United States Patent
Walensky et al.

(10) Patent No.: US 11,834,520 B2
(45) Date of Patent: *Dec. 5, 2023

(54) SELECTIVE TARGETING OF APOPTOSIS PROTEINS BY STRUCTURALLY-STABILIZED AND/OR CYSTEINE-REACTIVE NOXA PEPTIDES

(71) Applicant: Dana-Farber Cancer Institute, Inc., Boston, MA (US)

(72) Inventors: Loren D. Walensky, Newton, MA (US); Gregory H. Bird, Pelham, NH (US); Rachel Guerra, Cambridge, MA (US); Edward Harvey, Weston, MA (US)

(73) Assignee: Dana-Farber Cancer Institute, Inc., Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/766,201

(22) PCT Filed: Dec. 13, 2018

(86) PCT No.: PCT/US2018/065438
§ 371 (c)(1),
(2) Date: May 21, 2020

(87) PCT Pub. No.: WO2019/118719
PCT Pub. Date: Jun. 20, 2019

(65) Prior Publication Data
US 2021/0070802 A1 Mar. 11, 2021

Related U.S. Application Data

(60) Provisional application No. 62/599,229, filed on Dec. 15, 2017.

(51) Int. Cl.
*C07K 7/08* (2006.01)
*A61K 38/00* (2006.01)
*A61K 45/06* (2006.01)

(52) U.S. Cl.
CPC .............. *C07K 7/08* (2013.01); *A61K 38/00* (2013.01); *A61K 45/06* (2013.01)

(58) Field of Classification Search
None
See application file for complete search history.

(56) References Cited

U.S. PATENT DOCUMENTS

| | | |
|---|---|---|
| 5,446,090 A | 8/1995 | Harris |
| 6,348,558 B1 | 2/2002 | Harris et al. |
| 7,723,468 B2 | 5/2010 | Daffre et al. |
| 8,889,632 B2 | 11/2014 | Bernal et al. |
| 9,464,125 B2 | 10/2016 | Link et al. |
| 9,493,510 B2 | 11/2016 | Skerlj |
| 10,023,613 B2 | 7/2018 | Guerlavais |
| 11,078,246 B2 | 8/2021 | Walensky et al. |
| 2004/0093164 A1 | 5/2004 | Carlson et al. |
| 2005/0250680 A1 | 11/2005 | Walensky et al. |
| 2009/0048164 A1 | 2/2009 | Colman et al. |
| 2010/0168388 A1 | 7/2010 | Bernal et al. |
| 2010/0286057 A1 | 11/2010 | Walensky et al. |
| 2012/0172285 A1* | 7/2012 | Walensky ............... A61P 37/00 435/375 |
| 2014/0296160 A1 | 9/2014 | Walensky et al. |
| 2014/0370042 A1 | 12/2014 | Walensky et al. |
| 2015/0051249 A1 | 2/2015 | Walensky |
| 2015/0119551 A1 | 4/2015 | Bernal et al. |
| 2019/0002506 A1 | 1/2019 | Walensky et al. |
| 2019/0002514 A1 | 1/2019 | Walensky et al. |
| 2022/0213146 A1 | 7/2022 | Walensky et al. |

FOREIGN PATENT DOCUMENTS

| | | |
|---|---|---|
| JP | 2008-509378 | 3/2008 |
| JP | 2012-511512 | 5/2012 |
| JP | 2015-504064 | 2/2015 |
| WO | WO 1999/14259 | 3/1999 |

(Continued)

OTHER PUBLICATIONS

Huhn et al. (Cell Chemical Biology 23, 1123-1134, Sep. 22, 2016) (Year: 2016).*
Adams et al., "Phenix: A Comprehensive Python-based System for Macromolecular Structure Solution," Acta Crystallogr D Biol Crystallogr, 2010, 66(pt. 2)213-221.
Ali et al., "Stapled Peptides Inhibitors: A New Window for Target Drug Discovery," Comput Struct Biotechnol J. 2019, 17: 263-281.
Altschul et al., "Gapped BLAST and PSI-BLAST: a new generation of protein database search programs," Nucleic Acids Research, 1997, 25(17):3389-3402.
Anderson et al., "CCT241533 is a potent and selective inhibitor of CHK2 that potentiates the cytotoxicity of PARP inhibitors," Cancer Research, 2011, 74:463-472.

(Continued)

*Primary Examiner* — Sergio Coffa
(74) *Attorney, Agent, or Firm* — Fish & Richardson P.C.

(57) ABSTRACT

This disclosure features structurally-stabilized and/or cysteine-reactive peptide inhibitors for selective targeting of BFL-1, or dual targeting of BFL-1 and MCL-1. Also disclosed are methods of using such structurally-stabilized and cysteine-reactive peptides in the treatment of BFL-1- and/or MCL-1-expressing or -dependent cancers or diseases of cellular excess (e.g., autoimmune or inflammatory conditions). Also provided are combination therapies comprising such structurally-stabilized and/or cysteine-reactive peptides and inhibitors of the DNA damage response pathway, such as an ATM kinase inhibitor, ATR kinase inhibitor, CHK1/2 inhibitor, or PARP inhibitor; or an inhibitor of MCL-1, or a selective inhibitor of BCL-2, or an inhibitor of BCL-2/BCL-XL, for the treatment of BFL-1-expressing or -dependent cancers (e.g., AML), BFL-1 and MCL-1-expressing or -dependent cancers, or diseases of cellular excess (e.g., autoimmune or inflammatory conditions).

26 Claims, 82 Drawing Sheets
Specification includes a Sequence Listing.

(56) References Cited

FOREIGN PATENT DOCUMENTS

| WO | WO 1999/34833 | | 7/1999 |
|---|---|---|---|
| WO | WO 2005/075645 | | 8/2005 |
| WO | WO 2008/121767 | | 10/2008 |
| WO | WO 2009/108261 | | 9/2009 |
| WO | WO 2010/060112 | | 5/2010 |
| WO | WO 2010/068684 | | 6/2010 |
| WO | WO 2010/148335 | | 12/2010 |
| WO | WO 2014/110420 | * | 7/2014 |
| WO | WO 2014/151369 | | 9/2014 |
| WO | WO 2017/040323 | | 3/2017 |
| WO | WO 2017 /040329 | * | 3/2017 |
| WO | WO 2017/040329 | | 3/2017 |
| WO | WO 2019/118719 | | 6/2019 |

OTHER PUBLICATIONS

Awasthi et al., "ATM and ATR signaling at a glance," Journal of the Cell Science, 2016, 128:4255-4262.
Ayaz et al., "Conformational Adaption May Explain the Slow Dissociation Kinetics of Roniciclib (BAY 1000394), a Type I CDK Inhibitor With Kinetic Selectivity for CDK2 and CDK9," ACS Chem Biol, 2016, 11(6):1710-1719.
Baggio et al., "1V-locking stabilization of covalent helical peptides: Application to Bfl-1 antagonists," Chem Biol Drug Des, 2020, 00:1-15.
Balaram, "Non standard amino acids in peptide design and protein engineering," Current Opinion in Structural Biology, 1992, 2(6):845-851.
Bang et al., "Total Chemical Synthesis of Crambin," J. Am. Chem. Soc., 2004, 126:1377-1383.
Barile et al., "hBfl-I /hNOXA Interaction Studies Provide New Insights on the Role of Bfl-1 in Cancer Cell Resistance and for the Design of Novel Anticancer Agents," ACS Chem Biol, 2017, 12:444-455.
Beroukhim et al., "The landscape of somatic copy-number alteration across human cancers," Nature, Feb. 2010, 463(7283):899-905.
Billard "Design of novel BH3 mimetics for the treatment of chronic lymphocytic leukemia", Leukemia, 2012, 26(9):2032-2038.
Bird et al., "Biophysical determinants for cellular uptake of hydrocarbon-stapled peptide helices," Nat Chem Biol., 2016, 12(10):845-52.
Bird et al., "Chemical Synthesis and Hydrocarbon-stapled peptides for protein interaction research and therapeutic targeting." Current Protocol in Chemical Biology, Sep. 2011, 3(3):99-117.
Bird et al., "Synthesis and Biophysical Characterization of Stabilized a-Helices of BCL-2 Domains." Methods Enzymol., 2008, 446:369-386.
Blackwell et al., "Highly Efficient Synthesis of Covalently Cross-Linked Peptide Helices by Ring-Closing Metathesis," Angewandte Chem. Int. Ed., 1994, 37(23):3281-4.
Blackwell et al., "Ring-closing metathesis of olefinic peptides: Design, synthesis, and structural characterization of macrocyclic helical peptides," Journal of Organic Chemistry, 2001, 16:5291-5302.
Boehrer et al., "Suppression of the DNA damage response in acute myeloid leukemia versus myelodysplastic syndrome," Oncogene, 2009, 28(22):2205-2218.
Booth et al., "The Chk 1 inhibitor SRA737 synergizes with PARP1 inhibitors to kill carcinoma cells," Cancer Biology and Therapy, 2018, 9:786-796.
Bork et al., "Go hunting in sequence databases but watch out for traps," Trends in Genetics, 1996, 12:425-427.
Bork, "Powers and Pitfalls in Sequence Analysis: The 70% Hurdle," Genome Research, 2000, 10:398-400.
Brenner, "Errors in genome annotation," Trends in Genetics, 1999, 15:132-133.
Bridges et al., "Niraparib (MK-4827), a Novel poly(ADP-Ribose) Polymerase Inhibitor, Radiosensitizes Human Lung and Breast Cancer Cells," Oncotarget, 2014, 5(13):5076-5086.
Brock et al., "Radiosensitization of human and rodent cell lines by INO-1001, a novel inhibitor of poly(ADP-ribose) polymerase," Cancer Letters, 2004, 205(2):155-160.
Brunel et al., "Synthesis of constrained helical peptides by thioether ligation application to analogs of gp41," Chemical Communications, 2005, 20:2552-4.
Caenepeel et al., "Abstract 2027: Preclinical evaluation of AMG 176, a novel, potent and selective Mcl-1 inhibitor with robust anti-tumor activity in Mcl-1 dependent cancer models," Cancer Research, 2017, 4 pages.
Chapman et al., "A highly stable short a-helix constrained by a main-chain hydrogen-bond surrogate," Journal of the American Chemical Society, 2004, 126(39):12252-12253.
Chin et al., "Design and Evolution of a Miniature Bcl-2 Binding Protein," Angew Chem Int Ed Engl., 2001, 40:3806-09.
Chonghaile et al., "Mimicking the BH3 domain to kill cancer cells," Oncogene, 2009, 27: S149-S157.
Clinicaltrials. gov, [online], "Phase I Study of MIK665, a Mcl-1 Inhibitor, in Patients With Refractory or Relapsed Lymphoma or Multiple Myeloma," Dec. 14, 2016, retrieved on Nov. 16, 2020, retrieved from URL<https://www.clinicaltrials.gov/ct2/show/NCT02992483?term=NCT02992483&draw=2&rank=1>, Clinical Trial ID NCT02992483, 8 pages.
Clinicaltrials. gov, [online], "Phase I Study of S64315 Administred Intravenously in Patients With Acute Myeloid Leukaemia or Myelodysplastic Syndrome," Dec. 1, 2016, retrieved on Nov. 16, 2020, retrieved from URL<https://www.clinicaltrials.gov/ct2/show/NCT02979366?term=NCT02979366&draw=2&rank=1>, Clinical Trial ID NCT02979366, 10 pages.
Clinicaltrials.gov, [online], "Safety, Tolerability, Pharmacokinetics and Efficacy of AMG 397 in Subjects With Selected Relapsed or Refractory Hematological Malignancies," Mar. 14, 2018, retrieved on Nov. 16, 2020, retrieved from URL<https://www.clinicaltrials.gov/ct2/show/NCT03465540?term=NCT03465540&draw=2&rank=1>, Clinical Trial ID NCT03465540, 20 pages.
Curtin et al., "Novel poly(ADP-ribose) polymerase-1 Inhibitor, AG14361, Restores Sensitivity to Temozolomide in Mismatch Repair-Deficient Cells," Clin Cancer Res, 2004, 10(3):881-889.
Daniel et al., "Inhibition of poly(ADP-ribose) polymerase-1 enhances temozolomide and topotecan activity against childhood neuroblastoma," Cancer Therapy: Preclinical, 2009, 15(4):1241-1249.
Day et al., "Structure of the BH3 Domains From the p53-inducible BH3-only Proteins Noxa and Puma in Complex With Mcl-1," J Mol. Biol., 2008, 380(5):958-971.
Devi et al., "Antibodies to poly[((2->8)-alpha-N-acetylneuraminic Acid] and poly [(2->9))-alpha-N-acetylneuraminic Acid] Are Elicited by Immunization of Mice With *Escherichia coli*K92 Conjugates: Potential Vaccines for Groups B and C Meningococci and *E. coli* K1" Proc. Natl. Acad. Sci. USA, 1991, 88(16):7175-7179.
Doerks et al., "Protein annotation: detective work for function prediction," Trends in Genetics, 1998, 14:248-250.
Donawho et al., "ABT-888, and orally active poly(ADP-Ribose) polymerase inhibitor that potentiates DNA-damaging agents in preclinical tumor models," Clinical Cancer Research, 2007, 13(9):2728-2737.
Emsley et al., "Coot: Model-Building Tools for Molecular Graphics," Acta Crystallogr D Biol Crystallogr, 2004, 60:2126-2132.
European Search Report in European Application No. 16842712.8, dated Jan. 24, 2019, 19 pages.
Evans, "Scaling and Assessment of Data Quality," Acta Crystallogr D Biol Crystallogr, 2006, 62(Pt. 1):72-82.
Fattom et al., "Serum Antibody Response in Adult Volunteers Elicited by Injection of *Streptococcus pneumoniae* Type 12F Polysaccharide Alone or Conjugated to Diphtheria Toxoid," Infect. Immun., 1990, 58(7):2309-2312.
Fields et al., Chapter 3 in Synthetic Peptides: A users guide ed. Grant, W.H. Freeman & Co. New York, NY., 1992 p. 77-183.
Golding et al., "Improved ATM kinase inhibitor KU-60019 radiosensitizes glioma cells, compromises insulin, AKT and ERK prosurvival signaling, and inhibits migration and invasion," Mol. Cancer Ther, 2009, 8(10):2894-2902.

(56) References Cited

OTHER PUBLICATIONS

Gunnoo et al., "Bioconjugation—Using selective chemistry to enhance the properties of proteins and peptides as therapeutics and carriers," Organic & Biomolecular Chemistry, 2016, 14(34):8002-8013.

Haney et al., "Promoting peptide a-helix formation with dynamic covalent oxime side-chain cross-links." Chemical Communications, Jun. 2011, 47:10915-10917.

Haq et al., "BCL2A1 is a lineage-specific antiapoptotic melanoma oncogene that confers resistance to BRAF inhibition," Proc Natl Acad Sci USA, 2013, 110(11):4321-4326.

Harvey et al., "Crystal Structures of Anti-apoptotic BFL-1 and Its Complex with a Covalent Stapled Peptide Inhibitor," Structure, 2018, 26: 153-160.

Hickson et al., "Identification and characterization of a novel and specific inhibitor of the ataxia-telangiectasia mutated kinase ATM," Cancer Res, 2004, 64(24):9152-9159.

Hong et al., "Phase I Study of LY2606368, a Checkpoint Kinase 1 Inhibitor, in Patients With Advanced Cancer," J Clin Oncol, 2016, 34(15):1764-1771.

Horne et al., "Sequence-based Design of alpha/beta-peptide Foldamers That Mimic BH3 Domains," Angew Chen Int Ed Engl., 2008, 47(15):2853-6.

Huhn et al., "Selective Covalent Targeting of Anti-Apoptotic BFL-1 by Cysteine-Reactive Stapled Peptide Inhibitors," Cell Chem Biol., 2016, 23(9):1123-1134.

Jackson et al., "An indolocarbazole inhibitor of human checkpoint kinase (Chk1) abrogates cell cycle arrest caused by DNA damage," Cancer Research, 2000, 60:566-572.

Jackson et al., "General Approach to the synthesis of short a-helical peptides," Journal of American Chemical Society, 1991, 113:9391-9392.

Jobson et al., "Identification of a Bis-guanylhydrazone [4,4'-Diacetyldiphenylurea-bis(guanylhydrazone); NSC 109555] as a novel chemotype for inhibition of Chk2 Kinase," Molecular Pharmacology, 2007, 72:876-884.

Kabsch, "Integration, Scaling, Space-Group Assignment and Post-Refinement," Acta Crystallogr D Biol Crystallogr, 2010, 66(Pt 2):133-144.

Kawamoto et al., "Design of Triazole-Stapled BCL9 a-Helical Peptides to Target the b-Catenin/B-Cell CLL/Lymphoma 9 (BCL9) Protein-Protein Interaction," Journal of Medicinal Chemistry, 2012, 55(3):1137-1146.

Kemp et al., "The Structure and Energetics of Helix Formation by Short Templated Peptides in Aqueous Solution. 2. Characterization of Helical Structure of Ac-Hell-Ala6-OH," Journal of the American Chemical Society, 1996, 118(18):4240-4248.

Kim et al., "Oxidative stress attenuates Fas-mediated apoptosis in Jurkat T cell line through Bfl-1 induction," Oncogene, 2005, 24. 1252-1261.

Kotschy et al., "The MCL1 Inhibitor S63845 Is Tolerable and Effective in Diverse Cancer Models," Nature, 2016, 538(7626):477-482.

Kumita et al., "Photo control of helix content in a short peptide," Proceedings of the National Academy of Sciences, 2000, 3803-3808.

LaBelle et al., "A stapled BIM peptide overcomes apoptotic resistance in hematologic cancers," J Clin Invest, 2012, 122(6): 2018-2031.

Laird et al., "Talazoparib Is a Potent Radiosensitizer in Small Cell Lung Cancer Cell Lines and Xenografts," Clin Cancer Res, 2018, 24(20):5143-5152.

Lau et al., "Functionalised staple linkages for modulating the cellular activity of stapled peptides," Chemical Science, 2014, 5(5):1804-1809.

Lau et al., "Peptide stapling techniques based on different macrocyclisation chemistries," Chemical Society Reviews, 2015, 44:91-102.

Leshchiner et al., "Direct activation of full-length proapoptotic BAK, Proc Natl Acad Sci USA," 2013, 110(11):E986-95.

Leverson, "A New Staple: Peptide-Targeted Covalent Inhibitors," Cell chemical biology, 2016, 23(9):1043-1044.

Li et al., "Comparative Immunogenicities of Vi Polysaccharide-Protein Conjugates Composed of Cholera Toxin or Its B Subunit as a Carrier Bound to High- Or Lower-Molecular-Weight Vi" Infect. Immun., 1989, 57(12):3823-3827.

Liu et al., "Iniparib nonselectively modifies cysteine containing proteins in tumor cells and is not a bona fide PARP inhibitor," Cancer Therapy: Preclinical, 2012, 18(2):510-523.

Lovell et al., "Membrane Binding by tBid Initiates an Ordered Series of Events Culminating in Membrane Permeabilization by Bax," Cell, 2008, 135, 1074-1084.

Madden et al., "Facile synthesis of stapled, structurally reinforced peptide helices via a photoinduced intramolecular 1,3-dipolar cycloaddition reaction," Chem. Commun. (Camb), Oct. 2009, 7(37):5588-5590.

Madden et al., "Synthesis of Cell-Permeable Stapled Peptide Dual Inhibitors of the p53-Mdm2/Mdmx Interactions via Photoinduced Cycloaddition," Bioorg. Med. Chem. Letter, 2011, 21(5):1472-1475.

McCoy et al., "Phaser Crystallographic Software," J Appl Crystallogr, 2007, 40(Pt 4):658-674.

McGonigle et al., "E7449: A Dual Inhibitor of PARP1/2 and tankyrase 1/2 Inhibits Growth of DNA Repair Deficient Tumors and Antagonizes Wnt Signaling," Oncotarget, 2015, 6(38):41307-41323.

Menear et al., "4-[3-(4-Cyclopropanecarbonylpiperazine-1-carbonyl)-4-flurobenzyl]-2H-phthalazin-l-one: a novel bioavailable inhibitor of poly(ADP-ribose_Polymerase-1," Journal of Medicinal Chemistry, 2008, 51(20):6581-6591.

Meyers et al., "Computational correction of copy number effect improves specificity of CRISPR-Cas9 essentiality screens in cancer cells," Nat. Genet, 2017, 49(12):1779-1784.

Nakajima et al., "Noxa determines localization and stability of MCL-1 and consequently ABT-737 sensitivity in small cell lung cancer", Cell Death & Disease, 2014, 5(2):e1052, 10 pages.

Ngo et al., "Computational Complexity, Protein Structure Prediction, and the Levinthal Paradox," The Protein Folding Problem and Tertiary Structure Prediction, 1994, 433-506.

O'Connor et al., "The PARP Inhibitor AZD2461 Provides Insights Into the Role of PARP3 Inhibition for Both Synthetic Lethality and Tolerability With Chemotherapy in Preclinical Models," Cancer Res, 2016, 76(20):6084-6094.

Orner et al., "Toward Proteomimetics: Terphenyl Derivatives as Structural and Functional Mimics of Extended Regions of an a-Helix," Journal of the American Chemical Society, 2001, 123(22):5382-5383.

PCT International Preliminary Report on Patentability in International Appln. No. PCT/US2016/049083, dated Mar. 6, 2018, 13 pages.

PCT International Preliminary Report on Patentability in International Appln. No. PCT/US2016/049095, dated Mar. 6, 2018, 12 pages.

PCT International Preliminary Report on Patentability in International Appln. No. PCT/US2018/065438. dated Jun. 16, 2020, 10 pages.

PCT International Search Report and Written Opinion in International Appln. No. PCT/US2016/049083, dated Feb. 16, 2017, 19 pages.

PCT International Search Report and Written Opinion in International Appln. No. PCT/US2018/065438, dated May 22, 2019, 18 pages.

PCT International Search Report and Written Opinion in International Appln. No. PCT/US2016/049095, dated Feb. 21, 2017, 17 pages.

Penning et al., "Optimization of Phenyl-Substituted Benzimidazole Carboxamide poly(ADP-ribose) Polymerase Inhibitors: Identification of (S)-2-(2-fluoro-4-(pyrrolidin-2-yl)phenyl)-1H-benzimidazole-4-carboxamide (A-966492), a Highly Potent and Efficacious Inhibitor," J Med Chem, 2010, 53(8):3142-3153.

Phelan et al., "A general method for constraining short peptides to an a-helical conformation," Journal of the American Chemical Society, 1997, 119(3):455-460.

(56) References Cited

OTHER PUBLICATIONS

Pitter et al., "Dissection of the BCL-2 Family Signaling Network With Stabilized Alpha-Helices of BCL-2 Domains," Methods Enzymol., 2008, 446:387-408.
Roberts et al., "Targeting BCL2 With Venetoclax in Relapsed Chronic Lymphocytic Leukemia," N Engl J Med, 2016, 374(4):311-322.
Scagliotti et al., "Phase II evaluation of LY2603618, a first generation CHK1 inhibitor, in combination with pemetrexed in patients with advanced or metastatic non small cell lung cancer," Invest New Drugs, 2016, 34(5):625-635.
Schafmeister et al., "An All-Hydrocarbon cross-linking system for enhancing the helicity and metabolic stability of peptides," Journal of the American Chemical Society, 2000, 122(24):5891-5892.
Shepherd et al., "Single Turn Peptide Alpha Helices with Exceptional Stability in Water," Journal of the American Chemical Society, 2005, 127(9):2974-2983.
Skolnick et al., "From genes to protein structure and function: novel applications of computational approaches in the genomic era," Trends in Biotech., 2000, 18(1):34-39.
Smaill et al., "Synthesis and structure—activity relationships of N-6 substituted analogues of 9-hydroxy-4-phenylpyrrolo[3,4-c]carbazole-1,3(2H,6H)-diones as inhibitors of Wee1 and Chk1 checkpoint kinases," European Journal of Medicinal Chemistry, 2008, 43:1276-1296.
Smith et al., "The challenges of genome sequence annotation or "The devil is in the details,"" Nature Biotechnology, 1997 15:1222-1223.
Spokoyny et al., "A perfluoroaryl-cysteine SnAr Chemistry approach to unprotected peptide stapling," Journal of American Chemical Society, 2013, 135(16):5946-5949.
Stewart et al., "The MCL-1 BH3 Helix Is an Exclusive MCL-1 Inhibitor and Apoptosis Sensitizer," Nature Chemical Biology, 2010, 6(8):595-601.
Szu et al., "Laboratory and Preliminary Clinical Characterization of Vi Capsular Polysaccharide-Protein Conjugate Vaccines," Infect. Immun., 1994, 62(10):4440-4444.
Szu et al., "Relation Between Structure and Immunologic Properties of the Vi Capsular Polysaccharide," Infect. Immun., 1991, 59:4555-4561.
Szu et al., "Vi Capsular Polysaccharide-Protein Conjugates for Prevention of Typhoid Fever. Preparation, Characterization, and Immunogenicity in Laboratory Animals," J Exp. Med., 1987, 166(5):1510-1524.
Teng et al., "Structure-based Design and Synthesis of (5-arylamino-2H-pyrazol-3-yl)-biphenyl-2',4'-diols as Novel and Potent Human CHK1 Inhibitors," J Med Chem, 2007, 50(22):5253-6.
Tokuriki et al., "Stability effects of mutations and protein evolvability," Current Opinion in Structural Biology, 2009, 19: 596-604.
Tsherniak et al., "Defining a Cancer Dependency Map," Cell, 2017, 170(3):564-576.
Walensky et al., "Activation of Apoptosis in Vivo by a Hydrocarbon-Stapled BH3 Helix," Science, 2004, 305(5689):1466-1470.
Walensky et al., "Hydrocarbon-stapled peptides: Principles, practice and progress," Journal of Medicinal Chemistry, 2014, 57:6275-6288.
Weber et al., "ATM and ATR as therapeutic targets in cancer," Pharmacology and Therapeutics, 2014, 149:124-138.
Wells, "Additivity of Mutational Effects in Proteins," Biochemistry, 1990, 29:8509-8517.
Wilen et al., "Strategies in Optical Resolutions," Tetrahedron 33:2725, 1977.
Wilen, "Tables of Resolving Agents and Optical Resolutions," EX. Eliel, Ed., Univ. of Notre Dame Press, Notre Dame, IN, 1972, 268-308.
Williams et al., "Asymmetric synthesis of monosubstituted and a,a-Disubstituted a-Amino acids via diastereoselective glycine enolate alkylations," Journal of the American Chemical Society, 1991, 113(24):9276-9286.
Williams et al., "Efficient asymmetric synthesis of n-tert-butoxycarbonyl a-aminoacids using 4-tert-butoxycarbonyl-5,6-diphenylmorpholin-2-one(R)-(N-tert-butoxycarbonyl) Allylglycine: (4-pentenoic acid, 2-[[(1, 1-dimethylethoxy)carbonyl] amino]-,(2 R)-)" Organic Synthesis, 2003, 80:31-37.
Winter, "xia2: an expert system for macromolecular crystallography data reduction," Appl Crystallogr, 2010, 43(1):186-190.
Yang et al., "[11] Calculation of Protein conformation from circular dichroism," Macromolecular Conformation: Spectroscopy, 1986, 208-269.
Youle et al., "The BCL-2 protein family: opposing activities that mediate cell death," Nature reviews Molecular cell biology, 2008, 9(1):47-59.
Zabludoff et al., "AZD7762, a novel checkpoint kinase inhibitor, drives checkpoint abrogation and potentiates DNA-targeted therapies," Molecular Cancer Therapeutics, 2008, 7(9):2955-2966.
Zhu et al., "Identification of a Novel Senolytic Agent, Navitoclax, Targeting the Bel-2 Family of Anti-Apoptotic Factors," Aging Cell, 2016, 15(3):428-35.
Holm et al., "Electrophilic Affibodies Forming Covalent Bonds to Protein Targets," The Journal of Biological Chemistry, Nov. 2009, 284(47):32906-32913.
Walensky et al., "A Stapled BID BH3 Helix Directly Binds and Activates BAX," Molecular Cell, Oct. 2006, 24:199-210.
Wikipedia.org, [online], "Acetylation," Feb. 17, 2021, retrieved on Mar. 22, 2021, retrieved from URL<https://en.wikipedia.org/wiki/Acetylation#N-terminal_acetylation>, 16 pages.
U.S. Appl. No. 15/752,358, 2019/0002514, filed Feb. 13, 2018, Walensky.
U.S. Appl. No. 15/752,358, filed Feb. 13, 2018, 2019/0002514, U.S. Pat. No. 11,078,246, Walensky.
U.S. Appl. No. 15/752,372, filed Feb. 13, 2018, 2019/0002506, Walensky.
U.S. Appl. No. 17/389,761, filed Jul. 30, 2021, Walensky.
Guerra et al., "Precision Targeting of BFL-1/A1 and an ATM Co-dependency in Human Cancer," Cell Reports, Sep. 25, 2018, 24(13):3393-403.
U.S. Appl. No. 15/752,358, 2019/0002514, U.S. Pat. No. 11,078,246, filed Feb. 13, 2018, Walensky.
U.S. Appl. No. 17/353,206, filed Jun. 21, 2021, Walensky.
U.S. Appl. No. 17/674,379, filed Feb. 17, 2022, Walensky.
U.S. Appl. No. 15/752,372, 2019/0002506, filed Feb. 13, 2018, Walensky.
U.S. Appl. No. 17/389,761, 2022/0213146, filed Jul. 30, 2021, Walensky.

* cited by examiner

| | |
|---|---|
| NOXA SAHB$_{26-40}$ | ATQLRRFGDKLNFRQ |
| NOXA SAHB-1 | XTQLXRFGDKLNFRQ |
| NOXA SAHB-2 | AXQLRXFGDKLNFRQ |
| NOXA SAHB-3 | ATXLRRXGDKLNFRQ |
| NOXA SAHB-4 | ATQXRRFXDKLNFRQ |
| NOXA SAHB-5 | ATQLXRFGXKLNFRQ |
| NOXA SAHB-6 | ATQLRXFGDXLNFRQ |
| NOXA SAHB-7 | ATQLRRXGDKXNFRQ |
| NOXA SAHB-8 | ATQLRRFXDKLXFRQ |
| NOXA SAHB-9 | ATQLRRFGXKLNXRQ |
| NOXA SAHB-10 | ATQLRRFGDXLNFXQ |
| NOXA SAHB-11 | ATQLRRFGDKXNFRX |
| NOXA SAHB-12 | ATQLRRFGDKLXFRQX |
| NOXA SAHB-13 | 8TQLRRFXDKLNFRQ |
| NOXA SAHB-14 | A8QLRRFGXKLNFRQ |
| NOXA SAHB-15 | AT8LRRFGDXLNFRQ |
| NOXA SAHB-16 | ATQ8RRFGDKXNFRQ |
| NOXA SAHB-17 | ATQL8RFGDKLXFRQ |
| NOXA SAHB-18 | ATQLR8FGDKLNXRQ |
| NOXA SAHB-19 | ATQLRR8GDKLNFXQ |
| NOXA SAHB-20 | ATQLRRF8DKLNFRX |

Note: D-nipecotic acid derivatization placed at the stapled peptide N-terminus

FIG. 2

| | |
|---|---|
| NOXA SAHB-15 A26E | ET8LRRFGDXLNFRQ |
| NOXA SAHB-15 T27A | AA8LRRFGDXLNFRQ |
| NOXA SAHB-15 L29A | AT8ARRFGDXLNFRQ |
| NOXA SAHB-15 R30A | AT8LARFGDXLNFRQ |
| NOXA SAHB-15 R31A | AT8LRAFGDXLNFRQ |
| NOXA SAHB-15 F32A | AT8LRRAGDXLNFRQ |
| NOXA SAHB-15 G33A | AT8LRRFADXLNFRQ |
| NOXA SAHB-15 D34A | AT8LRRFGAXLNFRQ |
| NOXA SAHB-15 L36A | AT8LRRFGDXANFRQ |
| NOXA SAHB-15 N37A | AT8LRRFGDXLAFRQ |
| NOXA SAHB-15 F38A | AT8LRRFGDXLNARQ |
| NOXA SAHB-15 R39A | AT8LRRFGDXLNFAQ |
| NOXA SAHB-15 Q40A | AT8LRRFGDXLNFRA |

Note: D-nipecotic acid derivatization placed at the stapled peptide N-terminus

FIG. 6

NOXA SAHB-15 R31E    ATθLREFGDXLNFRQ
NOXA SAHB-15 R39E    ATθLRRFGDXLNEEQ
NOXA SAHB-15 N37D    ATθLRRFGDXLDFRQ
NOXA SAHB-15 Q40L    ATθLRRFGDXLNFRL

Note: D-nipecotic acid derivatization placed at the stapled peptide N-terminus

FIG. 10

| | Pearson Correlation Combined CRISPR | Pearson Correlation CERES Avana | Spearman Correlation CERES Avana |
|---|---|---|---|
| BCL2A1 | 1 | 1 | 1 |
| ATM | 0.986 | 0.857 | 0.881 |
| SLFNL1 | 0.983 | 0.694 | 0.762 |
| RFTN2 | 0.98 | 0.51 | 0.667 |
| EDC4 | 0.975 | 0.89 | 0.881 |
| DCST2 | 0.963 | -0.073 | -0.071 |
| SULT1C4 | 0.95 | 0.868 | 0.857 |
| TR1QK | 0.946 | 0.749 | 0.905 |
| TAS2R50 | 0.945 | 0.887 | 0.857 |
| IQCA1 | 0.943 | 0.818 | 0.905 |

FIG. 25

Table 1 Crystallization conditions and data collection and refinement statistics for crystal structures

| Structure Name | BFL-1 apo | BFL-1/Peptide |
|---|---|---|
| Ligand | - | Peptide |
| RCSB accession code | 5WHI | 5WHH |
| Data collection [a] | | |
| Space group | $P2_1$ | $P3_221$ |
| Cell dimensions | | |
| $\quad a, b, c$ (Å) | 39.51 43.09 43.44 | 86.71 86.71 40.36 |
| $\quad a, b, g$ (°) | 90 104.15 90 | 90 90 120 |
| Resolution (Å) | 28.63 - 1.69 (1.75 - 1.69) [b] | 43.35 - 2.38 (2.46 - 2.38) |
| $R_{pim}$ | 0.027 (0.677) | 0.056 (0.683) |
| $I / sI$ | 13.56 (1.14) | 11.23 (1.09) |
| Completeness (%) | 97.98 (98.12) | 99.03 (92.60) |
| Redundancy | 3.3 (3.3) | 9.8 (6.1) |
| Structure solution | | |
| PDB entries used for molecular replacement | 3I1H | 3I1H |
| Refinement | | |
| Resolution (Å) | 28.63 - 1.69 | 43.35 - 2.38 |
| No. reflections, unique | 15702 | 7157 |
| $R_{work} / R_{free}$ | 0.1955/0.2340 | 0.2102/0.2882 |
| No. atoms | 1245 | 1326 |
| $\quad$ Protein | 1186 | 1272 |
| $\quad$ Ligand/ion | 5 | 1 |
| $\quad$ Water | 54 | 53 |
| B-factors | | |
| $\quad$ Protein | 47.3 | 45.4 |
| $\quad$ Ligand/ion | 157.5 | 32.0 |
| $\quad$ Water | 50.4 | 44.8 |
| R.m.s. deviations | | |
| $\quad$ Bond lengths (Å) | 0.008 | 0.007 |
| $\quad$ Bond angles (°) | 0.86 | 0.96 |
| Ramachandran Plot | | |
| $\quad$ Preferred | 97.9% | 92.7% |
| $\quad$ Allowed | 1.4% | 7.3% |
| $\quad$ Not Allowed | 0.7% | 0.0% |

[a] A single crystal was used to collect data for each of the structures reported here.
[b] Values in parentheses are for highest-resolution shell.

FIG. 30

```
                                    α1
  1 MTDCEFGYIY RLAQDYLQCY LQIPQPGSGP SKTSRVLQNV AFSVQKEVEK 50
                                              α2
           α3                    α4      BH3        α5
 51 NLKSCLDNVN VVSVDTARTL FNQVMEKEFE DGIINWGRIV TIFAFEGILI 100
                             α6               BH1    α7      α8
101 KKLLRQQIAP DVDTYKEISY FVAEFIMNNT GEWIRQNGGW ENGFVKKFEP 150
                                                BH2
151 K
```

FIG. 31A

| Amino Acids | Apo Distance (Å) |
|---|---|
| BFL-1 Cys 55 to Leu 70 | 10.2 |
| MCL-1 Met 231 to Leu 246 | 10.9 |
| BCL-$X_L$ Leu 108 to Ser 122 | 10.6 |
| BFL-1 Cys 55 to Val 74 | 11.3 |
| MCL-1 Met 231 to Val 249 | 10.7 |
| BCL-$X_L$ Leu 108 to Val 126 | 6.5 |
| BFL-1 Val 59 to Leu 70 | 8.3 |
| MCL-1 Leu 235 to Leu 246 | 8.0 |
| BCL-$X_L$ Leu 112 to Ser 122 | 7.0 |

FIG. 31D

```
           α2                                              α3                        α4                                        α5
BFL-1  KTSRVLQNVAFSVQKEVEVEKNLKSCLDNVNVVSVDTARTLFNQVMEKEFED--GIINWGRIVTIFAFEGILIKKLLRQ
MCL-1  TSRKALETLRRVGDGVQRNHETAFQGMLRK-LDIKNEDDVKLSRVMIHVFSD--GVTNWGRIVTLISFGAFVAKHLKT
BCL-2    VVHKTLRQAGDDFSRRYRRDFAEMSSQ-LHLTPFTARGRFATVEELFRD-GV-NWGRIVAFFEFGGVMCVESVN
BCL-XL MAAVKQALREAGDEFELRYRRAFSDLTSQ-LHITPGTAYQSFEQVVNELFRD-GV NWGRIVAFFSFGGALCVESVD
BCL-W    PLHQAMRAAGDEFETRFRRTFSDLAAQ-LLHVTPGSAQQRFTQVSDELQG-GP-NWGRLVAFFVFGAALCAESVN
BCL-B         PEAAVLRSAAARLRQIHRSFFSAYLG-----YPGNRFELVALMADSVLSDSPGP-TWGRVVTLTFAGTL
BAX     ASTKKLLSECLKRIGDELDSNME-IQRMIAA----VDTDSPREVFFRVAADMFSD--GNFNWGRVVALFYFASKLVLKALC
BAK         TMGQVRQLAIIGDDINRRYDSEFQTMLQH-LQPTAENAYEYETKIATSLFES-GI-NWGRVVALLGFGYRLALHVVQ
```

FIG. 31E

NOXA SAHB: [26]*AT8LRRFGDXLNFRQ[40]
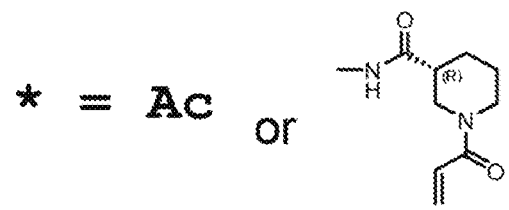
D-Nipecotic Acid
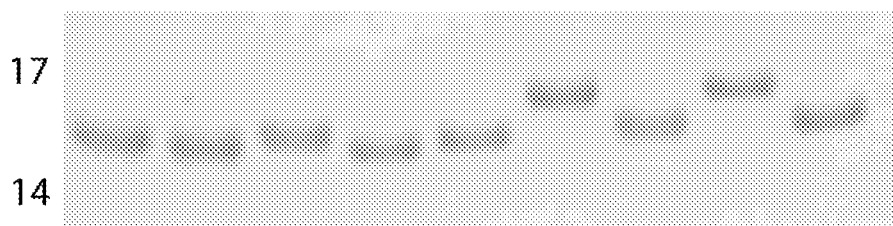
FIG. 32A

| Amino Acids | Apo Distance (Å) | NOXA Bound Distance (Å) |
|---|---|---|
| BFL-1 Cys 55 to Leu 70 | 10.2 | 13.0 |
| MCL-1 Met 231 to Leu 246 | 10.9 | 10.4 |
| BFL-1 Cys 55 to Val 74 | 10.6 | 12.9 |
| MCL-1 Met 231 to Val 249 | 10.7 | 10.6 |
| BFL-1 Val 59 to Leu 70 | 8.3 | 9.6 |
| MCL-1 Leu 235 to Leu 246 | 8.0 | 7.3 |

FIG. 34B

Apo BFL-1ΔC

BFL-1ΔC/D-NA-NOXA SAHB

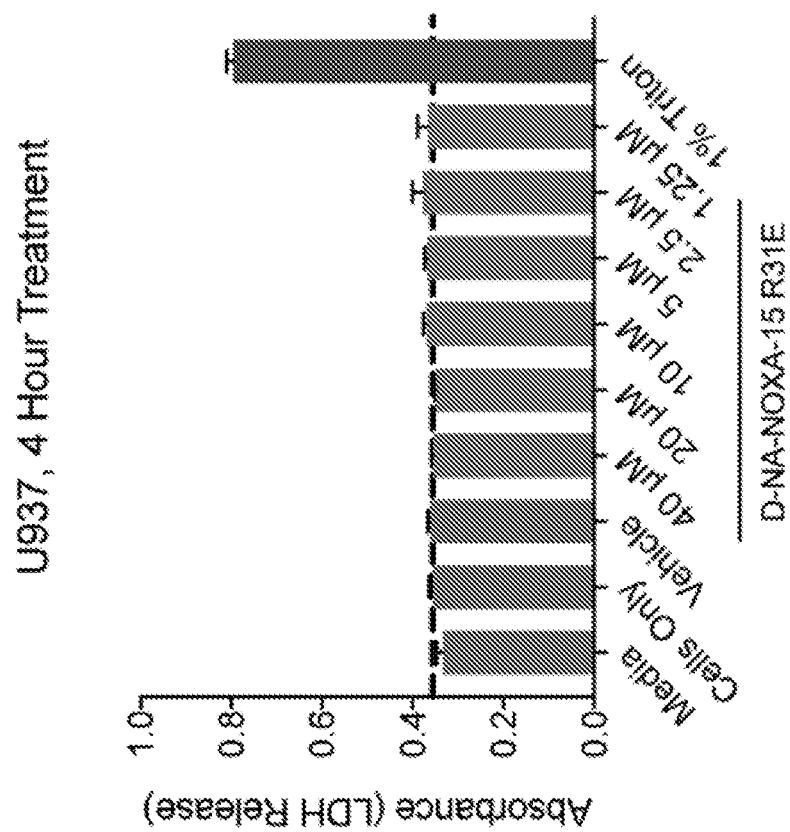
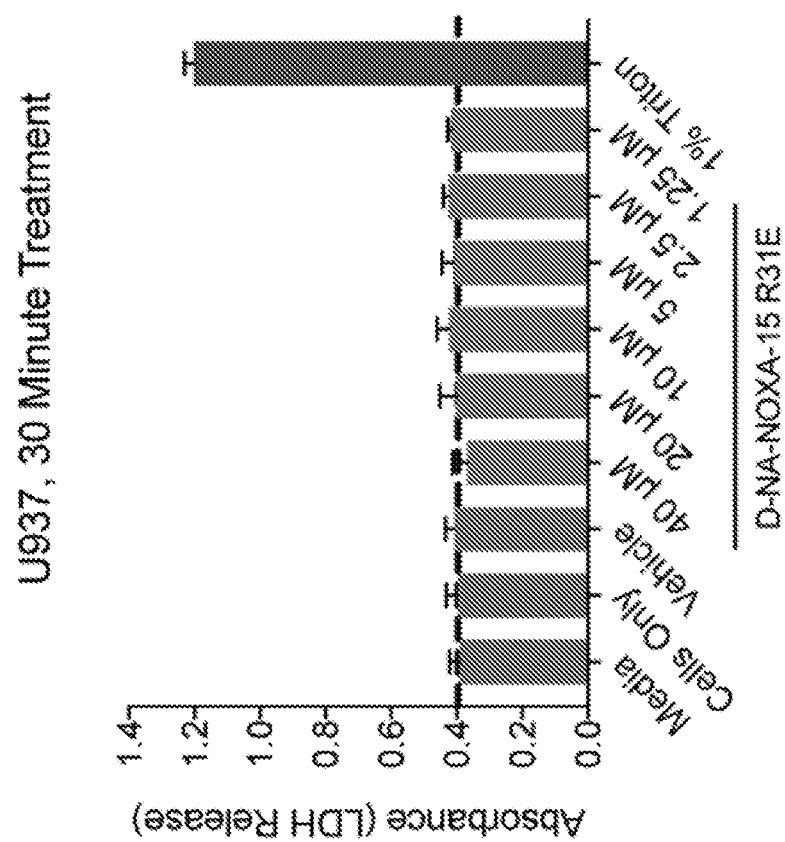
FIG. 60

Fraction of cells plasma-membrane permeabilized
(20 μM, 2 hr)

A

|  | BFL-1 Depedency Z-score | BFL-1 Scaled Rank |
|---|---|---|
| U937 | -2.880572590 | 0.133559706 |
| NB4 | -2.137596737 | 0.187775891 |
| THP1 | -1.558836432 | 0.164799095 |
| P31FUJ | -1.255901014 | 0.258064516 |
| TF1 | -0.960518814 | 0.304753820 |
| MOLM13 | -0.323784907 | 0.419524618 |
| NOMO1 | 0.276081075 | 0.536672326 |
| MV4;11 | 0.498330955 | 0.563950198 |

B

| Cell Line | Cancer Type | BFL-1 Dependency Z-Score | BFL-1 Scaled Rank |
|---|---|---|---|
| DU4475 | Breast | -5.145431813 | 0.090548953 |
| IMR32 | Autonomic Ganglia | -4.058526463 | 0.116525184 |
| PSN1 | Pancreas | -3.975630696 | 0.134352009 |
| COLO679 | Skin | -3.494531252 | 0.140350877 |
| U178 | CNS | -3.468540224 | 0.153027731 |
| NB1 | Autonomic Ganglia | -3.247641011 | 0.178494624 |
| ASPC1 | Pancreas | -3.112237399 | 0.147934352 |
| U787MG | CNS | -2.963316233 | 0.163893605 |
| U937 | Hematopoetic/Lymphoid | -2.880572590 | 0.133559706 |
| HT144 | Skin | -2.796976029 | 0.200565931 |
| SKMEL30 | Skin | -2.667202852 | 0.160611205 |
| NCIH2110 | Lung | -2.516536028 | 0.182795699 |
| MDST8 | Large Intestine | -2.470023481 | 0.178720996 |
| NCIH2122 | Lung | -2.465532621 | 0.182229768 |
| NCIN87 | Stomach | -2.370858183 | 0.218222977 |
| MORCPR | Lung | -2.161270828 | 0.210526316 |
| NB4 | Hematopoetic/Lymphoid | -2.137596737 | 0.187775891 |
| UACC62 | Skin | -2.111832692 | 0.171533673 |
| KELLY | Autonomic Ganglia | -2.071612986 | 0.177589134 |
| SKNMC | Bone | -2.043786655 | 0.213186191 |

C

|  | Pearson Correlation Coefficient | Spearman Correlation Coefficient |
|---|---|---|
| BFL1 | 1 | 1 |
| DCTPP1 | 0.941102590 | 0.928571429 |
| ATM | 0.937773368 | 0.976190476 |
| GEN1 | 0.936089024 | 0.904761905 |
| ASCC1 | 0.934906261 | 0.928571429 |
| NSUN6 | 0.916185332 | 0.904761905 |
| FBXO42 | 0.911441405 | 0.904761905 |
| DYNC2LI1 | 0.907170948 | 0.904761905 |
| JRKL | 0.904267905 | 0.928571429 |
| C3orf62 | 0.902864788 | 0.904761905 |

SELECTIVE TARGETING OF APOPTOSIS PROTEINS BY STRUCTURALLY-STABILIZED AND/OR CYSTEINE-REACTIVE NOXA PEPTIDES

CROSS REFERENCE TO RELATED APPLICATIONS

This application is a national stage entry of International Application No. PCT/US2018/065438, filed Dec. 13, 2018, which claims priority to U.S. Provisional Application No. 62/599,229, filed Dec. 15, 2017, each of which is incorporated by reference herein in its entirety.

STATEMENT REGARDING FEDERALLY SPONSORED RESEARCH

This invention was made with government support under grant numbers 5R35CA197583 and R50CA211399 awarded by the National Institutes of Health. The government has certain rights in the invention.

TECHNICAL FIELD

This disclosure relates to structurally-stabilized and/or cysteine-reactive NOXA peptides and methods for using such peptides alone or in combination with an inhibitor of a DNA damage response pathway member (e.g., ATM kinase inhibitor, ATR kinase inhibitor, CHK1/2 inhibitor, PARP inhibitor), or an inhibitor of MCL-1, or a selective inhibitor of BCL-2, or an inhibitor of BCL-2/BCL-XL in the treatment of cancer and diseases of cellular excess such as autoimmune and inflammatory conditions.

BACKGROUND

The BCL-2 protein family, which includes both pro-apoptotic and anti-apoptotic members, forms a complex network of checks and balances that dictate cell fate. The family is structurally defined by the presence of up to four conserved "BCL-2 homology" (BH) domains, all of which include alpha-helical portions. Anti-apoptotic proteins such as BFL-1 and MCL-1 display sequence conservation in all BH domains, whereas pro-apoptotic proteins are divided into "multi-BH domain" members (e.g., BAX and BAK) and "BH3-only" members (e.g., BIM and NOXA) that display sequence similarity only in the alpha-helical BH3 domain. The BH3-only subgroup is diverse and transmits pro-death signals from disparate stimuli to the apoptotic machinery located at the mitochondria. The BH3-only protein's death signal will either be neutralized by anti-apoptotic proteins or delivered, directly or indirectly, to the mitochondrial executioners BAX and BAK. When activated, BAX/BAK induce outer mitochondrial membrane permeabilization, enabling released mitochondrial factors to induce caspases, which irreversibly execute the death program.

Human cancers invariably suppress mitochondrial apoptosis to resist treatment and ensure cell survival. The most common strategy involves overexpression of one or more anti-apoptotic BCL-2 family proteins, such as BCL-2, BCL-$X_L$, MCL-1, or BFL-1. These proteins share a common mechanism of mitochondrial apoptosis suppression, involving entrapment of the BH3 helices of pro-apoptotic members, including the multidomain proteins BAX and BAK, and the BH3-only stress-sensor proteins, such as BIM, BID, BAD, and NOXA. Given the overlap in binding specificity among anti-apoptotic proteins, molecular targeting of one member often leads to upregulation of another—resulting in the oncologic version of "whack-a-mole." For example, small molecule targeting of BCL-2 by the selective small molecule inhibitor ABT-737 has been shown to trigger upregulation of MCL-1 or BFL-1 in lymphoma cell lines. With a selective small molecule inhibitor of BCL-2 now FDA-approved and selective compounds for MCL-1 recently advanced to clinical trials, BFL-1 remains a high priority, undrugged cancer target. Indeed, in addition to its capacity to confer resistance to selective BCL-2 and MCL-1 inhibitors, BFL-1 is an independent oncogenic driver in a host of human cancers, including melanoma, leukemia, and lymphoma.

BCL-2-related protein BFL-1/A1 has been implicated in suppressing the mitochondrial apoptotic pathway in a wide variety of liquid and solid tumors. For example, when overexpressed or mutated to resist ubiquitin-mediated degradation, BFL-1 induces chemoresistance in discrete lymphomas, including the BCR-dependent/elevated NFκB subclass of germinal center lymphomas and diffuse large B-cell lymphomas. BFL-1 was also identified as a pathologic survival factor in approximately 30% of human melanomas, including those with clinically relevant BRAF V600E resistance mutations.

Myeloid Cell Leukemia-1 (MCL-1), an anti-apoptotic BCL-2 family survival protein, has been implicated in the development, maintenance, and chemoresistance of a broad range of cancers and is one of the top ten most widely expressed pathologic factors in human cancers (see, e.g., Beroukhim, Nature, 463(7283):899-905 (2010)). Highly overexpressed in human cancers, MCL-1 mounts formidable apoptotic resistance by binding and sequestering the essential BH3 domain helices of pro-apoptotic BCL-2 family members.

Thus, compounds that interfere with BFL-1 and/or MCL-1 activity could be useful in treating a variety of cancers and diseases of cellular excess such as autoimmune and inflammatory conditions.

SUMMARY

This disclosure relates to structurally-stabilized and/or cysteine-reactive NOXA BH3 peptides that can covalently bind to BFL-1 and also engage BFL-1 and/or MCL-1 through non-covalent interactions. This disclosure also features methods for using such peptides alone or in combination with other therapeutic agents (e.g., an inhibitor of a DNA damage response pathway member (e.g., ATM kinase inhibitor, ATR kinase inhibitor, CHK1/2 inhibitor, PARP inhibitor), a selective inhibitor of MCL-1, a selective inhibitor of BCL-2, an inhibitor of BCL-2/BCL-XL) in the treatment of BFL-1- and/or MCL-1-dependent or expressing cancers (e.g., hematologic malignancies, melanoma).

In a first aspect, this disclosure provides a peptide that includes an electrophilic warhead; and a modified amino acid sequence of the sequence set forth in SEQ ID NO:39. The modified amino acid sequence is at least five amino acids in length; comprises at least one peptide structure stabilizing modification, and one or more (e.g., 1, 2, 3, 4, 5, 6, 7, 8, 9, 10, 11, 12, 13, 14) amino acids of SEQ ID NO:39 are substituted by another amino acid. The peptide binds BFL-1/A1 or binds both BFL-1/A1 and MCL-1. The at least five amino acids can be a variant of, e.g., ATQLR (SEQ ID NO:110), RFGDK (SEQ ID NO:143), LNFRQ (SEQ ID NO:124), TQLRR (SEQ ID NO:145), FGDKL (SEQ ID NO:146), QLRRF (SEQ ID NO:147), GDKLN (SEQ ID NO:148), LRRFG (SEQ ID NO:149), DKLNF (SEQ ID NO:150), RRFGD (SEQ ID NO:142), and KLNFR (SEQ ID NO:144). For example, at least two of the five amino acids are modified for structure stabilization (e.g., by substituting with non-natural amino acids that can form a hydrocarbon staple) and one or more (e.g., 1, 2, 3) amino acids are substituted with other amino acids. In certain instances, the substitution(s) are on the non-interacting face of the helix. In certain instances, the substitution(s) are on the non-interacting face of the helix. In some cases, the substitutions are conservative amino acid substitutions. In certain embodiments, the one or more amino acids of the at least five amino acids are substituted by an amino acid or amino acids selected from the group consisting of L-alanine, D-alanine, α-aminoisobutyric acid, N-methyl glycine, serine, a substituted alanine, and a glycine derivative.

In some embodiments, the modified amino acid sequence is 5 to 35 amino acids in length (e.g., 5, 6, 7, 8, 9, 10, 11, 12, 13, 14, 15, 20, 25, 30, 32, 35). In some embodiments, the modified amino acid sequence is 8 to 18 (e.g., 8, 9, 10, 11, 12, 13, 14, 15, 16, 17, 18) amino acids in length.

In some embodiments, the peptide structure stabilizing modification is a staple and/or stitch. In some instances, the staple is at one or more of position i and i+3; i and i+4; or i and i+7. In some embodiments, the peptide structure stabilizing modification comprises substitution of at least two (e.g., 2, 3, 4, 5, 6) amino acids of SEQ ID NO:39 with non-natural amino acids with olefinic side chains. In some instances, the non-natural amino acids with olefinic side chains are selected from the group consisting of: S-pentenyl alanine, R-octenyl alanine; R-propenylalanine, S-pentenylalanine; R-pentenylalanine, S-pentenylalanine; Bis-pentenylglycine, S-pentenylalanine, R-octenylalanine; and Bis-pentenylglycine, S-octenylalanine, R-octenylalanine. In certain embodiments, the staple and/or stitch involves positions: 1 and 5; 2 and 6; 3 and 7; 6 and 10; 10 and 14; 11 and 15; 12 and 16; 1 and 8; 3 and 10; 6 and 13; 7 and 14; or 8 and 15 (wherein the positions are based on SEQ ID NO:39).

In certain embodiments, the peptide structure stabilizing modification is a hydrocarbon staple/stitch, a lactam staple/stitch; a UV-cycloaddition staple/stitch; an oxime staple/stitch; a thioether staple/stitch; a double-click staple/stitch; a bis-lactam staple/stitch; a bis-arylation staple/stitch; or a combination of any two or more thereof.

In certain embodiments, the one or more (e.g., 1, 2, 3, 4, 5, 6) amino acids of SEQ ID NO:39 that are substituted by another amino acid are on the BFL-1/A1 non-interacting face of the helix of SEQ ID NO:39. In some embodiments, 0 to 5 amino acids in SEQ ID NO:39 are removed from the C-terminal or are removed and replaced with 1 to 6 amino acids from the group consisting of alanine, D-alanine, α-aminoisobutyric acid, N-methyl glycine, serine, a substituted alanine, and a glycine derivative. In some embodiments, 0 to 6 amino acids on the non-interacting face in SEQ ID NO:39 are substituted with an amino acid selected from the group consisting of alanine, D-alanine, α-aminoisobutyric acid, N-methyl glycine, serine, a substituted alanine, and a glycine derivative. In some embodiments, one or more of the following amino acids A1, L4, R5, F7, G8, L11, N12, and Q15 of SEQ ID NO:39 are substituted with an alpha-methylated or alpha-ethylated natural amino acids. In some embodiments, one or more of the following amino acids A1, L4, R5, F7, G8, L11, N12, and Q15 of SEQ ID NO:39 are substituted with an amino acid selected from the group consisting of L-alanine, D-alanine, α-aminoisobutyric acid, N-methyl glycine, serine, a substituted alanine, and a glycine derivative. In some embodiments, one or more of the following amino acids T2, Q3, R6, K10, F13, and R14 of SEQ ID NO:39 are substituted with an alpha-methylated or alpha-ethylated natural amino acids. In certain embodiments, one or more of the following amino acids T2, Q3, R6, K10, F13, and R14 of SEQ ID NO:39 are substituted with an amino acid selected from the group consisting of L-alanine, D-alanine, α-aminoisobutyric acid, N-methyl glycine, serine, a substituted alanine, and a glycine derivative. In certain embodiments, one or more of the following amino acids A1, T2, Q3, R5, R6, F7, G8, K10, L11, N12, F13, R14, and Q15 of SEQ ID NO:39 are modified with an alpha methyl or ethyl, or are substituted with an amino acid selected from the group consisting of L-alanine, D-alanine, α-aminoisobutyric acid, N-methyl glycine, serine, a substituted alanine, and a glycine derivative. In certain instances, the one or more amino acids of SEQ ID NO:39 that are substituted by another amino acid are on the BFL-1/A1 interacting face of the helix of SEQ ID NO:39. In other instances, the one or more amino acids of SEQ ID NO:39 that are substituted by another amino acid are on the BFL-1/A1 non-interacting and interacting faces of the helix of SEQ ID NO:39. In certain embodiments, the one or more amino acids of SEQ ID NO:39 are substituted by an amino acid or amino acids selected from the group consisting of L-alanine, D-alanine, α-aminoisobutyric acid, N-methyl glycine, serine, a substituted alanine, and a glycine derivative.

In some embodiments, one or more of the following (numbering based on SEQ ID NO: 39) are not substituted, stapled, or stitched: L4 and G8 together; R5 and D9 together; F7 and L11 together; G8 and N12 together; D9 and F13 together; T2 and D9 together; L4 and L11 together; R5 and N12 together; A1; L4; G8; or D9.

In some embodiments, overall hydrophobicity of the peptide is reduced relative to a peptide of SEQ ID NO:39 or 16. In some embodiments, overall positive charge of the peptide is reduced relative to a peptide of SEQ ID NO:39 or 16. In certain embodiments, overall hydrophobicity and overall positive charge of the peptide is reduced relative to a peptide of SEQ ID NO:39 or 16.

In some embodiments, the electrophilic warhead is a non-natural amino acid bearing an electrophilic group. In certain instances, the non-natural amino acid bearing an electrophilic group has an electrophilic acrylamide or substituted acrylamide linked to the polypeptide backbone. In some instances, the non-natural amino acid bearing an electrophilic group is selected from the group consisting of: (S)-1-acryloylpyrrolidine-3-carboxamide; 1-acryloylpiperidine-4-carboxamide, (R)-1 acryloylpiperidine-3-carboxamide; (S)-1-acryloylpiperidine-3-carboxamide; (S)-1-acryloylpyrrolidine-2-carboxamide; (R)-1-acryloylpyrrolidine-2-carboxamide; (E)-4-(dimethylamino)but-2-enamide; acrylamide; aziridine, diaziridine, azetidine, pyrrolidine, imidazolidine, pyrazolidine, oxazolidine, isoxazolidine, thiazolidine, isothiazolidine, piperidine, piperazine, morpholine, thiomorpholine, azepaneazirine, diazirine, azete, pyrrole, imidazole, pyrazole, oxazole, isoxazole, thiazole, isothiazole, pyridine, diazines, oxazine, thiazine, azepine phenyl (aniline); naphthalene, anthracene, phenanthrene, indole, isoindole, indolizine, quinolone, isoquinoline, quinoxaline, phthalazine, quinazoline, purine, carbazole, indazole, benzimidazole, azaindole, α-cyanoacrylamide, propiolamide, trans 4-dimethylamino-2-butenamide, trans 4-piperidinyl-2-butenamide, a substituted acrylamide, and a vinyl-sulfonamide. In one embodiment, the electrophilic warhead is a cysteine-reactive D-nipecotic acid moiety. In another embodiment, the electrophilic warhead is a cysteine-reactive moiety. In certain instances, the electrophilic warhead is at the N-terminus of the peptide. In other instances, the electrophilic warhead is not at the N-terminus of the peptide.

In a second aspect, the disclosure features a peptide comprising an electrophilic warhead and five or more amino acids of: A0B0C0D0E0A1B1C1D1E1A2B2C2D2E2 (SEQ ID NO:93), wherein:
(a) A0 is absent, A, D-alanine, α-aminoisobutyric acid, or a staple/stitch position;
(b) B0 is absent, T, A, D-alanine, α-aminoisobutyric acid, I, M, B (norleucine), or a staple/stitch position;
(c) C0 is absent, Q, A, D-alanine, α-aminoisobutyric acid, or a staple/stitch position;
(d) D0 is absent, L, A, D-alanine, α-aminoisobutyric acid, I, or F;
(e) E0 is R, A, D-alanine, α-aminoisobutyric acid, K, T, or a staple/stitch position;
(f) A1 is R, A, D-alanine, α-aminoisobutyric acid, E, or a staple/stitch position;
(g) B1 is F, A, D-alanine, α-aminoisobutyric acid, I, L, V, or a staple/stitch position;
(h) C1 is G, A, D-alanine, α-aminoisobutyric acid, or a staple/stitch position;
(i) D1 is D;
(j) E1 is absent, K, A, D-alanine, α-aminoisobutyric acid, or a staple/stitch position;
(k) A2 is absent, L, A, D-alanine, α-aminoisobutyric acid, W, V, or a staple/stitch position;
(l) B2 is absent, N, A, D-alanine, α-aminoisobutyric acid, S, D, or a staple/stitch position;
(m) C2 is absent, F, A, L, D-alanine, α-aminoisobutyric acid, or a staple/stitch position;
(n) D2 is absent, R, A, D-alanine, α-aminoisobutyric acid, E, or a staple/stitch position; and
(o) E2 is absent, Q, A, D-alanine, α-aminoisobutyric acid, L, or a staple/stitch position.
The peptide binds BFL-1/A1 (covalently and/or non-covalently); or the peptide binds BFL-1/A1 (covalently) and MCL-1 (non-covalently).

In certain embodiments, the peptide is 5 to 35 (e.g., 5, 6, 7, 8, 9, 10, 11, 12, 13, 14, 15, 20, 22, 25, 30, 35) amino acids in length. In certain embodiments, the peptide is 8 to 18 (e.g., 8, 9, 10, 11, 12, 13, 14, 15, 16, 17, 18) amino acids in length.

In some embodiments, overall hydrophobicity of the peptide is reduced relative to a peptide of SEQ ID NO:39 or 16. In some embodiments, overall positive charge of the peptide is reduced relative to a peptide of SEQ ID NO:39 or 16. In certain embodiments, overall hydrophobicity and overall positive charge of the peptide is reduced relative to a peptide of SEQ ID NO:39 or 16.

In some embodiments, the electrophilic warhead is a non-natural amino acid bearing an electrophilic group. In certain instances, the non-natural amino acid bearing an electrophilic group has an electrophilic acrylamide or substituted acrylamide linked to the polypeptide backbone. In some instances, the non-natural amino acid bearing an electrophilic group is selected from the group consisting of: (S)-1-acryloylpyrrolidine-3-carboxamide; 1-acryloylpiperidine-4-carboxamide, (R)-1 acryloylpiperidine-3-carboxamide; (S)-1-acryloylpiperidine-3-carboxamide; (S)-1-acryloylpyrrolidine-2-carboxamide; (R)-1-acryloylpyrrolidine-2-carboxamide; (E)-4-(dimethylamino)but-2-enamide; acrylamide; aziridine, diaziridine, azetidine, pyrrolidine, imidazolidine, pyrazolidine, oxazolidine, isoxazolidine, thiazolidine, isothiazolidine, piperidine, piperazine, morpholine, thiomorpholine, azepaneazirine, diazirine, azete, pyrrole, imidazole, pyrazole, oxazole, isoxazole, thiazole, isothiazole, pyridine, diazines, oxazine, thiazine, azepine phenyl (aniline); naphthalene, anthracene, phenanthrene, indole, isoindole, indolizine, quinolone, isoquinoline, quinoxaline, phthalazine, quinazoline, purine, carbazole, indazole, benzimidazole, azaindole, α-cyanoacrylamide, propiolamide, trans 4-dimethylamino-2-butenamide, trans 4-piperidinyl-2-butenamide, a substituted acrylamide, and a vinyl-sulfonamide. In one embodiment, the electrophilic warhead is a cysteine-reactive D-nipecotic acid moiety. In another embodiment, the electrophilic warhead is a cysteine-reactive moiety. In certain instances, the electrophilic warhead is at the N-terminus of the peptide. In other instances, the electrophilic warhead is not at the N-terminus of the peptide.

In some embodiments, the peptide contains a staple and/or stitch. In some instances, the staple, if present, is at one or more of positions i and i+3; i and i+4; or i and i+7. In some embodiments, the peptide structure stabilizing modification comprises substitution of at least two (e.g., 2, 3, 4, 5, 6) amino acids of SEQ ID NO:93 with non-natural amino acids with olefinic side chains. In some instances, the non-natural amino acids with olefinic side chains are selected from the group consisting of: S-pentenyl alanine; R-octenyl alanine; R-propenylalanine, S-pentenylalanine; R-pentenylalanine, S-pentenylalanine; Bis-pentenylglycine, S-pentenylalanine, R-octenylalanine; and Bis-pentenylglycine, S-octenylalanine, R-octenylalanine. In certain embodiments, the peptide comprises a hydrocarbon staple/stitch, a lactam staple/stitch; a UV-cycloaddition staple/stitch; an oxime staple/stitch; a thioether staple/stitch; a double-click staple/stitch; a bis-lactam staple/stitch; a bis-arylation staple/stitch; or a combination of any two or more thereof. In certain embodiments any two or more of the following positions in SEQ ID NO:93 are involved in a staple or stitch: A0, B0, C0, E0, A1, B1, C1, E1, A2, B2, C2, D2, E2. In certain instances, a staple position can be introduced after position E2.

In a third aspect, the disclosure provides a peptide that covalently binds to BFL-1/A1 (e.g., to C55). The peptide comprising an electrophilic warhead and a sequence that is at least 14% identical to an amino acid sequence set forth in any one of SEQ ID NOs.: 94-109. The peptide selectively binds BFL-1/A1 over MCL-1. In some embodiments, the peptide is 8 to 18 (e.g., 8, 9, 10, 11, 12, 13, 14, 15, 16, 17, 18) amino acids in length.

In certain embodiments, the electrophilic warhead is at the N-terminus of the peptide. In other embodiments, the electrophilic warhead is not at the N-terminus of the peptide. In some embodiments, the electrophilic warhead is a non-natural amino acid bearing an electrophilic group. In certain instances, the non-natural amino acid bearing an electrophilic group has an electrophilic acrylamide or substituted acrylamide linked to the polypeptide backbone. In some cases, the linker is a nitrogen containing heterocycle, a nitrogen containing heterocyclic amino acid, an amino-functionalized benzene ring, a carbocycle, a polycycle, or a heterocycle. In some instances, the non-natural amino acid bearing an electrophilic group is selected from the group consisting of: (S)-1-acryloylpyrrolidine-3-carboxamide; 1-acryloylpiperidine-4-carboxamide, (R)-1 acryloylpiperidine-3-carboxamide; (S)-1-acryloylpiperidine-3-carboxamide; (S)-1-acryloylpyrrolidine-2-carboxamide; (R)-1-acryloylpyrrolidine-2-carboxamide; (E)-4-(dimethylamino)but-2-enamide; acrylamide; aziridine, diaziridine, azetidine, pyrrolidine, imidazolidine, pyrazolidine, oxazolidine, isoxazolidine, thiazolidine, isothiazolidine, piperidine, piperazine, morpholine, thiomorpholine, azepaneazirine, diazirine, azete, pyrrole, imidazole, pyrazole, oxazole, isoxazole, thiazole, isothiazole, pyridine, diazines, oxazine, thiazine, azepine phenyl (aniline); naphthalene, anthracene, phenanthrene, indole, isoindole, indolizine, quinolone, isoquinoline, quinoxaline, phthalazine, quinazoline, purine, carbazole, indazole, benzimidazole, azaindole, α-cyanoacrylamide, propiolamide, trans 4-dimethylamino-2-butenamide, trans 4-piperidinyl-2-butenamide, a substituted acrylamide, and a vinyl-sulfonamide. In one embodiment, the electrophilic warhead is a cysteine-reactive D-nipecotic acid moiety.

In certain instances, the peptide comprises a hydrocarbon staple/stitch, a lactam staple/stitch; a UV-cycloaddition staple/stitch; an oxime staple/stitch; a thioether staple/stitch; a double-click staple/stitch; a bis-lactam staple/stitch; a bis-arylation staple/stitch; or a combination of any two or more thereof.

In some instances, wherein the peptide comprises a sequence that is at least 15%, 20%, 27%, 34%, 40%, 47%, 50%, 53%, 60%, 65%, 70%, 75%, 80%, 85%, 90%, 95%, or 97%, or 100% identical to the amino acid sequence. In some instances, the variation from the amino acid sequence is on the BFL-1 non-interacting alpha-helical face of the amino acid sequence. In certain instances, the amino acid sequence is modified to contain an alpha-methyl or alpha-ethyl natural amino acid, and/or is substituted with one or more amino acids selected from the group consisting of alanine, D-alanine, α-aminoisobutyric acid, N-methyl glycine, serine, a substituted alanine, and a glycine derivative.

In a fourth aspect, this disclosure features a peptide that covalently binds to BFL-1/A1 (e.g., to C55 of BFL-1/A1), wherein the peptide comprises a sequence that is at least 14% identical to an amino acid sequence set forth in SEQ ID NOs.: 60-75. In certain instances, the peptide selectively binds BFL-1/A1 over MCL-1. In some instances, the peptide covalently binds BFL-1/A1 and non-covalently binds MCL-1.

In certain embodiments, the electrophilic warhead is a non-natural amino acid bearing an electrophilic group.

In some embodiments, the peptide comprises a sequence that is at least 15%, 20%, 27%, 34%, 40%, 47%, 50%, 53%, 60%, 65%, 70%, 75%, 80%, 85%, 90%, 95%, 97%, or 100% identical to the amino acid sequence. In certain instances, the variation from the amino acid sequence is on the BFL-1 non-interacting alpha-helical face of the amino acid sequence. In some instances, the amino acid at one or more of positions 2, 3, 6, 7, 8, 9, 12, 13, 14, 15, or 16 (wherein position 1 is "J") of the recited sequences can be substituted to another amino acid. In some instances, one or more of the amino acids at these positions is substituted to one or more of alanine, D-alanine, or α-aminoisobutyric acid. In some instances, the amino acid at positions 7 and/or 15 is substituted with a glutamic acid, and/or the amino acid at position 13 is substituted with an aspartic acid, and/or the amino acid at position 16 is substituted with a leucine, and/or the amino acids at one or more of positions 2, 3, 6, 8, 9, 12, 14, and 15 is substituted with alanine, D-alanine, or α-aminoisobutyric acid (wherein position 1 is "J"). In some instances, the amino acids at positions 8 and/or 12 is/are substituted with alanine, D-alanine, or α-aminoisobutyric acid (wherein position 1 is "J").

In some instances, the peptide comprises or consists of the sequence JATX$_1$LREFGDX$_2$LNFRQ (SEQ ID NO:62), wherein the peptide selectively binds BFL-1/A1 over MCL-1, and wherein the peptide covalently binds BFL-1/A1 and non-covalently binds MCL-1; and wherein J is an electrophilic warhead; and X$_1$ and X$_2$ are non-natural amino acids.

In some instances, the peptide comprises or consists of the sequence JATX$_1$LRRAGDX$_2$LNFRQ (SEQ ID NO:60), wherein the peptide selectively binds BFL-1/A1 over MCL-1, and wherein the peptide covalently binds BFL-1/A1 and non-covalently binds MCL-1; and wherein J is an electrophilic warhead; and X$_1$ and X$_2$ are non-natural amino acids.

In some instances, the electrophilic warhead has an electrophilic moiety linked to the polypeptide backbone. In some cases, the linker is a nitrogen containing heterocycle, a nitrogen containing heterocyclic amino acid, an amino-functionalized benzene ring, a carbocycle, a polycycle, or a heterocycle. In some embodiments, the electrophilic moiety is an electrophilic acrylamide, substituted acrylamide, a vinyl-sulfonamide, or an α, β unsaturated amide. In some embodiments, the electrophilic warhead is a non-natural amino acid bearing an electrophilic group. In some instances, the non-natural amino acid bearing an electrophilic group is selected from the group consisting of: (S)-1-acryloylpyrrolidine-3-carboxamide; 1-acryloylpiperidine-4-carboxamide, (R)-1 acryloylpiperidine-3-carboxamide; (S)-1-acryloylpiperidine-3-carboxamide; (S)-1-acryloylpyrrolidine-2-carboxamide; (R)-1-acryloylpyrrolidine-2-carboxamide; (E)-4-(dimethylamino)but-2-enamide; acrylamide; aziridine, diaziridine, azetidine, pyrrolidine, imidazolidine, pyrazolidine, oxazolidine, isoxazolidine, thiazolidine, isothiazolidine, piperidine, piperazine, morpholine, thiomorpholine, azepaneazirine, diazirine, azete, pyrrole, imidazole, pyrazole, oxazole, isoxazole, thiazole, isothiazole, pyridine, diazines, oxazine, thiazine, azepine phenyl (aniline); naphthalene, anthracene, phenanthrene, indole, isoindole, indolizine, quinolone, isoquinoline, quinoxaline, phthalazine, quinazoline, purine, carbazole, indazole, benzimidazole, azaindole, α-cyanoacrylamide, propiolamide, trans 4-dimethylamino-2-butenamide, trans 4-piperidinyl-2-butenamide, a substituted acrylamide, and a vinyl-sulfonamide. In one embodiment, the electrophilic warhead is a cysteine-reactive D-nipecotic acid moiety.

In certain embodiments, the peptide is 15 to 35 (e.g., 15, 16, 17, 18, 19, 20, 21, 22, 23, 24, 25, 26, 27, 28, 29, 30, 35) amino acids in length. In some embodiments, the modified amino acid sequence is 8 to 18 (e.g., 8, 9, 10, 11, 12, 13, 14, 15, 16, 17, 18) amino acids in length.

In a fifth aspect, the disclosure provides a peptide that covalently binds to BFL-1/A1 (e.g., to C55 of BFL-1/A1), wherein the peptide comprises at least two (e.g., 2, 3, 4, 5, 6, 7, 8, 9) amino acids of the BFL-1/A1 interacting face of the alpha helix of an amino acid sequence set forth in any one of SEQ ID NOs.:60-75.

In certain embodiments, the peptide is 5, 6, 7, 8, 9, 10, 11, 12, 13, 14, 15, 16, 17, 18, 19, 20, 21, 22, 23, 24, 25, 26, 27, 28, 29, or 30 amino acids in length.

In certain embodiments, the peptide includes at least five (e.g., 5, 6, 7, 8, 9, 10, 11, 12, 13, 14, 15, 16, 17, 18, 19, 20, 21, 22, 23, 24, 25) amino acids of SEQ ID NOs.:60-75, of which three, two, or one amino acid are substituted. In some instances, the substitution(s) is to alanine, D-alanine, or α-aminoisobutyric acid.

In some embodiments, the electrophilic warhead is a cysteine-reactive D-nipecotic acid moiety. In other embodiments, the electrophilic warhead is a cysteine-reactive moiety.

In certain instances, the non-natural amino acids are non-natural amino acids with olefinic side chains. In some instances, the non-natural amino acids with olefinic side chains are S-pentenyl alanine and/or R-octenyl alanine.

In a sixth aspect, the disclosure features a peptide that covalently binds to BFL-1/A1, the peptide comprising an amino acid sequence set forth in any one of SEQ ID NOs.:60-75. In some embodiments, the peptide comprises or consists of the amino acid sequence set forth in SEQ ID NO: 62. In some embodiments, the peptide comprises or consists of the amino acid sequence set forth in SEQ ID NO: 60.

In some embodiments, $X_1$ is R-octenyl alanine and $X_2$ is S-pentenyl alanine. In some embodiments, $X_1$ is S-pentenyl alanine and $X_2$ is R-octenyl alanine. In certain embodiments, $X_1$ is S-pentenyl alanine and $X_2$ is S-pentenyl alanine. In other embodiments, $X_1$ is R-propenylalanine and $X_2$ is S-pentenyl alanine. In yet other embodiments, $X_1$ is R-pentenylalanine and $X_2$ is S-pentenyl alanine.

In certain embodiments, the electrophilic warhead comprises an electrophilic moiety linked to the polypeptide backbone. In some embodiments, the electrophilic moiety is a non-natural amino acid bearing an electrophilic group. In certain instances, the non-natural amino acid bearing an electrophilic group comprises an electrophilic acrylamide, substituted acrylamide, a vinyl-sulfonamide, or an α, β unsaturated amide. In some instances, the non-natural amino acid bearing an electrophilic group is selected from the group consisting of: (S)-1-acryloylpyrrolidine-3-carboxamide; 1-acryloylpiperidine-4-carboxamide, (R)-1 acryloylpiperidine-3-carboxamide; (S)-1-acryloylpiperidine-3-carboxamide; (S)-1-acryloylpyrrolidine-2-carboxamide; (R)-1-acryloylpyrrolidine-2-carboxamide; (E)-4-(dimethylamino)but-2-enamide; acrylamide; aziridine, diaziridine, azetidine, pyrrolidine, imidazolidine, pyrazolidine, oxazolidine, isoxazolidine, thiazolidine, isothiazolidine, piperidine, piperazine, morpholine, thiomorpholine, azepaneazirine, diazirine, azete, pyrrole, imidazole, pyrazole, oxazole, isoxazole, thiazole, isothiazole, pyridine, diazines, oxazine, thiazine, azepine phenyl (aniline); naphthalene, anthracene, phenanthrene, indole, isoindole, indolizine, quinolone, isoquinoline, quinoxaline, phthalazine, quinazoline, purine, carbazole, indazole, benzimidazole, azaindole, α-cyanoacrylamide, propiolamide, trans 4-dimethylamino-2-butenamide, trans 4-piperidinyl-2-butenamide, a substituted acrylamide, and a vinyl-sulfonamide. In certain instances, the electrophilic warhead is a cysteine-reactive D-nipecotic acid moiety. In other instances, the electrophilic warhead is a cysteine-reactive moiety.

In some embodiments, the peptide is 15 to 35 (e.g., 15, 16, 17, 18, 19, 20, 21, 22, 23, 24, 25, 26, 27, 28, 29, 30, 35) amino acids in length. In some embodiments, the peptide is 8 to 18 (e.g., 8, 9, 10, 11, 12, 13, 14, 15, 16, 17, 18) amino acids in length.

In a seventh aspect the disclosure relates to a pharmaceutical composition comprising a NOXA peptide described herein and a pharmaceutically acceptable carrier.

In an eighth aspect, the disclosure features a method of treating a BFL-1/A1-expressing or BFL-1/A1-dependent disease in a human subject in need thereof. The method involves administering to the human subject a therapeutically effective amount of a NOXA peptide described herein, or a pharmaceutical composition described herein.

In some embodiments, the BFL-1/A1-expressing or BFL-1/A1-dependent disease is selected from the group consisting of a hematologic malignancy, a solid tumor, an autoimmune disease, and an inflammatory disease. In certain instances, the hematologic malignancy is a leukemia or a lymphoma. In certain instances, the solid tumor that is a melanoma, a breast cancer, or a lung cancer. In certain instances, the autoimmune disease that is autoimmune colitis, thyroiditis, arthritis, nephritis, dermatitis, vasculitis, system lupus erythematosus, diabetes, or Sjogren's disease. In certain instances, the inflammatory disease that is asthma, psoriasis, inflammatory colitis, thyroiditis, arthritis, nephritis, dermatitis, or vasculitis.

In some embodiments, the BFL-1/A1-expressing or BFL-1/A1-dependent disease is a cancer. In some embodiments, the cancer is a solid tumor or a liquid tumor. In some embodiments, the cancer is a breast cancer, an autonomic ganglia cancer, a pancreatic cancer, a skin cancer, a CNS cancer, a hematopoietic or lymphoid cancer, a lung cancer, a large intestine cancer, a stomach cancer, a soft tissue sarcoma, or a bone cancer. In some embodiments, the hematologic malignancy is acute myeloid leukemia, acute lymphoblastic leukemia, chronic myeloid leukemia, chronic lymphocytic leukemia, myelodysplastic syndrome, or multiple myeloma.

In some embodiments, the NOXA peptide is selected from SEQ ID NOs.: 60-79, 151, and 153. In some embodiments, the NOXA peptide is SEQ ID NO: 62. In some embodiments, the NOXA peptide is SEQ ID NO: 60.

In some embodiments, the method involves further administering an inhibitor of a DNA damage response pathway member. In some embodiments, the DNA damage response pathway member inhibitor is an ataxia-telangiectasia mutated (ATM) kinase inhibitor, an ataxia telangiectasia and rad3-related (ATR) kinase inhibitor, a checkpoint kinase 1 and/or a checkpoint kinase 2 (CHK1/2) inhibitor, and/or a poly(ADP-ribose) polymerase (PARP) inhibitor. In some instances, the ATM inhibitor is selected from the group consisting of KU-559403, KU-55933, KU-60019, CP-466722, chloroquine phosphate, CGK733, and AZD0156. In certain instances, the ATR inhibitor is selected from the group consisting of schisandrin B, NU6027, NVP-BEZ235, VE-821, VE-822/VX-970, AZ20, and AZD6738. In certain instances, the CHK1/2 inhibitor is selected from the group consisting of AZD7762, CCT 241533, LY 2603618, LY 2606368, NSC 109555 ditosylate, PD 407824, PF47736, SB 218078, TCS 2312, and SRA737. In certain instances, the PARP inhibitor is selected from the group consisting of olaparib, A-966492, veliparib, rucaparib, AG-14361, iniparib, INO-1001, niraparib, talazoparib, AZD2461, 2X-121, BMN 673, and E7449.

In a ninth aspect, the disclosure features a method of treating a MCL-1-expressing or MCL-1-dependent disease in a human subject in need thereof. The method involves administering to the human subject a therapeutically effective amount of a NOXA peptide described herein, or a pharmaceutical composition described herein.

In some embodiments, the NOXA peptide is selected from SEQ ID NOs.: 60-79, 151, and 153 or a structurally-stabilized version of a sequence set forth in SEQ ID NOs.: 126-141.

In some embodiments, the method further involves administering an inhibitor of a DNA damage response pathway member. In some embodiments, the DNA damage response pathway member inhibitor is an ATM kinase inhibitor, an ATR kinase inhibitor, a CHK1/2 inhibitor, and/or a PARP inhibitor. In some instances, the ATM inhibitor is selected from the group consisting of KU-559403, KU-55933, KU-60019, CP-466722, chloroquine phosphate, CGK733, and AZD0156. In certain instances, the ATR inhibitor is selected from the group consisting of schisandrin B, NU6027, NVP-BEZ235, VE-821, VE-822/VX-970, AZ20, and AZD6738. In certain instances, the CHK1/2 inhibitor is selected from the group consisting of AZD7762, CCT 241533, LY 2603618, LY 2606368, NSC 109555 ditosylate, PD 407824, PF47736, SB 218078, TCS 2312, and SRA737. In certain instances, the PARP inhibitor is selected from the group consisting of olaparib, A-966492, veliparib, rucaparib, AG-14361, iniparib, INO-1001, niraparib, talazoparib, AZD2461, 2X-121, BMN 673, and E7449.

In a tenth aspect, the disclosure features a method of treating a BFL-1/A1-expressing or BFL-1/A1-dependent disease and an MCL-1-expressing or MCL-1-dependent disease in a human subject in need thereof. The method involves administering to the human subject a therapeutically effective amount of a NOXA peptide described herein, or a pharmaceutical composition described herein.

In some embodiments, the NOXA peptide is selected from SEQ ID NOs.: 60-79, 151, and 153 or a structurally-stabilized version of a sequence set forth in SEQ ID NOs.: 126-141. In some embodiments, the NOXA peptide is selected from SEQ ID NOs.: 60 and 62 or a structurally-stabilized version of a sequence set forth in SEQ ID NOs.: 126 and 128.

In some embodiments, the method further involves administering an inhibitor of a DNA damage response pathway member. In some embodiments, the DNA damage response pathway member inhibitor is an ATM kinase inhibitor, an ATR kinase inhibitor, a CHK1/2 inhibitor, and/or a PARP inhibitor. In some instances, the ATM inhibitor is selected from the group consisting of KU-559403, KU-55933, KU-60019, CP-466722, chloroquine phosphate, CGK733, and AZD0156. In certain instances, the ATR inhibitor is selected from the group consisting of schisandrin B, NU6027, NVP-BEZ235, VE-821, VE-822/VX-970, AZ20, and AZD6738. In certain instances, the CHK1/2 inhibitor is selected from the group consisting of AZD7762, CCT 241533, LY 2603618, LY 2606368, NSC 109555 ditosylate, PD 407824, PF47736, SB 218078, TCS 2312, and SRA737. In certain instances, the PARP inhibitor is selected from the group consisting of olaparib, A-966492, veliparib, rucaparib, AG-14361, iniparib, INO-1001, niraparib, talazoparib, AZD2461, 2X-121, BMN 673, and E7449.

In an eleventh aspect, the disclosure provides a combination therapy for treating a BFL-1/A1-expressing or BFL-1/A1-dependent disease (e.g., hematologic malignancy, a solid tumor, an autoimmune disease, and an inflammatory disease) comprising a NOXA peptide described herein and an inhibitor of a DNA damage response pathway member. In some embodiments, the DNA damage response pathway member inhibitor is an ATM kinase inhibitor, an ATR kinase inhibitor, a CHK1/2 inhibitor, and/or a PARP inhibitor.

In a twelfth aspect, the disclosure provides a combination therapy for treating a MCL-1 expressing or MCL-1-dependent disease (e.g., hematologic malignancy, a solid tumor, an autoimmune disease, and an inflammatory disease) comprising a NOXA peptide described herein and an inhibitor of a DNA damage response pathway member. In some embodiments, the DNA damage response pathway member inhibitor is an ATM kinase inhibitor, an ATR kinase inhibitor, a CHK1/2 inhibitor, and/or a PARP inhibitor.

In a thirteenth aspect, the disclosure provides a combination therapy for treating a BFL-1/A1-expressing or BFL-1/A1-dependent disease and MCL-1 expressing or MCL-1-dependent disease (e.g., hematologic malignancy, a solid tumor, an autoimmune disease, and an inflammatory disease) comprising a NOXA peptide described herein and an inhibitor of a DNA damage response pathway member. In some embodiments, the DNA damage response pathway member inhibitor is an ATM kinase inhibitor, an ATR kinase inhibitor, a CHK1/2 inhibitor, and/or a PARP inhibitor.

These embodiments apply to the eleventh to thirteenth aspects. In some embodiments, the ATM inhibitor is selected from the group consisting of KU-559403, KU-55933, KU-60019, CP-466722, chloroquine phosphate, CGK733, and AZD0156. In certain embodiments, the ATR inhibitor is selected from the group consisting of schisandrin B, NU6027, NVP-BEZ235, VE-821, VE-822/VX-970, AZ20, and AZD6738. In certain instances, the CHK1/2 inhibitor is selected from the group consisting of AZD7762, CCT 241533, LY 2603618, LY 2606368, NSC 109555 ditosylate, PD 407824, PF47736, SB 218078, TCS 2312, and SRA737. In certain instances, the PARP inhibitor is selected from the group consisting of olaparib, A-966492, veliparib, rucaparib, AG-14361, iniparib, INO-1001, niraparib, talazoparib, AZD2461, 2X-121, BMN 673, and E7449. In some embodiments, the NOXA peptide is selected from SEQ ID NOs.: 60-79, 151, and 153 or a structurally-stabilized version of a sequence set forth in SEQ ID NOs.: 126-141. In some embodiments, the NOXA peptide is selected from SEQ ID NOs.: 60 and 62 or a structurally-stabilized version of a sequence set forth in SEQ ID NOs.: 126 and 128.

In a fourteenth aspect, the disclosure provides a stapled peptide comprising an amino acid sequence that is at least 50% identical (e.g., at least 55%, 60%, 65%, 70%, 75%, 80%, 85%, 90%, 95%, or 100% identical) to the amino acid sequence set forth in SEQ ID NO:44. In certain instances, the stapled peptide comprises an amino acid sequence set forth in SEQ ID NO:44 except that it has one to ten (e.g., 1, 2, 3, 4, 5, 6, 7, 8, 9, or 10) amino acid substitutions. In certain instances, the substitution(s) is to an amino acid or amino acids selected from the group consisting of L-alanine, D-alanine, α-aminoisobutyric acid, N-methyl glycine, serine, a substituted alanine, and a glycine derivative. The stapled peptide binds BFL-1 and/or MCL-1.

In a fourteenth aspect, the disclosure provides a stapled peptide comprising an amino acid sequence that is at least 50% identical (e.g., at least 55%, 60%, 65%, 70%, 75%, 80%, 85%, 90%, 95%, or 100% identical) to the amino acid sequence set forth in SEQ ID NO:46. In certain instances, the stapled peptide comprises an amino acid sequence set forth in SEQ ID NO:46 except that it has one to ten (e.g., 1, 2, 3, 4, 5, 6, 7, 8, 9, or 10) amino acid substitutions. In certain instances, the substitution(s) is to an amino acid or amino acids selected from the group consisting of L-alanine, D-alanine, α-aminoisobutyric acid, N-methyl glycine, serine, a substituted alanine, and a glycine derivative. The stapled peptide binds BFL-1 and/or MCL-1.

These embodiments apply to the fourteenth aspect. In some embodiments, the stapled peptide further comprises a cysteine-reactive moiety. In some embodiments, the stapled peptide further comprises a cysteine-reactive D-nipecotic acid moiety. These moieties can be attached or included at the N-terminus of the stapled peptide. In some embodiments, the stapled peptide is combined with a DNA damage response pathway inhibitor. In some embodiments, the DNA damage response pathway inhibitor is an ATM kinase inhibitor. In some embodiments, the DNA damage response pathway inhibitor is an ATR kinase inhibitor. In some embodiments, the DNA damage response pathway inhibitor is a CHK1/2 inhibitor. In some embodiments, the DNA damage response pathway inhibitor is a PARP inhibitor. In some embodiments, the ATM inhibitor is selected from the group consisting of KU-559403, KU-55933, KU-60019, CP-466722, chloroquine phosphate, CGK733, and AZD0156. In certain embodiments, the ATR inhibitor is selected from the group consisting of schisandrin B, NU6027, NVP-BEZ235, VE-821, VE-822/VX-970, AZ20, and AZD6738. In certain embodiments, the CHK1/2 inhibitor is selected from the group consisting of AZD7762, CCT 241533, LY 2603618, LY 2606368, NSC 109555 ditosylate, PD 407824, PF47736, SB 218078, TCS 2312, and SRA737. In certain embodiments, the PARP inhibitor is selected from the group consisting of olaparib, A-966492, veliparib, rucaparib, AG-14361, iniparib, INO-1001, niraparib, talazoparib, AZD2461, 2X-121, BMN 673, and E7449. The stapled peptides disclosed herein can be used to treat a BFL-1-expressing or -dependent condition (e.g., cancer, autoimmune disease, inflammatory disease). The stapled peptides disclosed herein can be used to treat a MCL-1-expressing or -dependent condition (e.g., cancer, autoimmune disease, inflammatory disease).

In a fifteenth aspect, the disclosure provides a combination therapy for treating a MCL-1-expressing and a BFL-1/A1-expressing, or MCL-1-dependent and BFL-1/A1-dependent, disease in a human subject in need thereof, comprising a NOXA stabilized peptide described herein and an inhibitor of MCL-1. In certain instances, the MCL-1 inhibitor is selected from the group consisting of S64315, S63845, BAY 1000394, MIK665, AMG397, and AMG176.

In a sixteenth aspect, the disclosure provides a combination therapy for treating a BCL-2-expressing and a BFL-1/A1-expressing, or BCL-2-dependent and BFL-1/A1-dependent, disease in a human subject in need thereof, comprising a NOXA stabilized peptide described herein and an inhibitor of BCL-2. In certain instances, the BCL-2 inhibitor is venetoclax.

In a seventeenth aspect, the disclosure provides a combination therapy for treating a BCL-XL-expressing and a BFL-1/A1-expressing, or BCL-XL-dependent and BFL-1/A1-dependent, disease in a human subject in need thereof, comprising a NOXA stabilized peptide described herein and an inhibitor of BCL-XL. In certain instances, the BCL-XL inhibitor is navitoclax.

In an eighteenth aspect, the disclosure provides a combination therapy for treating a BCL-XL-, BCL-2-, and/or MCL-1-expressing and a BFL-1/A1-expressing, or BCL-XL-, BCL-2-, and MCL-1-dependent and BFL-1/A1-dependent, disease in a human subject in need thereof, comprising a NOXA stabilized peptide described herein and an inhibitor of BCL-XL, BCL-2, and/or MCL-1. In certain instances, the MCL-1 inhibitor is selected from the group consisting of S64315, S63845, BAY 1000394, MIK665, AMG397, and AMG176. In certain instances, the BCL-2 inhibitor is venetoclax. In certain instances, the BCL-XL inhibitor is navitoclax.

These embodiments apply to each of the fifteenth to eighteenth aspects. In some embodiments, the NOXA peptide is selected from SEQ ID NOs.: 60-79, 151, and 153 or a structurally-stabilized version of a sequence set forth in SEQ ID NOs.: 126-141. In some embodiments, the NOXA peptide is selected from SEQ ID NOs.: 60 and 62 or a structurally-stabilized version of a sequence set forth in SEQ ID NOs.: 126 and 128.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description and from the claims.

BRIEF DESCRIPTION OF THE DRAWINGS

FIG. 2 provides the sequences of a NOXA BH3 staple scan peptide library, with all-hydrocarbon (i, 1+4) or (i, i+7) staples placed sequentially across the length of the peptide template bearing an N-terminal, cysteine-reactive, D-nipecotic acid moiety. The sequences (i.e., with the D-nipecotic acid derivatization placed at the stapled peptide N-terminus) are assigned SEQ ID NOs.: 1-21, from top to bottom.

FIG. 6 provides sequences of a NOXA-15 SAHB alanine scan library bearing an N-terminal, cysteine-reactive, D-nipecotic acid moiety. The sequences (i.e., with the D-nipecotic acid derivatization placed at the stapled peptide N-terminus) are assigned SEQ ID NOs.: 22-34, from top to bottom.

FIG. 10 lists the sequences of NOXA-15 SAHB mutants bearing N-terminal, cysteine-reactive, D-nipecotic acid moiety. The sequences (i.e., with the D-nipecotic acid derivatization placed at the stapled peptide N-terminus) are assigned SEQ ID NOs.: 35-38, from top to bottom.

FIG. 25 is a table showing genetic dependencies that are positively correlated with BFL-1 dependency in AML cell lines as determined by genome-wide CRISPR screening.

FIG. 30 is a table providing crystallization conditions and data collection and refinement statistics for the crystal structures of apo BFL-1 and its complex with a cysteine-reactive NOXA SAHB inhibitor.

FIG. 31A provides the amino acid sequence of BFL-1ΔC (SEQ ID NO:83) with α-helices shaded to correspond with the structure shown in FIG. 31B. BH1-3 domains are underlined.

FIG. 31D tabulates the comparative α-carbon distance measurements between apical and basal residues of the BH3-binding grooves of apo BFL-1, MCL-1, and BCL-$X_L$.

FIG. 31E shows an alignment of amino acid sequences of the α2-α5 regions of BCL-2 family proteins, shaded to correspond with the structures in FIG. 31D. BFL-1 is the only protein with a cysteine located at the indicated position within the BH3-binding groove (see C in α3). The sequences from top to bottom are assigned SEQ ID NOs.: 84-91.

FIG. 32A provides the results of in vitro crosslinking analysis demonstrating the selective derivatization of C55-bearing BFL-1 constructs by an i, i+7-stapled NOXA BH3 peptide (aa 26-40) containing an N-terminal, cysteine-reactive, D-nipecotic acid (D-NA). *AT8LRRFGDXLNFRQ, wherein *=Ac or D-Nipecotic Acid; 8=R-octenyl alanine; and X=S-pentenyl alanine. (SEQ ID NO:92).

FIG. 34B tabulates the comparative α-carbon distance measurements between apical and basal residues of the unliganded and NOXA BH3-bound grooves of BFL-1 and MCL-1.

FIG. 60 shows that treatment of U937 cells with the indicated doses of D-NA-NOXA SAHB-15 R31E for 30 min (A) and 4 hours (B) causes no LDH release.

FIG. 62 shows (A) BFL-1 dependency Z-scores and BFL-1 scaled rank values across AML cell lines evaluated in a genome-scale CRISPR-Cas9 screen, (B) BFL-1 dependency Z-scores and BFL-1 scaled rank values for top-scoring BFL-1 dependent human cancer cell lines among those evaluated in a genome-scale CRISPR-Cas9 screen, and (C) Pearson and Spearman correlations for BFL-1 co-dependencies in AML cell lines from a genome-scale CRISPR-Cas9 screen and identified based on the following criteria: (1) gene scored as a potential dependency in at least 2 AML cell lines (score <−0.1), (2) gene is expressed in at least 2 AML cell lines (TPM>1), (3) gene is not predicted to be a pan-lethal gene, and (4) Pearson and Spearman correlations are both >0.9.

DETAILED DESCRIPTION

Figure 1:
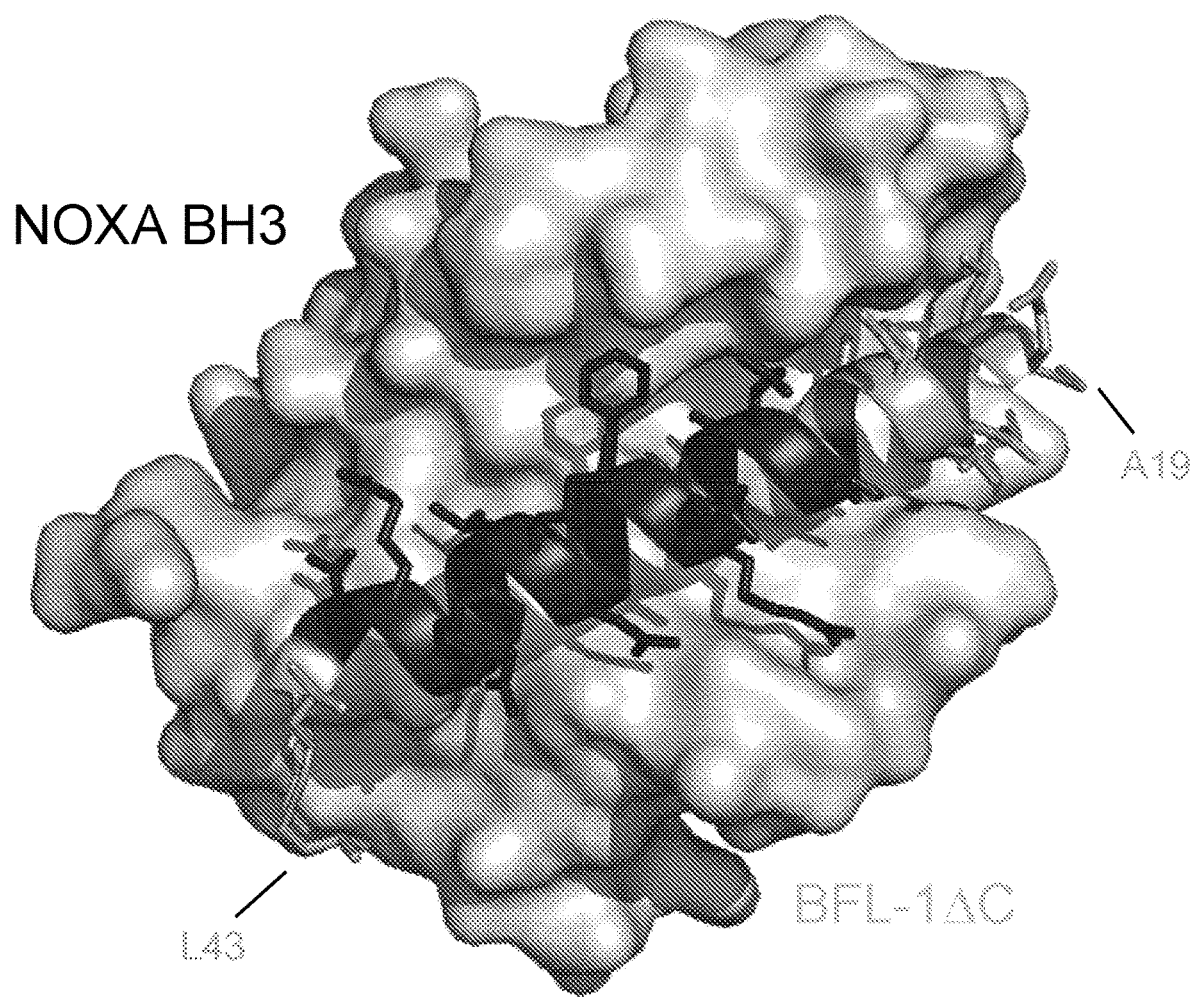
FIG. 1 shows the structure of the NOXA BH3/BFL-1ΔC complex (PDB: 3MQP), highlighting in dark gray the NOXA residues selected for the shortened NOXA peptide staple scan library.

There are currently no Food and Drug Administration approved drugs available for targeting the apoptotic resistance driven by MCL-1 and BFL-1/A1. In particular, no selective BFL-1 targeting agents, dual BFL-1/MCL-1-targeting agents, nor the combination of a covalent and non-covalent dual inhibitor have been advanced to clinical testing. This disclosure provides structurally-stabilized and cysteine-reactive NOXA BH3 peptides that demonstrate the properties of selective covalent BFL-1 targeting agents and dual BFL-1/MCL-1-targeting agents that can covalently bind to BFL-1 and non-covalently bind to MCL-1. This disclosure also features methods for using such stabilized peptides alone or in combination with other therapeutic agents (e.g., ATM kinase/ATR kinase inhibitors) in the treatment of BFL-1 and/or MCL-1-dependent and/or -expressing cancers (e.g., hematologic malignancies, melanoma or other solid tumors, diseases of cellular excess such as autoimmune or inflammatory diseases, or other cancers described herein below). Such stapled peptides are useful to reactivate apoptosis, singly and in combination, in cancers or diseases of cellular excess that express and/or are dependent on MCL-1 and/or BFL-1.

Proteins

The amino acid sequence of human MCL-1 is provided below (UniProtKB—Q07820):

```
                                              (SEQ ID NO: 80)
         10         20         30         40
MFGLKRNAVI GLNLYCGGAG LGAGSGGATR PGGRLLATEK 50         60         70         80
EASARREIGG GEAGAVIGGS AGASPPSTLT PDSRRVARPP 90        100        110        120
PIGAEVPDVT ATPARLLFFA PTRRAAPLEE MEAPAADAIM 130        140        150        160
SPEEELDGYE PEPLGKRPAV LPLLELVGES GNNTSTDGSL 170        180        190        200
PSTPPPAEEE EDELYRQSLE IISRYLREQA TGAKDTKPMG 210        220        230        240
RSGATSRKAL ETLRRVGDGV QRNHETAFQG MLRKLDIKNE
```

```
                    -continued
        250        260        270        280
DDVKSLSRVM IHVFSDGVTN WGRIVTLISF GAFVAKHLKT 290        300        310        320
INQESCIEPL AESITDVLVR TKRDWLVKQR GWDGFVEFFH 330        340        350
VEDLEGGIRN VLLAFAGVAG VGAGLAYLIR
```

The amino acid sequence of human BFL-1 is provided below (UniProtKB—Q16548):

```
                                              (SEQ ID NO: 81)
         10         20         30         40
MTDCEFGYIY RLAQDYLQCV LQIPQPGSGP SKTSRVLQNV 50         60         70         80
AFSVQKEVE KNLKSCLDNVN VVSVDTARTL FNQVMEKEFE 90        100        110        120
DGIINWGRIV TIFAFEGILI KKLLRQQIAP DVDTYKEISY 130        140        150        160
FVAEFIMNNT GEWIRQNGGW ENGFVKKFEP KSGWMTFLEV

170
TGKICEMLSL LKQYC
```

The amino acid sequence of human NOXA is provided below (UniProtKB—Q13794):

```
                                              (SEQ ID NO: 82)
         10         20         30         40
MPGKKARKNA QPSPARAPAE LEVECATQLR RFGDKLNFRQ

50
KLLNLISKLF CSGT
```

NOXA Peptides

An exemplary NOXA peptide of this disclosure is the BH3 peptide starting from amino acid 26 to amino acid 40 of SEQ ID NO:82. This peptide has the amino acid sequence: ATQLRRFGDKLNFRQ (SEQ ID NO:39) and interacts with BFL-1/A1. The numbering used for this peptide is provided below.

| Position | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Amino Acid | A | T | Q | L | R | R | F | G | D | K | L | N | F | R | Q |

The BFL-1 interacting residues (i.e., the residues of the NOXA BH3 alpha helix that interact with BFL-1) for NOXA are: Leu-21, Glu-22, Val-23, Glu-24, Cys-25, Ala-26, Leu-29, Arg-30, Phe-32, Gly-33, Asp-34, Leu-36, Asn-37, and Gln-40 (wherein the amino acid numbering is based on SEQ ID NO:82). In the context of the position numbering for SEQ ID NO:39 provided above, the BFL-1 interacting residues are: Ala-1, Leu-4, Arg-5, Phe-7, Gly-8, Asp-9, Leu-11, Asn-12, and Gln-15. Alanine-1, Leucine-4, Phenylalanine-7, Glycine-8, and Leucine-11 are involved in hydrophobic interactions; while Arginine-5, Aspartate-9, and Asparagine-12 are involved in hydrogen bond interactions.

The residues of NOXA that do not interact with BFL-1 (i.e., the residues of the NOXA BH3 alpha helix that are on the non-interacting side of the helix) are: Thr-27, Gln-28, Arg-31, Lys-35, Phe-38, and Arg-39 (wherein the amino acid numbering is based on SEQ ID NO:82). In the context of the position numbering for SEQ ID NO:39 provided above, the residues that are non on the interacting face of the NOXA peptide alpha helix are residues: Thr-2, Gln-3, Arg-6, Lys-10, Phe-13, and Arg-14.

The MCL-1 interacting residues (i.e., the residues of the NOXA BH3 alpha helix that interact with MCL-1) of the NOXA alpha-helix are: Gln-28, Leu-29, Arg-30, Phe-32, Gly-33, Leu-36, Asn-37, Gln-40 (wherein the amino acid numbering is based on SEQ ID NO:82).

The residues of NOXA that do not interact with MCL-1 (i.e., the residues of the NOXA BH3 alpha helix that are on the non-interacting side of the helix) are: Ala-26, Thr-27, Arg-31, Asp-34, Lys-35, Phe-38, and Arg-39 (wherein the amino acid numbering is based on SEQ ID NO:82).

In certain embodiments, the NOXA BH3 peptides of this disclosure can have 1, 2, 3, 4, 5, 6, 7, 8, 9, 10, 11, 12, or 13 amino acid substitutions in SEQ ID NO:39 (e.g., 1, 2, 3, 4, 5, 6, 7, 9, 10, 11, 12, or 13 amino acids are conservatively or non-conservatively substituted). In some instances, one to three amino acids of SEQ ID NO:39 are substituted. The amino acid substitutions in SEQ ID NO:39 can be on one or both the interacting and non-interacting side of the alpha helix. Much greater variability is permitted in the non-interacting side of the alpha helix of the NOXA peptide that does not interact with BFL-1 than on the interacting side. In fact, just about every one of those amino acids (e.g., 5, 4, 3, 2, or 1 amino acid of the non-interacting face of the helix) can be substituted (e.g., conservative or non-conservative amino acid substitutions or alanine). In certain embodiments, the interacting face of the helix of these peptides have 1 to 9, 1 to 8, 1 to 7, 1 to 6, 1 to 5, 1 to 4, 1 to 3, 1 to 2, or 1 amino acid substitution(s). In some instances, the substitution(s) is/are a conservative amino acid substitution. In other instances, the substitution(s) is/are a non-conservative amino acid substitution. In some instances, where there are more than one amino acid substitution, the substitutions are both conservative and non-conservative amino acid substitutions. In some cases, where one to three amino acids (e.g., 1, 2, or 3) of SEQ ID NO:39 are substituted, the substitutions are all on the non-interacting face of the NOXA helix. In some cases, where one to three amino acids (e.g., 1, 2, or 3) of SEQ ID NO:39 are substituted, the substitutions are all on the interacting face of the NOXA helix. In some cases, where one to three amino acids (e.g., 1, 2, or 3) of SEQ ID NO:39 are substituted, the substitutions are both on the interacting and non-interacting face of the NOXA helix. In certain instances, the substituted amino acid(s) are selected from the group consisting of L-Ala, D-Ala, Aib, Sar, Ser, a substituted alanine, or a substituted glycine derivative. In certain instances, one or more of A26, T27, Q28, R30, R31, F32, G33, K35, L36, N37, F38, R39, or Q40 (numbering according to SEQ ID NO:82) are substituted. In certain instances, the substituted amino acid(s) are selected from the group consisting of L-Ala, D-Ala, Aib, Sar, Ser, a substituted alanine, or a substituted glycine derivative. In certain instances, one or both of L29 and D34 (numbering according to SEQ ID NO:82) of SEQ ID NO:39 are not substituted. In some instances L29 (numbering according to SEQ ID NO:82) of SEQ ID NO:39 is substituted with isoleucine, phenylalanine, L-Ala, D-Ala, Aib, Sar, Ser, a substituted alanine, or a substituted glycine derivative.

In certain embodiments, the NOXA BH3 peptides of this disclosure can have 1, 2, 3, 4, 5, amino acid removed/deleted from the C-terminus of the sequence set forth in SEQ ID NO:39. In certain embodiments, the NOXA BH3 peptides of this disclosure can have 1, 2, 3, 4, 5, amino acid removed/deleted from the N-terminus of the sequence set forth in SEQ ID NO:39. In certain embodiments, the NOXA BH3 peptides of this disclosure can have 1, 2, 3, 4, 5, amino acid removed/deleted from both the N-terminus and C-terminus of the sequence set forth in SEQ ID NO:39. In certain instances, these removed amino acids can be replaced with 1-6 (1, 2, 3, 4, 5, or 6) amino acids selected from the group consisting of L-Ala, D-Ala, Aib, Sar, Ser, a substituted alanine, or a substituted glycine derivative.

Non-limiting examples of modifications to the sequence of SEQ ID NO:39 are provided below:

| Position (numbered according to SEQ ID NO: 82) | Exemplary Modifications |
| --- | --- |
| A26 | D-Ala, Aib, Sar, Ser, a substituted alanine, or a substituted glycine derivative; deletion |
| T27 | I, M, B; L-Ala, D-Ala, Aib, Sar, Ser, a substituted alanine, or a substituted glycine derivative; deletion |
| Q28 | L-Ala, D-Ala, Aib, Sar, Ser, a substituted alanine, or a substituted glycine derivative; deletion |
| L29 | I, F, L-Ala, D-Ala, Aib, Sar, Ser, a substituted alanine, or a substituted glycine derivative |
| R30 | K, T; L-Ala, D-Ala, Aib, Sar, Ser, a substituted alanine, or a substituted glycine derivative; deletion |
| R31 | E, L-Ala, D-Ala, Aib, Sar, Ser, a substituted alanine, or a substituted glycine derivative |
| F32 | I, L, V, L-Ala, D-Ala, Aib, Sar, Ser, a substituted alanine, or a substituted glycine derivative |
| G33 | L-Ala, D-Ala, Aib, Sar, Ser, a substituted alanine, or a substituted glycine derivative |
| D34 | — |
| K35 | L-Ala, D-Ala, Aib, Sar, Ser, a substituted alanine, or a substituted glycine derivative |
| L36 | W; V; L-Ala, D-Ala, Aib, Sar, Ser, a substituted alanine, or a substituted glycine derivative; deletion |
| N37 | D, S, L-Ala, D-Ala, Aib, Sar, Ser, a substituted alanine, or a substituted glycine derivative; deletion |
| F38 | A, L, L-Ala, D-Ala, Aib, Sar, Ser, a substituted alanine, or a substituted glycine derivative; deletion |
| R39 | E, L-Ala, D-Ala, Aib, Sar, Ser, a substituted alanine, or a substituted glycine derivative; deletion |
| Q40 | L, L-Ala or poly-L-Ala, D-Ala or poly-D-Ala, Aib, Sar, Ser, a substituted alanine, or a substituted glycine derivative; deletion |

The disclosure also encompasses NOXA peptides that are at least 14% (e.g., at least 14 to 50%, at least 14 to 45%, at least 14 to 40%, at least 14 to 35%, at least 14 to 30%, at least 14 to 25%, at least 14 to 20%, at least 20% to 50%, at least 20% to 45%, at least 20% to 40%, at least 20% to 35%, at least 20% to 30%, at least 20% to 25%, at least 15%, at least 20%, at least 27%, at least 34%, at least 40% at least 45%, at least 50%, at least 55%, at least 60%, at least 65%, at least 70%, at least 75%, at least 80%, at least 85%, at least 90%, at least 95%, at least 98%, at least 99%, or 100%) identical to SEQ ID NO:39. The variability in amino acid sequence of SEQ ID NO:39 can be on one or both the interacting and non-interacting side of the alpha helix. Just about every one of the amino acids on the non-interacting face of the NOXA BH3 helix can be varied. The amino acids on the interacting face of the helix can also be varied.

In some embodiments, the disclosure features variants of SEQ ID NO:39, wherein the NOXA peptide variants non-covalently bind to BFL-1. This disclosure also features variants of SEQ ID NO:39, wherein the NOXA peptide variants non-covalently bind to MCL-1. In some instances, the variants of SEQ ID NO:39 described herein non-covalently bind to both BFL-1 and MCL-1.

In certain instances, the NOXA peptide has an amino acid sequence set out below:

ATQLRRAGDKLNFRQ; (SEQ ID NO: 94)

ATQLRRFGDKANFRQ; (SEQ ID NO: 95)

ATQLREFGDKLNFRQ; (SEQ ID NO: 96)

ATQLRRFGDKLNFEQ; (SEQ ID NO: 97)

AAQLRAFGAKLNAA; (SEQ ID NO: 98)

AAQLRAFGAKLNAAAA; (SEQ ID NO: 99)

AAQLRAFGAKLNAE; (SEQ ID NO: 100)

AAQLRAFGAKLNAEAA; (SEQ ID NO: 101)

AAQLREFGAKLNAA; (SEQ ID NO: 102)

AAQLREFGAKLNAAAA; (SEQ ID NO: 103)

AAQLRAFGDKLNAA; (SEQ ID NO: 104)

AAQLRAFGDKLNAAAA; (SEQ ID NO: 105)

AAQLRAFGDKLNAE; (SEQ ID NO: 106)

AAQLRAFGDKLNAEAA; (SEQ ID NO: 107)

AAQLREFGDKLNAA; (SEQ ID NO: 108)
or

AAQLREFGDKLNAAAA. (SEQ ID NO: 109)

The NOXA peptides described herein can be optimized for therapeutic use. For example, if any of the above-described NOXA peptides cause membrane disruption (cell lysis), the peptides can be optimized by lowering the overall peptide hydrophobicity. This can for example be achieved by substituting especially hydrophobic residues with an amino acid with lower hydrophobicity (e.g., alanine). Membrane disruption can also be lowered by reducing the overall positive charge of the peptide. This can be accomplished by substituting basic residues with uncharged or acidic residues. In certain instances, both the overall peptide hydrophobicity and the overall positive charge of the peptide are lowered.

In certain embodiments, the NOXA peptides described herein are between 5 and 35 amino acids in length. In certain embodiments, the NOXA peptides described herein are between 5 and 25 amino acids in length. In certain embodiments, the NOXA peptides described herein are between 5 and 20 amino acids in length. In certain embodiments, the NOXA peptides described herein are between 5 and 18 amino acids in length. In certain embodiments, the NOXA peptides described herein are between 10 and 35 amino acids in length. In certain embodiments, the NOXA peptides described herein are between 10 and 25 amino acids in length. In certain embodiments, the NOXA peptides described herein are between 10 and 20 amino acids in length. In certain embodiments, the NOXA peptides described herein are between 10 and 18 amino acids in length. In certain embodiments, the NOXA peptides described herein are between 15 and 26 amino acids in length. In certain embodiments, the NOXA peptides described herein are between 15 and 18 amino acids in length.

In certain instances, the NOXA peptides are structurally stabilized. In order to stabilize these NOXA peptides, the peptides can include two or more substitutions to replace, e.g., an amino acid of the NOXA peptide with a non-natural amino acid, so that the peptide can be stapled and/or stitched.

Stabilized Peptides

A peptide helix is an important mediator of key protein-protein interactions that regulate many important biological processes such as apoptosis; however, when such a helix is taken out of its context within a protein and prepared in isolation, it usually adopts a random coil conformation, leading to a drastic reduction in biological activity and thus diminished therapeutic potential. The present disclosure provides structurally stabilized peptides of NOXA. The present disclosure includes structurally stabilized NOXA peptides (such as those described above) comprising at least two modified amino acids joined by an internal (intramolecular) cross-link (or staple) and, in certain instances, having a reactive group ("a warhead" such as a non-natural amino acid bearing an electrophilic group) that can form a covalent bond with a cysteine (Cys) residue within a target protein to which the structurally stabilized peptide binds (e.g., BFL-1). Stabilized peptides as described herein include stapled peptides and stitched peptides as well as peptides containing multiple stitches, multiple staples or a mix or staples and stitches, or other chemical strategies for structural reinforcement (see. e.g., Balaram P. *Cur. Opin. Struct. Biol.* 1992; 2:845; Kemp D S, et al., *J. Am. Chem. Soc.* 1996; 118:4240; Orner B P, et al., *J. Am. Chem. Soc.* 2001; 123:5382; Chin J W, et al., *Int. Ed.* 2001; 40:3806; Chapman R N, et al., *J. Am. Chem. Soc.* 2004; 126:12252; Horne W S, et al., *Chem., Int. Ed.* 2008; 47:2853; Madden et al., *Chem Commun* (Camb). 2009 Oct. 7; (37): 5588-5590; Lau et al., *Chem. Soc. Rev.,* 2015, 44:91-102; and Gunnoo et al., *Org. Biomol. Chem.,* 2016, 14:8002-8013; all of which are incorporated by reference herein in its entirety).

In certain embodiments, one or more of the NOXA polypeptides described herein can be stabilized by peptide stapling (see, e.g., Walensky, *J. Med. Chem.,* 57:6275-6288 (2014), the contents of which are incorporated by reference herein in its entirety). A peptide is "stabilized" in that it maintains its native secondary structure. For example, stapling allows a polypeptide, predisposed to have an α-helical secondary structure, to maintain its native α-helical conformation. This secondary structure increases resistance of the polypeptide to proteolytic cleavage and heat, and also may increase target binding affinity, hydrophobicity, and cell permeability. Accordingly, the stapled (cross-linked) polypeptides described herein have improved biological activity relative to a corresponding non-stapled (un-cross-linked) polypeptide.

"Peptide stapling" is a term coined from a synthetic methodology wherein two olefin-containing side-chains (e.g., cross-linkable side chains) present in a polypeptide chain are covalently joined (e.g., "stapled together") using a ring-closing metathesis (RCM) reaction to form a cross-linked ring (see, e.g., Blackwell et al., *J. Org. Chem.,* 66:

5291-5302, 2001; Angew et al., *Chem. Int. Ed.* 37:3281, 1994). As used herein, the term "peptide stapling" includes the joining of two (e.g., at least one pair of) double bond-containing side-chains, triple bond-containing side-chains, or double bond-containing and triple bond-containing side chain, which may be present in a polypeptide chain, using any number of reaction conditions and/or catalysts to facilitate such a reaction, to provide a singly "stapled" polypeptide. The term "multiply stapled" polypeptides refers to those polypeptides containing more than one individual staple, and may contain two, three, or more independent staples of various spacing. Additionally, the term "peptide stitching," as used herein, refers to multiple and tandem "stapling" events in a single polypeptide chain to provide a "stitched" (e.g., tandem or multiply stapled) polypeptide, in which two staples, for example, are linked to a common residue. Peptide stitching is disclosed, e.g., in WO 2008/121767 and WO 2010/068684, which are both hereby incorporated by reference in their entirety. In some instances, staples, as used herein, can retain the unsaturated bond or can be reduced.

In certain embodiments, one or more of the polypeptides described herein can be stabilized by, e.g., hydrocarbon stapling. In some embodiments, the stapled peptide is a polypeptide comprising or consisting of amino acids 26-40 of NOXA, or comprising 1 to 13 (e.g., 1, 2, 3, 4, 5, 6, 7, 8, 9, 10, 11, 12, or 13) amino acid substitutions, deletions and/or insertions therein). In certain instances, the stapled peptide includes at least two (e.g., 2, 3, 4, 5, 6) amino acid substitutions, wherein the substituted amino acids are separated by two, three, or six amino acids, and wherein the substituted amino acids are non-natural amino acids with olefinic side chains. There are many known non-natural or unnatural amino acids any of which may be included in the peptides of the present disclosure. Some examples of unnatural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and/para-substituted phenylalanines (e.g., substituted with —C(=O)C$_6$H$_5$; —CF$_3$; —CN; -halo; —NO$_2$; CH$_3$), disubstituted phenylalanines, substituted tyrosines (e.g., further substituted with —C=O)C$_6$H$_5$; —CF$_3$; —CN; -halo; —NO$_2$; CH$_3$), and statine. Additionally, amino acids can be derivatized to include amino acid residues that are hydroxylated, phosphorylated, sulfonated, acylated, or glycosylated.

Hydrocarbon stapled polypeptides include one or more tethers (linkages) between two non-natural amino acids, which tether significantly enhances the α-helical secondary structure of the polypeptide. Generally, the tether extends across the length of one or two helical turns (i.e., about 3.4 or about 7 amino acids). Accordingly, amino acids positioned at i and i+3; i and i+4; or i and i+7 are ideal candidates for chemical modification and cross-linking. Thus, for example, where a peptide has the sequence . . . X1, X2, X3, X4, X5, X6, X7, X8, X9 . . . , cross-links between X1 and X4, or between X1 and X5, or between X1 and X8 are useful hydrocarbon stapled forms of that peptide, as are cross-links between X2 and X5, or between X2 and X6, or between X2 and X9, etc. The use of multiple cross-links (e.g., 2, 3, 4, or more) is also contemplated. The use of multiple cross-links is very effective at stabilizing and optimizing the peptide, especially with increasing peptide length. Thus, the disclosure encompasses the incorporation of more than one cross-link within the polypeptide sequence to either further stabilize the sequence or facilitate the structural stabilization, proteolytic resistance, acid stability, thermal stability, cellular permeability, and/or biological activity enhancement of longer polypeptide stretches. Additional description regarding making and use of hydrocarbon stapled polypeptides can be found, e.g., in U.S. Patent Publication Nos. 2012/0172285, 2010/0286057, and 2005/0250680, the contents of all of which are incorporated by reference herein in their entireties.

In certain embodiments when a staple is at the i and i+3 residues, R-propenylalanine and S-pentenylalanine; or R-pentenylalanine and S-pentenylalanine are substituted for the amino acids at those positions. In certain embodiments when a staple is at the i and i+4 residues, S-pentenyl alanine is substituted for the amino acids at those positions. In certain embodiments when a staple is at the i and i+7 residues, S-pentenyl alanine and R-octenyl alanine are substituted for the amino acids at those positions. In some instances, when the peptide is stitched, the amino acids of the peptide to be involved in the "stitch" are substituted with Bis-pentenylglycine, S-pentenylalanine, and R-octenylalanine; or Bis-pentenylglycine, S-octenylalanine, and R-octenylalanine.

In certain embodiments, the staple and/or stitch is made at positions 1 and 5; 2 and 6; 3 and 7; 6 and 10; 10 and 14; 11 and 15; 12 and 16; 1 and 8; 3 and 10; 6 and 13; 7 and 14; or 8 and 15, wherein the positions provided are based on SEQ ID NO:39; or a modified version of SEQ ID NO:39 as described above (e.g., any one of SEQ ID NOs.:94 through 109). Staple positions can be varied by testing different staple locations in a staple walk.

Figure 36:
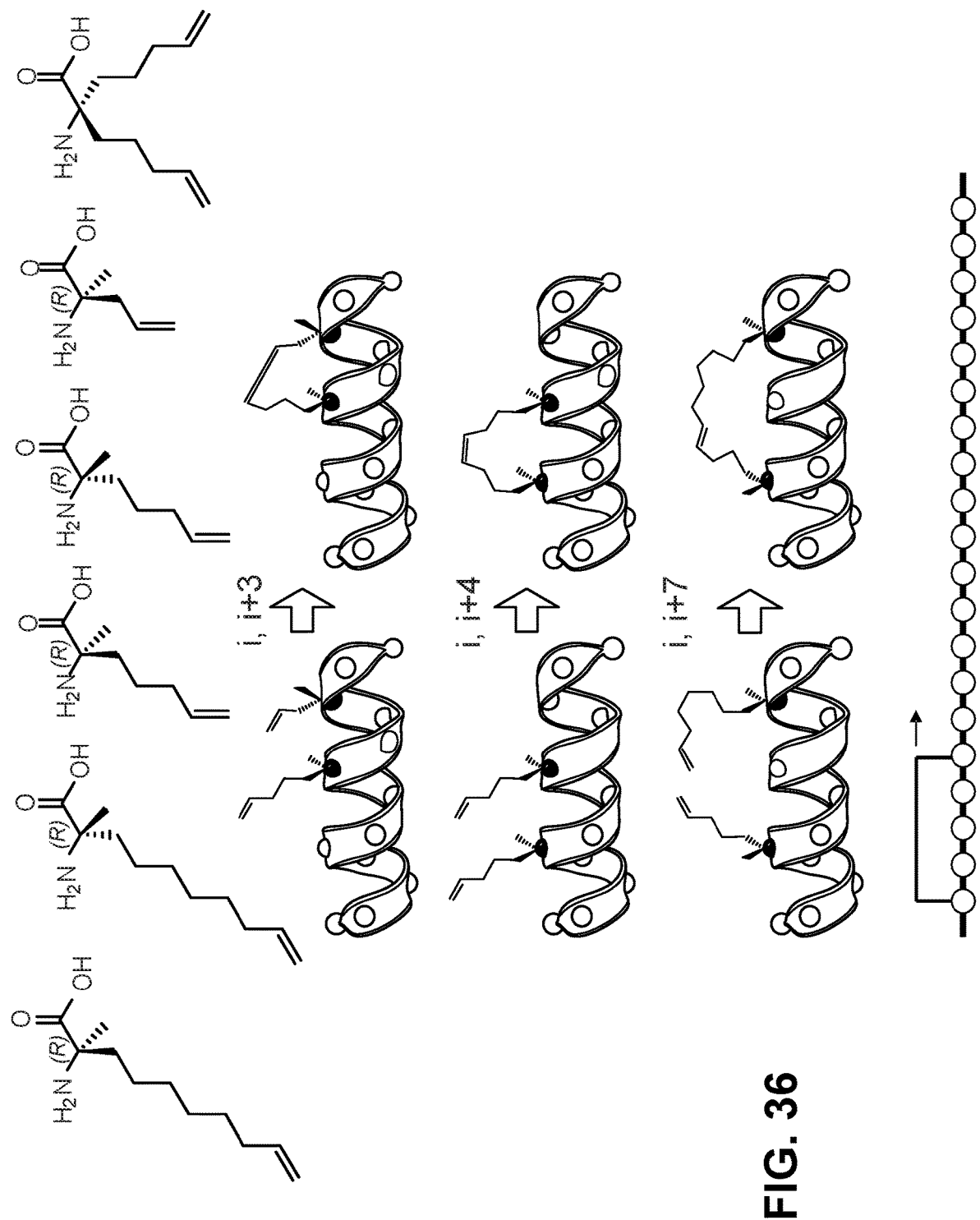
FIG. 36 shows the chemical structures of exemplary unnatural amino acids used to generate various kinds of staples (top). The middle panel illustrates peptides with staples of various lengths. The bottom panel illustrates a staple walk along a peptide sequence.
Figure 37:
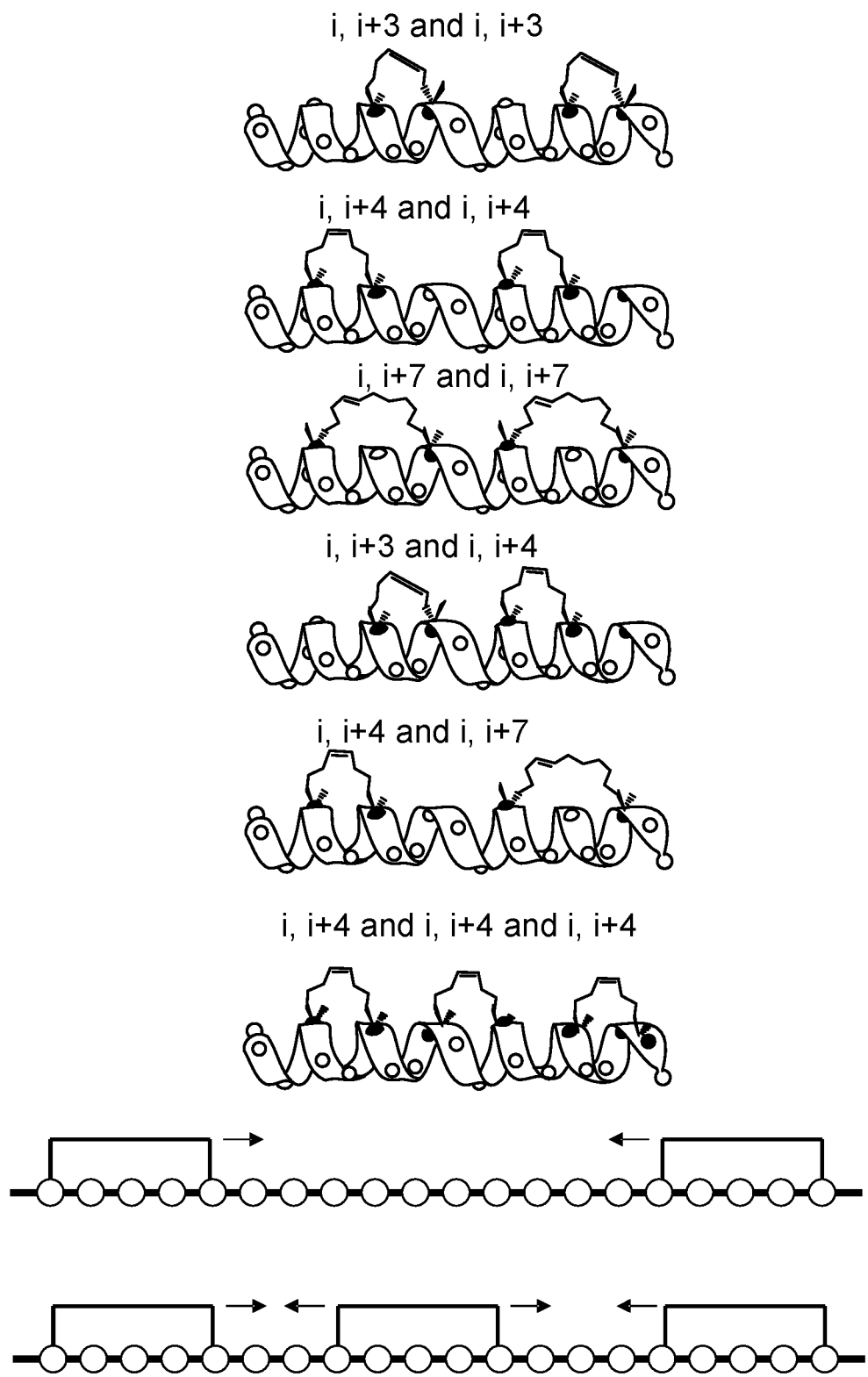
FIG. 37 is a schematic showing representations of various kinds of double and triple stapling strategies along with exemplary staple walks.
Figure 38:
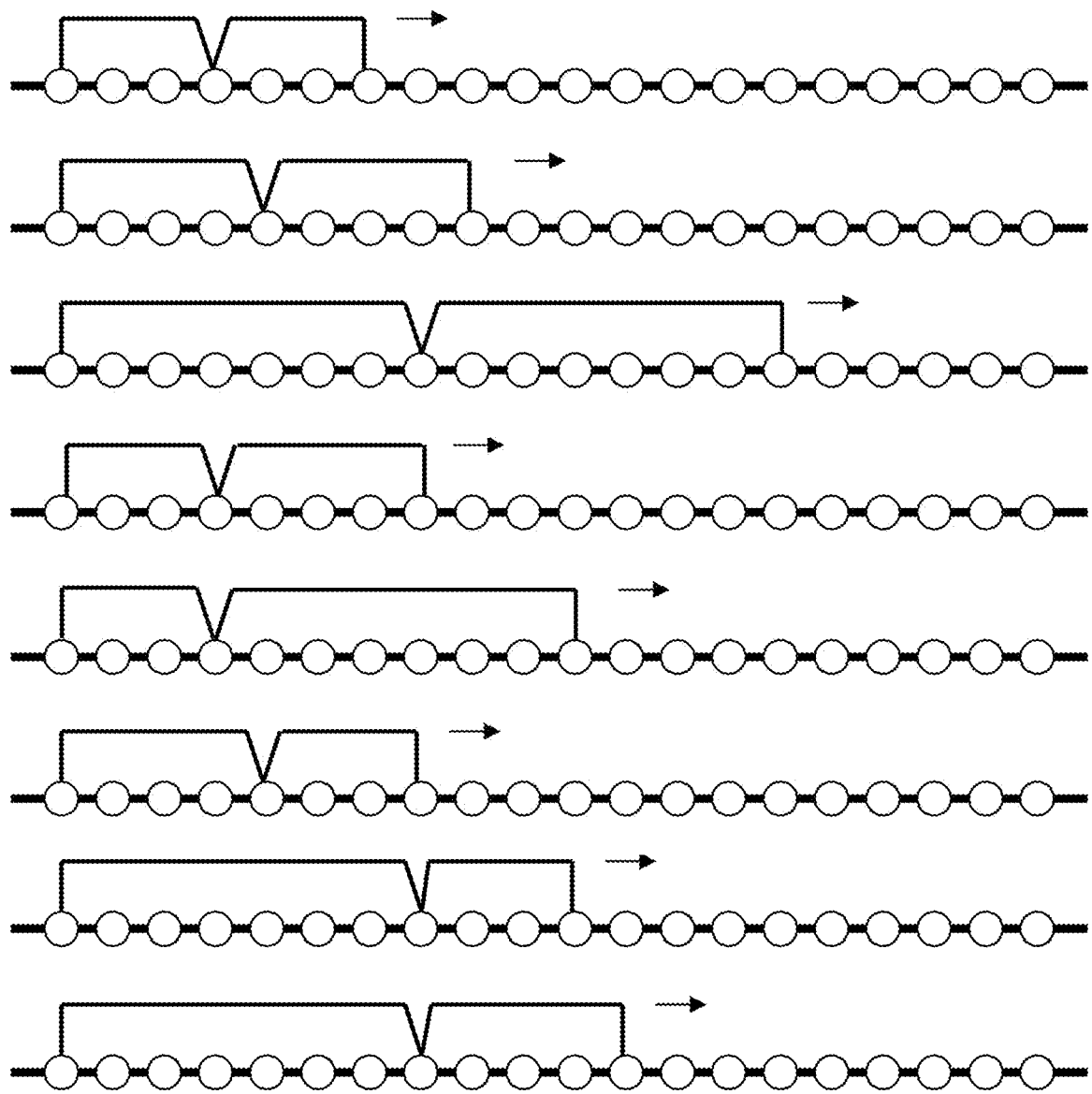
FIG. 38 is a schematic showing exemplary staple walks using various lengths of branched double staple moieties.
Figure 39:
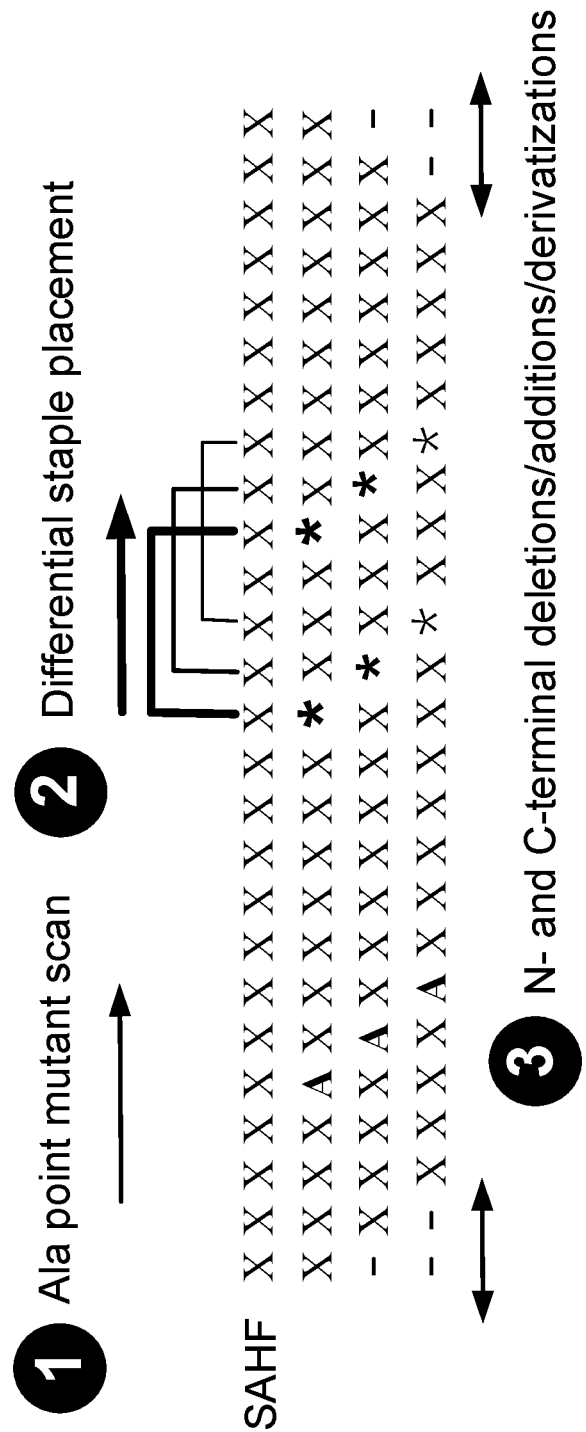
FIG. 39 is a schematic showing exemplary chemical alterations that are employed to generate stapled peptide derivatives.
Figure 40:
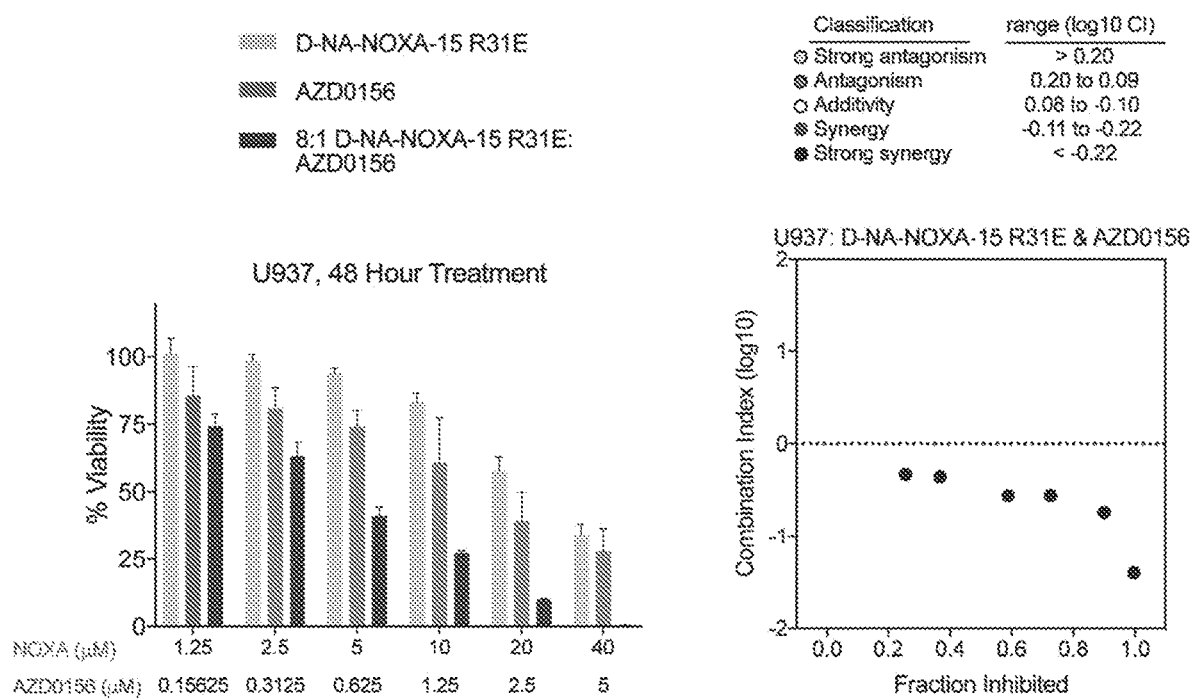
FIG. 40 are graphs showing that treatment of BFL-1-dependent U937 cells with the combination of cysteine-reactive NOXA-15 R31E and the ATM inhibitor AZD0156 caused a synergistic decrease in cell viability (left), as reflected by Calcusyn analysis dose-effect plot (right). Left panel: for each concentration in the left panel, the bars are (from left to right): (i) D-NA-NOXA-15 R31E, (ii) AZD0156, and (iii) 8:1 D-NA-NOXA-15 R31E:AZD0156. Right panel: each dot in the plot is classified as "Strong synergy".
Figure 41:
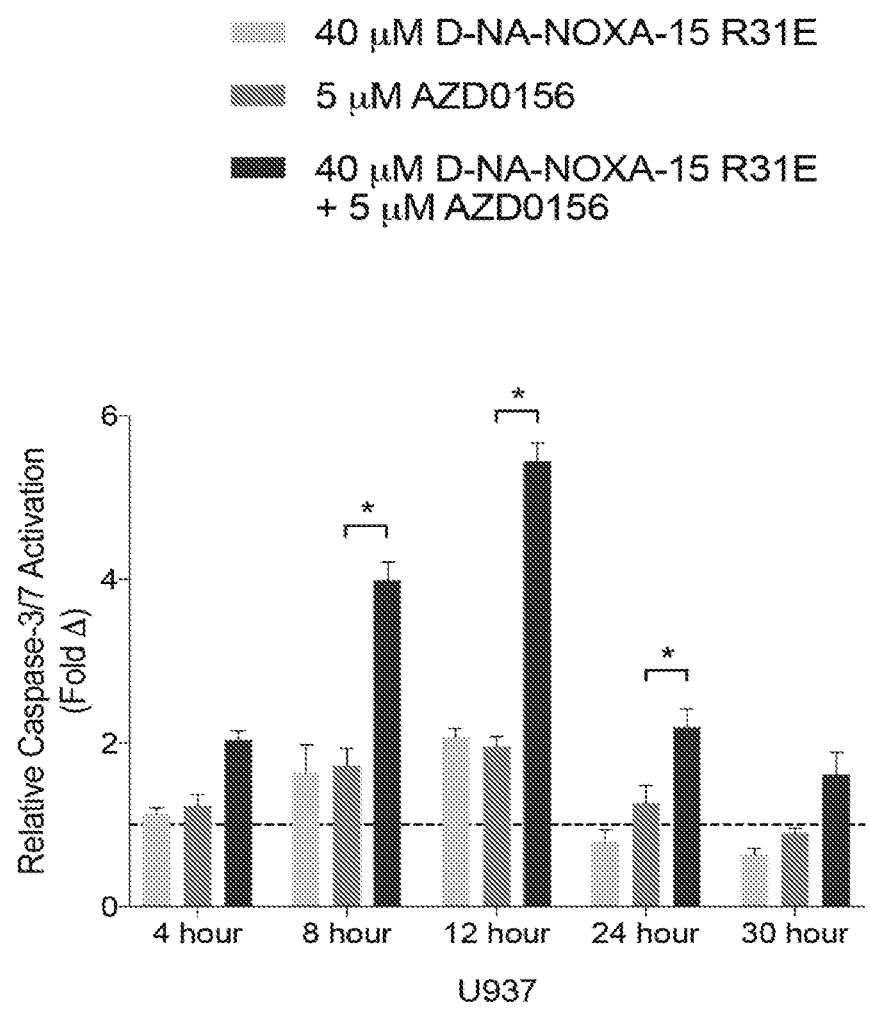
FIG. 41 is a bar graph showing that U937 cells treated with cysteine-reactive NOXA-15 R31E and AZD0156 singly and in combination exhibit significantly increased caspase-3/7 activation over time upon combination treatment compared to single agent treatment. For each time point, the bars are (from left to right): (i) 40 μM D-NA-NOXA-15 R31E, (ii) 5 μM AZD0156, and (ii) 40 μM D-NA-NOXA-15 R31E+5 μM AZD0156.
Figure 42:
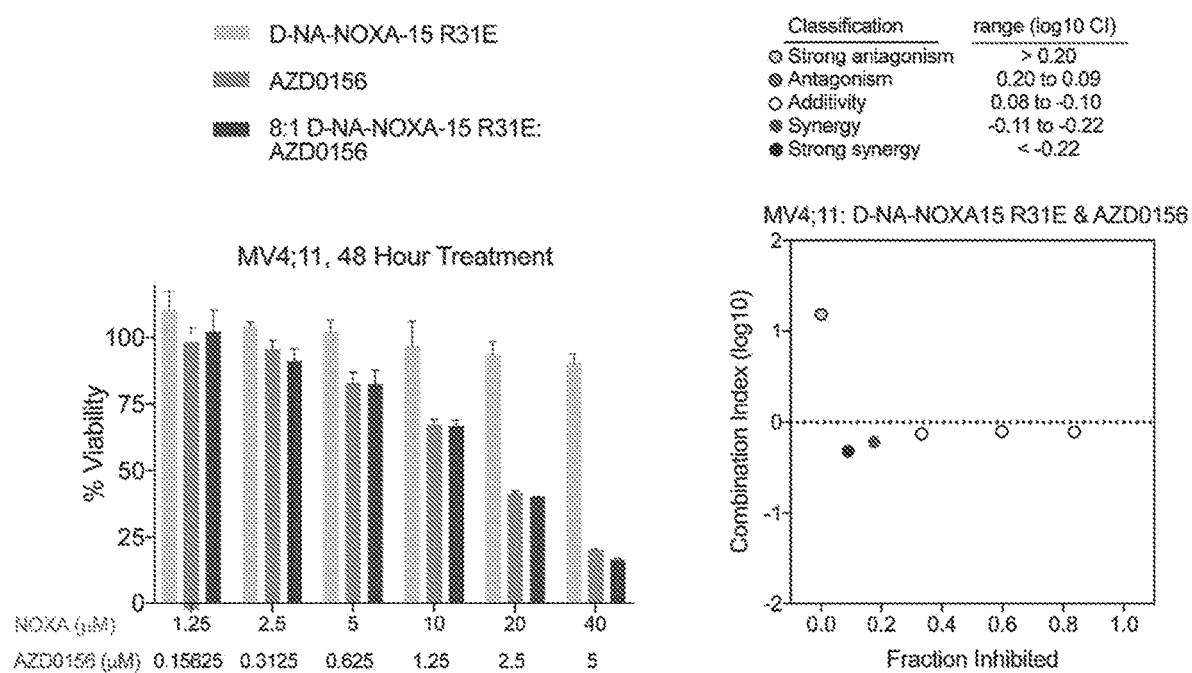
FIG. 42 are graphs showing that co-treatment of the MV4;11 cell line, which is not dependent on BFL-1, resulted in little to no cytotoxic synergy of cysteine-reactive NOXA-15 R31E and the ATM inhibitor AZD0156. Left panel: for each concentration in the left panel, the bars are (from left to right): (i) D-NA-NOXA-15 R31E, (ii) AZD0156, and (iii) 8:1 D-NA-NOXA-15 R31E:AZD0156. Right panel: the dots are (from left to right): (i) strong antagonism, (ii) strong synergy, (iii) synergy, (iv) additivity, (v) additivity, and (vi) additivity.
Figure 43:
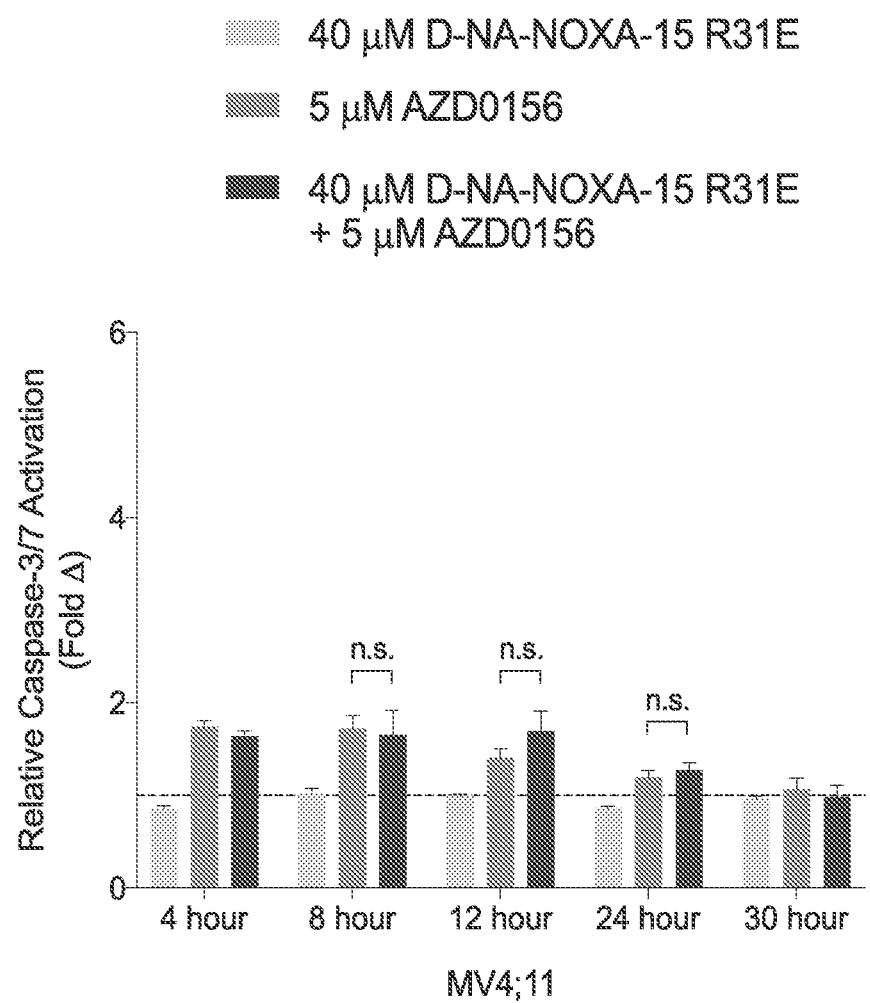
FIG. 43 is a bar graph showing that MV4;11 cells treated with cysteine-reactive NOXA-15 R31E and AZD0156 singly and in combination exhibit no increase in caspase-3/7 activation compared to single agent treatments. For each time point, the bars are (from left to right): (i) 40 μM D-NA-NOXA-15 R31E, (ii) 5 μM AZD0156, and (ii) 40 μM D-NA-NOXA-15 R31E+5 μM AZD0156.

FIG. 36 top panel shows exemplary chemical structures of non-natural amino acids that can be used to generate various crosslinked compounds. FIG. 36 middle panel illustrates peptides with hydrocarbon cross-links between positions i and i+3; i and i+4; and i and i+7 residues. FIG. 36 bottom panel illustrates a staple walk along a peptide sequence. FIG. 37 shows various peptide sequences with double and triple stapling strategies, and exemplary staple walks. FIG. 38 illustrates exemplary staple walks using various lengths of branched stitched moieties.

In one aspect, a NOXA SAHB polypeptide has the formula (I),

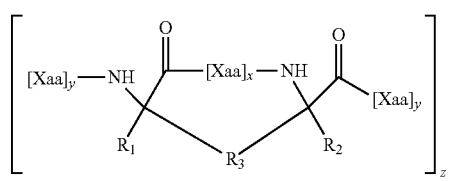

wherein:
each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;
$R_3$ is alkyl, alkenyl, alkynyl; [$R_4$—K—$R_4$]$_n$; each of which is substituted with 0-6 $R_5$;
R4 is alkyl, alkenyl, or alkynyl;
$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;

K is O, S, SO, $SO_2$, CO, $CO_2$, $CONR_6$, or

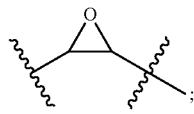 [SMILES: *C1OC1*]

$R_6$ is H, alkyl, or a therapeutic agent;
n is an integer from 1-4;
x is an integer from 2-10;
each y is independently an integer from 0-100;
z is an integer from 1-10 (e.g., 1, 2, 3, 4, 5, 6, 7, 8, 9, 10);
and each Xaa is independently an amino acid. In some embodiments, the N-terminal $[Xaa]_y$ of formula (I) is not present, A, AT, ATQLR (SEQ ID NO:110), ATQLRR (SEQ ID NO:111), ATQLRRF (SEQ ID NO:112), ATQLRRFGD (SEQ ID NO:113), ATQLRRFGDK (SEQ ID NO:114); or ATQLRRFGDKL (SEQ ID NO:115). In some embodiments, $[Xaa]_x$ is TQL, QLR, LRR, FGD, LNF, NFR, FRQ, TQLRRF (SEQ ID NO:116), LRRFGD (SEQ ID NO:117), FGDKLN (SEQ ID NO:118), GDKLNF (SEQ ID NO:119), or DKLNFR (SEQ ID NO:120). In some embodiments, the C-terminal $[Xaa]_y$ of formula (I) is RFGDKLNFRQ (SEQ ID NO:121); FGDKLN-FRQ (SEQ ID NO:122); GDKLNFRQ (SEQ ID NO:123); LNFRQ (SEQ ID NO:124); Q; DKLNFRQ (SEQ ID NO:125); or RQ. In certain instances, the sequences set forth above and in SEQ ID NOs.:110-125 can have at least one (e.g., 1, 2, 3, 4, 5, 6) amino acid substitution or deletion. The NOXA SAHB polypeptides can include any amino acid sequence described herein.

The tether can include an alkyl, alkenyl, or alkynyl moiety (e.g., $C_5$, $C_8$, or $C_{11}$ alkyl, a $C_5$, $C_8$, or $C_{11}$ alkenyl, or $C_5$, $C_8$, or $C_{11}$ alkynyl). The tethered amino acid can be alpha disubstituted (e.g., $C_1$-$C_3$ or methyl).

In some instances, x is 2, 3, or 6. In some instances, each y is independently an integer between 1 and 15, or 3 and 15. In some instances, $R_1$ and $R_2$ are each independently H or $C_1$-$C_6$ alkyl. In some instances, $R_1$ and $R_2$ are each independently $C_1$-$C_3$ alkyl. In some instances, at least one of $R_1$ and $R_2$ are methyl. For example, $R_1$ and $R_2$ can both be methyl. In some instances, $R_3$ is alkyl (e.g., $C_8$ alkyl) and x is 3. In some instances, $R_3$ is $C_{11}$ alkyl and x is 6. In some instances, $R_3$ is alkenyl (e.g., $C_8$ alkenyl) and x is 3. In some instances, x is 6 and $R_3$ is $C_{11}$ alkenyl. In some instances, $R_3$ is a straight chain alkyl, alkenyl, or alkynyl. In some instances, $R_3$ is —$CH_2$—$CH_2$—$CH_2$—CH=CH—$CH_2$—$CH_2$—$CH_2$—.

In another aspect, the two alpha, alpha disubstituted stereocenters are both in the R configuration or S configuration (e.g., i, i+4 cross-link), or one stereocenter is R and the other is S (e.g., i, i+7 cross-link). Thus, where formula I is depicted as:

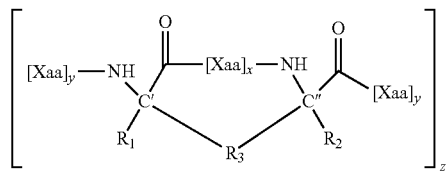

the C' and C" disubstituted stereocenters can both be in the R configuration or they can both be in the S configuration, e.g., when x is 3. When x is 6, the C' disubstituted stereocenter is in the R configuration and the C" disubstituted stereocenter is in the S configuration. The R3 double bond can be in the E or Z stereochemical configuration.

In some instances, $R_3$ is $[R_4—K—R_4]_n$; and $R_4$ is a straight chain alkyl, alkenyl, or alkynyl.

In some embodiments, the disclosure features internally cross-linked ("stapled" or "stitched") peptides comprising the amino acid sequence ATQLRRFGDKLNFRQ (SEQ ID NO:39), wherein the side chains of two amino acids separated by two, three, or six amino acids are replaced by an internal staple; the side chains of three amino acids are replaced by an internal stitch; the side chains of four amino acids are replaced by two internal staples, or the side chains of five amino acids are replaced by the combination of an internal staple and an internal stitch. In certain instances, the amino acids at one or more of positions 4, 8, and 9 of SEQ ID NO: 39 are not replaced with a staple or stitch. In certain instances, the amino acids at positions 4 and/or 9 of SEQ ID NO: 39 are not replaced with a staple or stitch. The stapled/stitched peptide can be 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length. In a specific embodiment, the stapled/stitched peptide is 15, 16, 17, 18, 19, 20, 21, 22, 23, 24, or 25 amino acids in length. In a specific embodiment, the stapled/stitched peptide is 8, 9, 10, 11, 12, 13, 14, 15, 16, 17, or 18 amino acids in length. Exemplary NOXA stapled peptides are shown in FIG. 2. In certain embodiments, the stapled polypeptide comprises or consists of the amino acid sequence set forth in any one of SEQ ID NOs:2 to 21. In one embodiment, the NOXA stapled peptide has the amino acid sequence set forth in SEQ ID NO:16. In certain embodiments, the stapled polypeptide comprises or consists of the amino acid sequence set forth in any one of SEQ ID NOs: 22 to 34. In certain embodiments, the stapled polypeptide comprises or consists of the amino acid sequence set forth in any one of SEQ ID NOs: 35 to 38. In certain embodiments, the stapled polypeptide comprises or consists of the amino acid sequence set forth in any one of SEQ ID NOs:94 to 109, wherein at least two amino acids separated by 2, 3 or 6 amino acids are modified to structurally stabilize the peptide (e.g., by substituting them with non-natural amino acids to permit hydrocarbon stapling).

While hydrocarbon tethers are common, other tethers can also be employed in the NOXA BH3 peptides described herein. For example, the tether can include one or more of an ether, thioether, ester, amine, or amide, or triazole moiety. In some cases, a naturally occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally occurring amino acids rather than using a tether that is made by coupling two non-naturally occurring amino acids. It is also possible to use a single non-naturally occurring amino acid together with a naturally occurring amino acid. Triazole-containing (e.g., 1, 4 triazole or 1, 5 triazole) crosslinks can be used (see, e.g., Kawamoto et al. 2012 *Journal of Medicinal Chemistry* 55:1137; WO 2010/060112). In addition, other methods of performing different types of stapling are well known in the art and can be employed with the NOXA BH3 peptides described herein (see, e.g., *Lactam stapling*: Shepherd et al., *J. Am. Chem.*

Soc., 127:2974-2983 (2005); *UV-cycloaddition stapling*: Madden et al., *Bioorg. Med. Chem. Lett.*, 21:1472-1475 (2011); *Disulfide stapling*: Jackson et al., *Am. Chem. Soc.*, 113:9391-9392 (1991); *Oxime stapling:* Haney et al., *Chem. Commun.*, 47:10915-10917 (2011); *Thioether stapling*: Brunel and Dawson, *Chem. Commun.*, 552-2554 (2005); *Photoswitchable stapling*: J. R. Kumita et al., *Proc. Natl. Acad. Sci. U.S.A.*, 97:3803-3808 (2000); *Double-click stapling*: Lau et al., *Chem. Sci.*, 5:1804-1809 (2014); *Bis-lactam stapling*: J. C. Phelan et al. *J. Am. Chem. Soc.*, 119:455-460 (1997); and *Bis-acylation stapling*: A. M. Spokoyny et al., *J. Am. Chem. Soc.*, 135:5946-5949 (2013)).

It is further envisioned that the length of the tether can be varied. For instance, a shorter length of tether can be used where it is desirable to provide a relatively high degree of constraint on the secondary alpha-helical structure, whereas, in some instances, it is desirable to provide less constraint on the secondary alpha-helical structure, and thus a longer tether may be desired.

Additionally, while tethers spanning from amino acids i to i+3, i to i+4, and i to i+7 are common in order to provide a tether that is primarily on a single face of the alpha helix, the tethers can be synthesized to span any combinations of numbers of amino acids and also used in combination to install multiple tethers.

In some instances, the hydrocarbon tethers (i.e., cross links) described herein can be further manipulated. In one instance, a double bond of a hydrocarbon alkenyl tether, (e.g., as synthesized using a ruthenium-catalyzed ring closing metathesis (RCM)) can be oxidized (e.g., via epoxidation, aminohydroxylation or dihydroxylation) to provide one of compounds below.

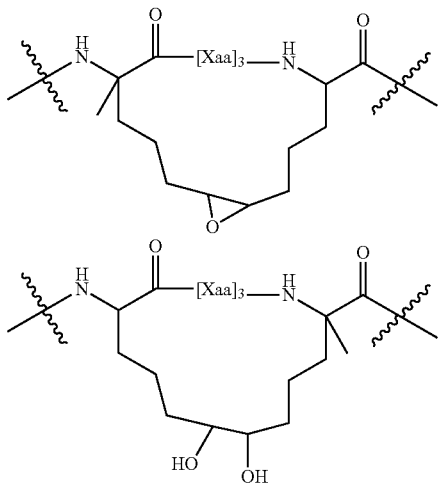

Either the epoxide moiety or one of the free hydroxyl moieties can be further functionalized. For example, the epoxide can be treated with a nucleophile, which provides additional functionality that can be used, for example, to attach a therapeutic agent. Such derivatization can alternatively be achieved by synthetic manipulation of the amino or carboxy-terminus of the polypeptide or via the amino acid side chain. Other agents can be attached to the functionalized tether, e.g., an agent that facilitates entry of the polypeptide into cells.

In some instances, alpha disubstituted amino acids are used in the polypeptide to improve the stability of the alpha helical secondary structure. However, alpha disubstituted amino acids are not required, and instances using mono-alpha substituents (e.g., in the tethered amino acids) are also envisioned.

The stapled polypeptides can include a drug, a toxin, a derivative of polyethylene glycol; a second polypeptide; a carbohydrate, etc. Where a polymer or other agent is linked to the stapled polypeptide is can be desirable for the composition to be substantially homogeneous.

The addition of polyethelene glycol (PEG) molecules can improve the pharmacokinetic and pharmacodynamic properties of the polypeptide. For example, PEGylation can reduce renal clearance and can result in a more stable plasma concentration. PEG is a water soluble polymer and can be represented as linked to the polypeptide as formula:

$XO—(CH_2CH_2O)_n—CH_2CH_2—Y$ where n is 2 to 10,000 and X is H or a terminal modification, e.g., a $C_{1-4}$ alkyl; and Y is an amide, carbamate or urea linkage to an amine group (including but not limited to, the epsilon amine of lysine or the N-terminus) of the polypeptide. Y may also be a maleimide linkage to a thiol group (including but not limited to, the thiol group of cysteine). Other methods for linking PEG to a polypeptide, directly or indirectly, are known to those of ordinary skill in the art. The PEG can be linear or branched. Various forms of PEG including various functionalized derivatives are commercially available.

PEG having degradable linkages in the backbone can be used. For example, PEG can be prepared with ester linkages that are subject to hydrolysis. Conjugates having degradable PEG linkages are described in WO 99/34833; WO 99/14259, and U.S. Pat. No. 6,348,558.

In certain embodiments, macromolecular polymer (e.g., PEG) is attached to an agent described herein through an intermediate linker. In certain embodiments, the linker is made up of from 1 to 20 amino acids linked by peptide bonds, wherein the amino acids are selected from the 20 naturally occurring amino acids. Some of these amino acids may be glycosylated, as is well understood by those in the art. In other embodiments, the 1 to 20 amino acids are selected from glycine, alanine, proline, asparagine, glutamine, and lysine. In other embodiments, a linker is made up of a majority of amino acids that are sterically unhindered, such as glycine and alanine. Non-peptide linkers are also possible. For example, alkyl linkers such as —NH(CH$_2$)$_n$C (O)—, wherein n=2-20 can be used. These alkyl linkers may further be substituted by any non-sterically hindering group such as lower alkyl (e.g., $C_1$-$C_6$) lower acyl, halogen (e.g., Cl, Br), CN, NH$_2$, phenyl, etc. U.S. Pat. No. 5,446,090 describes a bifunctional PEG linker and its use in forming conjugates having a peptide at each of the PEG linker termini.

The stapled peptides can also be modified, e.g., to further facilitate cellular uptake or increase in vivo stability, in some embodiments. For example, acylating or PEGylating a peptidomimetic macrocycle facilitates cellular uptake, increases bioavailability, increases blood circulation, alters pharmacokinetics, decreases immunogenicity and/or decreases the needed frequency of administration.

In some embodiments, the stapled peptides disclosed herein have an enhanced ability to penetrate cell membranes (e.g., relative to non-stapled peptides).

Methods of synthesizing the stabilized peptides described herein are known in the art. Nevertheless, the following exemplary method may be used. It will be appreciated that the various steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3d. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The peptides of this invention can be made by chemical synthesis methods, which are well known to the ordinarily skilled artisan. See, for example, Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the $\alpha$-$NH_2$ protected by either t-Boc or Fmoc chemistry using side chain protected amino acids on, for example, an Applied Biosystems Peptide Synthesizer Model 430A or 431.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides could be made by conjoining individual synthetic peptides using native chemical ligation. Alternatively, the longer synthetic peptides can be synthesized by well-known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptides can be made in a high-throughput, combinatorial fashion, e.g., using a high-throughput multiple channel combinatorial synthesizer available from Advanced Chemtech. Peptide bonds can be replaced, e.g., to increase physiological stability of the peptide, by: a retro-inverso bonds (C(O)—NH); a reduced amide bond (NH—$CH_2$); a thiomethylene bond (S—$CH_2$ or $CH_2$—S); an oxomethylene bond (O—$CH_2$ or $CH_2$—O); an ethylene bond ($CH_2$—$CH_2$); a thioamide bond (C(S)—NH); a trans-olefin bond (CH=CH); a fluoro substituted trans-olefin bond (CF=CH); a ketomethylene bond (C(O)—CHR) or CHR—C(O) wherein R is H or $CH_3$; and a fluoro-ketomethylene bond (C(O)—CFR or CFR—C(O) wherein R is H or F or $CH_3$.

The polypeptides can be further modified by: acetylation, amidation, biotinylation, cinnamoylation, farnesylation, fluoresceination, formylation, myristoylation, palmitoylation, phosphorylation (Ser, Tyr or Thr), stearoylation, succinylation and sulfurylation. As indicated above, peptides can be conjugated to, for example, polyethylene glycol (PEG); alkyl groups (e.g., C1-C20 straight or branched alkyl groups); fatty acid radicals; and combinations thereof a, $\alpha$-Disubstituted non-natural amino acids containing olefinic side chains of varying length can be synthesized by known methods (Williams et al. J. Am. Chem. Soc., 113:9276, 1991; Schafmeister et al., J. Am. Chem Soc., 122:5891, 2000; and Bird et al., Methods Enzymol., 446:369, 2008; Bird et al, Current Protocols in Chemical Biology, 2011). For peptides where an i linked to i+7 staple is used (two turns of the helix stabilized) either: a) one S5 amino acid and one R8 is used; or b) one S8 amino acid and one R5 amino acid is used. R8 is synthesized using the same route, except that the starting chiral auxiliary confers the R-alkyl-stereoisomer. Also, 8-iodooctene is used in place of 5-iodopentene. Inhibitors are synthesized on a solid support using solid-phase peptide synthesis (SPPS) on MBHA resin (see, e.g., WO 2010/148335).

Fmoc-protected $\alpha$-amino acids (other than the olefinic amino acids Fmoc-$S_5$—OH, Fmoc-$R_8$—OH, Fmoc-$R_8$—OH, Fmoc-$S_8$—OH and Fmoc-$R_5$—OH), 2-(6-chloro-1-H-benzotriazole-1-yl)-1,1,3,3-tetramethylammonium hexafluorophosphate (HCTU), and Rink Amide MBHA are commercially available from, e.g., Novabiochem (San Diego, CA). Dimethylformamide (DMF), N-methyl-2-pyrrolidinone (NMP), N,N-diisopropylethylamine (DIEA), trifluoroacetic acid (TFA), 1,2-dichloroethane (DCE), fluorescein isothiocyanate (FITC), and piperidine are commercially available from, e.g., Sigma-Aldrich. Olefinic amino acid synthesis is reported in the art (Williams et al., Org. Synth., 80:31, 2003).

Again, methods suitable for obtaining (e.g., synthesizing), stapling, and purifying the peptides disclosed herein are also known in the art (see, e.g., Bird et. al., Methods in Enzymol., 446:369-386 (2008); Bird et al, Current Protocols in Chemical Biology, 2011; Walensky et al., Science, 305:1466-1470 (2004); Schafmeister et al., J. Am. Chem. Soc., 122:5891-5892 (2000); U.S. patent application Ser. No. 12/525,123, filed Mar. 18, 2010; and U.S. Pat. No. 7,723,468, issued May 25, 2010, each of which are hereby incorporated by reference in their entirety).

In some embodiments, the peptides are substantially free of non-stapled peptide contaminants or are isolated. Methods for purifying peptides include, for example, synthesizing the peptide on a solid-phase support. Following cyclization, the solid-phase support may be isolated and suspended in a solution of a solvent such as DMSO, DMSO/dichloromethane mixture, or DMSO/NMP mixture. The DMSO/dichloromethane or DMSO/NMP mixture may comprise about 30%, 40%, 50% or 60% DMSO. In a specific embodiment, a 50%/50% DMSO/NMP solution is used. The solution may be incubated for a period of 1, 6, 12 or 24 hours, following which the resin may be washed, for example with dichloromethane or NMP. In one embodiment, the resin is washed with NMP. Shaking and bubbling an inert gas into the solution may be performed.

Properties of the stapled (cross-linked) polypeptides of the invention can be assayed, for example, using the methods described below.

Assays to Determine $\alpha$-Helicity: Compounds are dissolved in an aqueous solution (e.g. 5 mM potassium phosphate solution at pH 7, or distilled $H_2O$, to concentrations of 25-50 μM). Circular dichroism (CD) spectra are obtained on a spectropolarimeter (e.g., Jasco J-710, Aviv) using standard measurement parameters (e.g. temperature, 20° C.; wavelength, 190-260 nm; step resolution, 0.5 nm; speed, 20 nm/sec; accumulations, 10; response, 1 sec; bandwidth, 1 nm; path length, 0.1 cm). The $\alpha$-helical content of each peptide is calculated by dividing the mean residue ellipticity by the reported value for a model helical decapeptide (Yang et al., *Methods Enzymol.* 130:208 (1986)).

Assays to Determine Melting Temperature (Tm): Cross-linked or the unmodified template peptides are dissolved in distilled $H_2O$ or other buffer or solvent (e.g. at a final concentration of 50 µM) and Tm is determined by measuring the change in ellipticity over a temperature range (e.g. 4 to 95° C.) on a spectropolarimeter (e.g., Jasco J-710, Aviv) using standard parameters (e.g. wavelength 222 nm; step resolution, 0.5 nm; speed, 20 nm/sec; accumulations, 10; response, 1 sec; bandwidth, 1 nm; temperature increase rate: 1° C./min; path length, 0.1 cm).

In Vitro Protease Resistance Assays: The amide bond of the peptide backbone is susceptible to hydrolysis by proteases, thereby rendering peptidic compounds vulnerable to rapid degradation in vivo. Peptide helix formation, however, typically buries and/or twists and/or shields the amide backbone and therefore may prevent or substantially retard proteolytic cleavage. The peptidomimetic macrocycles of the present invention may be subjected to in vitro enzymatic proteolysis (e.g. trypsin, chymotrypsin, pepsin) to assess for any change in degradation rate compared to a corresponding uncrosslinked or alternatively stapled polypeptide. For example, the peptidomimetic macrocycle and a corresponding uncrosslinked polypeptide are incubated with trypsin agarose and the reactions quenched at various time points by centrifugation and subsequent HPLC injection to quantitate the residual substrate by ultraviolet absorption at 280 nm. Briefly, the peptidomimetic macrocycle and peptidomimetic precursor (5 mcg) are incubated with trypsin agarose (Pierce) (S/E ~125) for 0, 10, 20, 90, and 180 minutes. Reactions are quenched by tabletop centrifugation at high speed; remaining substrate in the isolated supernatant is quantified by HPLC-based peak detection at 280 nm. The proteolytic reaction displays first order kinetics and the rate constant, k, is determined from a plot of ln[S] versus time.

Peptidomimetic macrocycles and/or a corresponding uncrosslinked polypeptide can be each incubated with fresh mouse, rat and/or human serum (e.g. 1-2 mL) at 37° C. for, e.g., 0, 1, 2, 4, 8, and 24 hours. Samples of differing macrocycle concentration may be prepared by serial dilution with serum. To determine the level of intact compound, the following procedure may be used: The samples are extracted, for example, by transferring 100 µL of sera to 2 ml centrifuge tubes followed by the addition of 10 µL of 50% formic acid and 500 acetonitrile and centrifugation at 14,000 RPM for 10 min at 4+/−2° C. The supernatants are then transferred to fresh 2 ml tubes and evaporated on Turbovap under $N_2$<10 psi, 37° C. The samples are reconstituted in 100 µL of 50:50 acetonitrile:water and submitted to LC-MS/MS analysis. Equivalent or similar procedures for testing ex vivo stability are known and may be used to determine stability of macrocycles in serum.

In Vivo Protease Resistance Assays: A key benefit of peptide stapling is the translation of in vitro protease resistance into markedly improved pharmacokinetics in vivo.

In vitro Binding Assays: To assess the binding and affinity of peptidomimetic macrocycles and peptidomimetic precursors to acceptor proteins, a fluorescence polarization assay (FPA) can be used, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled peptides bound to a large protein) emit higher levels of polarized fluorescence due to their slower rates of rotation as compared to fluorescent tracers attached to smaller molecules (e.g. FITC-labeled peptides that are free in solution).

Stabilized NOXA Peptide Variants

The disclosure also provides NOXA SAHB peptide variants. These variants can differ by one or more amino acids from the amino acid sequence set forth in SEQ ID NO:39. In addition to amino acid substitutions, C- and/or N-terminal deletions are also envisioned.

In some embodiments, internally cross-linked peptides can be made by modifying (e.g., by amino acid substitution) a polypeptide of SEQ ID NO:39. Such NOXA SAHB variants can include peptides with reduced hydrophobicity and/or overall positive charge relative to the peptide of SEQ ID NO:39; or relative to the stapled counterpart of the variant peptide (i.e., a stapled version of the peptide without the variation from SEQ ID NO:39). In some embodiments, an internal staple replaces the side chains of 2 amino acids, i.e., each staple is between two amino acids separated by, for example, 3, 4, or 6 amino acids. In some embodiments, an internal stitch replaces the side chains of 3 amino acids, i.e., the stitch is a pair of crosslinks between three amino acids separated by, for example, 3 and 6 amino acids. In some embodiments, the internal staples and/or the internal stitch comprise at least two internal staples (replacing the side chains of 4 amino acids, i.e., each staple is between two amino acids separated by, for example, 3 amino acids). In some embodiments, the internal staples and/or the internal stitch comprise a combination of at least one internal staple and an internal stitch. In some embodiments, the internal stitch replaces the side chain of a first amino acid and a second and a third amino acid thereby cross-linking the first amino acid (which lies between the second and third amino acids) to the second and third amino acid via an internal cross-link, wherein the first and second amino acid are separated by two, three, or six amino acids, the first and the third amino acids are separated by two, three, or six amino acids, and the second and third amino acids are distinct amino acids. In some embodiments, the side chains of the four amino acids of the internally cross-linked polypeptides of the disclosure are replaced by two distinct internal staples. In some embodiments, a first of the two distinct internal staples cross-links a first pair of amino acids separated by two, three, or six amino acids, and a second of the at least two distinct internal staples cross-links a second pair of amino acids separated by two, three, or six amino acids. In some embodiments, internally cross-linked NOXA polypeptide variants of the disclosure are prepared from a polypeptide of SEQ ID NO: 39 and having e.g., 1, 2, 3, 4, 5, 6, 7, 8, or 9 amino acid substitutions (e.g., 1, 2, 3, 4, 5, 6, 7, 8, or 9 amino acids are conservatively or non-conservatively substituted). Exemplary NOXA stapled peptide variants are provided in FIG. 6 and FIG. 10.

In some instances, stabilized peptides can have 1 to 8 amino acid substitutions (e.g., 1, 2, 3, 4, 5, 6, 7, or 8) on the non-interacting face of the helix of the stabilized NOXA peptide (i.e., the part of the NOXA BH3 helix that does not interact with BFL-1). The "interacting face" of the polypeptides described herein includes those amino acid residues of the alpha helix that interact (e.g., interact specifically or bind specifically) with a BFL-1 protein. In certain instances, the peptides have 1 to 9, 1 to 8, 1 to 7, 1 to 6, 1 to 5, 1 to 4, 1 to 3, or 1 to 2 or 1 amino substitution on the interacting face of the helix of the peptide. In some instances, it can be useful to replace an amino acid on the interacting face of any one of the peptides of SEQ ID NOS: 2-38 with another amino acid, e.g., Ala or a derivative such as D-Ala, or α-aminoisobutyric acid. In certain embodiments, the amino acid substitutions are conservative amino acid substitution(s). In some instances, the peptides described herein can include one of SEQ ID NOs:2-38 with one or more (e.g., 1, 2, 3, 4, 5, 6, 7, 8, 9, 10, 11, 12, 13, or 1 to 2, 1 to 3, 1 to 4, 1 to 5, 1 to 6, 1 to 7, 1 to 8, 1 to 9, 1 to 10, 1 to 11, or 1 to 12) conservative amino acid substitutions. Significant variability is permitted in the amino acids that are not on the interacting face of the helix of the peptides described herein. For example, almost all, if not all, of these amino acids can be substituted (e.g., with a conservative amino acid). A "conservative amino acid substitution" means that the substitution replaces one amino acid with another amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In some instances, the peptides of this disclosure include sequences with at least 14%, 15%, 20%, 27%, 34%, 40%, 47%, 50%, 53%, 60%, 65%, 70%, 75%, 80%, 85%, 90%, 95%, or 97% identity to an amino acid sequence of SEQ ID NOs:2-38. In certain cases, the variability in the amino acid sequence is on the non-interacting face of the helix. In some cases, the variability in the amino acid sequence is on the interacting face of the helix. In certain cases, the variability in the amino acid sequence is on both the non-interacting and interacting face of the helix. In certain instances one or more of A-1, T-2, Q-3, R-5, R-6, F-7, G-8, K-10, L-11, N-12, F-13, R-14, and Q-15 (numbering according to SEQ ID NO:39) are substituted. In some instances, the substitution is to L-alanine, D-alanine, or α-aminoisobutyric acid. In some instances, 1 to 5 (e.g., 1, 2, 3, 4 or 5) amino acids at the C- and/or N-terminus are deleted. Methods for determining percent identity between amino acid sequences are known in the art. For example, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The determination of percent identity between two amino acid sequences is accomplished using the BLAST 2.0 program. Sequence comparison is performed using an ungapped alignment and using the default parameters (Blossom 62 matrix, gap existence cost of 11, per residue gapped cost of 1, and a lambda ratio of 0.85). The mathematical algorithm used in BLAST programs is described in Altschul et al. (Nucleic Acids Res. 25:3389-3402, 1997).

The stapled polypeptide comprises at least two modified amino acids joined by an internal intramolecular cross-link (or "staple"), wherein the at least two amino acids are separated by 2, 3, or 6 amino acids. Stabilized peptides herein include stapled peptides, including peptides having two staples and/or stitched peptides. The at least two modified amino acids can be unnatural alpha-amino acids (including, but not limited to α,α-disubstituted and N-alkylated amino acids). There are many known unnatural amino acids any of which may be included in the peptides of the present invention. Some examples of unnatural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and/para-substituted phenylalanines (e.g., substituted with —C(=O)C$_6$H$_5$; —CF$_3$; —CN; -halo; —NO$_2$; CH$_3$), disubstituted phenylalanines, substituted tyrosines (e.g., further substituted with -Q=O) C$_6$H$_5$; —CF$_3$; —CN; -halo; —NO$_2$; CH$_3$), and statine.

In certain embodiments, the stapled NOXA polypeptide variant comprises or consists of the amino acid sequence set forth in any one of SEQ ID NOs:22 to 34 (without including the N-terminal nipecotic acid).

In certain embodiments, the stapled NOXA polypeptide variant comprises or consists of the amino acid sequence set forth in any one of SEQ ID NOs:35 to 38 (without including the N-terminal nipecotic acid).

In certain embodiments, the stapled NOXA polypeptide variant comprises or consists of a structurally stabilized versions of the amino acid sequences set forth in any one of SEQ ID NOs:94 to 109. A non-limiting example of structural stabilization of these peptides is achieved by hydrocarbon stapling by introducing non-natural amino acids at positions separated by 2, 3, or 6 amino acids in these sequences.

In certain embodiments, the stapled polypeptide comprises or consists of an amino acid sequence selected from the group consisting of:

ATX$_1$LRR<u>A</u>GDX$_2$LNFRQ; (SEQ ID NO: 40)

ATX$_1$LRRFGDX$_2$<u>A</u>NFRQ; (SEQ ID NO: 41)

ATX$_1$LR<u>E</u>FGDX$_2$LNFRQ; (SEQ ID NO: 42)
and

ATX$_1$LRRFGDX$_2$LNF<u>E</u>Q, (SEQ ID NO: 43)

wherein X$_1$ and X$_2$ in the above sequences are non-natural amino acids which can be covalently joined ("stapled together") using a ring-closing metathesis (RCM) reaction to form a cross-linked ring.

In some embodiments, the stapled polypeptide variant comprises or consists of an amino acid sequence selected from the group consisting of:

AT8LRR<u>A</u>GDXLNFRQ; (SEQ ID NO: 44)

AT8LRRFGDX<u>A</u>NFRQ; (SEQ ID NO: 45)

-continued

AT8LREFGDXLNFRQ; (SEQ ID NO: 46)

AT8LRRFGDXLNFEQ; (SEQ ID NO: 47)

AA8LRAFGAXLNAA; (SEQ ID NO: 48)

AA8LRAFGAXLNAAAA; (SEQ ID NO: 49)

AA8LRAFGAXLNAE; (SEQ ID NO: 50)

AA8LRAFGAXLNAEAA; (SEQ ID NO: 51)

AA8LREFGAXLNAA; (SEQ ID NO: 52)

AA8LREFGAXLNAAAA; (SEQ ID NO: 53)

AA8LRAFGDXLNAA; (SEQ ID NO: 54)

AA8LRAFGDXLNAAAA; (SEQ ID NO: 55)

AA8LRAFGDXLNAE; (SEQ ID NO: 56)

AA8LRAFGDXLNAEAA; (SEQ ID NO: 57)

AA8LREFGDXLNAA; (SEQ ID NO: 58)
and

AA8LREFGDXLNAAAA, (SEQ ID NO: 59)

wherein "8"=R-octenyl alanine: and "X"=S-pentenyl alanine.

Warhead Bearing Stabilized NOXA Peptides

This disclosure features stabilized NOXA peptides that include a warhead—i.e., a reactive group such as a non-natural amino acid bearing an electrophilic group. Importantly, these warhead containing peptides allow for significant variability in the amino acid sequence of the associated NOXA peptide (much more than in the absence of the warhead) as the interaction between the NOXA peptide and BFL-1 is cemented by the covalent bond between the electrophile and the cysteine at position 55 of BFL-1. Thus, even if there are substitutions and/or deletions in SEQ ID NO:39, including substitutions on the BFL-1 interacting face of the NOXA helix, these warhead bearing peptides are likely to be effective in binding BFL-1. Furthermore, with the warhead present, the size of the NOXA peptide (e.g., any one of SEQ ID NOs:39-59) can be reduced in length (e.g., from 15 to 14, 13, 12, 11, 10, 9, 8, 7, 6, or 5 amino acids).

The electrophile can be installed not only in the context of a non-natural amino acid, but also as a chemical cap to the N or C terminus of the stabilized (e.g., cross-linked) NOXA polypeptide. In some instances, the electrophile can be installed within the stabilized peptide. Such warhead bearing stabilized peptides are able to form covalent bonds with at least some of the proteins they interact with. For example, such warhead bearing NOXA peptides can covalently modify BFL-1 (e.g., by covalent bonding with C55 of BFL-1), noncovalently interact with BFL-1 and/or non-covalently interact with MCL-1.

The warheads may be at the N-terminus, C-terminus, or within the polypeptide sequence. In some cases, the warhead is a non-natural electrophile bearing amino acid. In certain embodiments, the warhead is selected from the group consisting of: 3S-1-pyrrolidine-3-carboxylic acid terminating in acrylamide; D-homoproline terminating in acrylamide; L-homoproline terminating in acrylamide; isonipecotic acid terminating in acrylamide; D-nipecotic acid terminating in acrylamide; L-nipecotic acid terminating in acrylamide; D-proline terminating in acrylamide; L-proline terminating in acrylamide; trans-4-dimethylaminocrotonic acid; and acrylic acid.

In some embodiments, the electrophilic warhead is a cysteine-reactive D-nipecotic acid moiety. In other embodiments, the electrophilic warhead is a cysteine-reactive moiety.

In certain embodiments, the warhead is a non-natural amino acid bearing an electrophilic group that is selected from the group consisting of: (S)-1-acryloylpyrrolidine-3-carboxamide; 1-acryloylpiperidine-4-carboxamide, (R)-1 acryloylpiperidine-3-carboxamide; (S)-1-acryloylpiperidine-3-carboxamide; (S)-1-acryloylpyrrolidine-2-carboxamide; (R)-1-acryloylpyrrolidine-2-carboxamide; (E)-4-(dimethylamino)but-2-enamide; and acrylamide. In other embodiments, the warhead is not an amino acid. For example, the electrophilic moiety and peptide are linked via a nitrogen containing heterocycle, either saturated (aziridine, diaziridine, azetidine, pyrrolidine, imidazolidine, pyrazolidine, oxazolidine, isoxazolidine, thiazolidine, isothiazolidine, piperidine, piperazine, morpholine, thiomorpholine, azepane) or unsaturated (azirine, diazirine, azete, pyrrole, imidazole, pyrazole, oxazole, isoxazole, thiazole, isothiazole, pyridine, diazines, oxazine, thiazine, azepine). The peptide and electrophile can also be linked by a substituted amino-functionalized ring (e.g. N-arylacrylamide) such as phenyl (aniline) or by more complex bicyclic or polycyclic rings, for instance, naphthalene, anthracene, phenanthrene, indole, isoindole, indolizine, quinolone, isoquinoline, quinoxaline, phthalazine, quinazoline, purine, carbazole, indazole, benzimidazole, azaindole. The electrophilic warhead in some embodiments is an acrylamide, or more generally defined as an α,β-unsaturated carbonyl, such as α-cyano-acrylamide, propiolamide, trans 4-dimethylamino-2-butenamide, or trans 4-piperidinyl-2-butenamide, or any other substituted acrylamide, or N-functionalized vinylsulfonyl, alpha-fluoro acetyl, alpha-chloro acetyl, alpha-bromo acetyl, and alpha-iodo acetyl or other electrophilic moiety. The electrophile can not only be installed in the context of a non-natural amino acid, but also as a chemical cap to the N or C terminus of the cross-linked (e.g., stapled, stitched) polypeptide.

In one aspect, the BFL-1 binding warhead bearing NOXA peptide has an amino acid sequence set out in any one of SEQ ID NOs.: 94-109. In another aspect, the BFL-1 binding warhead bearing NOXA peptide has an amino acid sequence that contains 5 or more (e.g., 5, 6, 7, 8, 10, 11, 12, 13, 14) amino acids of a sequence set out in any one of SEQ ID NOs.: 94-109. In another aspect, the BFL-1 binding warhead bearing NOXA peptide has an amino acid sequence that contains 1-5 deletions (e.g., 1, 2, 3, 4, 5) at the C- or N-terminus of a sequence set out in any one of SEQ ID NOs.: 94-109. In some instances, the electrophilic warhead is at the N-terminus of the peptide. In other instances, the electrophilic warhead is within the peptide.

In one embodiment, the BFL-1 binding warhead-bearing NOXA peptide has a sequence selected from the sequences set out below:

JATQLRRAGDKLNFRQ; (SEQ ID NO: 126)

JATQLRRFGDKANFRQ; (SEQ ID NO: 127)

JATQLREFGDKLNFRQ; (SEQ ID NO: 128)

JATQLRRFGDKLNFEQ; (SEQ ID NO: 129)

JAAQLRAFGAKLNAA; (SEQ ID NO: 130)

JAAQLRAFGAKLNAAAA; (SEQ ID NO: 131)

JAAQLRAFGAKLNAE; (SEQ ID NO: 132)

JAAQLRAFGAKLNAEAA; (SEQ ID NO: 133)

JAAQLREFGAKLNAA; (SEQ ID NO: 134)

JAAQLREFGAKLNAAAA; (SEQ ID NO: 135)

JAAQLRAFGDKLNAA; (SEQ ID NO: 136)

JAAQLRAFGDKLNAAAA; (SEQ ID NO: 137)

JAAQLRAFGDKLNAE; (SEQ ID NO: 138)

JAAQLRAFGDKLNAEAA; (SEQ ID NO: 139)

JAAQLREFGDKLNAA; (SEQ ID NO: 140)
or

JAAQLREFGDKLNAAAA. (SEQ ID NO: 141)

In certain instances the above warhead-bearing sequences can be structurally stabilized by any method known in the art. For example, at least two amino acids (e.g., 2, 3, 4, 5) of the sequence separated by 2, 3, or 6 amino acids can be replaced with non-natural amino acids that can form a staple and/or stitch. In some embodiments, the electrophilic warhead (J) is a cysteine-reactive D-nipecotic acid moiety. In other embodiments, the electrophilic warhead (J) is a cysteine-reactive moiety.

In some embodiments, the stapled polypeptide comprises or consists of an amino acid sequence selected from the group consisting of:

JATX$_1$LRR<u>A</u>GDX$_2$LNFRQ; (SEQ ID NO: 60)

JATX$_1$LRRFGDX$_2$<u>A</u>NFRQ; (SEQ ID NO: 61)

JATX$_1$LR<u>E</u>FGDX$_2$LNFRQ; (SEQ ID NO: 62)
and

JATX$_1$LRRFGDX$_2$LNF<u>E</u>Q; (SEQ ID NO: 63)

JAAX$_1$LRAFGAX$_2$LNAA; (SEQ ID NO: 64)

JAAX$_1$LRAFGAX$_2$LNAAAA; (SEQ ID NO: 65)

JAAX$_1$LRAFGAX$_2$LNAE; (SEQ ID NO: 66)

JAAX$_1$LRAFGAX$_2$LNAEAA; (SEQ ID NO: 67)

JAAX$_1$LREFGAX$_2$LNAA; (SEQ ID NO: 68)

JAAX$_1$LREFGAX$_2$LNAAAA; (SEQ ID NO: 69)

JAAX$_1$LRAFGDX$_2$LNAA; (SEQ ID NO: 70)

JAAX$_1$LRAFGDX$_2$LNAAAA; (SEQ ID NO: 71)

JAAX$_1$LRAFGDX$_2$LNAE; (SEQ ID NO: 72)

JAAX$_1$LRAFGDX$_2$LNAEAA; (SEQ ID NO: 73)

JAAX$_1$LREFGDX$_2$LNAA; (SEQ ID NO: 74)
and

JAAX$_1$LREFGDX$_2$LNAAAA, (SEQ ID NO: 75)

wherein "X$_1$" and "X$_2$" in the above sequences are non-natural amino acids which can be covalently joined ("stapled together") using a ring-closing metathesis (RCM) reaction to form a cross-linked ring and "J" is a non-natural electrophile containing amino acid or an electrophilic warhead presented in the context of a moiety that is not an amino acid (the electrophile can serve as a chemical cap)). In a particular embodiment, "J" is a cysteine-reactive D-nipecotic acid moiety. In another particular embodiment, "J" is a cysteine-reactive moiety.

In some embodiments, the stapled polypeptide comprises or consists of an amino acid sequence listed above, or in SEQ ID NOs.: 2-21 where multiple residues (e.g., 1, 2, 3, 4, 5, 6) on the non-interacting face can be replaced with residues selected from the group consisting of Ala (alanine), D-Ala (D-alanine), Aib (α-aminoisobutyric acid), Sar (N-methyl glycine), and Ser (serine), other substituted alanine, and a glycine derivative. Additionally, one or more of these residues (e.g., 1, 2, 3, 4, 5, 6) can be appended to the C-terminus of the peptide. In some instances, 0 to 5 amino at the C-terminus of the above peptides (SEQ ID NOs:60-75) or those of SEQ ID NOs.: 2-21 are replaced with a residue or residues selected from the group consisting of Ala (alanine), D-Ala (D-alanine), Aib (α-aminoisobutyric acid), Sar (N-methyl glycine), and Ser (serine), other substituted alanine, and a glycine derivative.

In some embodiments, the stapled polypeptide comprises or consists of an amino acid sequence selected from the group consisting of:

JAT8LRR<u>A</u>GDXLNFRQ; (SEQ ID NO: 76)

JAT8LRRFGDX<u>A</u>NFRQ; (SEQ ID NO: 77)

JAT8LREFGDXLNFRQ; (SEQ ID NO: 78)

JAT8LRRFGDXLNFEQ (SEQ ID NO: 79)

JAA8LREFGAXLNAA; (SEQ ID NO: 151)
and

JAA8LREFGAXLNAAAA, (SEQ ID NO: 153)

wherein "8"=R-octenyl alanine, "X"=S-pentenyl alanine, and "J"=a non-natural electrophile containing amino acid or an electrophilic warhead presented in the context of a moiety that is not an amino acid. In a particular embodiment, "J" is a cysteine-reactive D-nipecotic acid moiety. In another particular embodiment, "J" is a cysteine-reactive moiety.

In some embodiments, the disclosure features a warhead-bearing NOXA stapled peptide that is at least 14%, 15%, 20%, 27%, 34%, 40%, 47%, 50%, 53%, 60%, 65%, 70%, 75%, 80%, 85%, 90%, 95%, or 97%, identical to the amino acid sequence set forth in any one of SEQ ID NOs.: 60-79, and wherein the modified peptide covalently binds BFL-1. In some embodiments, these modified peptides also non-covalently bind to BFL-1 and/or MCL-1. In some embodiments, these modified peptides have reduced hydrophobicity and/or overall positive charge relative to the stapled NOXA peptide prior to the amino acid variation. In some embodiments, hydrophobicity or positive charge are independently enhanced to optimize cell penetrance. In some embodiments, these modified peptides have reduced hydrophobicity and/or overall positive charge relative to the peptide of SEQ ID NO:16.

In certain embodiments, the disclosure features a warhead-bearing NOXA stapled peptide that has 1-10 (e.g., 1, 2, 3, 4, 5, 6, 7, 8, 9, or 10) amino acid substitutions relative to the amino acid sequence set forth in any one of SEQ ID NOs.: 60-79, and wherein the modified peptide covalently binds BFL-1. In some embodiments, these modified peptides also non-covalently bind to BFL-1 and/or MCL-1. In some embodiments, these modified peptides have reduced hydrophobicity and/or overall positive charge relative to the stapled NOXA peptide prior to the amino acid substitution. In some embodiments, these modified peptides have reduced hydrophobicity and/or overall positive charge relative to the peptide of SEQ ID NO:16. In some embodiments, hydrophobicity or positive charge are independently enhanced to optimize cell penetrance.

Exemplary Stabilized NOXA Peptide Variants and Warhead Bearing Stabilized NOXA Peptides In a specific embodiment, the stapled peptide comprises the amino acid sequence AT8LREFGDXLNFRQ (SEQ ID NO:46) with 0 to 6 (i.e., 0, 1, 2, 3, 4, 5, 6) amino acid substitutions, insertions, and/or deletions, wherein "8"=R-octenyl alanine: and "X"=S-pentenyl alanine. In a particular embodiment, the stapled peptide further comprises one or more of the modifications described in the sections "NOXA Peptides" and "Stabilized Peptides" above. In another particular embodiment, the stapled peptide consists of the amino acid sequence AT8LREFGDXLNFRQ (SEQ ID NO:46), wherein "8"=R-octenyl alanine: and "X"=S-pentenyl alanine. In certain embodiments, the zero to six (i.e., 0, 1, 2, 3, 4, 5, 6) amino acids of SEQ ID NO:46 that are substituted by another amino acid are on the BFL-1/A1 non-interacting face of the helix of SEQ ID NO:46. In some embodiments, 0 to 3 amino acids in SEQ ID NO:46 are removed from the C-terminal or are removed and replaced with 1 to 6 amino acids from the group consisting of alanine, D-alanine, α-aminoisobutyric acid, N-methyl glycine, serine, a substituted alanine, and a glycine derivative. In some embodiments, 0 to 6 amino acids on the non-interacting face in SEQ ID NO:46 are substituted with an amino acid selected from the group consisting of alanine, D-alanine, α-aminoisobutyric acid, N-methyl glycine, serine, a substituted alanine, and a glycine derivative. In some embodiments, one or more of the following amino acids A1, L4, R5, F7, G8, L11, N12, and Q15 of SEQ ID NO:46 are substituted with an alpha-methylated or alpha-ethylated natural amino acids. In some embodiments, one or more of the following amino acids A1, L4, R5, F7, G8, L11, N12, and Q15 of SEQ ID NO:46 are substituted with an amino acid selected from the group consisting of L-alanine, D-alanine, α-aminoisobutyric acid, N-methyl glycine, serine, a substituted alanine, and a glycine derivative. In some embodiments, one or more of the following amino acids T2, R6, F13, and R14 of SEQ ID NO:46 are substituted with an alpha-methylated or alpha-ethylated natural amino acids. In certain embodiments, one or more of the following amino acids T2, R6, F13, and R14 of SEQ ID NO:46 are substituted with an amino acid selected from the group consisting of L-alanine, D-alanine, α-aminoisobutyric acid, N-methyl glycine, serine, a substituted alanine, and a glycine derivative. In certain embodiments, one or more of the following amino acids A1, T2, R5, R6, F7, G8, L11, N12, F13, R14, and Q15 of SEQ ID NO:46 are modified with an alpha methyl or ethyl, or are substituted with an amino acid selected from the group consisting of L-alanine, D-alanine, α-aminoisobutyric acid, N-methyl glycine, serine, a substituted alanine, and a glycine derivative. In certain instances, the one to six amino acids of SEQ ID NO:46 that are substituted by another amino acid are on the BFL-1/A1 interacting face of the helix of SEQ ID NO:46. In other instances, the one to six amino acids of SEQ ID NO:46 that are substituted by another amino acid are on the BFL-1/A1 non-interacting and interacting faces of the helix of SEQ ID NO:46. In certain embodiments, the one to six amino acids of SEQ ID NO:46 are substituted by an amino acid or amino acids selected from the group consisting of L-alanine, D-alanine, α-aminoisobutyric acid, N-methyl glycine, serine, a substituted alanine, and a glycine derivative.

In another specific embodiment, the stapled peptide comprises the amino acid sequence AT8LRRAGDXLNFRQ (SEQ ID NO:44) with 0 to 6 (i.e., 0, 1, 2, 3, 4, 5, 6) amino acid substitutions, insertions, and/or deletions, wherein "8"=R-octenyl alanine: and "X"=S-pentenyl alanine. In a particular embodiment, the stapled peptide further comprises one or more of the modifications described in the sections "NOXA Peptides" and "Stabilized Peptides" above. In another particular embodiment, the stapled peptide consists of the amino acid sequence AT8LRRAGDXLNFRQ (SEQ ID NO:44), wherein "8"=R-octenyl alanine: and "X"=S-pentenyl alanine. In certain embodiments, the zero to six (i.e., 0, 1, 2, 3, 4, 5, 6) amino acids of SEQ ID NO:44 that are substituted by another amino acid are on the BFL-1/A1 non-interacting face of the helix of SEQ ID NO:44. In some embodiments, 0 to 3 amino acids in SEQ ID NO:44 are removed from the C-terminal or are removed and replaced with 1 to 6 amino acids from the group consisting of alanine, D-alanine, α-aminoisobutyric acid, N-methyl glycine, serine, a substituted alanine, and a glycine derivative. In some embodiments, 0 to 6 amino acids on the non-interacting face in SEQ ID NO:44 are substituted with an amino acid selected from the group consisting of alanine, D-alanine, α-aminoisobutyric acid, N-methyl glycine, serine, a substituted alanine, and a glycine derivative. In some embodiments, one or more of the following amino acids A1, L4, R5, G8, L11, N12, and Q15 of SEQ ID NO:44 are substituted with an alpha-methylated or alpha-ethylated natural amino acids. In some embodiments, one or more of the following amino acids A1, L4, R5, G8, L11, N12, and Q15 of SEQ ID NO:44 are substituted with an amino acid selected from the group consisting of L-alanine, D-alanine, α-aminoisobutyric acid, N-methyl glycine, serine, a substituted alanine, and a glycine derivative. In some embodiments, one or more of the following amino acids T2, R6, F13, and R14 of SEQ ID NO:44 are substituted with an alpha-methylated or alpha-ethylated natural amino acids. In certain embodiments, one or more of the following amino acids T2, R6, F13, and R14 of SEQ ID NO:44 are substituted with an amino acid selected from the group consisting of L-alanine, D-alanine, α-aminoisobutyric acid, N-methyl glycine, serine, a substituted alanine, and a glycine derivative. In certain embodiments, one or more of the following amino acids A1, T2, R5, R6, G8, L11, N12, F13, R14, and Q15 of SEQ ID NO:44 are modified with an alpha methyl or ethyl, or are substituted with an amino acid selected from the group consisting of L-alanine, D-alanine, α-aminoisobutyric acid, N-methyl glycine, serine, a substituted alanine, and a glycine derivative. In certain instances, the one to six amino acids of SEQ ID NO:44 that are substituted by another amino acid are on the BFL-1/A1 interacting face of the helix of SEQ ID NO:44. In other instances, the one to six amino acids of SEQ ID NO:44 that are substituted by another amino acid are on the BFL-1/A1 non-interacting and interacting faces of the helix of SEQ ID NO:44. In certain embodiments, the one to six amino acids of SEQ ID NO:44 are substituted by an amino acid or amino acids selected from the group consisting of L-alanine, D-alanine, α-aminoisobutyric acid, N-methyl glycine, serine, a substituted alanine, and a glycine derivative.

In another specific embodiment, the peptide is a BFL-1-binding warhead-bearing NOXA peptide described herein. For example, the peptides of SEQ ID NO:46, 44, or their variants described above, are modified to include a non-natural electrophile containing amino acid or an electrophilic warhead presented in the context of a moiety that is not an amino acid (the electrophile can serve as a chemical cap) (e.g., a cysteine-reactive moiety; a cysteine-reactive D-nipecotic acid moiety).

In a specific embodiment, the BFL-1-binding warhead bearing NOXA peptide comprises the sequence JATQLREFGDKLNFRQ (SEQ ID NO:128) with 0 to 6 (i.e., 0, 1, 2, 3, 4, 5, 6) amino acid substitutions, insertions, and/or deletions (as described above), wherein the peptide is structurally stabilized by any method known in the art, wherein the electrophilic warhead (J) is a cysteine-reactive moiety, (e.g., a D-nipecotic acid moiety). In a particular embodiment, the BFL-1-binding warhead-bearing NOXA peptide comprises the sequence JATX$_1$LREFGDX$_2$LNFRQ (SEQ ID NO:62) with 0 to 6 (i.e., 0, 1, 2, 3, 4, 5, 6) amino acid substitutions, insertions, and/or deletions (as described above), wherein "X$_1$" and "X$_2$" are non-natural amino acids which can be covalently joined ("stapled together") using a ring-closing metathesis (RCM) reaction to form a cross-linked ring and "J" is a non-natural electrophile containing amino acid or an electrophilic warhead presented in the context of a moiety that is not an amino acid (the electrophile can serve as a chemical cap) (e.g., wherein "J" is a cysteine-reactive moiety, e.g., wherein "J" is a cysteine-reactive D-nipecotic acid moiety). In another particular embodiment, the BFL-1-binding warhead-bearing NOXA peptide comprises the sequence JAT8LREFGDXLNFRQ (SEQ ID NO:78) with 0 to 6 (i.e., 0, 1, 2, 3, 4, 5, 6) amino acid substitutions, insertions, and/or deletions (as described above), wherein "8"=R-octenyl alanine, "X"=S-pentenyl alanine, and "J"=a non-natural electrophile containing amino acid or an electrophilic warhead presented in the context of a moiety that is not an amino acid (e.g., wherein "J is a cysteine-reactive moiety, e.g., wherein "J" is a cysteine-reactive D-nipecotic acid moiety). In a particular embodiment, the BFL-1-binding warhead-bearing NOXA peptide (e.g., SEQ ID NO:62, or 78, or 128) further comprises one or more of the modifications described in the sections "NOXA Peptides" and "Stabilized Peptides" above.

In a specific embodiment, the BFL-1-binding warhead bearing NOXA peptide consists of the sequence JATQLREFGDKLNFRQ (SEQ ID NO:128) with 0 to 6 (i.e., 0, 1, 2, 3, 4, 5, 6) amino acid substitutions, insertions, and/or deletions (as described above), wherein the peptide is structurally stabilized by any method known in the art, wherein the electrophilic warhead (J) is a cysteine-reactive moiety, (e.g., a D-nipecotic acid moiety). In a particular embodiment, the BFL-1-binding warhead-bearing NOXA peptide consists of the sequence JATX$_1$LREFGDX$_2$LNFRQ (SEQ ID NO:62) with 0 to 6 (i.e., 0, 1, 2, 3, 4, 5, 6) amino acid substitutions, insertions, and/or deletions (as described above), wherein "X$_1$" and "X$_2$" are non-natural amino acids which can be covalently joined ("stapled together") using a ring-closing metathesis (RCM) reaction to form a cross-linked ring and "J" is a non-natural electrophile containing amino acid or an electrophilic warhead presented in the context of a moiety that is not an amino acid (the electrophile can serve as a chemical cap) (e.g., wherein "J" is a cysteine-reactive moiety, e.g., wherein "J" is a cysteine-reactive D-nipecotic acid moiety). In another particular embodiment, the BFL-1-binding warhead-bearing NOXA peptide consists of the sequence JAT8LREFGDXLNFRQ (SEQ ID NO:78) with 0 to 6 (i.e., 0, 1, 2, 3, 4, 5, 6) amino acid substitutions, insertions, and/or deletions (as described above), wherein "8"=R-octenyl alanine, "X"=S-pentenyl alanine, and "J"=a non-natural electrophile containing amino acid or an electrophilic warhead presented in the context of a moiety that is not an amino acid (e.g., wherein "J is a cysteine-reactive moiety, e.g., wherein "J" is a cysteine-reactive D-nipecotic acid moiety).

In another specific embodiment, the BFL-1-binding warhead-bearing NOXA peptide comprises the sequence JATQLRRAGDKLNFRQ (SEQ ID NO:126), wherein the peptide is structurally stabilized by any method known in the art, wherein the electrophilic warhead (J) is a cysteine-reactive moiety, (e.g., a D-nipecotic acid moiety). In a particular embodiment, the BFL-1-binding warhead-bearing NOXA peptide comprises the JATX$_1$LRRAGDX$_2$LNFRQ (SEQ ID NO:60), wherein "X$_1$" and "X$_2$" are non-natural amino acids which can be covalently joined ("stapled together") using a ring-closing metathesis (RCM) reaction to form a cross-linked ring and "J" is a non-natural electrophile containing amino acid or an electrophilic warhead presented in the context of a moiety that is not an amino acid (the electrophile can serve as a chemical cap) (e.g., wherein "J" is a cysteine-reactive moiety, e.g., wherein "J" is a cysteine-reactive D-nipecotic acid moiety). In another particular embodiment, the BFL-1-binding warhead-bearing NOXA peptide comprises the sequence JAT8LRRAGDXLNFRQ (SEQ ID NO:76), wherein "8"=R-octenyl alanine, "X"=S-pentenyl alanine, and "J"=a non-natural electrophile containing amino acid or an electrophilic warhead presented in the context of a moiety that is not an amino acid (e.g., wherein "J" is a cysteine-reactive moiety, e.g., wherein "J" is a cysteine-reactive D-nipecotic acid moiety). In a particular embodiment, the BFL-1-binding warhead-bearing NOXA peptide (e.g., SEQ ID NO:60, or 76, or 126) further comprises one or more of the modifications described in the sections "NOXA Peptides" and "Stabilized Peptides" above. In another specific embodiment, the BFL-1-binding warhead-bearing NOXA peptide consists of the sequence JATQLRRAGDKLNFRQ (SEQ ID NO:126), wherein the peptide is structurally stabilized by any method known in the art, wherein the electrophilic warhead (J) is a cysteine-reactive moiety, (e.g., a D-nipecotic acid moiety). In a particular embodiment, the BFL-1-binding warhead-bearing NOXA peptide consists of the JATX$_1$LRRAGDX$_2$LNFRQ (SEQ ID NO:60), wherein "X$_1$" and "X$_2$" are non-natural amino acids which can be covalently joined ("stapled together") using a ring-closing metathesis (RCM) reaction to form a cross-linked ring and "J" is a non-natural electrophile containing amino acid or an electrophilic warhead presented in the context of a moiety that is not an amino acid (the electrophile can serve as a chemical cap) (e.g., wherein "J" is a cysteine-reactive moiety, e.g., wherein "J" is a cysteine-reactive D-nipecotic acid moiety). In another particular embodiment, the BFL-1-binding warhead-bearing NOXA peptide consists of the sequence JAT8LRRAGDXLNFRQ (SEQ ID NO:76), wherein "8"=R-octenyl alanine, "X"=S-pentenyl alanine, and "J"=a non-natural electrophile containing amino acid or an electrophilic warhead presented in the context of a moiety that is not an amino acid (e.g., wherein "J is a cysteine-reactive moiety, e.g., wherein "J" is a cysteine-reactive D-nipecotic acid moiety).

Methods of Treatment

The disclosure features methods of using any of the stabilized peptides (or pharmaceutical compositions comprising said stabilized peptides) described herein for the prophylaxis and/or treatment of a cancer, an autoimmune disease, or an inflammatory disease. The terms "treat" or "treating," as used herein, refers to alleviating, inhibiting, or ameliorating the disease or condition from which the subject is suffering.

The peptides described herein can be useful for treating a human subject with a BFL-1-expressing cancer. The peptides described herein can also be useful for treating a human subject with a BFL-1-dependent cancer. In certain embodiments, the cancer is a solid tumor or a liquid tumor. In certain embodiments, the BFL-1-dependent cancer is a melanoma, a leukemia, lymphoma, or other hematologic malignancy or solid tumor. In certain embodiments, the hematologic malignancy is acute myeloid leukemia, acute lymphoblastic leukemia, chronic myeloid leukemia, chronic lymphocytic leukemia, myelodysplastic syndrome, or multiple myeloma. In certain embodiments, the BFL-1-dependent cancer is a breast cancer, an autonomic ganglia cancer, a pancreatic cancer, a skin cancer, a CNS cancer, a hematopoietic or lymphoid cancer, a lung cancer, a large intestine cancer, a stomach cancer, a soft tissue sarcoma, or a bone cancer. In certain instances, the solid tumor is a melanoma, a breast cancer or a lung cancer. In some embodiments, the BFL-1-expressing or -dependent cell causes autoimmune disease or other inflammatory condition characteristic of a disease of cellular excess. In certain instances, the autoimmune disease is autoimmune colitis, thyroiditis, arthritis, nephritis, dermatitis, vasculitis, system lupus erythematosus, diabetes, or Sjogren's disease. In some instances, the inflammatory disease, asthma, psoriasis, inflammatory colitis, thyroiditis, arthritis, nephritis, dermatitis, or vasculitis. In a specific embodiment, the BFL-1-dependent cancer is acute myeloid leukemia, acute lymphoblastic leukemia, chronic myeloid leukemia, chronic lymphocytic leukemia, myelodysplastic syndrome, or multiple myeloma.

The peptides described herein can be useful for treating a human subject with an MCL-1-expressing cancer. The peptides described herein can also be useful for treating a human subject with a MCL-1-dependent cancer. In certain embodiments, the MCL-1-dependent cancer is a melanoma, a leukemia, lymphoma, or other hematologic malignancy or solid tumor. In certain embodiments, the hematologic malignancy is acute myeloid leukemia, acute lymphoblastic leukemia, chronic myeloid leukemia, chronic lymphocytic leukemia, myelodysplastic syndrome, or multiple myeloma. In certain instances, the solid tumor is a melanoma, a breast cancer or a lung cancer. In some embodiments, the BFL-1 expressing or dependent cell causes autoimmune disease or other inflammatory condition characteristic of a disease of cellular excess. In certain instances, the autoimmune disease is autoimmune colitis, thyroiditis, arthritis, nephritis, dermatitis, vasculitis, system lupus erythematosus, diabetes, or Sjogren's disease. In some instances, the inflammatory disease, asthma, psoriasis, inflammatory colitis, thyroiditis, arthritis, nephritis, dermatitis, or vasculitis. In a specific embodiment, the MCL-1-dependent cancer is acute myeloid leukemia.

The peptides described herein can be useful for treating a human subject with a BFL-1- and MCL-1 coexpressing cancer. The peptides described herein can also be useful for treating a human subject with a BFL-1 and MCL-1-dependent cancer. In certain embodiments, the BFL-1 and MCL-1-dependent cancer is a melanoma, a leukemia, lymphoma, or other hematologic malignancy or solid tumor. In certain embodiments, the hematologic malignancy is acute myeloid leukemia, acute lymphoblastic leukemia, chronic myeloid leukemia, chronic lymphocytic leukemia, myelodysplastic syndrome, or multiple myeloma. In certain instances, the solid tumor is a melanoma, a breast cancer or a lung cancer. In some embodiments, the BFL-1 expressing or dependent cell causes autoimmune disease or other inflammatory condition characteristic of a disease of cellular excess. In certain instances, the autoimmune disease is autoimmune colitis, thyroiditis, arthritis, nephritis, dermatitis, vasculitis, system lupus erythematosus, diabetes, or Sjogren's disease. In some instances, the inflammatory disease, asthma, psoriasis, inflammatory colitis, thyroiditis, arthritis, nephritis, dermatitis, or vasculitis. In a specific embodiment, the BFL-1 and MCL-1-dependent cancer is acute myeloid leukemia.

In certain embodiments, the human subject in need thereof is administered a peptide selected from the group consisting of SEQ ID NO:16 and SEQ ID NOs.: 60-79. In certain embodiments, the human subject in need thereof is administered the peptide of SEQ ID NO: 62. In certain embodiments, the human subject in need thereof is administered the peptide of SEQ ID NO:60. In certain embodiments, the human subject in need thereof is administered a peptide that is at least 14%, 15%, 20%, 27%, 34%, 40%, 47%, 50%, 53%, 60%, 65%, 70%, 75%, 80%, 85%, 90%, 95%, or 97% identical to an amino acid sequence of selected from the group consisting of SEQ ID NO:16 and SEQ ID NOs.: 60-79.

In a specific embodiment, the human subject in need thereof is administered the peptide AT8LREFGDXLNFRQ (SEQ ID NO:46), wherein "8"=R-octenyl alanine: and "X"=S-pentenyl alanine. In a specific embodiment, the human subject in need thereof is administered the peptide AT8LRRAGDXLNFRQ (SEQ ID NO:44), wherein "8"=R-octenyl alanine: and "X"=S-pentenyl alanine. In a specific embodiment, the human subject in need thereof is administered a BFL-1-binding warhead-bearing NOXA peptide described herein. In a specific embodiment, the BFL-1-binding warhead bearing NOXA peptide has the sequence JATQLREFGDKLNFRQ (SEQ ID NO:128), wherein the peptide is structurally stabilized by any method known in the art, wherein the electrophilic warhead (J) is a cysteine-reactive moiety, (e.g., a D-nipecotic acid moiety). In a particular embodiment, the BFL-1-binding warhead-bearing NOXA peptide has the sequence JATX$_1$LREFGDX$_2$LNFRQ (SEQ ID NO:62), wherein "X$_1$" and "X$_2$" are non-natural amino acids which can be covalently joined ("stapled together") using a ring-closing metathesis (RCM) reaction to form a cross-linked ring and "J" is a non-natural electrophile containing amino acid or an electrophilic warhead presented in the context of a moiety that is not an amino acid (the electrophile can serve as a chemical cap) (e.g., wherein "J" is a cysteine-reactive moiety, e.g., wherein "J" is a cysteine-reactive D-nipecotic acid moiety). In another particular embodiment, the BFL-1-binding warhead-bearing NOXA peptide has the sequence JAT8LREFGDXLNFRQ (SEQ ID NO:78), wherein "8"=R-octenyl alanine, "X"=S-pentenyl alanine, and "J"=a non-natural electrophile containing amino acid or an electrophilic warhead presented in the context of a moiety that is not an amino acid (e.g., wherein "J is a cysteine-reactive moiety, e.g., wherein "J" is a cysteine-reactive D-nipecotic acid moiety). In another specific embodiment, the BFL-1-binding warhead-bearing NOXA peptide has the sequence JATQLRRAGDKLNFRQ (SEQ ID NO:126), wherein the peptide is structurally stabilized by any method known in the art, wherein the electrophilic warhead (J) is a cysteine-reactive moiety, (e.g., a D-nipecotic acid moiety). In a particular embodiment, the BFL-1-binding warhead-bearing NOXA peptide has the sequence JATX$_1$LRRAGDX$_2$LNFRQ (SEQ ID NO:60), wherein "X$_1$" and "X$_2$" are non-natural amino acids which can be covalently joined ("stapled together") using a ring-closing metathesis (RCM) reaction to form a cross-linked ring and "J" is a non-natural electrophile containing amino acid or an electrophilic warhead presented in the context of a moiety that is not an amino acid (the electrophile can serve as a chemical cap) (e.g., wherein "J" is a cysteine-reactive moiety, e.g., wherein "J" is a cysteine-reactive D-nipecotic acid moiety). In another particular embodiment, the BFL-1-binding warhead-bearing NOXA peptide has the sequence JAT8LRRAGDXLNFRQ (SEQ ID NO:76), wherein "8"=R-octenyl alanine, "X"=S-pentenyl alanine, and "J"=a non-natural electrophile containing amino acid or an electrophilic warhead presented in the context of a moiety that is not an amino acid (e.g., wherein "J is a cysteine-reactive moiety, e.g., wherein "J" is a cysteine-reactive D-nipecotic acid moiety). The skilled artisan will understand that, for peptides comprising two non-natural amino acids that can be covalently joined ("stapled together") using a ring-closing metathesis reaction to form a cross-linked ring, the ring-closing metathesis reaction will have been performed on the peptide prior to administering the peptide (i.e., the stabilized peptide) to the subject in need of treatment. In other words, a cross-linked ring produced from covalent joining of the two non-natural amino acids will be present in the stabilized peptide prior to administering the stabilized peptide to the subject.

In some instances, the human subject in need thereof is co-administered with a NOXA stabilized peptide disclosed herein an inhibitor of a DNA damage response pathway member. Non-limiting examples of DNA damage response pathway members include Ataxia-telangiectasia mutated (ATM) kinase, ataxia-telangiectasia and rad3-related (ATR) kinase, checkpoint kinase 1 (CHK1), checkpoint kinase 2 (CHK2), and poly(ADP-ribose polymerase (PARP). In some instances, the human subject in need thereof is co-administered with a NOXA stabilized peptide disclosed herein an ATM kinase or ATR kinase inhibitor. ATM and ATR kinase inhibitors are known in the art (see, e.g., Weber et al., *Pharmacology & Therapeutics*, 149:124-0138 (2015); Awasthi et al., *J Cell Sci* 2015 128: 4255-4262). Non-limiting examples of ATM inhibitors include KU-559403, KU-55933, KU-60019, CP-466722, CGK733, and AZD0156. In some instances, the human subject in need thereof is co-administered with a NOXA stabilized peptide disclosed herein a checkpoint kinase 1/checkpoint kinase 2 (CHK1/2) inhibitor. CHK1/2 inhibitors are known in the art (see, e.g., Zabludoff et al., 2008; Anderson, V. E. et al. Cancer Res 71, 463-472, doi:10.1158/0008-5472.CAN-10-1252 (2011); Scagliotti, G. et al. Invest New Drugs 34, 625-635, doi:10.1007/s10637-016-0368-1 (2016); Hong, D. et al. J Clin Oncol 34, 1764-1771, doi:10.1200/JCO.2015.64.5788 (2016); Jobson, A. G. et al. Pharmacol 72, 876-884, doi:10.1124/mol.107.035832 (2007); Smaill, J. B. et al. Eur J Med Chem 43, 1276-1296, doi:10.1016/j.ejmech.2007.07.016 (2008); Jackson, J. R. et al. Cancer Res 60, 566-572 (2000); Teng, M. et al. J Med Chem 50, 5253 (2007); Booth, L. et al. 786-796 (2018)). Non-limiting examples of CHK1/2 inhibitors include AZD7762 (CHK1/2), CCT 241533 (CHK2), LY 2603618, (CHK1), LY 2606368 (CHK1/2), NSC 109555 ditosylate (CHK2), PD 407824 (CHKE1), PF47736 (CHEK1), SB 218078 (CHK1), TCS 2312 (CHK1), and SRA737 (CHK1). In some instances, the human subject in need thereof is co-administered with a NOXA stabilized peptide disclosed herein a PARP inhibitor. PARP inhibitors are known in the art (see, e.g., Menear et al., 2008; Penning, T. D. et al. J Med Chem 53, 3142-3153, doi:10.1021/jm901775y (2010); Donawho, C. K. et al. Clin Cancer Res 13, 2728-2737, doi:10.1158/1078-0432.CCR-06-3039 (2007); Daniel, R. A. et al. Clin Cancer Res 15, 1241-1249, doi:10.1158/1078-0432.CCR-08-1095 (2009); Curtin, N. J. e. a. Clin Cancer Res 10, 881-889 (2004); Liu, X. et al. Clin Cancer Res 18, 510-523, doi:10.1158/1078-0432.CCR-11-1973 (2012); Brock, W. A. et al. Cancer Lett 205, 155-160, doi:10.1016/j.canlet.2003.10.029 (2004); Bridges, B. A. et al. Oncotarget 5, 5076-5086 (2014); Laird, J. H. et al. Clin Cancer Res 24, 5143-5152, doi:10.1158/1078-0432.CCR-18-0401 (2018); Oplustil O'Connor, L. et al. Cancer Res 76, 6084-6094, doi:10.1158/0008-5472.CAN-15-3240 (2016); McGonigle, S. et al. Oncotarget 6, 41307-41323 (2015)). Non-limiting examples of PARP inhibitors include olaparib, A-966492, veliparib, rucaparib, AG-14361, iniparib, INO-1001, niraparib, talazoparib, AZD2461, 2X-121, BMN 673 (talazoparib), and E7449.

In certain embodiments, the human subject in need thereof is administered a peptide selected from the group consisting of SEQ ID NO:16 and SEQ ID NOs.: 60-79, 151, and 153 and a DNA damage response pathway member inhibitor. In certain embodiments, the human subject in need thereof is administered a peptide that is at least 14%, 15%, 20%, 27%, 34%, 40%, 47%, 50%, 53%, 60%, 65%, 70%, 75%, 80%, 85%, 90%, 95%, or 97% identical to an amino acid sequence of selected from the group consisting of SEQ ID NO:16 and SEQ ID NOs.: 60-79, 151, and 153 and a DNA damage response pathway member inhibitor. In certain embodiments, the human subject in need thereof is administered a peptide selected from the group consisting of SEQ ID NO:16 and SEQ ID NOs.: 60-79, 151, and 153 and an ATM inhibitor or an ATR kinase inhibitor. In certain embodiments, the human subject in need thereof is administered a peptide that is at least 14%, 15%, 20%, 27%, 34%, 40%, 47%, 50%, 53%, 60%, 65%, 70%, 75%, 80%, 85%, 90%, 95%, or 97% identical to an amino acid sequence of selected from the group consisting of SEQ ID NO:16 and SEQ ID NOs.: 60-79, 151, and 153 and an ATM kinase or ATR kinase inhibitor. In certain embodiments, the human subject in need thereof is administered a peptide selected from the group consisting of SEQ ID NO:16 and SEQ ID NOs.: 60-79, 151, and 153 and CHK1/2 inhibitor or PARP inhibitor. In certain embodiments, the human subject in need thereof is administered a peptide that is at least 14%, 15%, 20%, 27%, 34%, 40%, 47%, 50%, 53%, 60%, 65%, 70%, 75%, 80%, 85%, 90%, 95%, or 97% identical to an amino acid sequence of selected from the group consisting of SEQ ID NO:16 and SEQ ID NOs.: 60-79, 151, and 153 and a CHK1/2 inhibitor or a PARP inhibitor.

In certain embodiments, the peptide co-administered to the human subject in need thereof with a DNA damage response pathway member inhibitor (e.g., an ATM inhibitor, an ATR kinase inhibitor, a CHK1/2 inhibitor, or a PARP inhibitor) is AT8LREFGDXLNFRQ (SEQ ID NO:46), wherein "8"=R-octenyl alanine: and "X"=S-pentenyl alanine. In a specific embodiment, the peptide co-administered to the human subject in need thereof with a DNA damage response pathway member inhibitor (e.g., an ATM inhibitor, an ATR kinase inhibitor, a CHK1/2 inhibitor, or a PARP inhibitor) is AT8LRRAGDXLNFRQ (SEQ ID NO:44), wherein "8"=R-octenyl alanine: and "X"=S-pentenyl alanine. In a specific embodiment, the peptide co-administered to the human subject in need thereof with a DNA damage response pathway member inhibitor (e.g., an ATM inhibitor, an ATR kinase inhibitor, a CHK1/2 inhibitor, or a PARP inhibitor) is a BFL-1-binding warhead-bearing NOXA peptide described herein. In a specific embodiment, the BFL-1-binding warhead bearing NOXA peptide has the sequence JATQLREFGDKLNFRQ (SEQ ID NO:128), wherein the peptide is structurally stabilized by any method known in the art, wherein the electrophilic warhead (J) is a cysteine-reactive moiety, (e.g., a D-nipecotic acid moiety). In a particular embodiment, the BFL-1-binding warhead-bearing NOXA peptide has the sequence JATX1LREFGDX2LNFRQ (SEQ ID NO:62), wherein "X1" and "X2" are non-natural amino acids which can be covalently joined ("stapled together") using a ring-closing metathesis (RCM) reaction to form a cross-linked ring and "J" is a non-natural electrophile containing amino acid or an electrophilic warhead presented in the context of a moiety that is not an amino acid (the electrophile can serve as a chemical cap) (e.g., wherein "J" is a cysteine-reactive moiety, e.g., wherein "J" is a cysteine-reactive D-nipecotic acid moiety). In another particular embodiment, the BFL-1-binding warhead-bearing NOXA peptide has the sequence JAT8LREFGDXLNFRQ (SEQ ID NO:78), wherein "8"=R-octenyl alanine, "X"=S-pentenyl alanine, and "J"=a non-natural electrophile containing amino acid or an electrophilic warhead presented in the context of a moiety that is not an amino acid (e.g., wherein "J is a cysteine-reactive moiety, e.g., wherein "J" is a cysteine-reactive D-nipecotic acid moiety). In another specific embodiment, the BFL-1-binding warhead-bearing NOXA peptide has the sequence JATQLRRAGDKLNFRQ (SEQ ID NO:126), wherein the peptide is structurally stabilized by any method known in the art, wherein the electrophilic warhead (J) is a cysteine-reactive moiety, (e.g., a D-nipecotic acid moiety). In a particular embodiment, the BFL-1-binding warhead-bearing NOXA peptide has the JATX1LRRAGDX2LNFRQ (SEQ ID NO:60), wherein "X1" and "X2" are non-natural amino acids which can be covalently joined ("stapled together") using a ring-closing metathesis (RCM) reaction to form a cross-linked ring and "J" is a non-natural electrophile containing amino acid or an electrophilic warhead presented in the context of a moiety that is not an amino acid (the electrophile can serve as a chemical cap) (e.g., wherein "J" is a cysteine-reactive moiety, e.g., wherein "J" is a cysteine-reactive D-nipecotic acid moiety). In another particular embodiment, the BFL-1-binding warhead-bearing NOXA peptide has the sequence JAT8LRRAGDXLNFRQ (SEQ ID NO:76), wherein "8"=R-octenyl alanine, "X"=S-pentenyl alanine, and "J"=a non-natural electrophile containing amino acid or an electrophilic warhead presented in the context of a moiety that is not an amino acid (e.g., wherein "J is a cysteine-reactive moiety, e.g., wherein "J" is a cysteine-reactive D-nipecotic acid moiety). The skilled artisan will understand that, for peptides comprising two non-natural amino acids that can be covalently joined ("stapled together") using a ring-closing metathesis reaction to form a cross-linked ring, the ring-closing metathesis reaction will have been performed on the peptide prior to administering the peptide (i.e., the stabilized peptide) to the subject in need of treatment. In other words, a cross-linked ring produced from covalent joining of the two non-natural amino acids will be present in the stabilized peptide prior to administering the stabilized peptide to the subject.

In some instances, the human subject in need thereof (e.g., a human subject having a cancer that expresses, or is dependent on, both BFL-1 and MCL-1) is co-administered with a NOXA stabilized peptide disclosed herein an inhibitor of MCL-1. MCL-1 inhibitors are known in the art (see, e.g., Clinical Trial ID NCT02979366; Kotschy et al. Nature, 538(7626):477-482 (2016); Ayaz et al. ACS Chem Biol, 11(6):1710-1719 (2016); Clinical Trial ID NCT02992483; Clinical Trial ID NCT03465540; Caenepeel et al., Proceedings: AACR Annual Meeting 2017, DOI: 10.1158/1538-7445.AM2017-2027). Non-limiting examples of MCL-1 inhibitors include S64315, S63845, BAY 1000394, MIK665, AMG397, and AMG176. In certain embodiments, the human subject in need thereof is administered a peptide selected from the group consisting of SEQ ID NO:16 and SEQ ID NOs.: 60-79, 151, and 153 and an MCL-1 inhibitor. In certain embodiments, the human subject in need thereof is administered a peptide that is at least 14%, 15%, 20%, 27%, 34%, 40%, 47%, 50%, 53%, 60%, 65%, 70%, 75%, 80%, 85%, 90%, 95%, or 97% identical to an amino acid sequence of selected from the group consisting of SEQ ID NO:16 and SEQ ID NOs.: 60-79, 151, and 153 and an MCL-1 inhibitor. In certain embodiments, the peptide co-administered to the human subject in need thereof with an MCL-1 inhibitor is AT8LREFGDXLNFRQ (SEQ ID NO:46), wherein "8"=R-octenyl alanine: and "X"=S-pentenyl alanine. In a specific embodiment, the peptide co-administered to the human subject in need thereof with an MCL-1 inhibitor is AT8LRRAGDXLNFRQ (SEQ ID NO:44), wherein "8"=R-octenyl alanine: and "X"=S-pentenyl alanine. In a specific embodiment, the peptide co-administered to the human subject in need thereof with an MCL-1 inhibitor is a BFL-1-binding warhead-bearing NOXA peptide described herein. In a specific embodiment, the BFL-1-binding warhead bearing NOXA peptide has the sequence JATQLREFGDKLNFRQ (SEQ ID NO:128), wherein the peptide is structurally stabilized by any method known in the art, wherein the electrophilic warhead (J) is a cysteine-reactive moiety, (e.g., a D-nipecotic acid moiety). In a particular embodiment, the BFL-1-binding warhead-bearing NOXA peptide has the sequence JATX$_1$LREFGDX$_2$LNFRQ (SEQ ID NO:62), wherein "X$_1$" and "X$_2$" are non-natural amino acids which can be covalently joined ("stapled together") using a ring-closing metathesis (RCM) reaction to form a cross-linked ring and "J" is a non-natural electrophile containing amino acid or an electrophilic warhead presented in the context of a moiety that is not an amino acid (the electrophile can serve as a chemical cap) (e.g., wherein "J" is a cysteine-reactive moiety, e.g., wherein "J" is a cysteine-reactive D-nipecotic acid moiety). In another particular embodiment, the BFL-1-binding warhead-bearing NOXA peptide has the sequence JAT8LREFGDXLNFRQ (SEQ ID NO:78), wherein "8"=R-octenyl alanine, "X"=S-pentenyl alanine, and "J"=a non-natural electrophile containing amino acid or an electrophilic warhead presented in the context of a moiety that is not an amino acid (e.g., wherein "J is a cysteine-reactive moiety, e.g., wherein "J" is a cysteine-reactive D-nipecotic acid moiety). In another specific embodiment, the BFL-1-binding warhead-bearing NOXA peptide has the sequence JATQLRRAGDKLNFRQ (SEQ ID NO:126), wherein the peptide is structurally stabilized by any method known in the art, wherein the electrophilic warhead (J) is a cysteine-reactive moiety, (e.g., a D-nipecotic acid moiety). In a particular embodiment, the BFL-1-binding warhead-bearing NOXA peptide has the JATX$_1$LRRAGDX$_2$LNFRQ (SEQ ID NO:60), wherein "X$_1$" and "X$_2$" are non-natural amino acids which can be covalently joined ("stapled together") using a ring-closing metathesis (RCM) reaction to form a cross-linked ring and "J" is a non-natural electrophile containing amino acid or an electrophilic warhead presented in the context of a moiety that is not an amino acid (the electrophile can serve as a chemical cap) (e.g., wherein "J" is a cysteine-reactive moiety, e.g., wherein "J" is a cysteine-reactive D-nipecotic acid moiety). In another particular embodiment, the BFL-1-binding warhead-bearing NOXA peptide has the sequence JAT8LRRAGDXLNFRQ (SEQ ID NO:76), wherein "8"=R-octenyl alanine, "X"=S-pentenyl alanine, and "J"=a non-natural electrophile containing amino acid or an electrophilic warhead presented in the context of a moiety that is not an amino acid (e.g., wherein "J is a cysteine-reactive moiety, e.g., wherein "J" is a cysteine-reactive D-nipecotic acid moiety). The skilled artisan will understand that, for peptides comprising two non-natural amino acids that can be covalently joined ("stapled together") using a ring-closing metathesis reaction to form a cross-linked ring, the ring-closing metathesis reaction will have been performed on the peptide prior to administering the peptide (i.e., the stabilized peptide) to the subject in need of treatment. In other words, a cross-linked ring produced from covalent joining of the two non-natural amino acids will be present in the stabilized peptide prior to administering the stabilized peptide to the subject.

In some instances, the human subject in need thereof (e.g., a human subject having a cancer that expresses, or is dependent on, both BFL-1 and BCL-2) is co-administered with a NOXA stabilized peptide disclosed herein an inhibitor of BCL-2. BCL-2 inhibitors are known in the art (see, e.g., Roberts et al. N Engl J Med 374(4):311-322 (2016)). An example of a BCL-2 inhibitor is venetoclax. In certain embodiments, the human subject in need thereof is administered a peptide selected from the group consisting of SEQ ID NO:16 and SEQ ID NOs.: 60-79, 151, and 153 and a BCL-2 inhibitor. In certain embodiments, the human subject in need thereof is administered a peptide that is at least 14%, 15%, 20%, 27%, 34%, 40%, 47%, 50%, 53%, 60%, 65%, 70%, 75%, 80%, 85%, 90%, 95%, or 97% identical to an amino acid sequence of selected from the group consisting of SEQ ID NO:16 and SEQ ID NOs.: 60-79, 151, and 153 and a BCL-2 inhibitor. In certain embodiments, the peptide co-administered to the human subject in need thereof with a BCL-2 inhibitor is AT8LREFGDXLNFRQ (SEQ ID NO:46), wherein "8"=R-octenyl alanine: and "X"=S-pentenyl alanine. In a specific embodiment, the peptide co-administered to the human subject in need thereof with a BCL-2 inhibitor is AT8LRRAGDXLNFRQ (SEQ ID NO:44), wherein "8"=R-octenyl alanine: and "X"=S-pentenyl alanine. In a specific embodiment, the peptide co-administered to the human subject in need thereof with a BCL-2 inhibitor is a BFL-1-binding warhead-bearing NOXA peptide described herein. In a specific embodiment, the BFL-1-binding warhead bearing NOXA peptide has the sequence JATQLREFGDKLNFRQ (SEQ ID NO:128), wherein the peptide is structurally stabilized by any method known in the art, wherein the electrophilic warhead (J) is a cysteine-reactive moiety, (e.g., a D-nipecotic acid moiety). In a particular embodiment, the BFL-1-binding warhead-bearing NOXA peptide has the sequence JATX$_1$LREFGDX$_2$LNFRQ (SEQ ID NO:62), wherein "X$_1$" and "X$_2$" are non-natural amino acids which can be covalently joined ("stapled together") using a ring-closing metathesis (RCM) reaction to form a cross-linked ring and "J" is a non-natural electrophile containing amino acid or an electrophilic warhead presented in the context of a moiety that is not an amino acid (the electrophile can serve as a chemical cap) (e.g., wherein "J" is a cysteine-reactive moiety, e.g., wherein "J" is a cysteine-reactive D-nipecotic acid moiety). In another particular embodiment, the BFL-1-binding warhead-bearing NOXA peptide has the sequence JAT8LREFGDXLNFRQ (SEQ ID NO:78), wherein "8"=R-octenyl alanine, "X"=S-pentenyl alanine, and "J"=a non-natural electrophile containing amino acid or an electrophilic warhead presented in the context of a moiety that is not an amino acid (e.g., wherein "J is a cysteine-reactive moiety, e.g., wherein "J" is a cysteine-reactive D-nipecotic acid moiety). In another specific embodiment, the BFL-1-binding warhead-bearing NOXA peptide has the sequence JATQLRRAGDKLNFRQ (SEQ ID NO:126), wherein the peptide is structurally stabilized by any method known in the art, wherein the electrophilic warhead (J) is a cysteine-reactive moiety, (e.g., a D-nipecotic acid moiety). In a particular embodiment, the BFL-1-binding warhead-bearing NOXA peptide has the JATX$_1$LRRAGDX$_2$LNFRQ (SEQ ID NO:60), wherein "X$_1$" and "X$_2$" are non-natural amino acids which can be covalently joined ("stapled together") using a ring-closing metathesis (RCM) reaction to form a cross-linked ring and "J" is a non-natural electrophile containing amino acid or an electrophilic warhead presented in the context of a moiety that is not an amino acid (the electrophile can serve as a chemical cap) (e.g., wherein "J" is a cysteine-reactive moiety, e.g., wherein "J" is a cysteine-reactive D-nipecotic acid moiety). In another particular embodiment, the BFL-1-binding warhead-bearing NOXA peptide has the sequence JAT8LRRAGDXLNFRQ (SEQ ID NO:76), wherein "8"=R-octenyl alanine, "X"=S-pentenyl alanine, and "J"=a non-natural electrophile containing amino acid or an electrophilic warhead presented in the context of a moiety that is not an amino acid (e.g., wherein "J is a cysteine-reactive moiety, e.g., wherein "J" is a cysteine-reactive D-nipecotic acid moiety). The skilled artisan will understand that, for peptides comprising two non-natural amino acids that can be covalently joined ("stapled together") using a ring-closing metathesis reaction to form a cross-linked ring, the ring-closing metathesis reaction will have been performed on the peptide prior to administering the peptide (i.e., the stabilized peptide) to the subject in need of treatment. In other words, a cross-linked ring produced from covalent joining of the two non-natural amino acids will be present in the stabilized peptide prior to administering the stabilized peptide to the subject.

In some instances, the human subject in need thereof (e.g., a human subject having a cancer that expresses, or is dependent on, both BFL-1 and BCL-XL) is co-administered with a NOXA stabilized peptide disclosed herein an inhibitor of BCL-XL. BCL-XL inhibitors are known in the art (see, e.g., Zhu et al. Aging Cell; 15(3):428-35 (2016)). An example of a BCL-XL inhibitor is navitoclax. In certain embodiments, the human subject in need thereof is administered a peptide selected from the group consisting of SEQ ID NO:16 and SEQ ID NOs.: 60-79, 151, and 153 and a BCL-XL inhibitor. In certain embodiments, the human subject in need thereof is administered a peptide that is at least 14%, 15%, 20%, 27%, 34%, 40%, 47%, 50%, 53%, 60%, 65%, 70%, 75%, 80%, 85%, 90%, 95%, or 97% identical to an amino acid sequence of selected from the group consisting of SEQ ID NO:16 and SEQ ID NOs.: 60-79, 151, and 153 and a BCL-XL inhibitor. In certain embodiments, the peptide co-administered to the human subject in need thereof with a BCL-XL inhibitor is AT8LREFGDXLNFRQ (SEQ ID NO:46), wherein "8"=R-octenyl alanine: and "X"=S-pentenyl alanine. In a specific embodiment, the peptide co-administered to the human subject in need thereof with a BCL-XL inhibitor is AT8LRRAGDXLNFRQ (SEQ ID NO:44), wherein "8"=R-octenyl alanine: and "X"=S-pentenyl alanine. In a specific embodiment, the peptide co-administered to the human subject in need thereof with a BCL-XL inhibitor is a BFL-1-binding warhead-bearing NOXA peptide described herein. In a specific embodiment, the BFL-1-binding warhead bearing NOXA peptide has the sequence JATQLREFGDKLNFRQ (SEQ ID NO:128), wherein the peptide is structurally stabilized by any method known in the art, wherein the electrophilic warhead (J) is a cysteine-reactive moiety, (e.g., a D-nipecotic acid moiety). In a particular embodiment, the BFL-1-binding warhead-bearing NOXA peptide has the sequence JATX$_1$LREFGDX$_2$LNFRQ (SEQ ID NO:62), wherein "X$_1$" and "X$_2$" are non-natural amino acids which can be covalently joined ("stapled together") using a ring-closing metathesis (RCM) reaction to form a cross-linked ring and "J" is a non-natural electrophile containing amino acid or an electrophilic warhead presented in the context of a moiety that is not an amino acid (the electrophile can serve as a chemical cap) (e.g., wherein "J" is a cysteine-reactive moiety, e.g., wherein "J" is a cysteine-reactive D-nipecotic acid moiety). In another particular embodiment, the BFL-1-binding warhead-bearing NOXA peptide has the sequence JAT8LREFGDXLNFRQ (SEQ ID NO:78), wherein "8"=R-octenyl alanine, "X"=S-pentenyl alanine, and "J"=a non-natural electrophile containing amino acid or an electrophilic warhead presented in the context of a moiety that is not an amino acid (e.g., wherein "J is a cysteine-reactive moiety, e.g., wherein "J" is a cysteine-reactive D-nipecotic acid moiety). In another specific embodiment, the BFL-1-binding warhead-bearing NOXA peptide has the sequence JATQLRRAGDKLNFRQ (SEQ ID NO:126), wherein the peptide is structurally stabilized by any method known in the art, wherein the electrophilic warhead (J) is a cysteine-reactive moiety, (e.g., a D-nipecotic acid moiety). In a particular embodiment, the BFL-1-binding warhead-bearing NOXA peptide has the JATX$_1$LRRAGDX$_2$LNFRQ (SEQ ID NO:60), wherein "X$_1$" and "X$_2$" are non-natural amino acids which can be covalently joined ("stapled together") using a ring-closing metathesis (RCM) reaction to form a cross-linked ring and "J" is a non-natural electrophile containing amino acid or an electrophilic warhead presented in the context of a moiety that is not an amino acid (the electrophile can serve as a chemical cap) (e.g., wherein "J" is a cysteine-reactive moiety, e.g., wherein "J" is a cysteine-reactive D-nipecotic acid moiety). In another particular embodiment, the BFL-1-binding warhead-bearing NOXA peptide has the sequence JAT8LRRAGDXLNFRQ (SEQ ID NO:76), wherein "8"=R-octenyl alanine, "X"=S-pentenyl alanine, and "J"=a non-natural electrophile containing amino acid or an electrophilic warhead presented in the context of a moiety that is not an amino acid (e.g., wherein "J is a cysteine-reactive moiety, e.g., wherein "J" is a cysteine-reactive D-nipecotic acid moiety). The skilled artisan will understand that, for peptides comprising two non-natural amino acids that can be covalently joined ("stapled together") using a ring-closing metathesis reaction to form a cross-linked ring, the ring-closing metathesis reaction will have been performed on the peptide prior to administering the peptide (i.e., the stabilized peptide) to the subject in need of treatment. In other words, a cross-linked ring produced from covalent joining of the two non-natural amino acids will be present in the stabilized peptide prior to administering the stabilized peptide to the subject.

In some instances, the human subject in need thereof (e.g., a human subject having a cancer that expresses, or is dependent on, BFL-1 and BCL-XL, BCL-2, and/or MCL-1) is co-administered with a NOXA stabilized peptide disclosed herein an inhibitor of BCL-XL, BCL-2, and/or MCL-1. In some instances, the human subject in need thereof (e.g., a human subject having a cancer that expresses, or is dependent on, each of BFL-1, BCL-XL, BCL-2, and MCL-1) is co-administered with a NOXA stabilized peptide disclosed herein an inhibitor of BCL-XL, BCL-2, and MCL-1. In some instances, the human subject in need thereof (e.g., a human subject having a cancer that expresses, or is dependent on, each of BFL-1, BCL-XL, and BCL-2) is co-administered with a NOXA stabilized peptide disclosed herein an inhibitor of BCL-XL and BCL-2. In some instances, the human subject in need thereof (e.g., a human subject having a cancer that expresses, or is dependent on, each of BFL-1, BCL-XL, and MCL-1) is co-administered with a NOXA stabilized peptide disclosed herein an inhibitor of BCL-XL and MCL-1. In some instances, the human subject in need thereof (e.g., a human subject having a cancer that expresses, or is dependent on, each of BFL-1, BCL-2, and MCL-1) is co-administered with a NOXA stabilized peptide disclosed herein an inhibitor of BCL-2 and MCL-1. BCL-XL inhibitors are known in the art (see, e.g., Zhu et al. Aging Cell; 15(3):428-35 (2016)). An example of a BCL-XL inhibitor is navitoclax. BCL-2 inhibitors are known in the art (see, e.g., Roberts et al. N Engl J Med 374(4):311-322 (2016)). An example of a BCL-2 inhibitor is venetoclax. MCL-1 inhibitors are known in the art (see, e.g., Clinical Trial ID NCT02979366; Kotschy et al. Nature, 538(7626):477-482 (2016); Ayaz et al. ACS Chem Biol, 11(6):1710-1719 (2016); Clinical Trial ID NCT02992483; Clinical Trial ID NCT03465540; Caenepeel et al., Proceedings: AACR Annual Meeting 2017, DOI: 10.1158/1538-7445.AM2017-2027). Non-limiting examples of MCL-1 inhibitors include S64315, S63845, BAY 1000394, MIK665, AMG397, and AMG176. In certain embodiments, the human subject in need thereof is administered a peptide selected from the group consisting of SEQ ID NO:16 and SEQ ID NOs.: 60-79, 151, and 153 and a BCL-XL inhibitor, a BCL-2 inhibitor, and/or a MCL-1 inhibitor. In certain embodiments, the human subject in need thereof is administered a peptide that is at least 14%, 15%, 20%, 27%, 34%, 40%, 47%, 50%, 53%, 60%, 65%, 70%, 75%, 80%, 85%, 90%, 95%, or 97% identical to an amino acid sequence of selected from the group consisting of SEQ ID NO:16 and SEQ ID NOs.: 60-79, 151, and 153 and a BCL-XL inhibitor, a BCL-2 inhibitor, and/or a MCL-1 inhibitor. In certain embodiments, the peptide co-administered to the human subject in need thereof with a BCL-XL inhibitor, a BCL-2 inhibitor, and/or a MCL-1 inhibitor is AT8LREFGDXLNFRQ (SEQ ID NO:46), wherein "8"=R-octenyl alanine: and "X"=S-pentenyl alanine. In a specific embodiment, the peptide co-administered to the human subject in need thereof with a BCL-XL inhibitor, a BCL-2 inhibitor, and/or a MCL-1 inhibitor is AT8LRRAGDXLNFRQ (SEQ ID NO:44), wherein "8"=R-octenyl alanine: and "X"=S-pentenyl alanine. In a specific embodiment, the peptide co-administered to the human subject in need thereof with a BCL-XL inhibitor, a BCL-2 inhibitor, and/or a MCL-1 inhibitor is a BFL-1-binding warhead-bearing NOXA peptide described herein. In a specific embodiment, the BFL-1-binding warhead bearing NOXA peptide has the sequence JATQLREFGDKLNFRQ (SEQ ID NO:128), wherein the peptide is structurally stabilized by any method known in the art, wherein the electrophilic warhead (J) is a cysteine-reactive moiety, (e.g., a D-nipecotic acid moiety). In a particular embodiment, the BFL-1-binding warhead-bearing NOXA peptide has the sequence JATX$_1$LREFGDX$_2$LNFRQ (SEQ ID NO:62), wherein "X$_1$" and "X$_2$" are non-natural amino acids which can be covalently joined ("stapled together") using a ring-closing metathesis (RCM) reaction to form a cross-linked ring and "J" is a non-natural electrophile containing amino acid or an electrophilic warhead presented in the context of a moiety that is not an amino acid (the electrophile can serve as a chemical cap) (e.g., wherein "J" is a cysteine-reactive moiety, e.g., wherein "J" is a cysteine-reactive D-nipecotic acid moiety). In another particular embodiment, the BFL-1-binding warhead-bearing NOXA peptide has the sequence JAT8LREFGDXLNFRQ (SEQ ID NO:78), wherein "8"=R-octenyl alanine, "X"=S-pentenyl alanine, and "J"=a non-natural electrophile containing amino acid or an electrophilic warhead presented in the context of a moiety that is not an amino acid (e.g., wherein "J is a cysteine-reactive moiety, e.g., wherein "J" is a cysteine-reactive D-nipecotic acid moiety). In another specific embodiment, the BFL-1-binding warhead-bearing NOXA peptide has the sequence JATQLRRAGDKLNFRQ (SEQ ID NO:126), wherein the peptide is structurally stabilized by any method known in the art, wherein the electrophilic warhead (J) is a cysteine-reactive moiety, (e.g., a D-nipecotic acid moiety). In a particular embodiment, the BFL-1-binding warhead-bearing NOXA peptide has the JATX$_1$LRRAGDX$_2$LNFRQ (SEQ ID NO:60), wherein "X$_1$" and "X$_2$" are non-natural amino acids which can be covalently joined ("stapled together") using a ring-closing metathesis (RCM) reaction to form a cross-linked ring and "J" is a non-natural electrophile containing amino acid or an electrophilic warhead presented in the context of a moiety that is not an amino acid (the electrophile can serve as a chemical cap) (e.g., wherein "J" is a cysteine-reactive moiety, e.g., wherein "J" is a cysteine-reactive D-nipecotic acid moiety). In another particular embodiment, the BFL-1-binding warhead-bearing NOXA peptide has the sequence JAT8LRRAGDXLNFRQ (SEQ ID NO:76), wherein "8"=R-octenyl alanine, "X"=S-pentenyl alanine, and "J"=a non-natural electrophile containing amino acid or an electrophilic warhead presented in the context of a moiety that is not an amino acid (e.g., wherein "J is a cysteine-reactive moiety, e.g., wherein "J" is a cysteine-reactive D-nipecotic acid moiety). The skilled artisan will understand that, for peptides comprising two non-natural amino acids that can be covalently joined ("stapled together") using a ring-closing metathesis reaction to form a cross-linked ring, the ring-closing metathesis reaction will have been performed on the peptide prior to administering the peptide (i.e., the stabilized peptide) to the subject in need of treatment. In other words, a cross-linked ring produced from covalent joining of the two non-natural amino acids will be present in the stabilized peptide prior to administering the stabilized peptide to the subject.

In some embodiments, the human subject has a MCL-1 and/or BFL-1 expression/dependent-cancer (e.g., melanoma, a leukemia, lymphoma, or other hematologic malignancy or solid tumor, or another cancer described herein. In some cases, the solid tumor is a melanoma, a breast cancer or lung cancer. In some embodiments, the BFL-1 expressing or dependent cell causes autoimmune disease or other inflammatory condition characteristic of a disease of cellular excess.). In certain instances, the autoimmune disease is autoimmune colitis, thyroiditis, arthritis, nephritis, dermatitis, vasculitis, system lupus erythematosus, diabetes, or Sjogren's disease. In some instances, the inflammatory disease, asthma, psoriasis, inflammatory colitis, thyroiditis, arthritis, nephritis, dermatitis, or vasculitis. In a specific embodiment, the human subject has AML.

In general, methods include selecting a subject and administering to the subject an effective amount of one or more of the peptides herein, e.g., in or as a pharmaceutical composition, and optionally repeating administration as required for the prophylaxis or treatment of a cancer, e.g., melanoma or lymphoma, and can be administered orally, intravenously or topically. A subject can be selected for treatment based on, e.g., determining that the subject has a cancer that expresses BFL-1; determining that the subject has a cancer that expresses MCL-1; or determining that the subject has a cancer that expresses both BFL-1 and MCL-1. The peptides of this disclosure can be used to determine if a subject's cancer expresses BFL-1, or if a subject's cancer is dependent on BFL-1.

Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments. For example, effective amounts can be administered at least once.

Pharmaceutical Compositions

One or more of any of the stabilized peptides described herein (e.g., one or more of SEQ ID NOs: 2-38 and 60-79, 151, and 153) can be formulated for use as or in pharmaceutical compositions. The pharmaceutical compositions may be used in the methods of treatment described herein (see above). In certain embodiments, the pharmaceutical composition comprises an amino acid sequence that is identical to an amino acid sequence set forth in SEQ ID NOs: 2-38 and 60-79, except for 1 to 10, 1 to 9, 1 to 8, 1 to 7, 1 to 6, 1 to 5, 1 to 4, 1 to 3, 1 to 2, or 1 amino acid substitution, insertion, or deletion. These changes to the amino acid sequences can be made on the BFL-1 non-interacting alpha-helical face of these peptides and/or on the BFL-1 interacting alpha-helical face. Such compositions can be formulated or adapted for administration to a subject via any route, e.g., any route approved by the Food and Drug Administration (FDA). Exemplary methods are described in the FDA's CDER Data Standards Manual, version number 004 (which is available at fda.give/cder/dsm/DRG/drg00301.htm). For example, compositions can be formulated or adapted for administration by inhalation (e.g., oral and/or nasal inhalation (e.g., via nebulizer or spray)), injection (e.g., intravenously, intra-arterial, subdermally, intraperitoneally, intramuscularly, and/or subcutaneously); and/or for oral administration, transmucosal administration, and/or topical administration (including topical (e.g., nasal) sprays and/or solutions).

In some instances, pharmaceutical compositions can include an effective amount of one or more stabilized peptides. The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome (e.g., treatment of infection).

Pharmaceutical compositions of this invention can include one or more peptides and any pharmaceutically acceptable carrier and/or vehicle. In some instances, pharmaceuticals can further include one or more additional therapeutic agents in amounts effective for achieving a modulation of disease or disease symptoms. For example, the pharmaceutical composition may include an ATM or ATR inhibitor. Non-limiting examples of ATM kinase inhibitors include KU-559403, KU-55933, KU-60019, CP-466722, CGK733, and AZD0156. Non-limiting examples of ATR kinase inhibitors include schisandrin B, NU6027, NVP-BEZ235, VE-821, VE-822/VX-970, AZ20, and AZD6738.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intra-cutaneous, intra-venous, intra-muscular, intra-articular, intra-arterial, intra-synovial, intra-sternal, intra-thecal, intra-lesional and intra-cranial injection or infusion techniques.

Pharmaceutical compositions can be in the form of a solution or powder for inhalation and/or nasal administration. Such compositions may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and/or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

Pharmaceutical compositions can be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

Alternatively or in addition, pharmaceutical compositions can be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

In some instances, one or more peptides disclosed herein can be conjugated, for example, to a carrier protein. Such conjugated compositions can be monovalent or multivalent. For example, conjugated compositions can include one peptide disclosed herein conjugated to a carrier protein. Alternatively, conjugated compositions can include two or more peptides disclosed herein conjugated to a carrier.

As used herein, when two entities are "conjugated" to one another they are linked by a direct or indirect covalent or non-covalent interaction. In certain embodiments, the association is covalent. In other embodiments, the association is non-covalent. Non-covalent interactions include hydrogen bonding, van der Waals interactions, hydrophobic interactions, magnetic interactions, electrostatic interactions, etc. An indirect covalent interaction is when two entities are covalently connected, optionally through a linker group.

Carrier proteins can include any protein that increases or enhances immunogenicity in a subject. Exemplary carrier proteins are described in the art (see, e.g., Fattom et al., *Infect. Immun.*, 58:2309-2312, 1990; Devi et al., *Proc. Natl. Acad. Sci. USA* 88:7175-7179, 1991; Li et al., Infect. Immun. 57:3823-3827, 1989; Szu et al., *Infect. Immun.* 59:4555-4561, 1991; Szu et al., *J. Exp. Med.* 166:1510-1524, 1987; and Szu et al., *Infect. Immun.* 62:4440-4444, 1994). Polymeric carriers can be a natural or a synthetic material containing one or more primary and/or secondary amino groups, azido groups, or carboxyl groups. Carriers can be water soluble.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art can develop equivalent means or reactants without the exercise of inventive capacity and without departing from the scope of the invention.

Example 1: Development of Potent, Selective, Cell Permeable, Cysteine-Reactive Stapled NOXA BH3 Inhibitors of BFL-1

We previously developed selective, covalent stapled peptide inhibitors of BFL-1 based on the sequence of BIM BH3, combining the high-affinity non-covalent interactions of a natural BH3 domain helix with the irreversible blockade resulting from covalent reaction of an electrophilic warhead. A covalent BIM SAHB that selectively neutralized the anti-apoptotic activity of BFL-1 in vitro and effectively triggered apoptosis in the context of BFL-1-driven melanoma was successfully designed and characterized (Huhn et al., *Cell Chem Biol.*, 23(9):1123-1134 (2016)). Although this cysteine-reactive BIM SAHB only targets BFL-1 covalently, it retains the ability to form non-covalent interactions with a broad spectrum of BCL-2 family proteins, including BCL-$X_L$, MCL-1, and potentially BAX. The BH3-only protein NOXA, however, has a narrower spectrum of BCL-2 protein binding activity, exhibiting dual selectivity for MCL-1 and BFL-1 (Stewart et al., *Nature Chemical Biology*, 6, 595-601 (2010)). Here, the NOXA BH3 template was used to tune the covalent and non-covalent selectivity of a warhead-bearing SAHB for BFL-1 so that such stapled peptides are sufficiently potent or cell permeable for ultimate therapeutic use. These new constructs are unique in that they either only target BFL-1 (by covalent and/or non-covalent means) or exhibit exclusive dual-targeting of BFL-1 (by covalent and/or non-covalent means) and MCL-1 (by non-covalent means).

Figure 3:
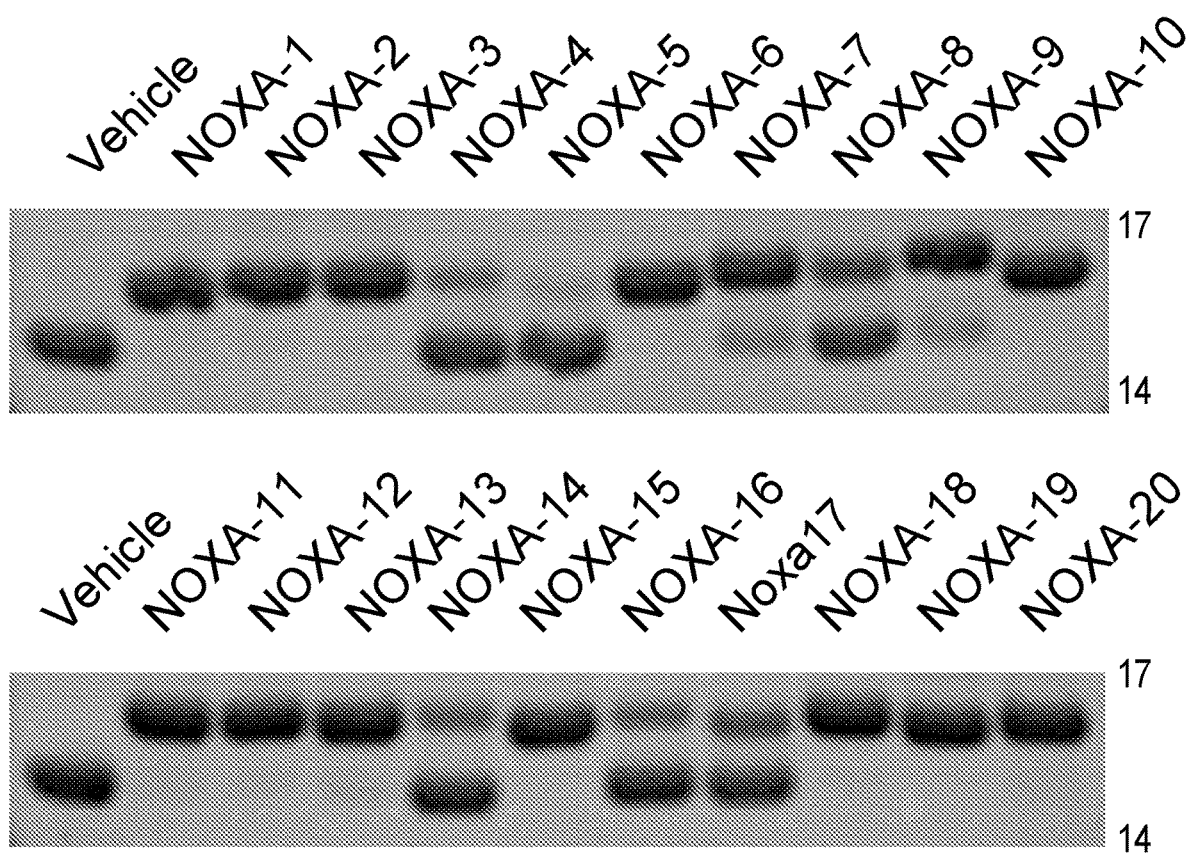
FIG. 3 shows the reactivity of D-nipecotic acid (D-NA)-bearing NOXA SAHBs with BFL-1ΔC C4S/C19S, which only retains the native Cys55.
Figure 4:
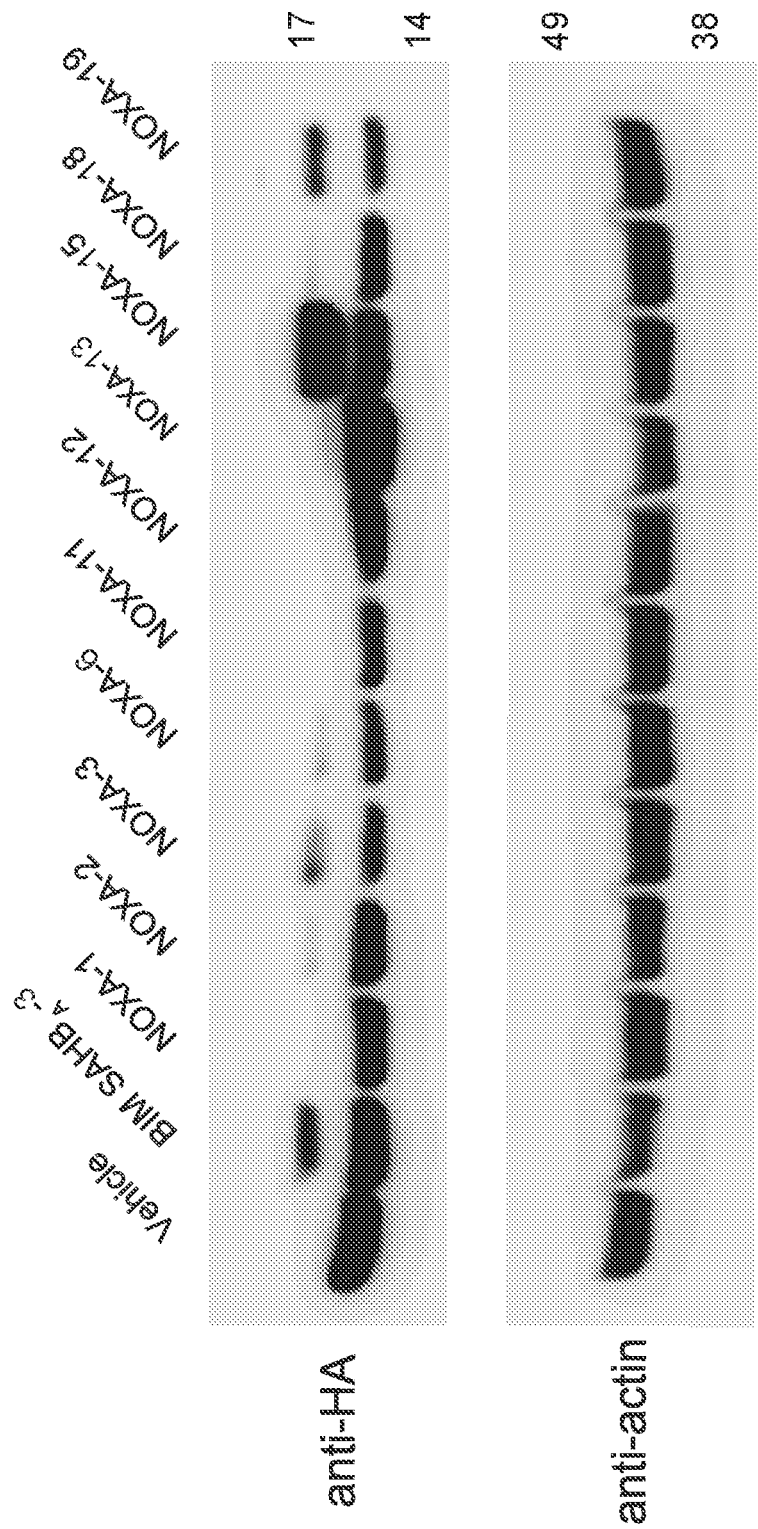
FIG. 4 shows cell permeability and reactivity of D-NA-NOXA SAHBs toward BFL-1 in 293T cells expressing HA-BFL-1ΔC C4S/C19S.
Figure 5:
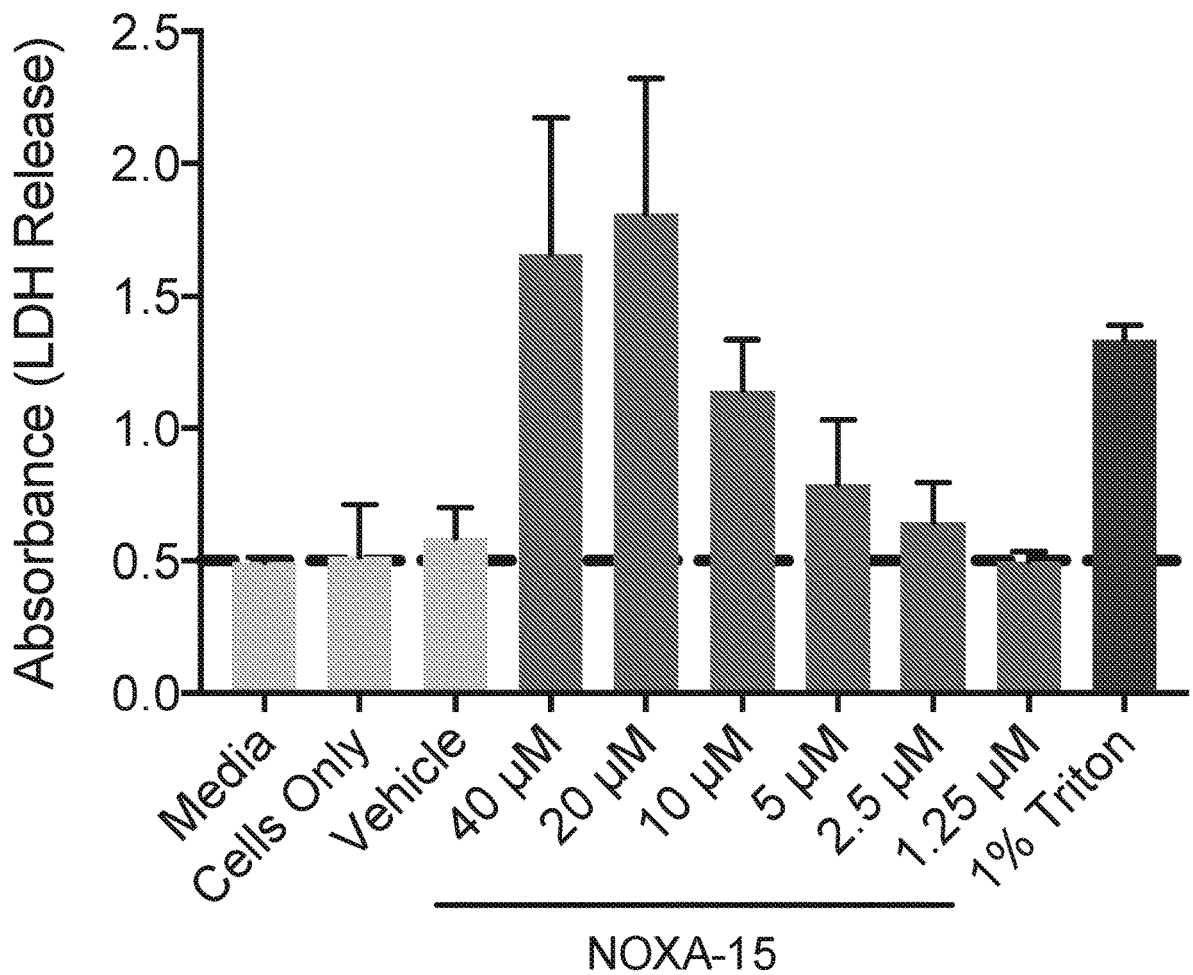
FIG. 5 shows the quantification of LDH release upon treatment of A375P cells with NOXA-15 for 30 min, demonstrating the induction of non-specific cell lysis by NOXA-15.

To generate constructs with particular binding selectivities, cell penetrance properties, in vivo stability, and biological activity to enable the development of a drug for clinical use, staple scanning methodology was first used to generate a library of cysteine-reactive NOXA SAHBs to optimize binding potency, selectivity, and cellular penetrance. Importantly, a novel, shortened template NOXA sequence was designed lacking N- and C-terminal residues of the classic BH3 domain sequence that did not appear to make critical contacts with the protein target based on structural data (FIG. 1). Staple scanning was achieved by sequential placement of (i, 1+4) and (i, i+7) staples across the length of the peptide template, while keeping the N-terminal D-nipecotic acid (D-NA) reactive group constant (FIG. 2). We measured the reactivity of this NOXA library by incubating each peptide with BFL-1ΔC and detecting a higher molecular weight conjugate upon reducing and denaturing gel electrophoresis, and Coomassie staining (FIG. 3). Those peptides capable of covalent reaction with BFL-1 were advanced to cellular testing for peptide uptake. 293T cells transfected with HA-BFL-1ΔC C4S/C19S were treated with peptide (20 µM, 6 hr), and then harvested and lysates analyzed by anti-HA western blotting (FIG. 4). The presence of a BFL-1 doublet indicated that the warhead-bearing peptide was both capable of gaining intracellular access and binding to BFL-1 covalently. The NOXA peptide with (i, i+7) staple position 15 exhibited a dramatic increase in covalent targeting efficiency compared to BIM SAHB$_A$-3. However, upon LDH release testing in A375P cells, this peptide was unexpectedly found to cause membrane disruption (FIG. 5).

Figure 7:
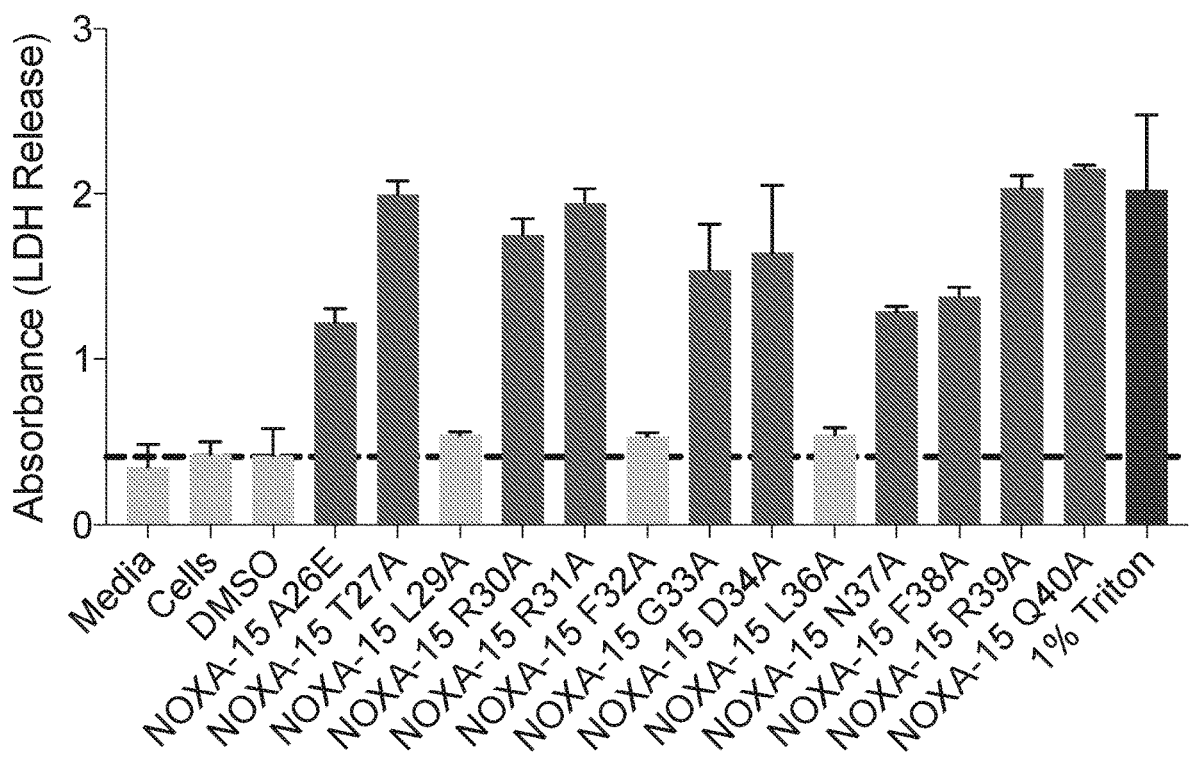
FIG. 7 is a bar graph LDH release of a D-NA-NOXA-15 SAHB alanine scan library demonstrating three peptides that lack lytic activity as a result of alanine mutation.
Figure 8:
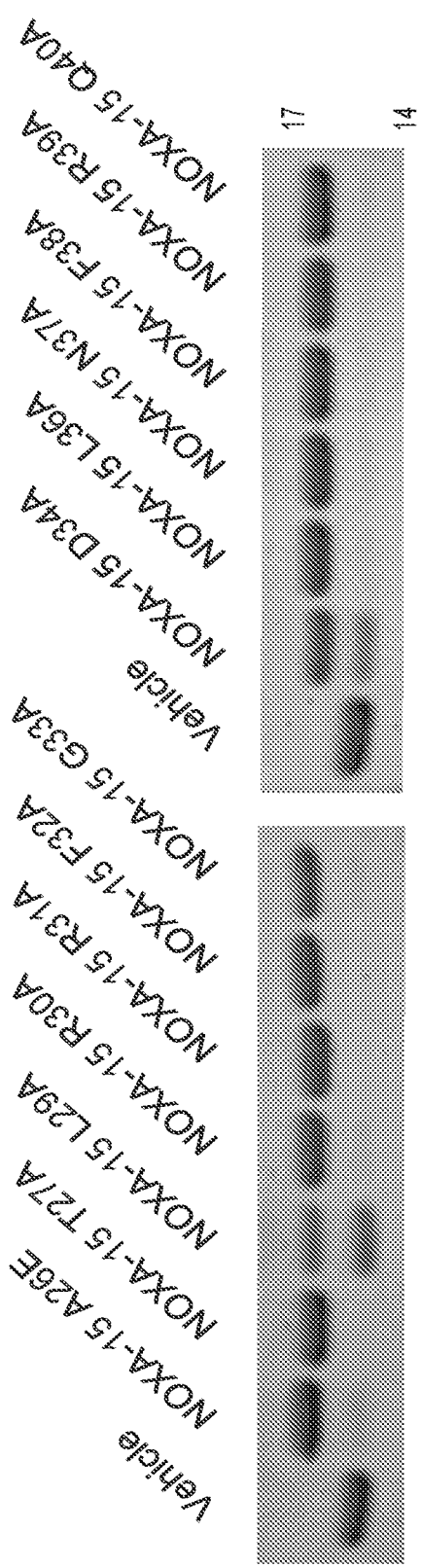
FIG. 8 is a Coomassie-stained gel showing reactivity of a D-NA-NOXA-15 SAHB alanine scan library with recombinant BFL-1ΔC C4S/C19S, emphasizing the broad tolerance for alanine mutation except at select positions, such as L29A and D34A, which show reduced or partial reactivity due to focal alanine mutagenesis.
Figure 9:
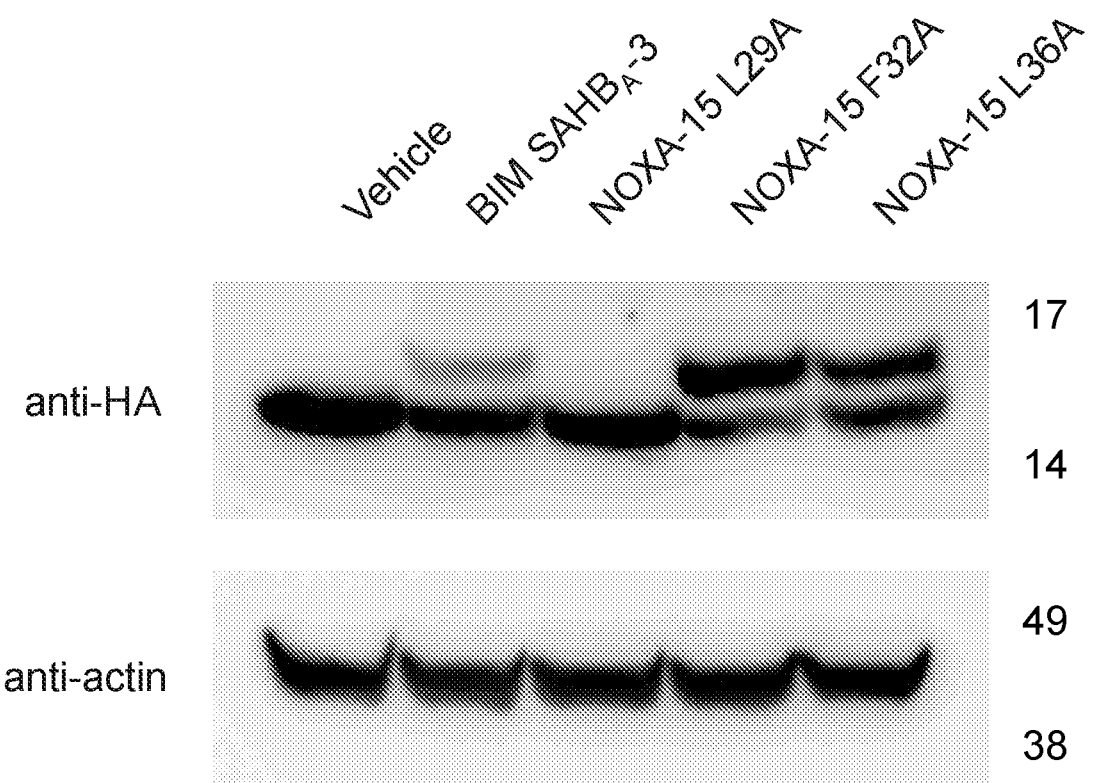
FIG. 9 is a western blot showing the cell permeability and reactivity of non-lytic, D-NA-NOXA-15 alanine-mutant SAHBs toward BFL-1 in 293T cells expressing HA-BFL-1ΔC C4S/C19S.

To remedy this shortcoming, the NOXA 15 construct was subjected to alanine scanning mutagenesis in an effort to identify changes in composition that could mitigate lytic behavior (FIG. 6). Especially hydrophobic residues were converted to alanine as one design strategy for eliminating lytic properties by decreasing hydrophobic content. Indeed, the sequential mutation of alanine across the length of the NOXA sequence yielded three warhead-bearing NOXA SAHBs with little to no lytic activity (FIG. 7). Notably, each of the mutations that reduced lysis lowered the overall peptide hydrophobicity. Surprisingly, the majority of mutations along the sequence of NOXA had no negative influence on BFL-1 covalent binding activity, except for Leu29 and Asp34 (FIG. 8), which are two residues of the "LXXXGDE" minimal consensus BH3 domain binding motif (Day et al., *J. Mol. Biol.*, 380(5):958-971 (2008)). These data indicate that stapled peptides bearing an electrophilic warhead for C55 targeting of BFL-1 are strikingly less sensitive to alteration of particular amino acid residues, even if they reside on the BFL-1 interaction surface of the NOXA helix. The cysteine-reactive NOXA-15 F32A and NOXA-15 L36A SAHBs were both cell permeable and covalently targeted BFL-1 (FIG. 9).

Figure 11:
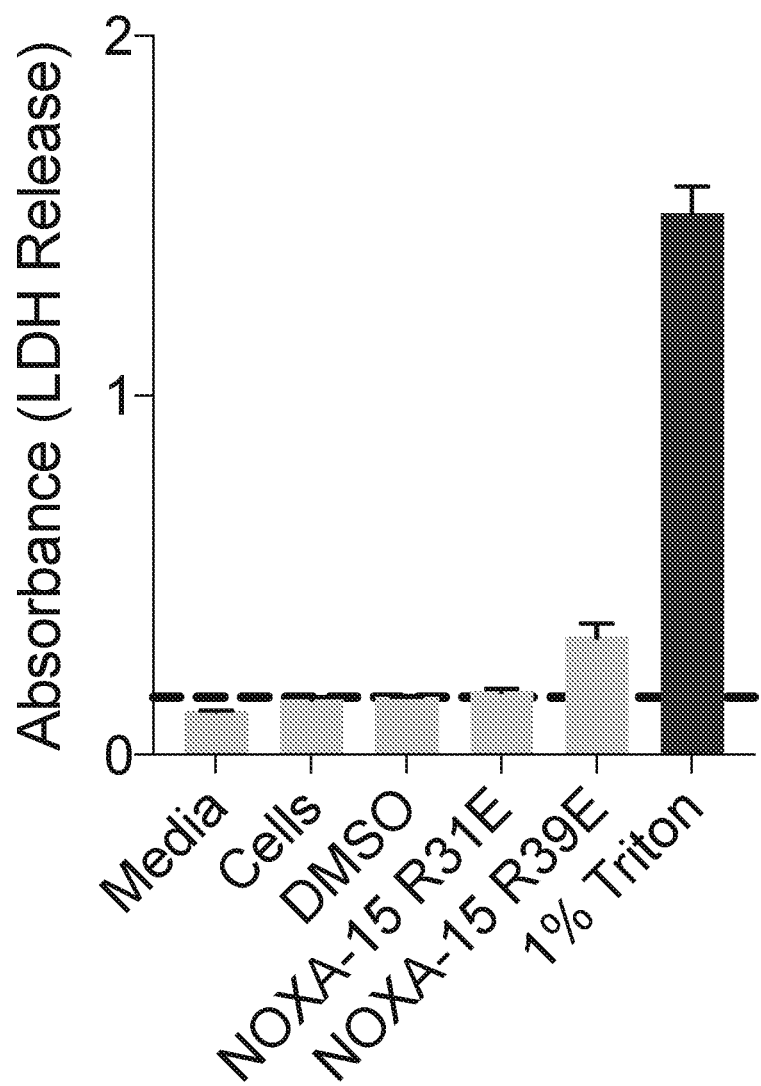
FIG. 11 is a bar graph depicting LDH release of D-NA-NOXA-15 SAHB Arg to Glu charge reversal mutant peptides demonstrating marked reduction or elimination of lytic activity.
Figure 12:
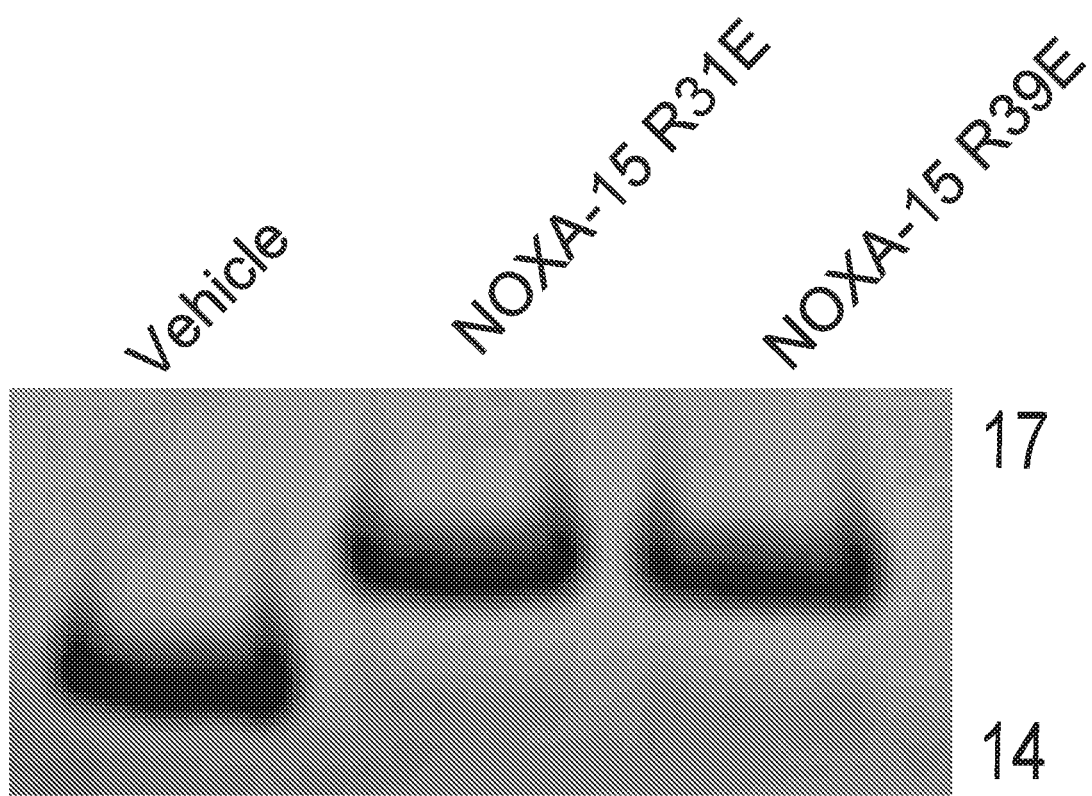
FIG. 12 is a Coomassie-stained gel showing the reactivity of D-NA-NOXA-15 SAHB Arg to Glu charge reversal mutants with recombinant BFL-1ΔC C4S/C19S.
Figure 13:
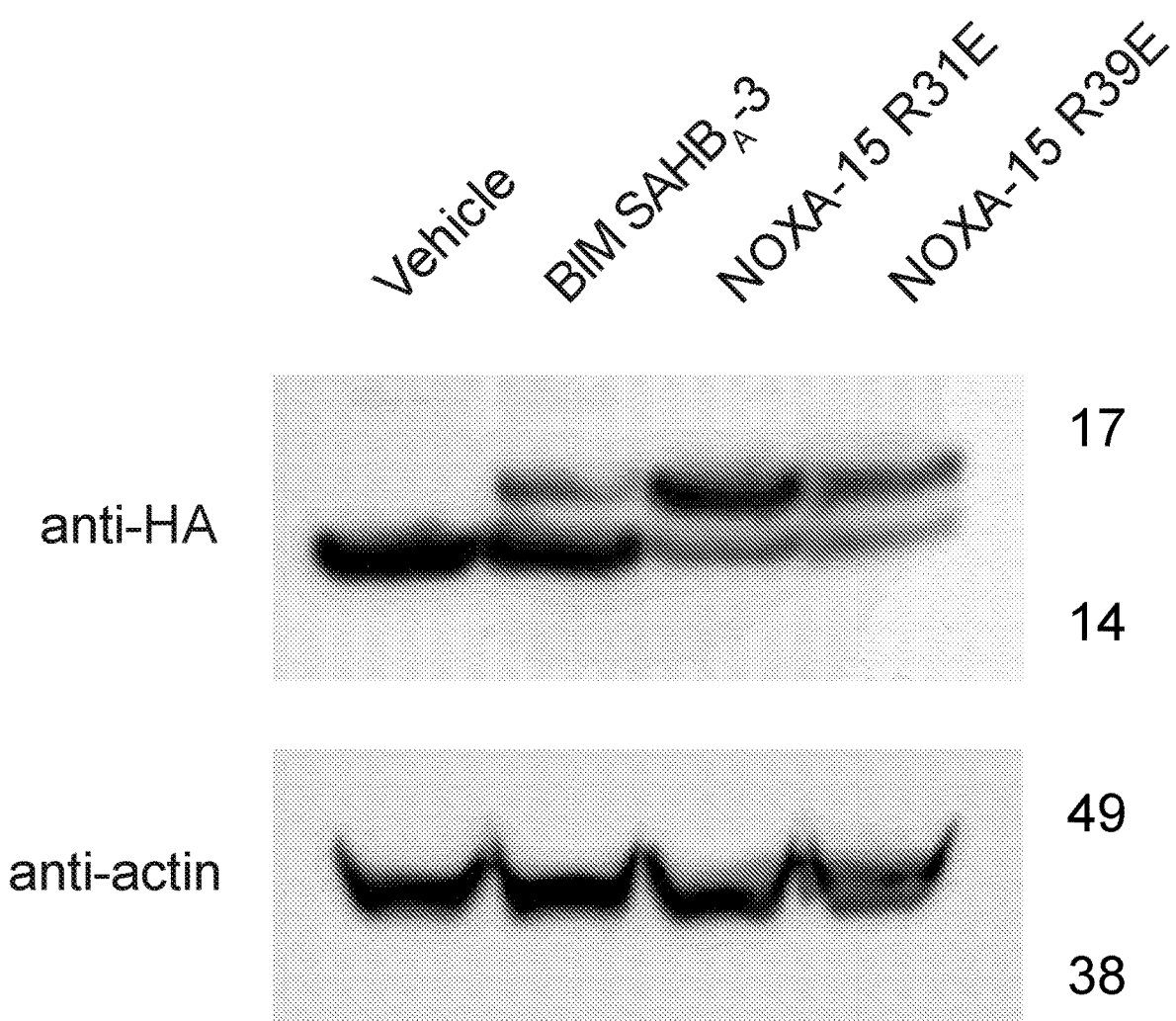
FIG. 13 are blots showing cell permeability and reactivity of non-lytic, D-NA-NOXA-15 SAHBs Arg to Glu charge reversal mutants toward BFL-1 in 293T cells expressing HA-BFL-1ΔC C4S/C19S.

In an alternative iterative approach to neutralizing the lytic activity of the cysteine-reactive NOXA-15 peptide, two different arginines were mutated to glutamic acid residues within the NOXA sequence, with the goal of reducing the overall positive charge of the peptide (FIG. 10). Indeed both peptides, whose overall charge was reduced from +2 to 0, retained covalent activity for BFL-1 (FIG. 12), demonstrated little-to-no cell lysis (FIG. 11), and achieved improved cellular uptake (FIG. 13).

Thus, using two distinct approaches, non-lytic, cell-permeable, cysteine-reactive NOXA SAHBs were inventively generated for advancement to biochemical characterization and cellular studies.

Example 2: Biochemical Characterization of the Selectivity of a Cell-Permeable, Cysteine-Reactive Stapled NOXA Peptides Reveals Decreased Non-Covalent Affinity for MCL-1 with Retained Covalent Selectivity for BFL-1

Figure 14:
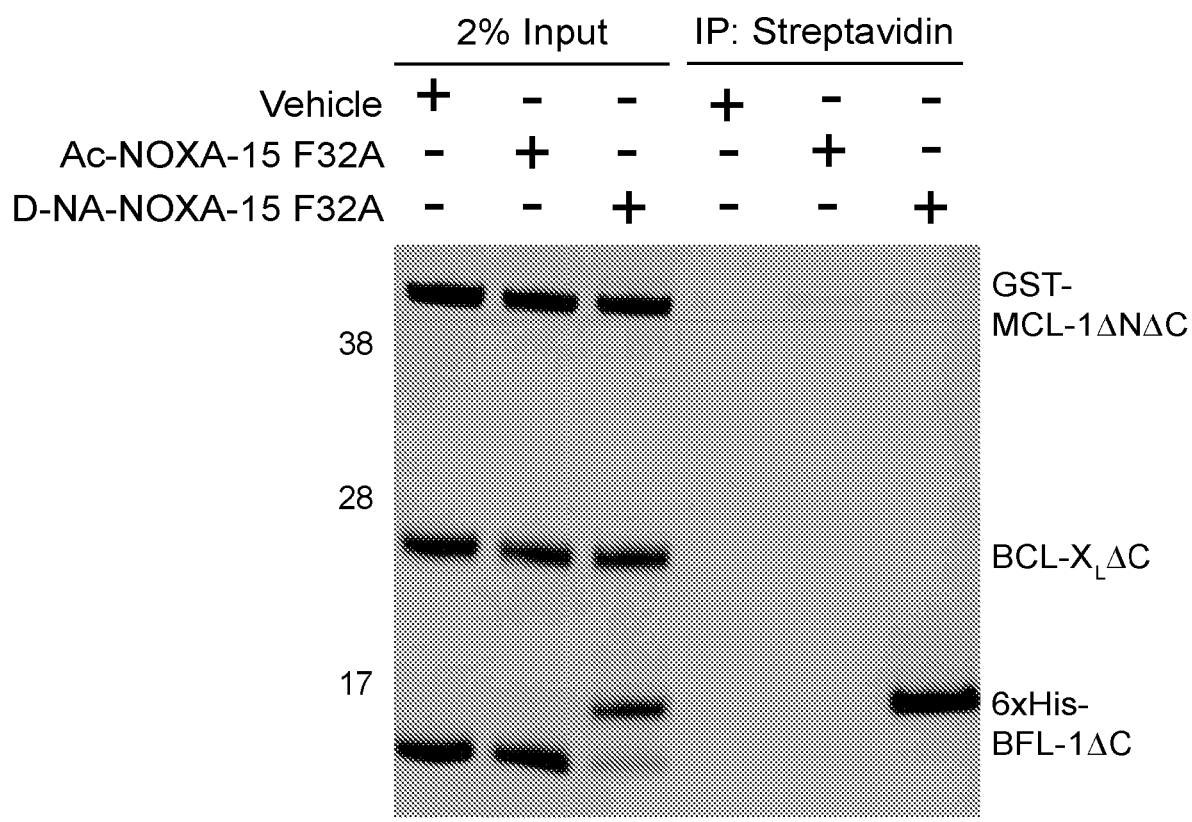
FIG. 14 is a silver-stained gel showing that D-NA-NOXA-15 F32A exhibits a striking competitive advantage for BFL-1 targeting over its acetylated counterpart as demonstrated by streptavidin pulldown of an equimolar mixture of recombinant GST-MCL-ΔNΔC, BCL-$X_L$ΔC (tagless), His-BFL-1ΔC, and biotinylated SAHB.
Figure 15:
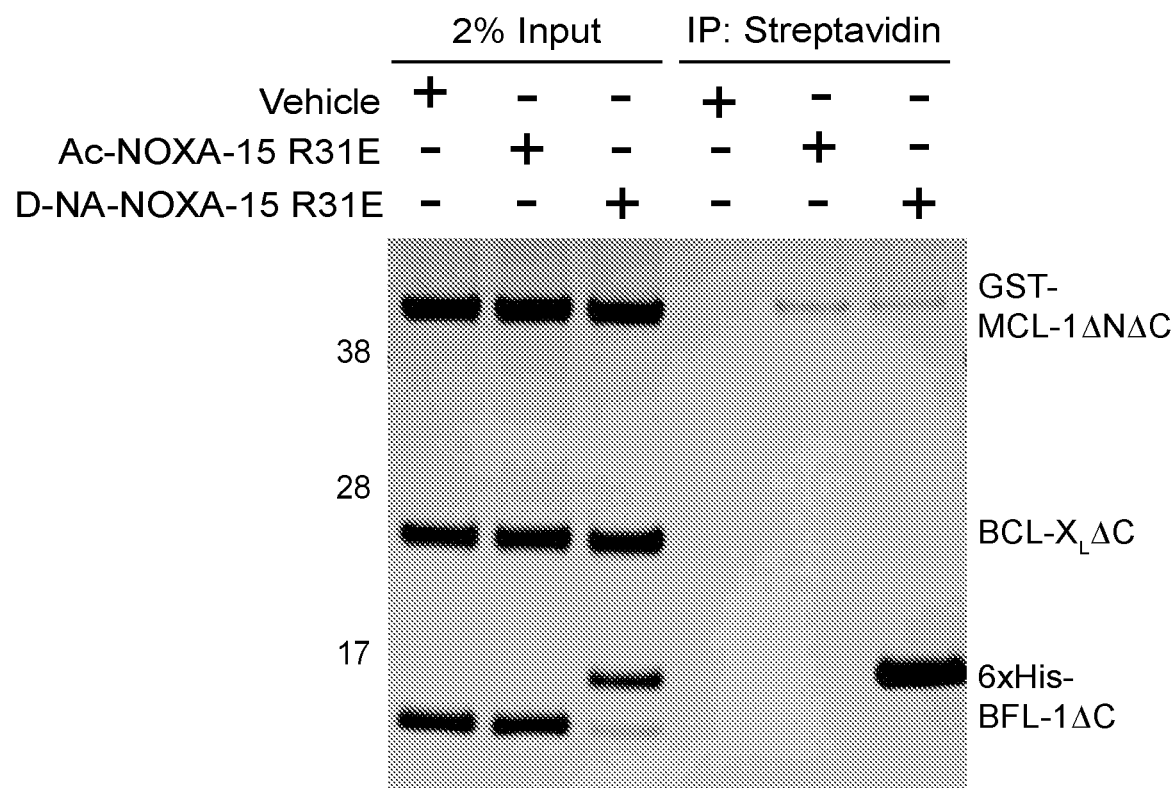
FIG. 15 is a silver-stained gel showing that D-NA-NOXA-15 R31E exhibits a striking competitive advantage for BFL-1 targeting over its acetylated counterpart as demonstrated by streptavidin pulldown of an equimolar mixture of recombinant GST-MCL-ΔNΔC, BCL-$X_L$ΔC (tagless), His-BFL-1ΔC, and biotinylated SAHB.
Figure 16:
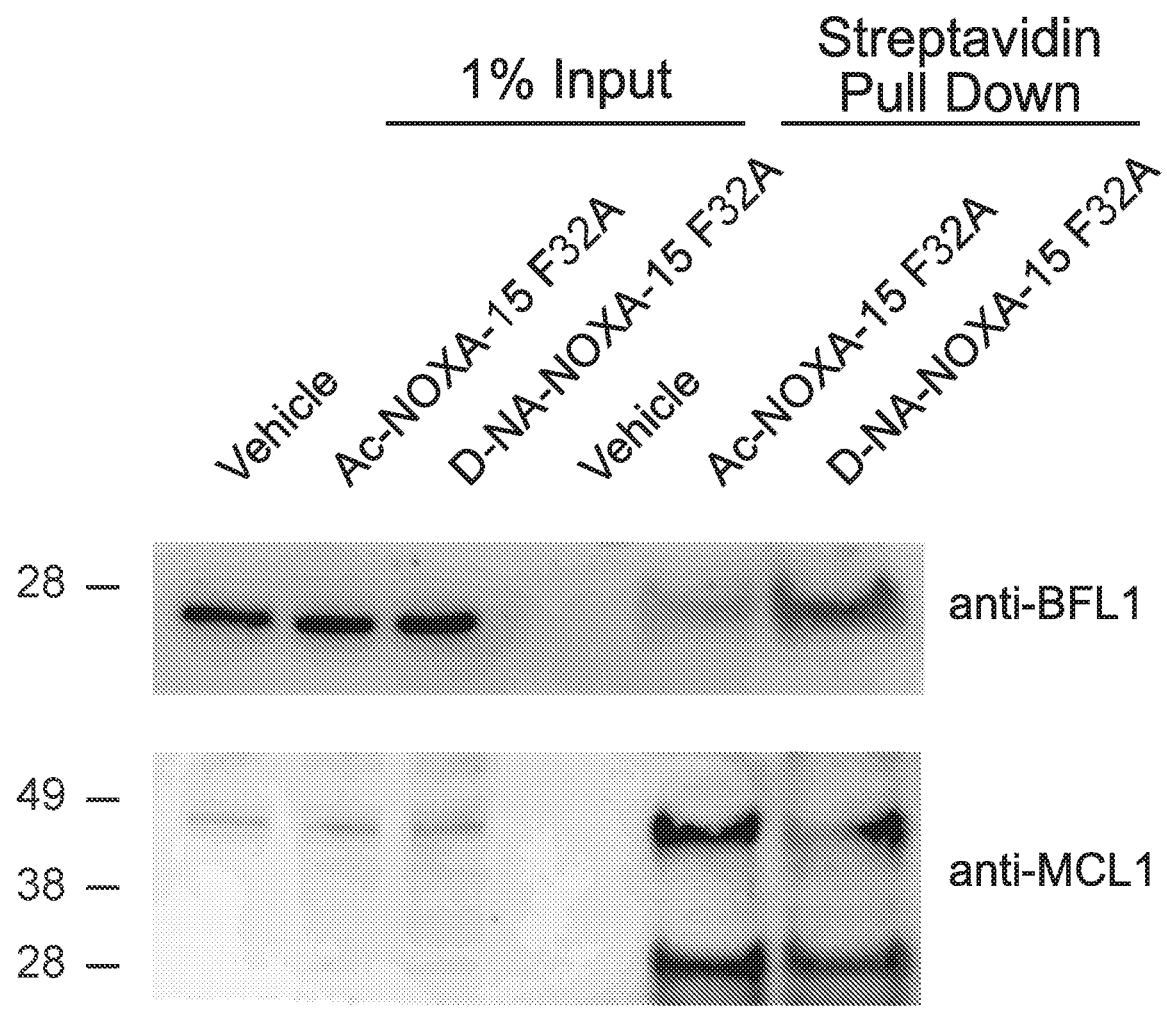
FIG. 16 is a blot showing that D-NA-NOXA-15 F32A displays enhanced targeting of native BFL-1 compare to the corresponding acetylated construct in A375P lysates, as monitored by streptavidin pulldown and BFL-1 western analysis. Both constructs similarly engage MCL-1, as demonstrated by MCL-1 western analysis of the streptavidin pull down.
Figure 17:
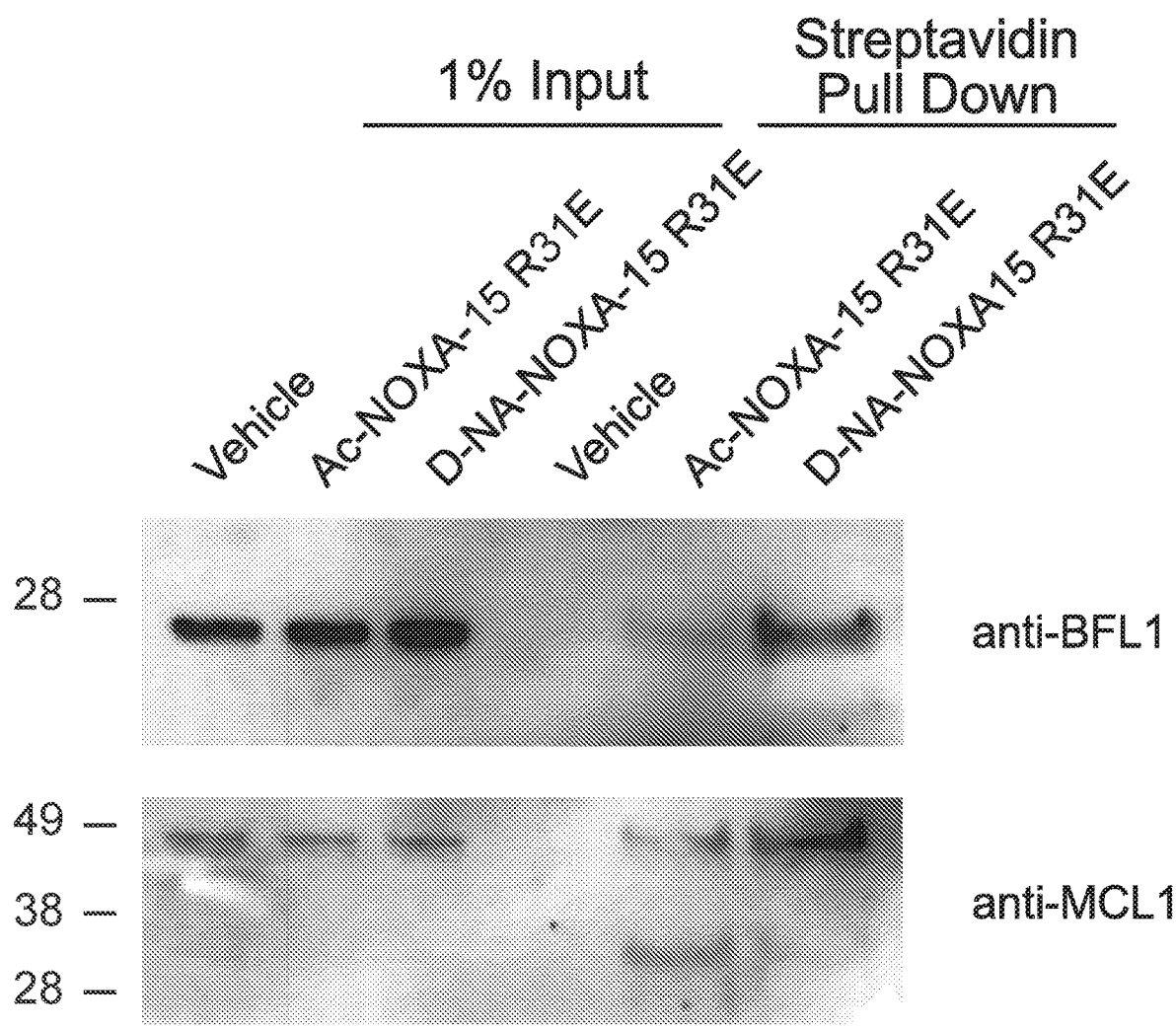
FIG. 17 is a blot showing that D-NA-NOXA-15 R31E displays enhanced targeting of native BFL-1 compare to the corresponding acetylated construct in A375P lysates, as monitored by streptavidin pulldown and BFL-1 western analysis. Both constructs similarly engage MCL-1, as demonstrated by MCL-1 western analysis of the streptavidin pull down.

Having made significant changes to the native NOXA BH3 sequence, including peptide length, staple placement, and mutagenesis, it was next sought to determine the effect of these modifications on the selectivity of two lead cell permeable peptides, the cysteine-reactive D-NA-NOXA-15 F32A and R31E. It was first examined how these changes coupled with the addition of a cysteine-reactive electrophile influenced the balance between non-covalent and covalent SAHB interactions in the context of an anti-apoptotic protein mixture. The biotinylated D-NA-NOXA-15 F32A SAHB or corresponding acetylated construct was incubated in an equimolar mixture with recombinant BFL-1, BCL-$X_L$, and MCL-1, and then subjected to streptavidin pull-down. The acetylated (Ac-) NOXA-15 F32A SAHB demonstrated no binding to BFL-1, BCL-$X_L$, and detectable but minimal direct interaction with MCL-1 (FIG. 14), consistent with the new design feature of significant truncation of the native BH3 sequence. However, D-NA-NOXA-15 F32A SAHB displayed a shift in the interaction propensity toward BFL-1, with notably more BFL-1 engagement as a result of covalent BFL-1ΔC conjugation (FIG. 14). The same covalent versus non-covalent interactions were observed for Ac- versus D-NA-NOXA-15 R31E in the same experimental context (FIG. 15). Additionally, the preferential interactions of these peptides were assessed with endogenous protein in lysates from the A375P melanoma cell line. When subjected to streptavidin pulldown, the biotinylated Ac- and D-NA-NOXA-15 F32A or R31E SAHBs demonstrated approximately equivalent binding to MCL-1, whereas the warhead-bearing constructs again showed markedly increased engagement of BFL-1 (FIGS. 16 and 17).

Figure 18:
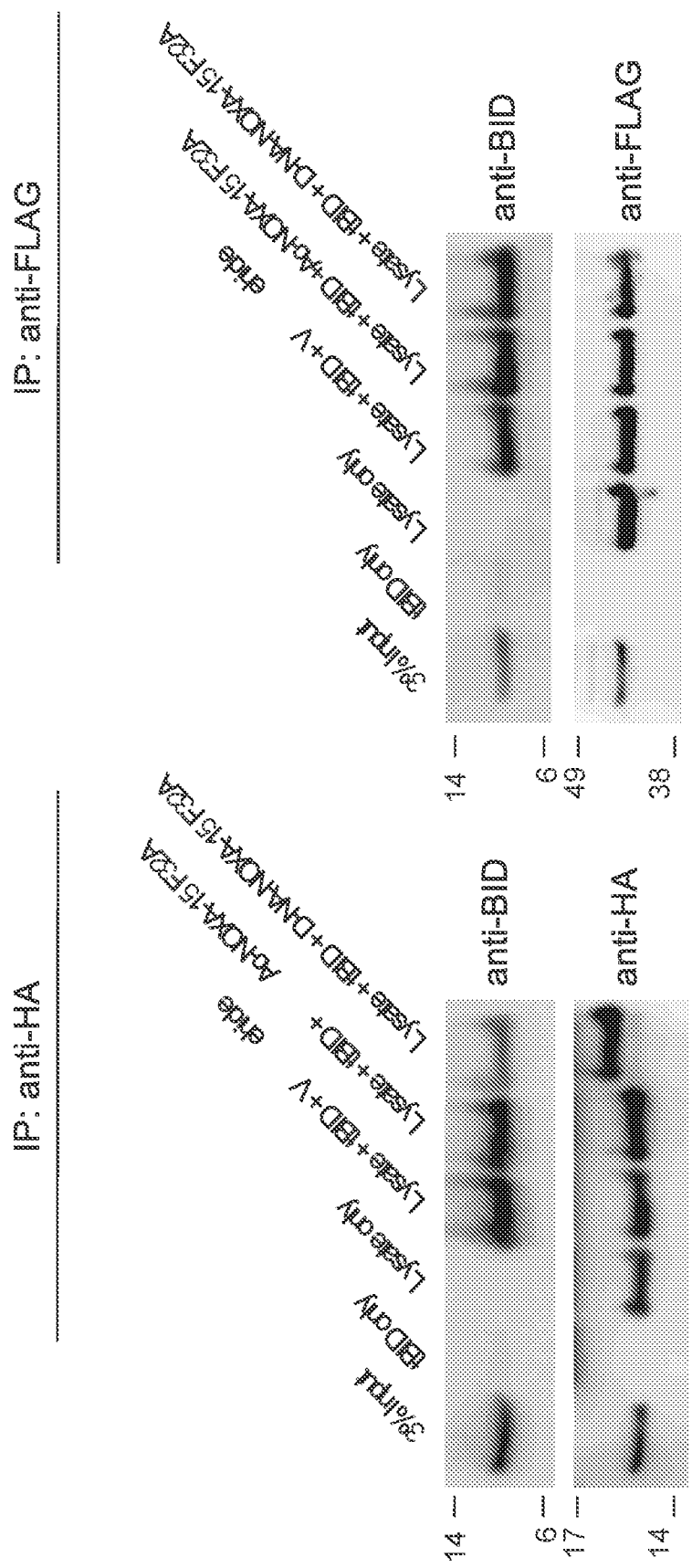
FIG. 18 includes blots showing that D-NA-NOXA15 F32A, but not its acetylated counterpart, effectively competes with tBID for HA-BFL-1ΔC C4S/C19S interaction in 293T lysates and achieves robust covalent conjugation, as measured by immunoprecipitation and western analysis (left). In contrast, neither D-NA- nor Ac-NOXA15 F32A is able to dissociate the interaction of FLAG-MCL-1 and tBID (right).
Figure 19:
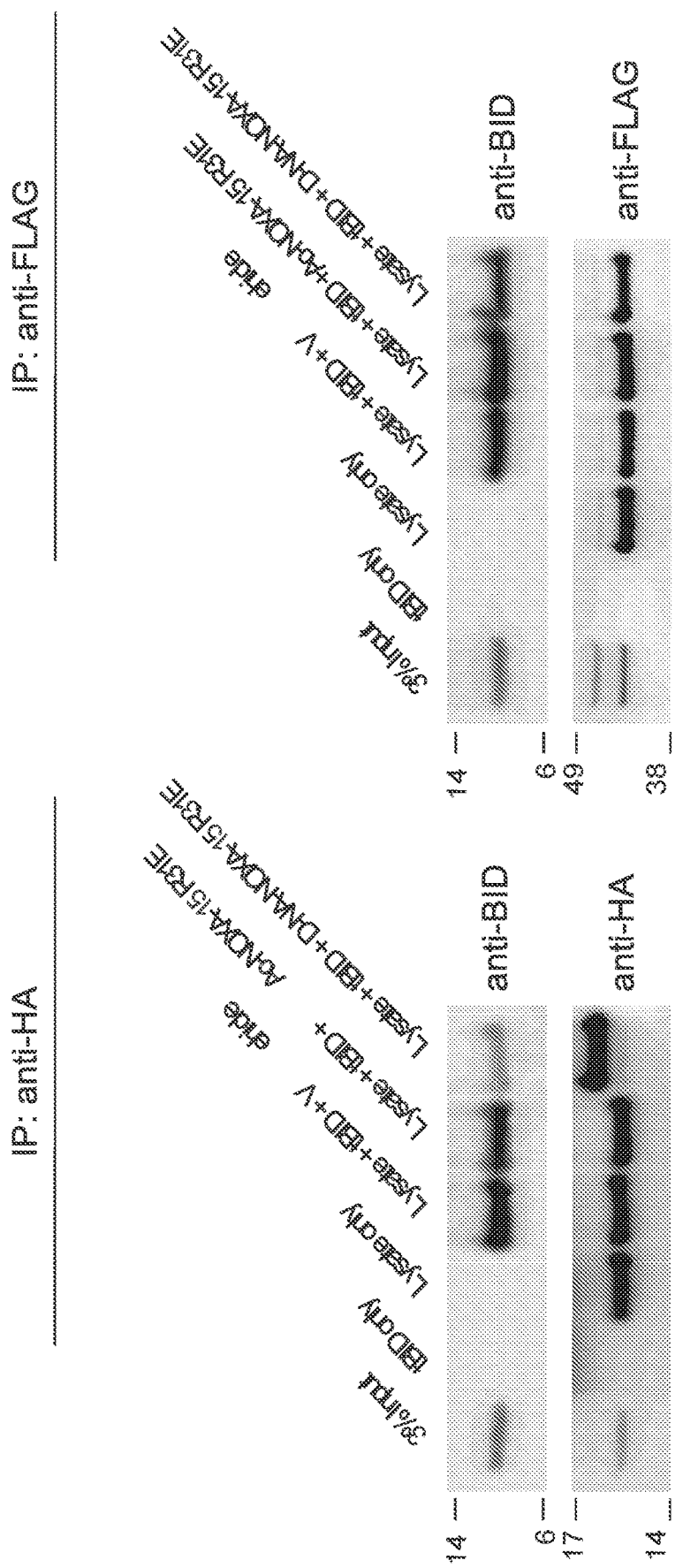
FIG. 19 shows blots that indicate that D-NA-NOXA15 R31E, but not its acetylated counterpart, effectively competes with tBID for HA-BFL-1ΔC C4S/C19S interaction in 293T lysates and achieves robust covalent conjugation, as measured by immunoprecipitation and western analysis (left). In contrast, neither D-NA- nor Ac-NOXA15 R31E is able to dissociate the interaction of FLAG-MCL-1 and tBID (right).
Figure 20:
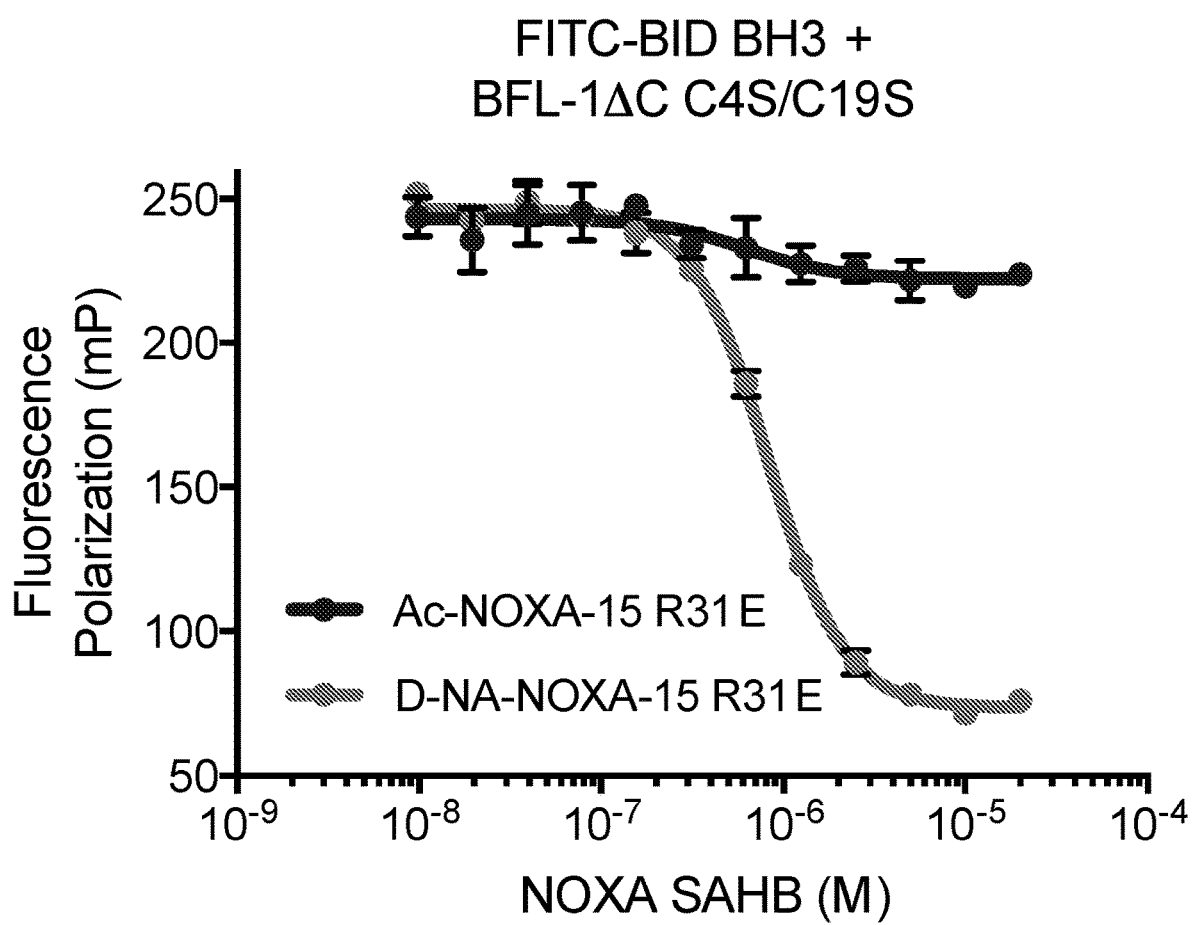
FIG. 20 is a graph showing that D-NA-NOXA-15 R31E, but not its acetylated counterpart, displays the ability to disrupt the interaction of BFL-1ΔC C4S/C19S and FITC-BID BH3 in a fluorescence polarization competitive binding assay.

In addition to studying the direct binding of the lead D-NA-NOXA-15 SAHBs to anti-apoptotic proteins, their capacity to competitively disrupt inhibitory BFL-1 complexes were also evaluated. For clinically useful biological activity, the capacity to inhibit unoccupied anti-apoptotic protein(s) to lower the apoptotic threshold and to competitively displace pro-apoptotic proteins from anti-apoptotic complexes to induce apoptosis are two distinct and desirable functionalities. For the competition experiment, tBID was added to lysates from 293T cells transiently transfected with HA-BFL-1ΔC C4S/C19S, the mixture was incubated with biotinylated Ac- or D-NA-NOXA-15 F32A SAHBs, anti-HA immunoprecipitation was performed, and blotted for HA and tBID. Acetylated NOXA-15 F32A was incapable of competing with tBID for HA-BFL-1 binding, whereas the warhead-bearing D-NA-NOXA-15 F32A construct covalently trapped HA-BFL-1, as exemplified by complete conversion of the protein to the higher molecular weight species and near total inhibition of tBID co-immunoprecipitation (FIG. 18, left). Strikingly, when the experiment was repeated using lysates from 293T cells transiently expressing FLAG-MCL-1, neither NOXA-15 F32A peptides were able to non-covalently disrupt the tBID/FLAG-MCL-1 co-immunoprecipitation (FIG. 18, right), demonstrating a distinct shift in the binding selectivity of NOXA-15 F32A SAHB toward BFL-1. The results were identical when performed with Ac- versus D-NA-NOXA-15 R31E (FIG. 19), establishing the same functional binding preferences for this construct.

Figure 21:
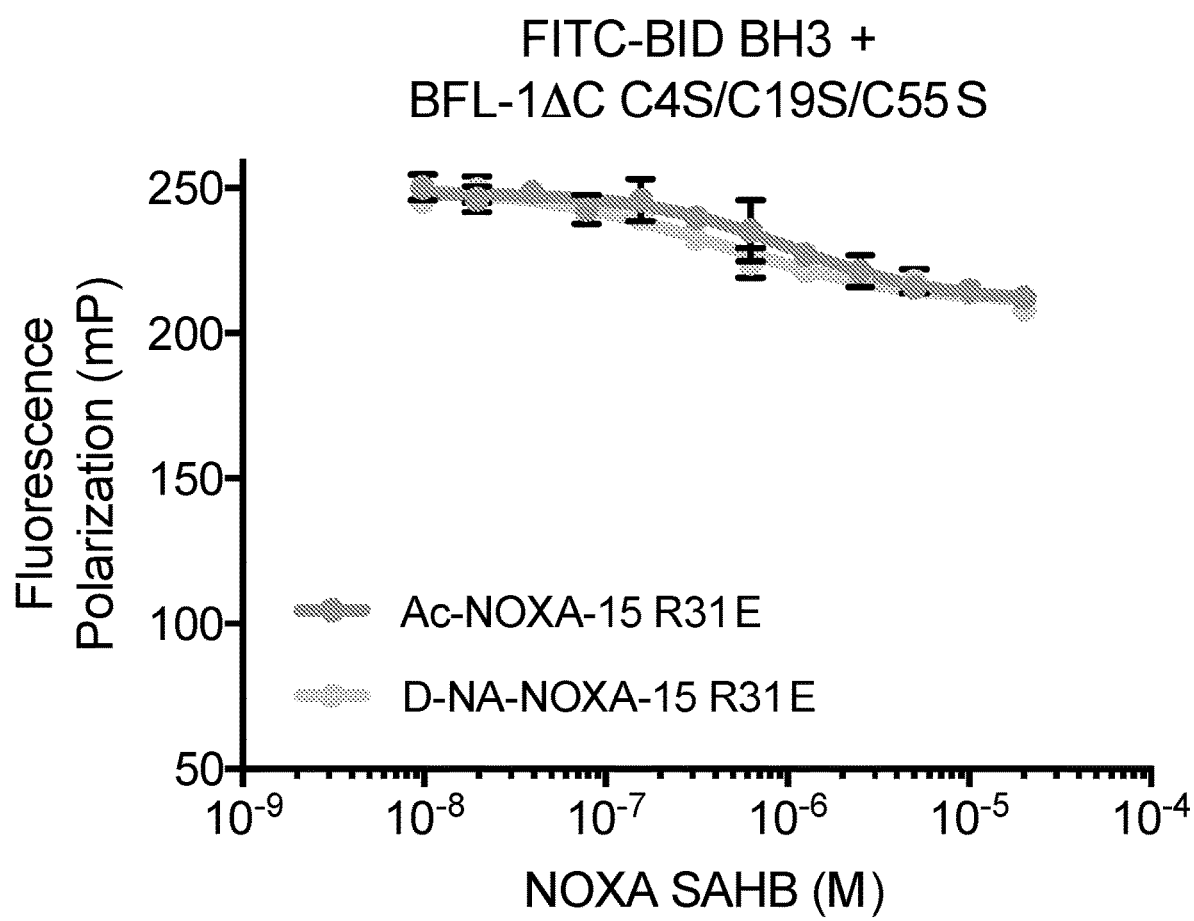
FIG. 21 is a graph showing that neither D-NA- nor Ac-NOXA15 R31E competes for FITC-BID BH3 binding to BFL-1ΔC C4S/C19S/C55S, demonstrating the necessity of C55 in the BH3 binding pocket of BFL-1 for selective covalent targeting.
Figure 22:
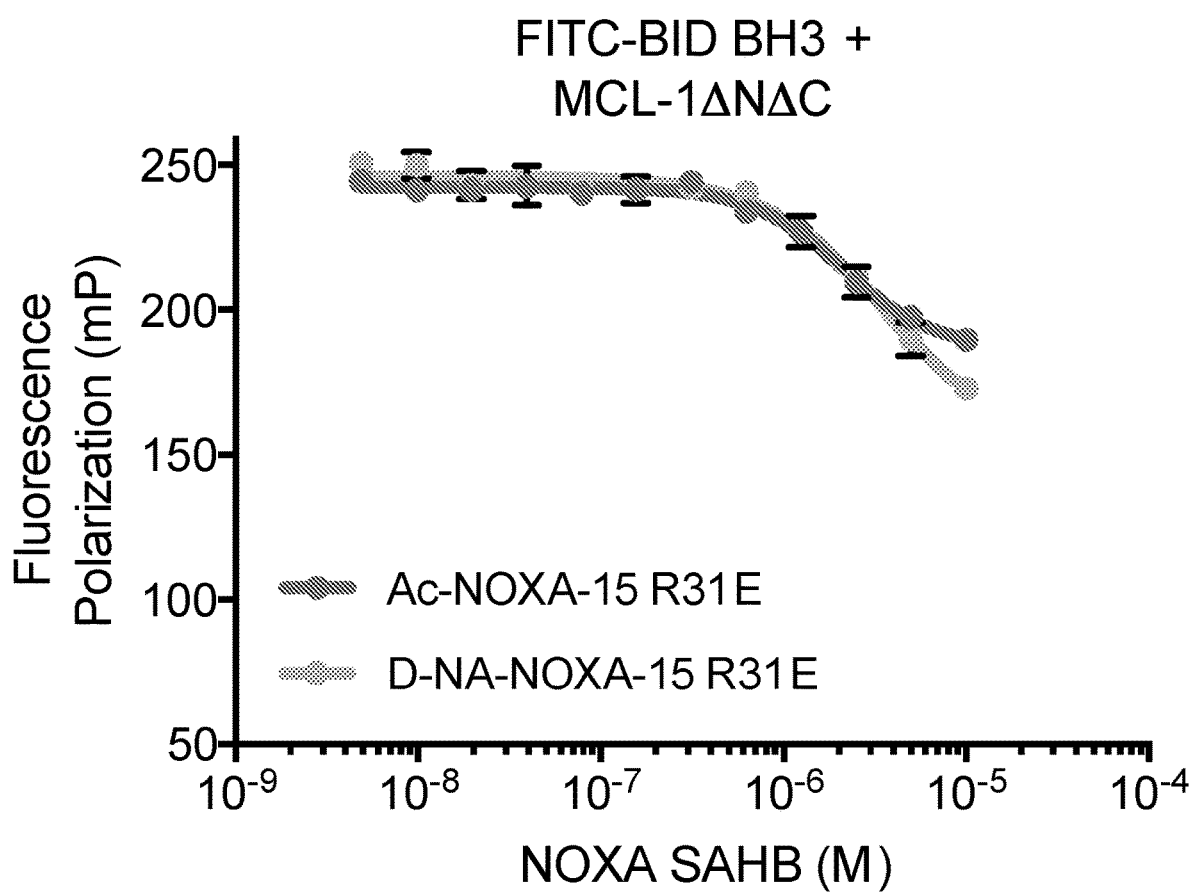
FIG. 22 is a graph depicting that both Ac- and D-NA-NOXA-15 R31E display a similar and relatively limited-to-moderate capacity to compete with FITC-BID BH3 binding to MCL-1ΔNΔC.
Figure 23:
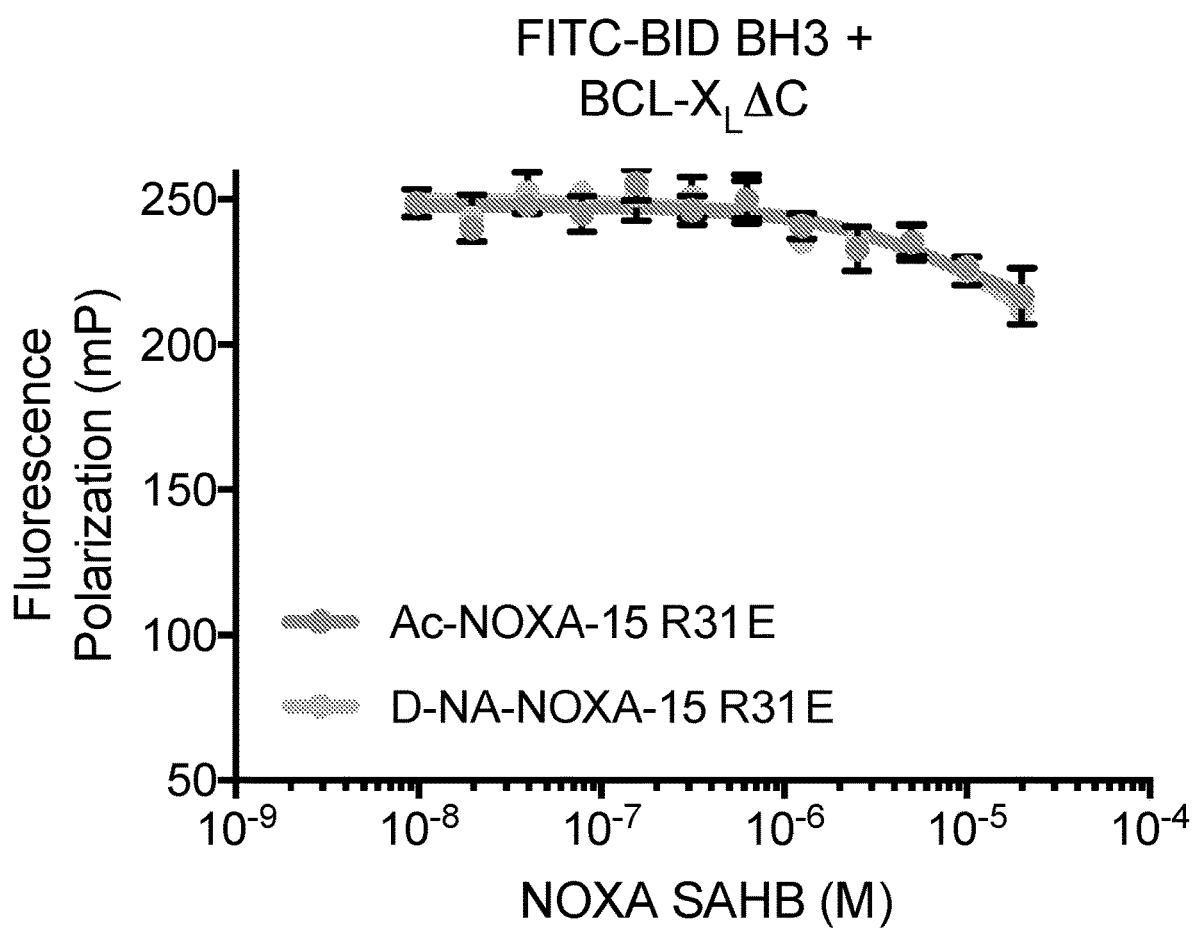
FIG. 23 is a graph showing that neither Ac- nor D-NA-NOXA-15 R31E is able to compete for FITC-BID BH3 binding to BCL-$X_L$ΔC.

Fluorescence polarization experiments comparing the capacity of acetylated versus cysteine-reactive NOXA-15 R31E SAHBs to compete with FITC-BID BH3 peptide for anti-apoptotic protein binding demonstrated a similar effect (FIGS. 20-23). The warhead-bearing D-NA-NOXA-15 R31E SAHB was only able to compete with FITC-BID BH3 for binding to BFL-1ΔC C4S/C19S (FIG. 20), and this activity was dependent on the presence of Cys55 in the BH3-binding pocket, as this effect was not observed with BFL-1ΔC C4S/C19S/C55S (FIG. 21). Neither Ac- nor D-NA-NOXA-15 R31E peptides were capable of significantly dissociating the interaction of FITC-BID BH3 with either MCL-1ΔNΔC (FIG. 22) or BCL-XLΔC (FIG. 23). These biochemical experiments demonstrated that the various modifications made to the NOXA BH3 sequence to impart cellular uptake and reduce lytic activity resulted in a stapled peptide with exquisite covalent selectivity for BFL-1, and diminished non-covalent affinity for MCL-1, in a competitive binding context.

Figure 24:
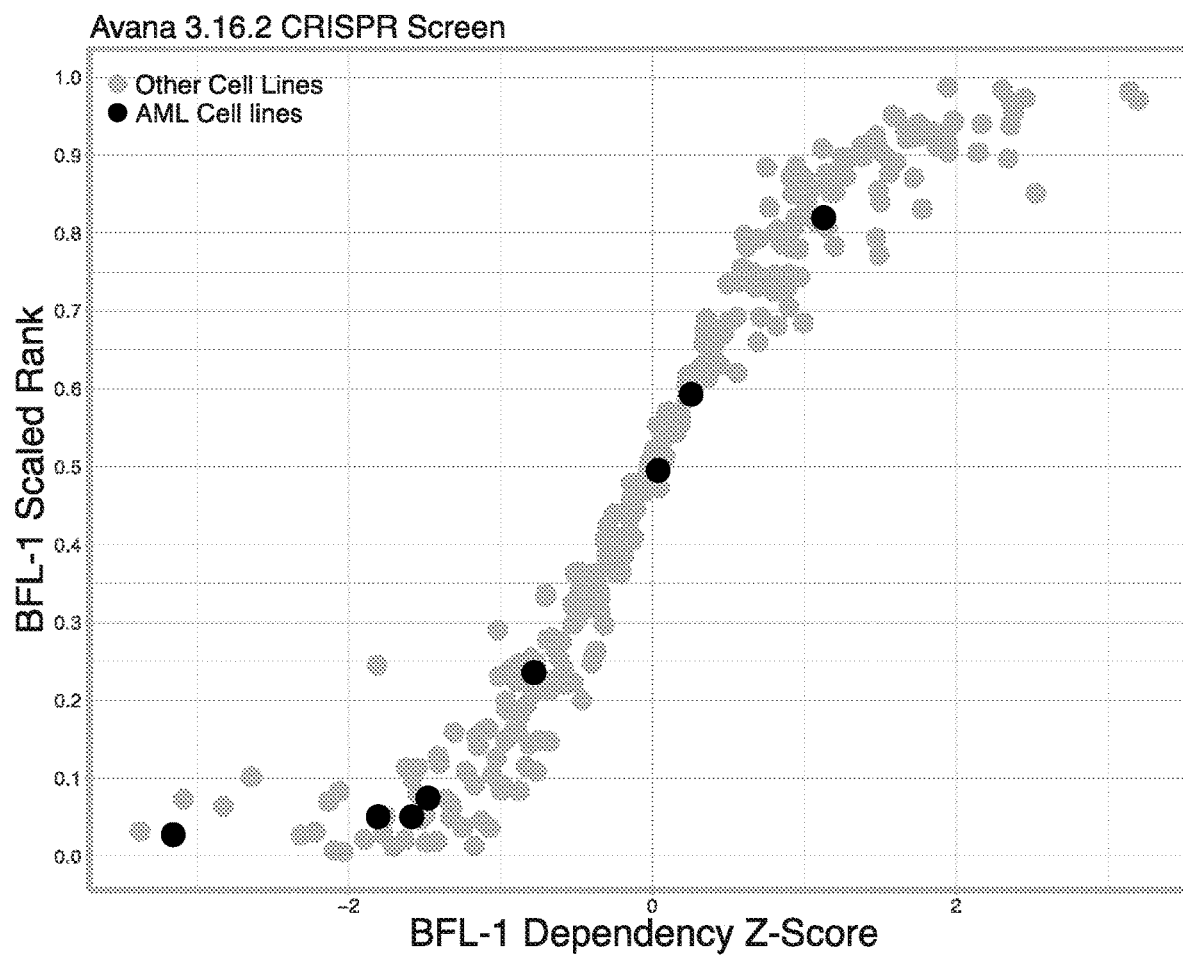
FIG. 24 is a plot of AML cell lines that display varying levels of dependency on BFL-1 for cell survival as determined by genome-wide CRISPR screening.
Figure 26:
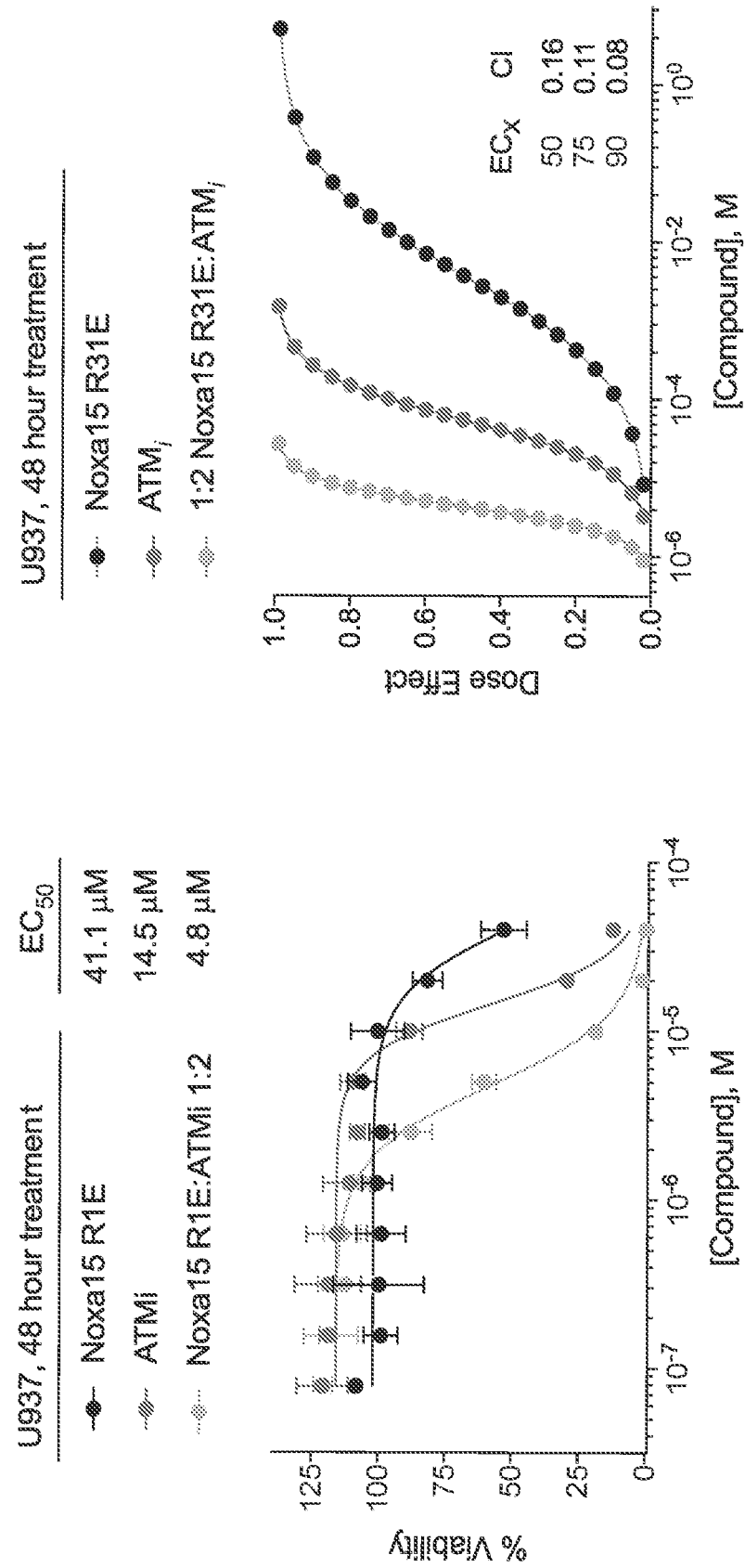
FIG. 26 are graphs showing that treatment of BFL-1-dependent U937 cells with the combination of the cysteine-reactive NOXA-15 R31E and the ATM inhibitor KU-55933 caused a synergistic decrease in cell viability (left), as reflected by Calcusyn analysis and the plotted dose-effect curves (right).
Figure 27:
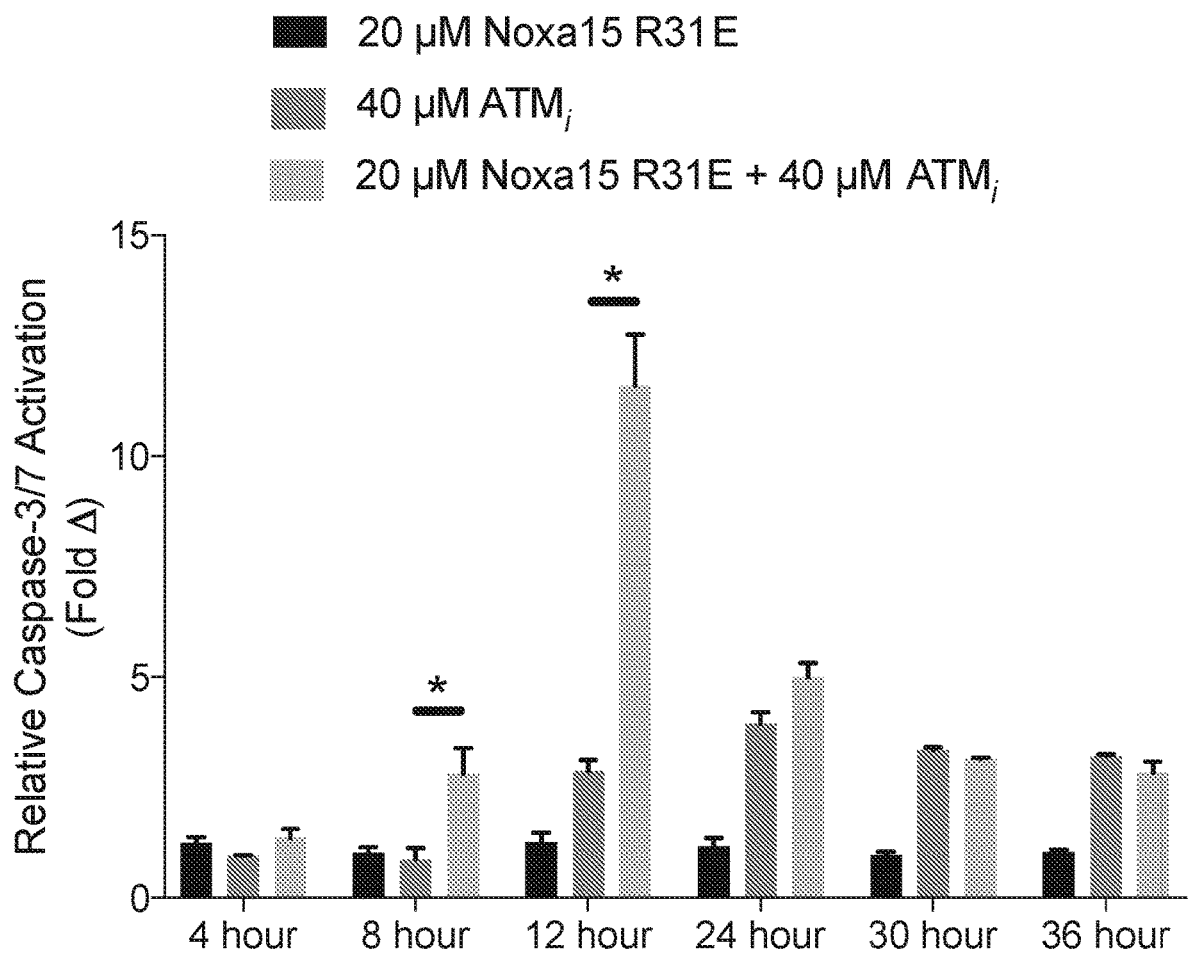
FIG. 27 is a bar graph showing that U937 cells treated with the cysteine-reactive NOXA-15 R31E and KU-55933 singly and in combination exhibit significantly increased caspase-3/7 activation over time upon combination treatment compared to single agent treatments.
Figure 28:
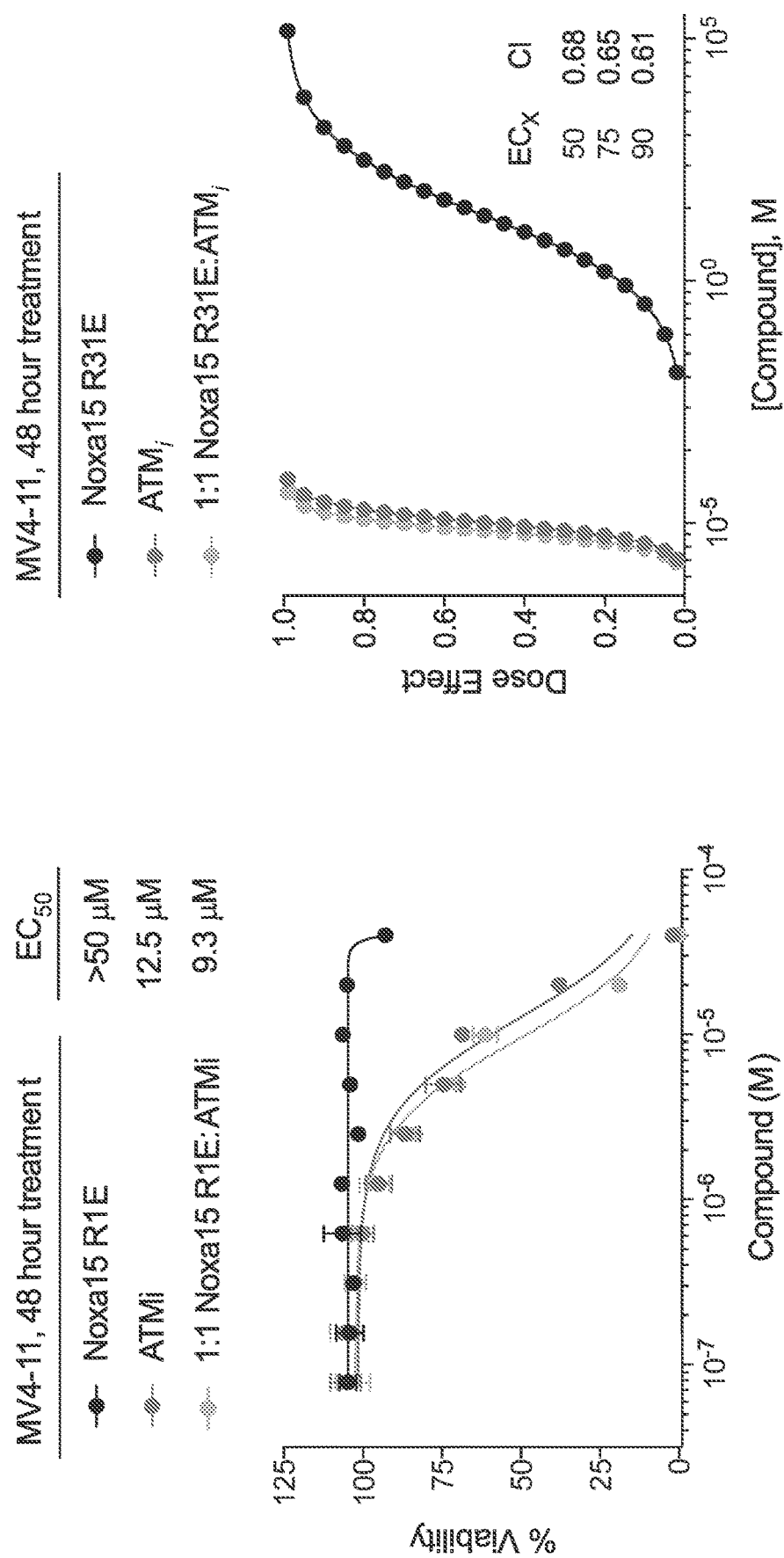
FIG. 28 are graphs showing that co-treatment of the MV4-11 cell line, which is not dependent on BFL-1, resulted in little to no cytotoxic synergy of cysteine-reactive NOXA-15 R31E and the ATM inhibitor.
Figure 29:
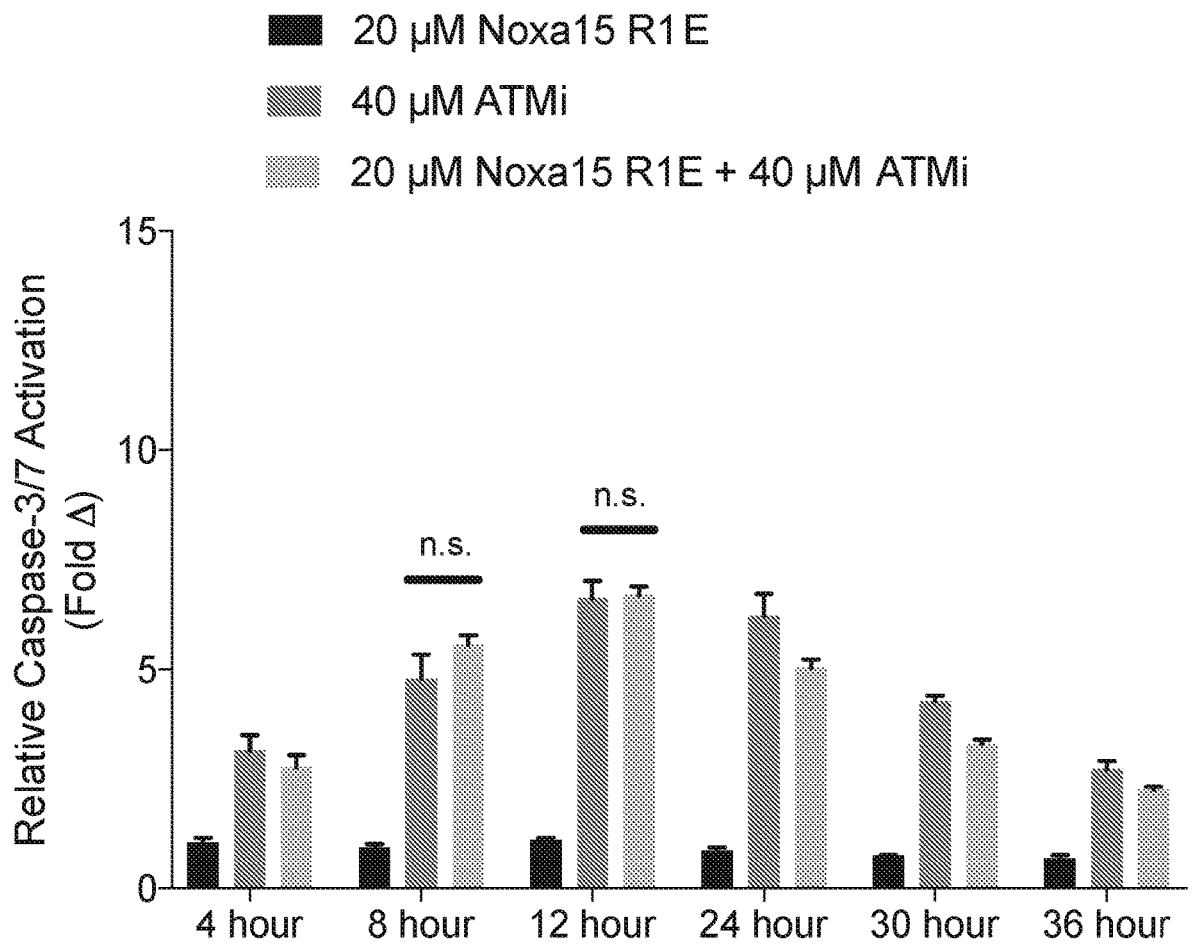
FIG. 29 is a bar graph showing that MV4-11 cells treated with a combination of the cysteine-reactive NOXA-15 R31E and KU-55933 demonstrate no increase in caspase-3/7 activation compared to the single agent treatments.

Example 3: Cysteine-Reactive NOXA SAHB Synergizes with ATM Inhibition in BFL-1-Dependent AML Cell Lines Given the selectivity of the cysteine-reactive NOXA-15 R31E SAHB for BFL-1, it was postulated that the ideal setting to test its cellular activity would be in cancer cell lines that are especially dependent on the expression of BFL-1 for survival. Large genome-wide RNAi screening efforts have been undertaken to map genetic dependencies across hundreds of cancer cell lines (Tsherniak, Cell, 170 (3):564-576 (2017)). A next-generation CRISPR-Cas9 screening data set for cancer cell lines, specifically focusing on AML, was queried and examined for which cells exhibit dependency on BFL-1 (FIG. 24). Cell lines with more positive dependency Z-score values exhibit little-to-no dependency on BFL-1 (e.g., MV4-11, top right), whereas more negative Z-score values represent increasing dependency on BFL-1 (e.g., U937, bottom left). Because most cancer cell lines express a spectrum of anti-apoptotic proteins, it was further hypothesized that combining a cysteine-reactive NOXA-15 R31E SAHB with a second dependency could potentially enhance cytotoxicity, particularly if the BFL-1 dependency was in the moderate range (Z-score values between −4 and −2). To inform this effort, genes were evaluated that showed significant co-dependency with BFL-1 dependency. ATM, a serine/threonine kinase activated by DNA double-strand breaks, was the most highly correlated co-dependent gene in AML (FIG. 25). Co-treatment of the AML cell line U937, which exhibited the highest dependency on BFL-1, with the cysteine-reactive NOXA-15 R31E SAHB and a small molecule ATM inhibitor KU-55933 resulted in highly synergistic cytotoxicity (CI<0.3, strong synergism), as analyzed by the CalcuSyn software (FIG. 26). Additionally, when treated with the cysteine-reactive NOXA-15 R31E and KU-55933 singly and in combination, the U937 cells exhibited significantly increased caspase-3/7 activation over time upon combination treatment compared to single agent treatments (FIG. 27), suggesting synergism in apoptosis induction as causal of the cytotoxic effects. Correspondingly, the AML cell line that was least dependent on BFL-1, MV4-11, is essentially insensitive to the cysteine-reactive NOXA-15 R31E SAHB alone over the same dose range as applied above, and displays little to no cytotoxic synergy when combined with the ATM inhibitor (FIG. 28), and no increase in caspase-3/7 activation for combination treatment compared to the single agent treatments (FIG. 29).

Example 4: Crystal Structures of Anti-Apoptotic BFL-1 and its Complex with a Covalent Stapled Peptide Inhibitor The structures of anti-apoptotic targets in complex with BH3 helices and their mimetics can provide a roadmap for molecular refinement and therapeutic development, so it was sought to solve the structures of BFL-1, alone and in complex with a covalent stapled peptide inhibitor, for the first time. The structure of apo BFL-1 provides the opportunity to compare unliganded anti-apoptotic protein structures, and also reveals the conformational consequences and molecular features of covalent targeting of BFL-1 with a cysteine-reactive stapled peptide inhibitor.

Structure of Apo BFL-1

Figure 31B:
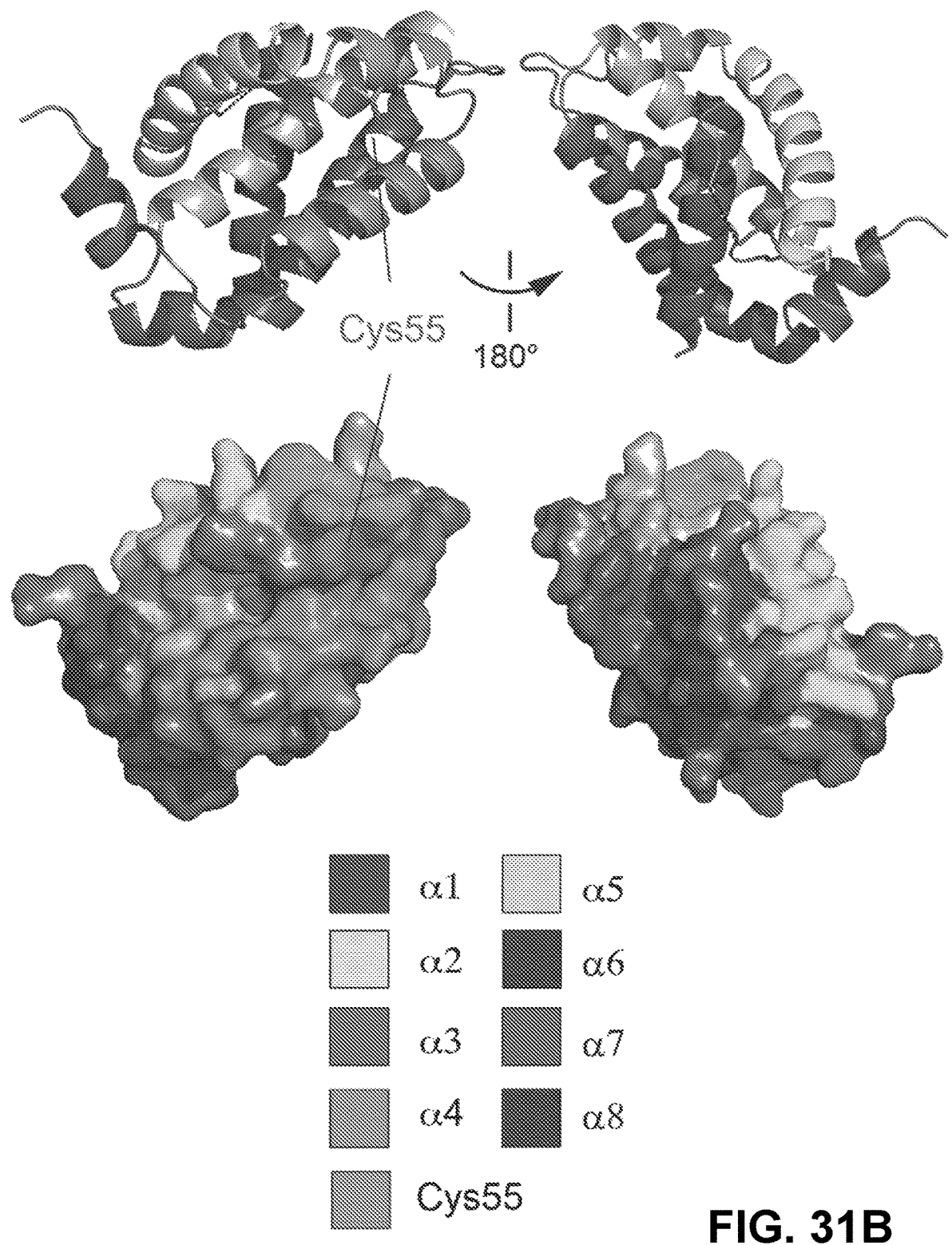
FIG. 31B shows ribbon and surface views of apo BFL-1ΔC (PDB ID: 5WHI) demonstrating the relative disposition of α-helices and the BH3-binding surface groove, which is formed by α-helices 2-4. A surface accessible cysteine located within the groove is noted.
Figure 31C:
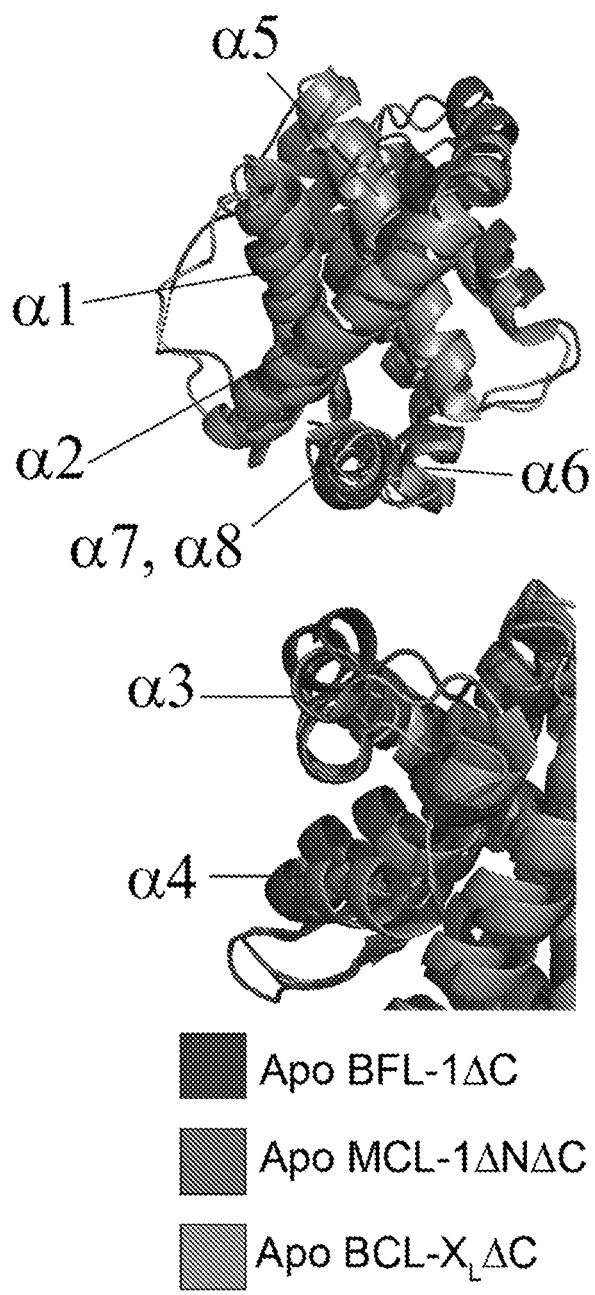
FIG. 31C shows ribbon diagram overlay of the apo structures of BFL-1 (PDB ID: 5WHI), MCL-1 (PDB ID: 4WMS), and BCL-$X_L$ (PDB ID: 1R2D) demonstrating the similarities (above) and differences (below) among the orientations of their α-helices.

The structure of unliganded BFL-1 was solved by X-ray crystallography at 1.69 Å resolution (FIG. 30, PDB ID: 5WHI) and revealed a globular protein comprised of a series of α-helices joined by loops, which typically contain helix-breaking glycines or prolines (FIG. 31A-B). BFL-1 shares all key elements of the conserved structure of multidomain BCL-2 family proteins, including a core α5-α6 hairpin that is surrounded by α-helices 1-4 and 7-8. At the site of α9 truncation, which is performed to facilitate anti-apoptotic protein expression and crystallization, lies the canonical surface groove lined by residues from α-helices 2-4. Specifically with respect to the only other apo structures of anti-apoptotic proteins, MCL-1 and BCL-$X_L$ the relative position, accessibility and conformation of the grooves show differences. An overlay of all three structures demonstrates near complete overlap of α-helices 1, 5, 6, 7, and 8, but notably less conservation of the orientation of α3 and the adjacent distal portion of α2 and proximal portion of α4 (FIG. 31C). The latter results in a variable pitch of the canonical groove, with that of BCL-$X_L$ displaced most downward, followed by MCL-1 and BFL-1, which progressively shift toward the horizontal. In these unbound structures, the width of the binding pockets, as assessed by measuring the distances between conserved residues at the roof and floor of the groove, are also distinct. Whereas the width of the empty BH3-binding pocket is essentially the same for MCL-1 and BFL-1 across multiple measurements, the BCL-$X_L$ groove is narrower, particularly between the midpoints of α-helices 3 and 4 (FIG. 31D). The latter derives from a notable difference in the relative disposition of these α-helices, which are oriented anti-parallel to one another in BCL-$X_L$ but progressively more V-shaped in MCL-1 and BFL-1. Whereas structure-based design of anti-apoptotic inhibitors have largely derived from BH3-bound protein complexes, such conformational distinctions among the apo structures inform alternative topographies for molecular targeting.

Figure 31F:
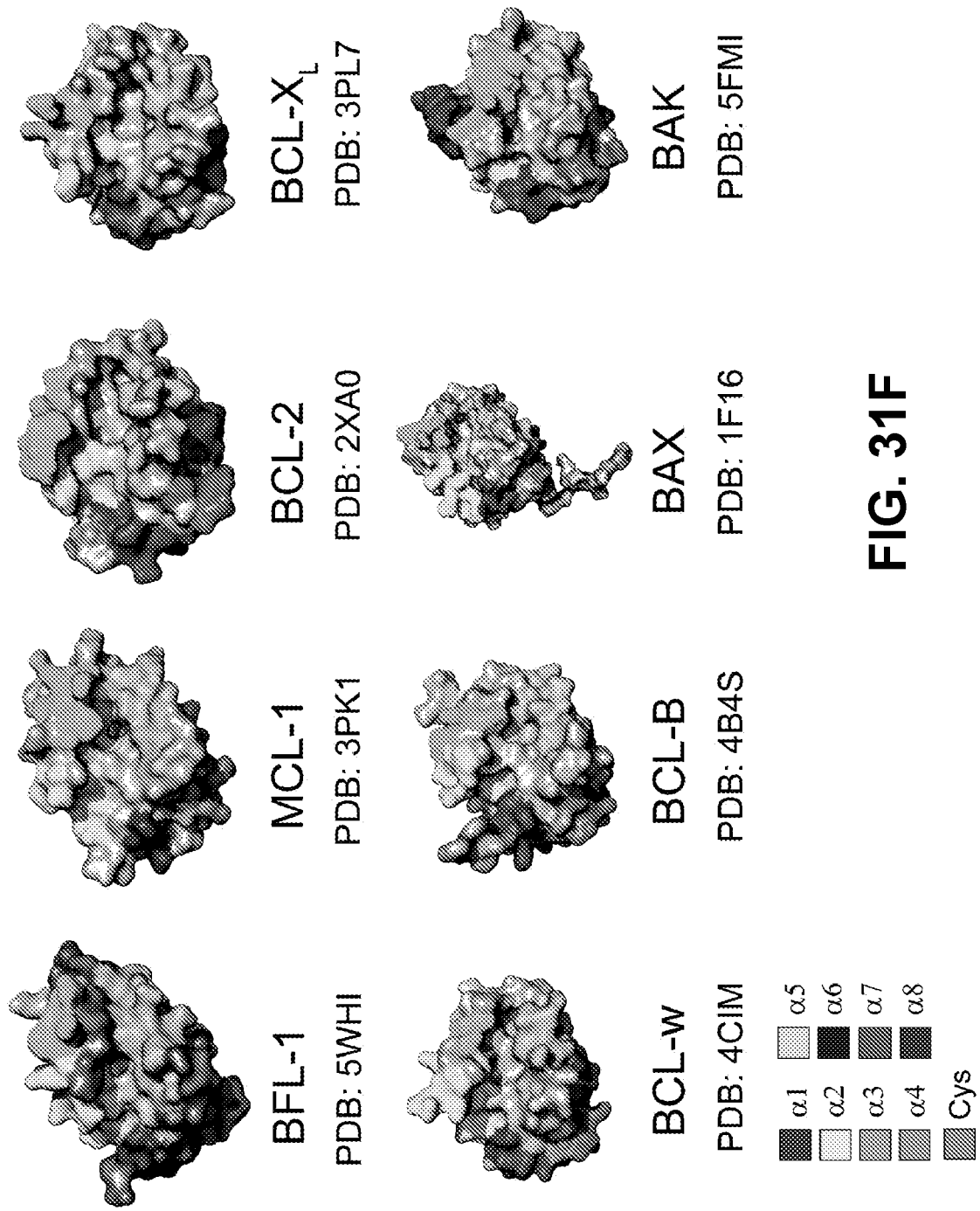
FIG. 31F shows a structural comparison of the BH3-binding grooves of BCL-2 family proteins, revealing that only BFL-1 contains a surface accessible cysteine residue.

One of the most intriguing differences among the structures of unliganded anti-apoptotic proteins is the presence of a solvent-exposed cysteine within the BH3-binding groove of apo BFL-1 (FIG. 31B). No such cysteine is found in apo MCL-1 or BCL-$X_L$, nor in any other BCL-2 family protein structure (FIG. 31E-F). This cysteine can indeed be exploited for stapled BIM and NOXA BH3-based covalent targeting of BFL-1 in vitro and in cells. Incorporation of cysteine-reactive warheads into small molecules resembling the BCL-2 or MCL-1 inhibitors can enable a switch in target specificity that favors BFL-1 inhibition. To provide a structural blueprint for such small molecule development and also analyze the conformational consequences of covalent BH3 engagement, the crystal structure of a cysteine-reactive stapled BH3 peptide in complex with BFL-1 was pursued next.

Covalent Targeting of BFL-1 C55 by DNA-NOXA SAHB

Figure 32B:
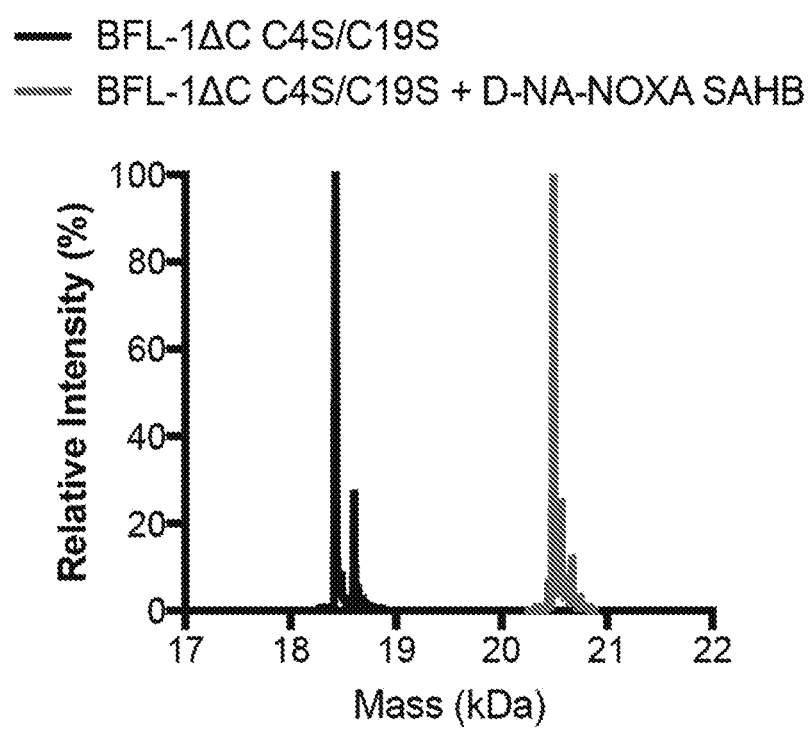
FIG. 32B provides intact mass spectrometry analysis demonstrating the gain in molecular weight of BFL-1ΔC C4S/C19S upon covalent reaction with D-NA-NOXA SAHB.
Figure 32C:
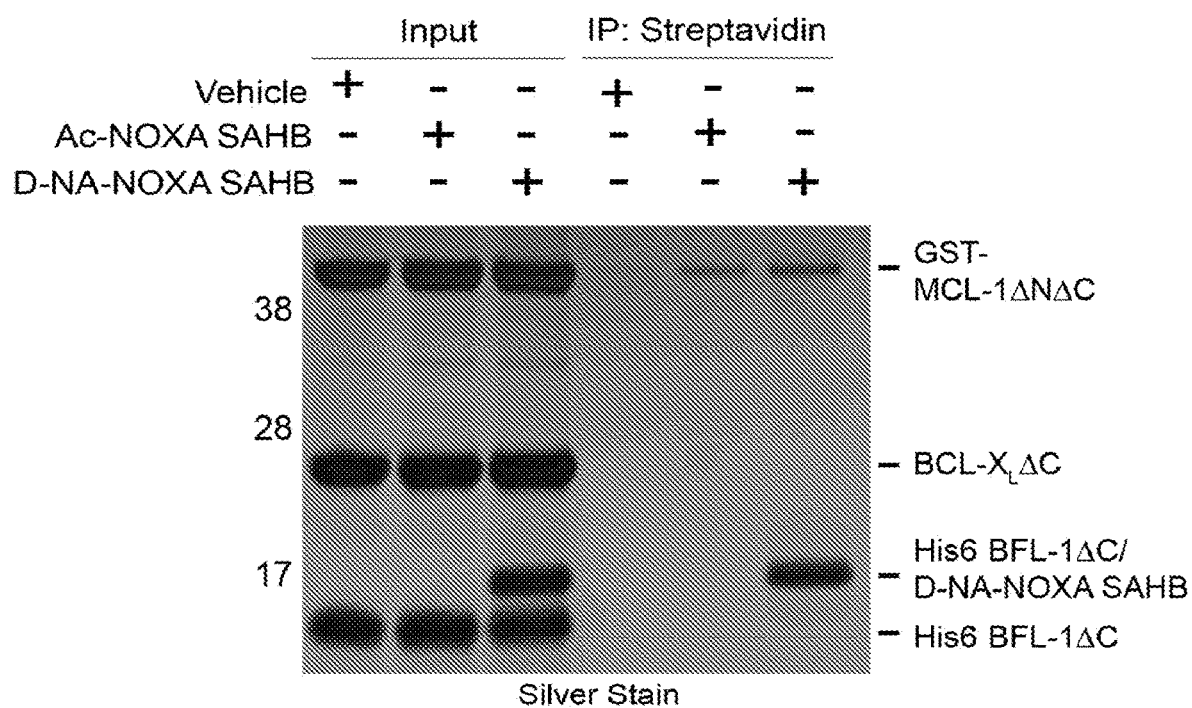
FIG. 32C shows the results of incubation of the indicated C-terminally biotinylated-NOXA SAHBs with a mixture of recombinant MCL-1, BCL-$X_L$, and BFL-1 proteins demonstrates selective covalent modification of BFL-1 by D-NA-NOXA SAHB (lane 3). Streptavidin pull downs revealed no interaction between NOXA SAHBs and BCL-$X_L$, and relatively minimal, equivalent engagement of MCL-1 (lanes 5-6). In contrast, D-NA-NOXA SAHB, but not Ac-NOXA SAHB, showed robust BFL-1 pull down, as demonstrated by silver stain (lane 6).
Figure 32D:
FIG. 32D is a blot showing lysates from BFL-1-expressing A375P melanoma cells that were subjected to the identical conditions described in FIG. 32C, followed by BFL-1 western blot of electrophoresed eluates from the streptavidin pull downs. Incubation with D-NA-NOXA SAHB resulted in markedly enhanced BFL-1 pull down compared to Ac-NOXA SAHB.

A series of D-nipecotic acid (D-NA)-derivatized stabilized alpha-helices of BCL-2 domains (SAHBs) modeled after the BH3-domain of human NOXA BH3 were generated—altering sequence composition, staple type and location—and the constructs were subjected to crystallization screening. Promising, reproducible crystals formed when BFL-1ΔC was complexed with a NOXA SAHB comprising amino acids 26-40 and an inserted i, i+7 staple at the 28,35 position (hereafter called D-NA-NOXA SAHB) (FIG. 32A). To verify the efficacy of site-selective derivatization of BFL-1 by D-NA-NOXA SAHB, a series of BFL-1 constructs (WT, C55S, C4S/C19S, C4S/C19S/C55S) were incubated with either an acetyl- or D-NA-capped NOXA SAHB, and BFL-1 crosslinking was monitored by electrophoresis and Coomassie stain. The only combinations of peptide and protein that led to a discrete increase in molecular weight was D-NA-NOXA SAHB with those BFL-1 constructs bearing C55, namely wild-type and C4S/C19S (FIG. 32A). Indeed, intact mass spectrometry documented complete conversion of BFL-1 C4S/C19S to the appropriately-sized D-NA-NOXA SAHB adduct upon peptide incubation (FIG. 32B). The BFL-1 targeting capability of biotinylated D-NA-NOXA SAHB was validated in a competitive streptavidin pull-down assay using a mixture of recombinant MCL-1, BCL-$X_L$, and BFL-1 proteins, all of which contain cysteines. Whereas both Ac-NOXA SAHB and D-NA-NOXA SAHB pulled down a similarly small amount of MCL-1, only D-NA-NOXA SAHB caused both robust derivatization of BFL-1, as seen in the input lane, and substantial pull-down of BFL-1 (FIG. 32C). Finally, to validate this activity in the context of a complex protein lysate, Ac- and D-NA-derivatized NOXA SAHBs were incubated with lysates from BFL-1-expressing A375P melanoma cells, and again markedly increased pull-down of native BFL-1 protein was noted for the warhead-bearing NOXA SAHB (FIG. 32D).

Crystal Structure of the/BFL-1/D-NA-NOXA SAHB Complex

Figure 33A:
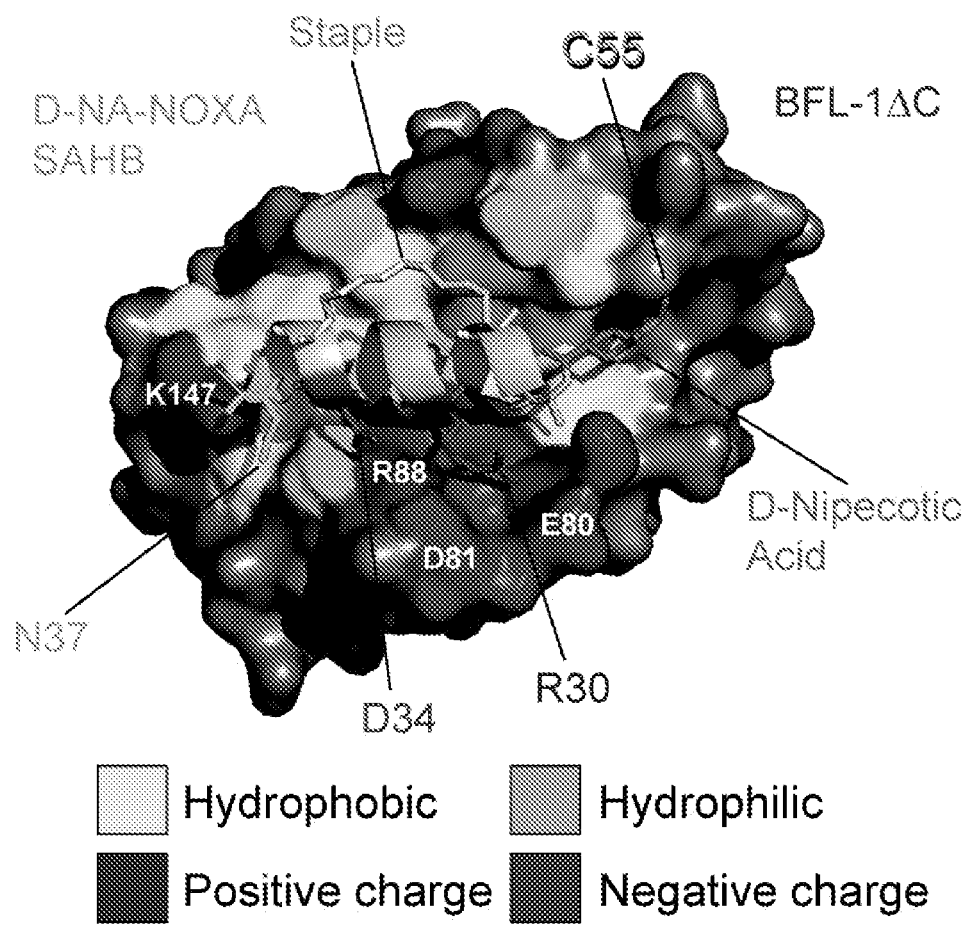
FIG. 33A shows the crystal structure of the D-NA-NOXA SAHB/BFL-1ΔC complex (PDB ID: 5WHH) demonstrating the complementary hydrophilic interactions between the amphipathic BH3 helix and BFL-1, with the i, i+7 staple observed in cis orientation and located on the non-interacting surface.
Figure 33B:
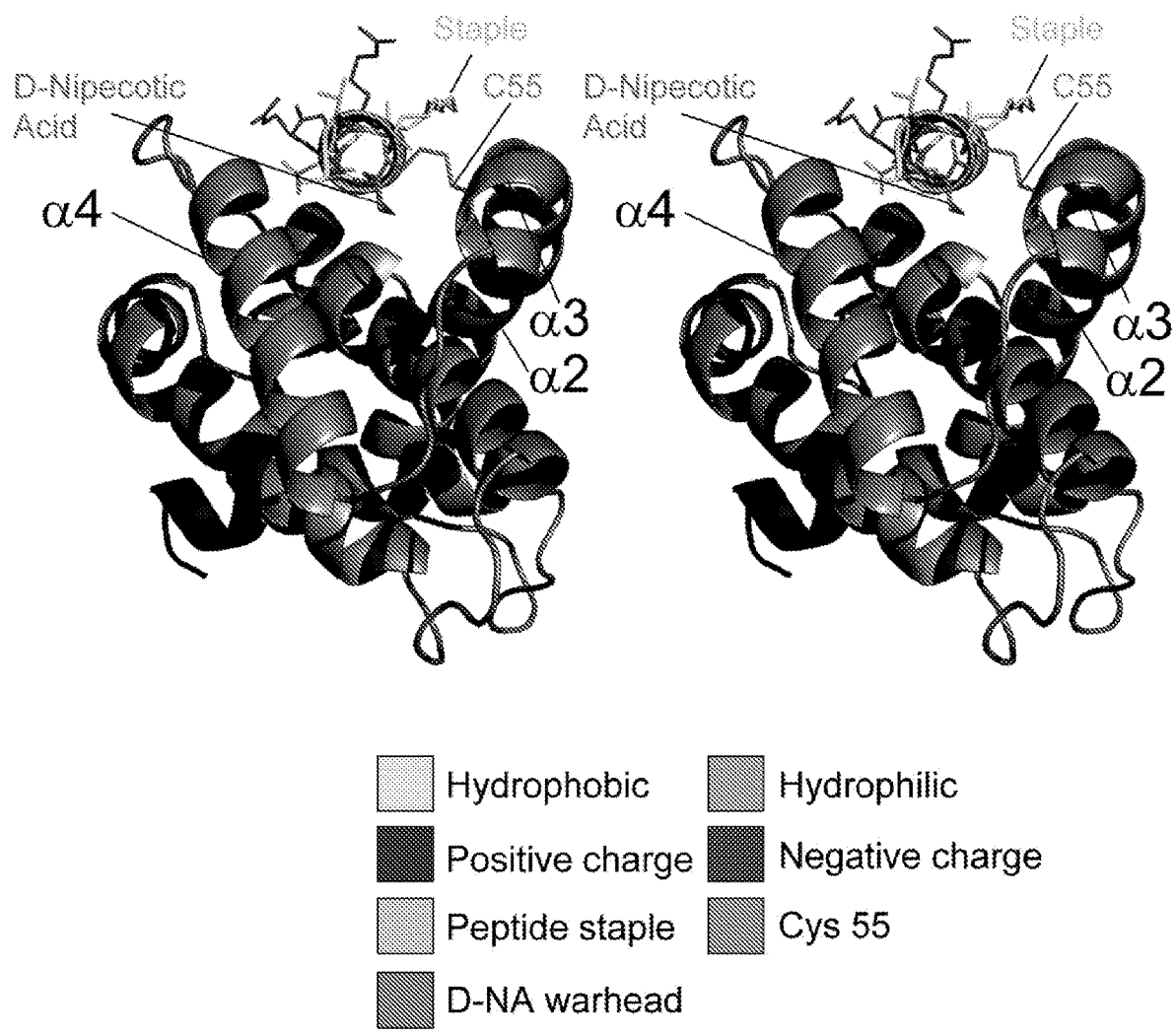
FIG. 33B shows a stereoview of the BFL-1/D-NA-NOXA SAHB covalent complex.
Figure 33C:
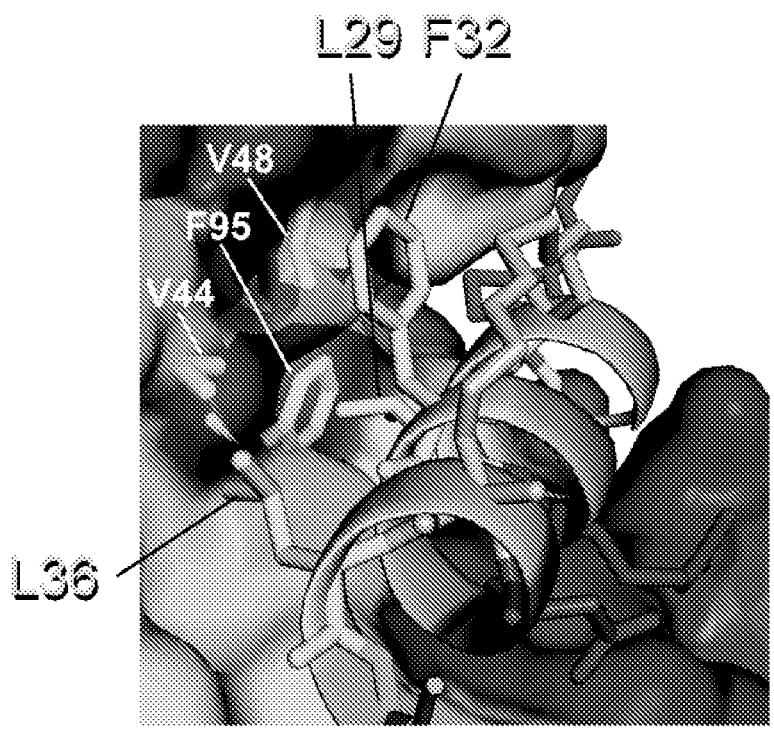
FIG. 33C shows the crystal structure of the D-NA-NOXA SAHB/BFL-1ΔC complex demonstrating the complementary hydrophobic interactions between the amphipathic BH3 helix and BFL-1, with the i, i+7 staple observed in cis orientation and located on the non-interacting surface.
Figure 33D:
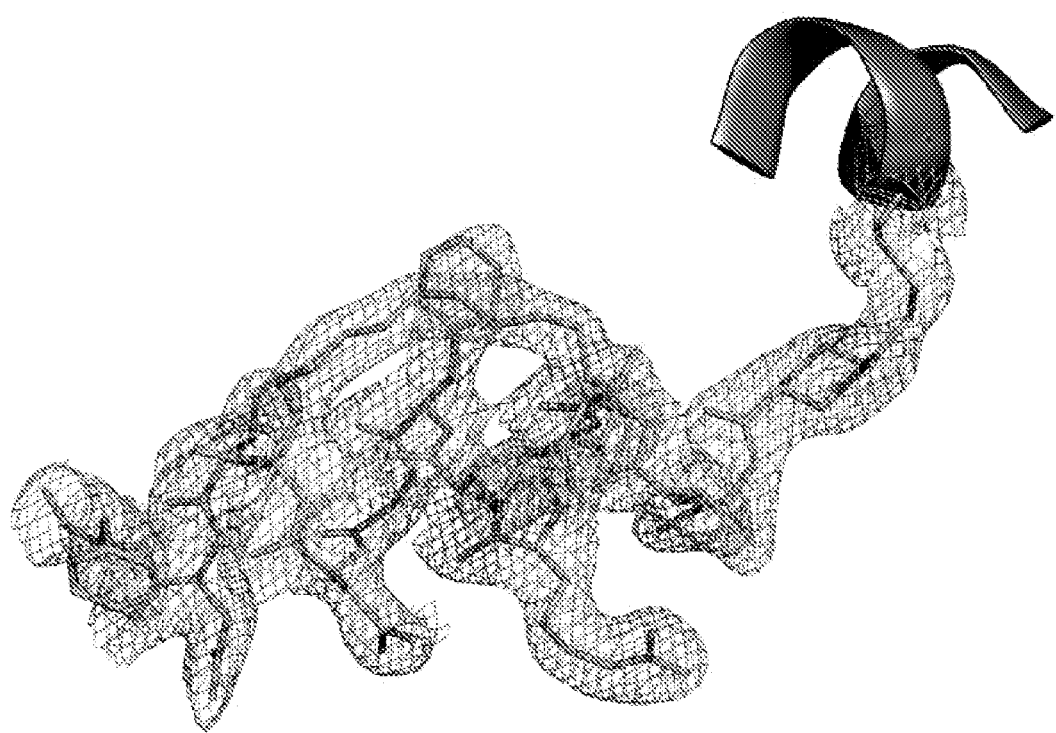
FIG. 33D identifies the covalent bond between C55 of BFL-1 and the D-NA moiety.
Figure 33E:
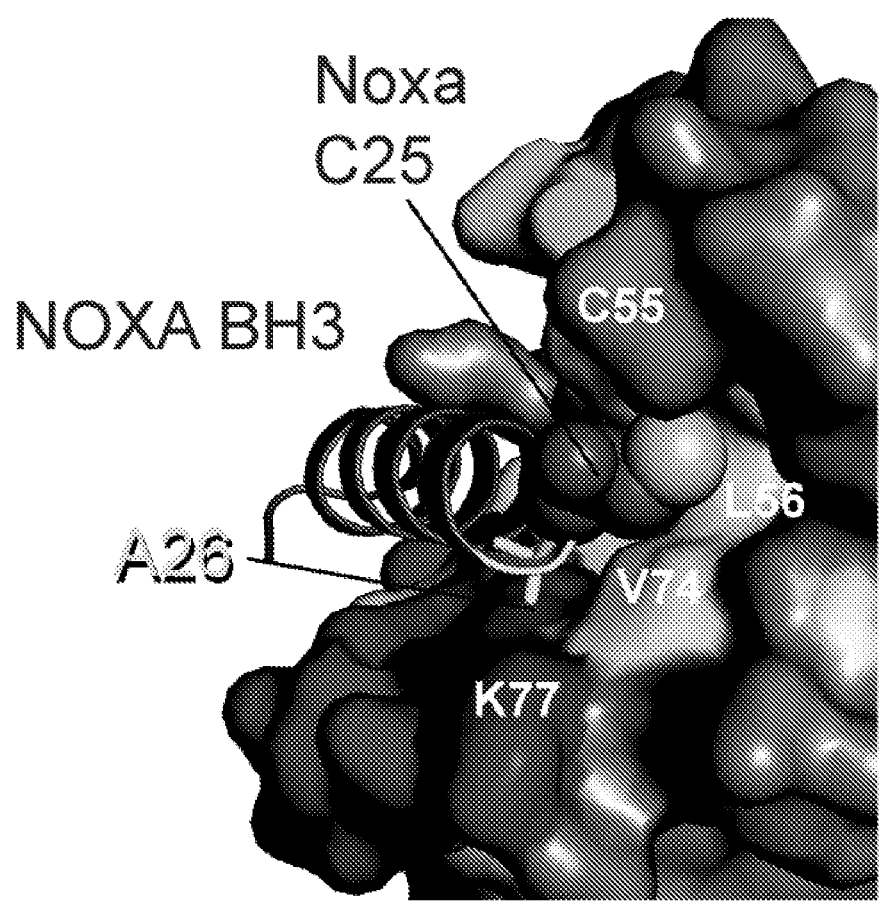
FIG. 33E shows the noncovalent NOXA BH3 (PDB ID: 3MQP) complexes with BFL-1/A1.
Figure 33F:
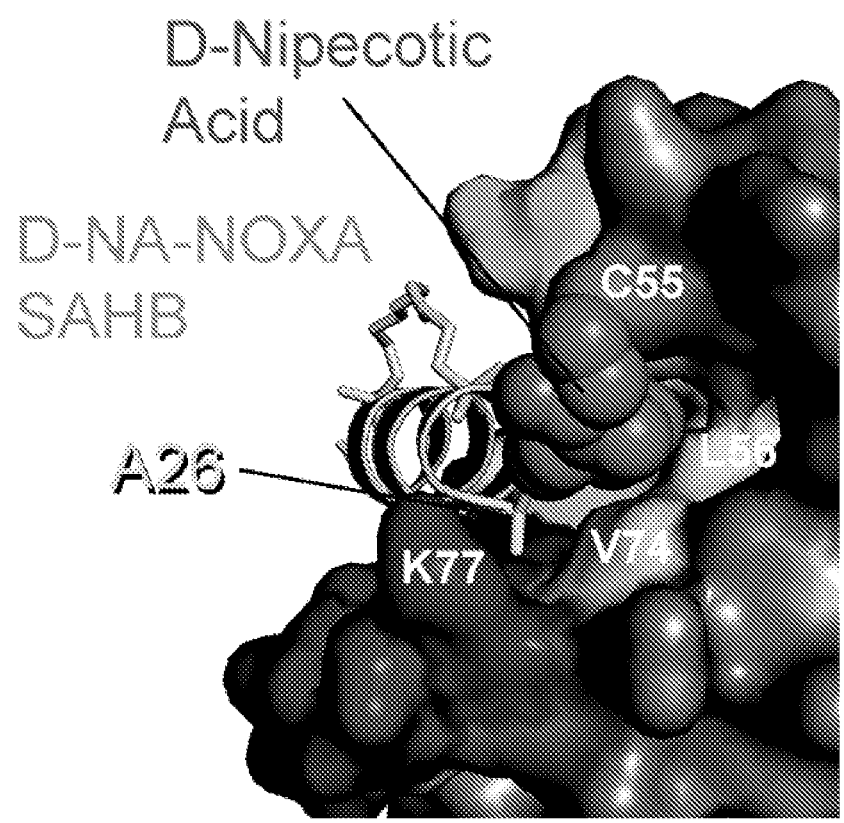
FIG. 33F shows the covalent D-NA-NOXA SAHB complex with BFL-1.

Having documented the robust BFL-1-targeting capacity of D-NA-NOXA SAHB, the crystal structure of its complex with BFL-1ΔC (C4S/C19S) was solved at 2.38 Å resolution (FIG. 33A-B, FIG. 30, PDB ID: 5WHH). All ligand atoms generated excellent electron density, showing the stapled peptide bound in the groove defined by α2-α4, with a calculated interface area per molecule of 771 Å². The hydrophilic residues R30, D34, and N37 of the amphipathic α-helix make complementary electrostatic and hydrogen-bonding interactions with E80/D81, R88, and K147 of the BFL-1 surface, respectively (FIG. 33A). Residues L29, F32, and L36 of the hydrophobic face of D-NA-NOXA SAHB directly engage the respective residues F95, V44/V48, and V40/V90 of the canonical hydrophobic groove (FIG. 33C). The i, i+7 staple is observed in the cis configuration and is predominantly solvent-exposed (FIG. 33A-C). In addition, the covalent bond between C55 and the acrylamide moiety of D-NA is readily visualized (FIG. 33D). Whereas the acrylamide moiety maintains a similar orientation as NOXA BH3 C25 with respect to BFL-1 C55 (FIG. 33E-F), the piperidine group of D-NA fortuitously engages a complementary hydrophobic pocket formed by residues L52, L56, V74, and F95 at the BFL-1 surface (FIG. 33F-3G). Thus, the chemical structure of the installed acrylamide-bearing moiety itself provides an opportunity to facilitate further BFL-1 interaction at the hydrophobic groove.

Figure 34A:
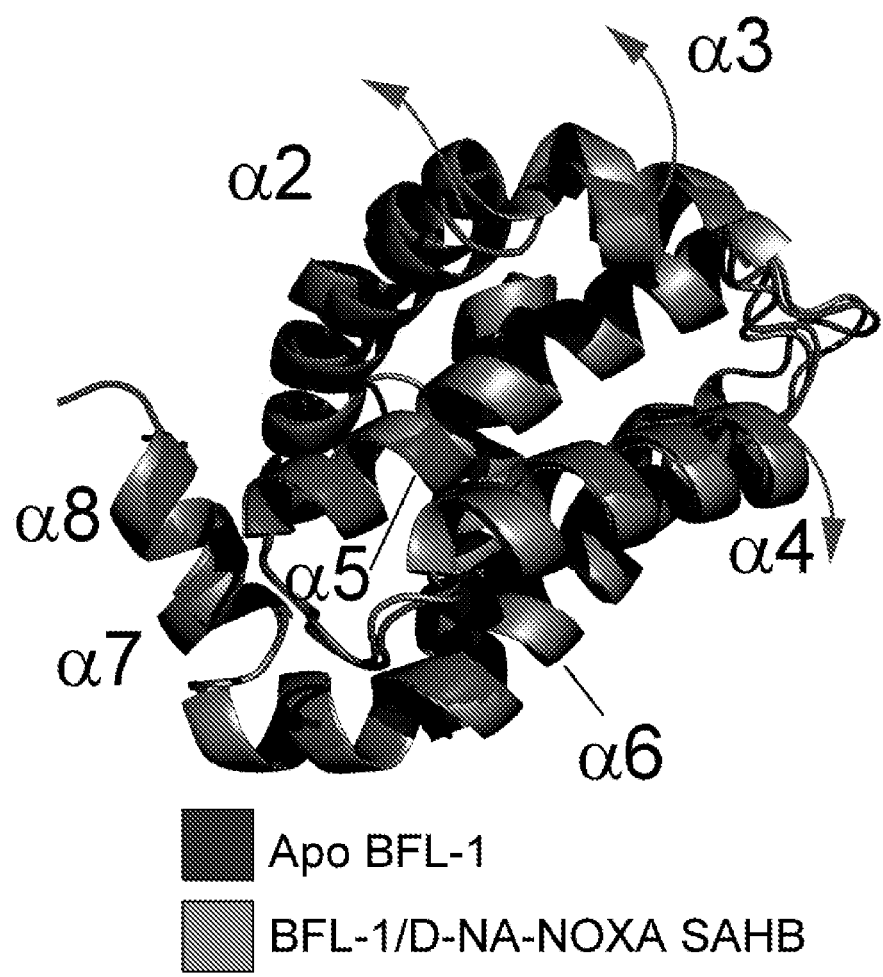
FIG. 34A is a ribbon overlay of the apo and D-NA-NOXA SAHB-bound structures of BFL-1, demonstrating the relative upward displacement of α2 and α3, and downward displacement of α4, upon covalent ligand interaction.
Figure 34C:
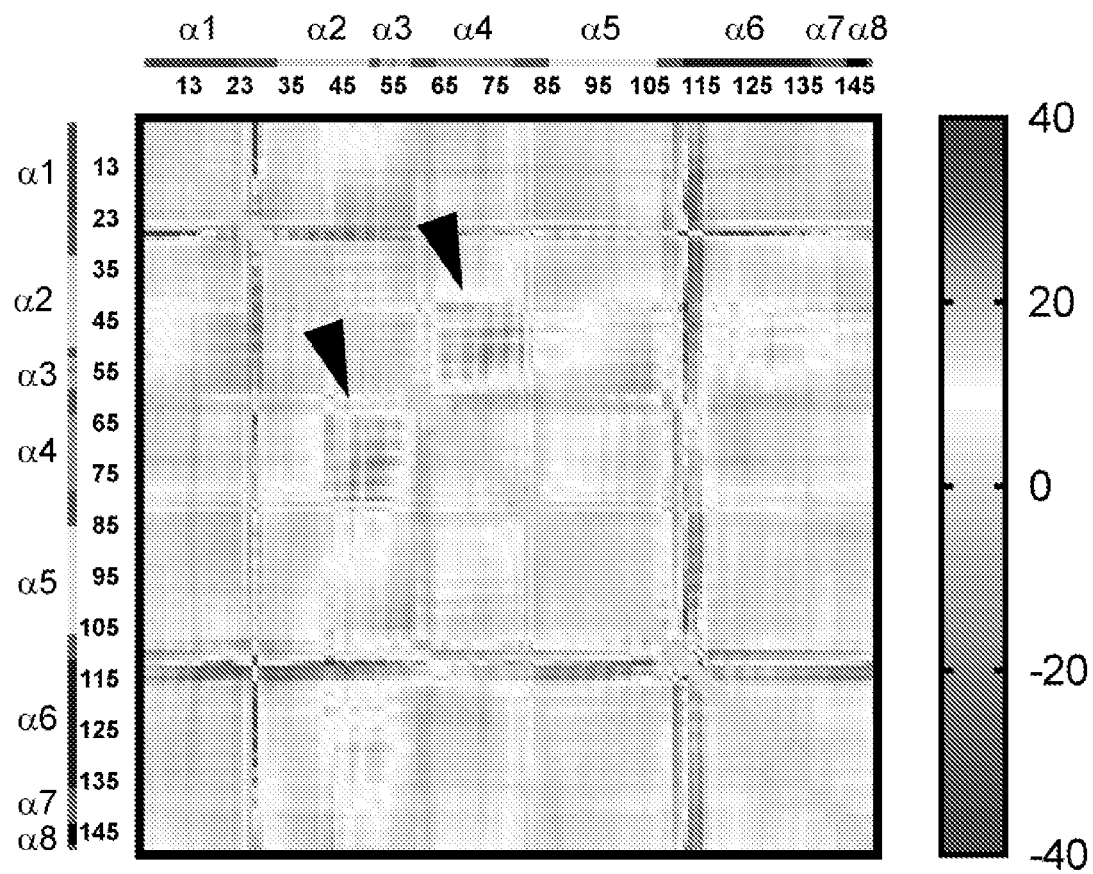
FIG. 34C shows focal changes that are evident in the corresponding difference distance matrix plot (see black arrowheads).
Figure 34D:
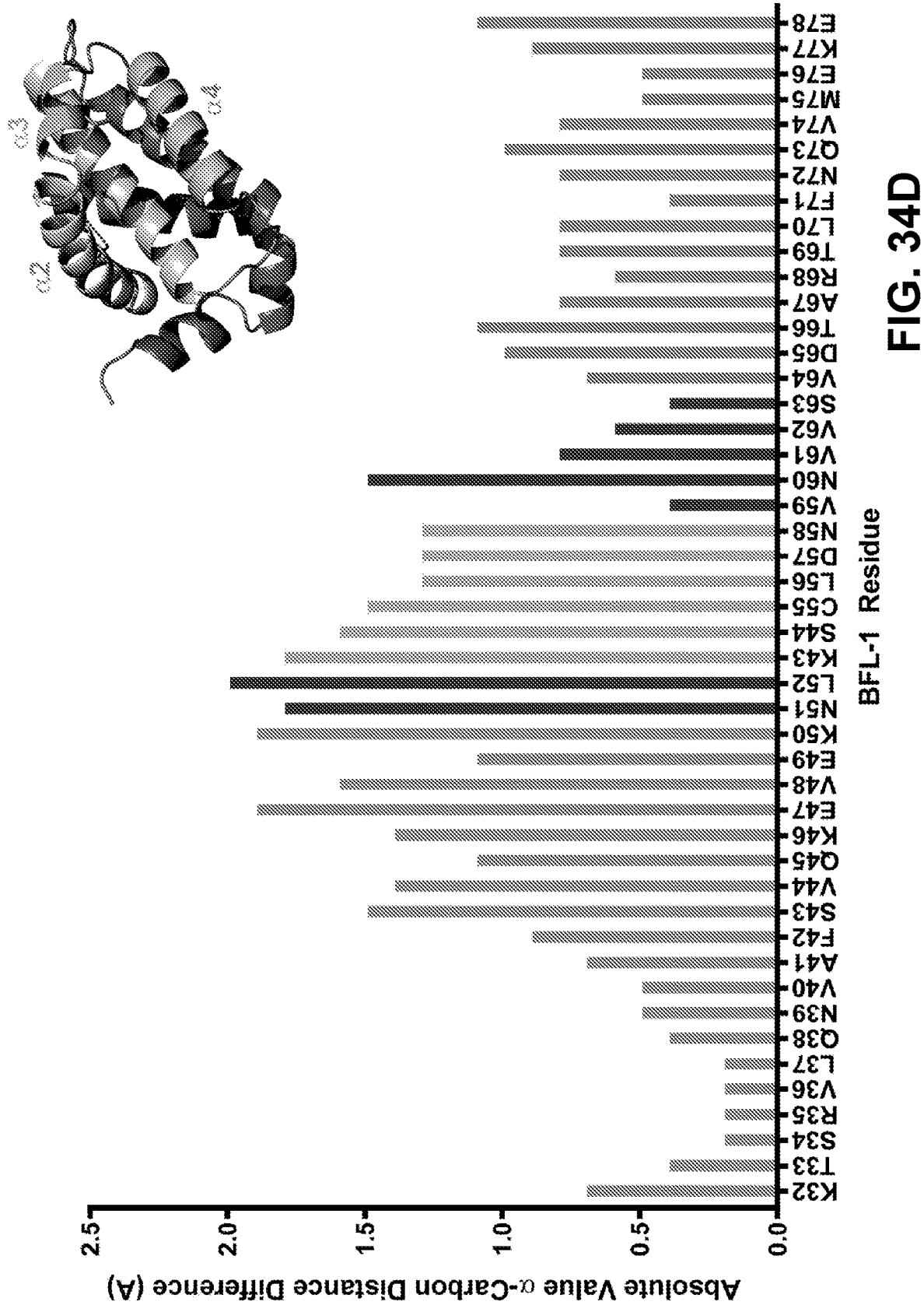
FIG. 34D shows a plot of the α-carbon distance differences upon covalent engagement of BFL-1 by D-NA-NOXA SAHB quantitatively demonstrates the displacement of residues within the α2-α4 region of the BH3-binding groove.

Solving both the apo and SAHB-derivatized structures of BFL-1 afforded a comparison of the unliganded and liganded conformations. Upon BFL-1 interaction, D-NA-NOXA SAHB induces a conformational "opening" of the groove, such that $\alpha 2/\alpha 3$ and $\alpha 4$ are displaced away from each other by 2.8 Å, when comparing, for example, the distances between the $\alpha$-carbons of residues 55 and 70 of the apo and BH3-bound forms (FIG. 34A-B). This discrete structural change is demonstrated quantitatively by a difference distance matrix plot of BFL-1/D-NA-NOXA SAHB versus apo BFL-1 (FIG. 34C-D). An RMSD value of 0.897 for the comparison between all conserved $\alpha$-carbons of the two BFL-1 structures underscores the significance of the conformational change.

Figure 33G:
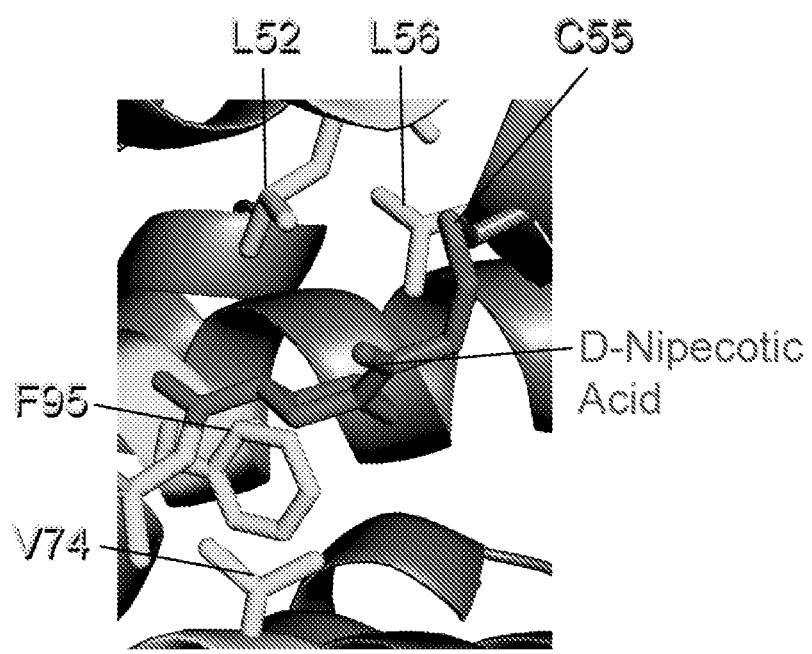
FIG. 33G demonstrates how the D-NA moiety engages in supplementary contacts with residues of a hydrophobic cavity located subjacent to C55.
Figure 34E:
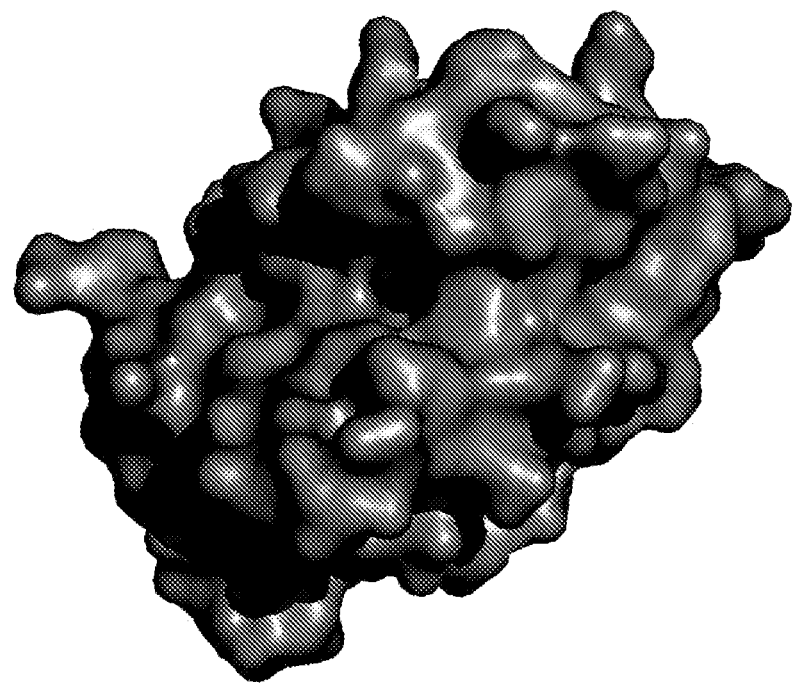
FIG. 34E shows the apo form of BFL-1ΔC.
Figure 34F:
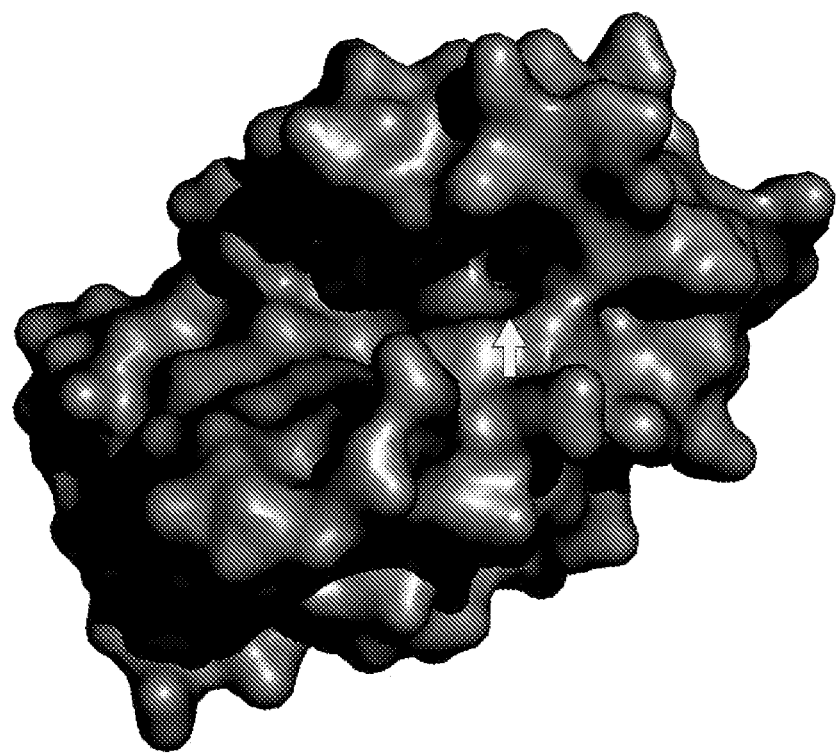
FIG. 34F shows that the liganded form of BFL-1ΔC results in a larger interaction surface, which includes the formation of a discrete hydrophobic cavity subjacent to C55 (see white arrow).
Figure 35A:
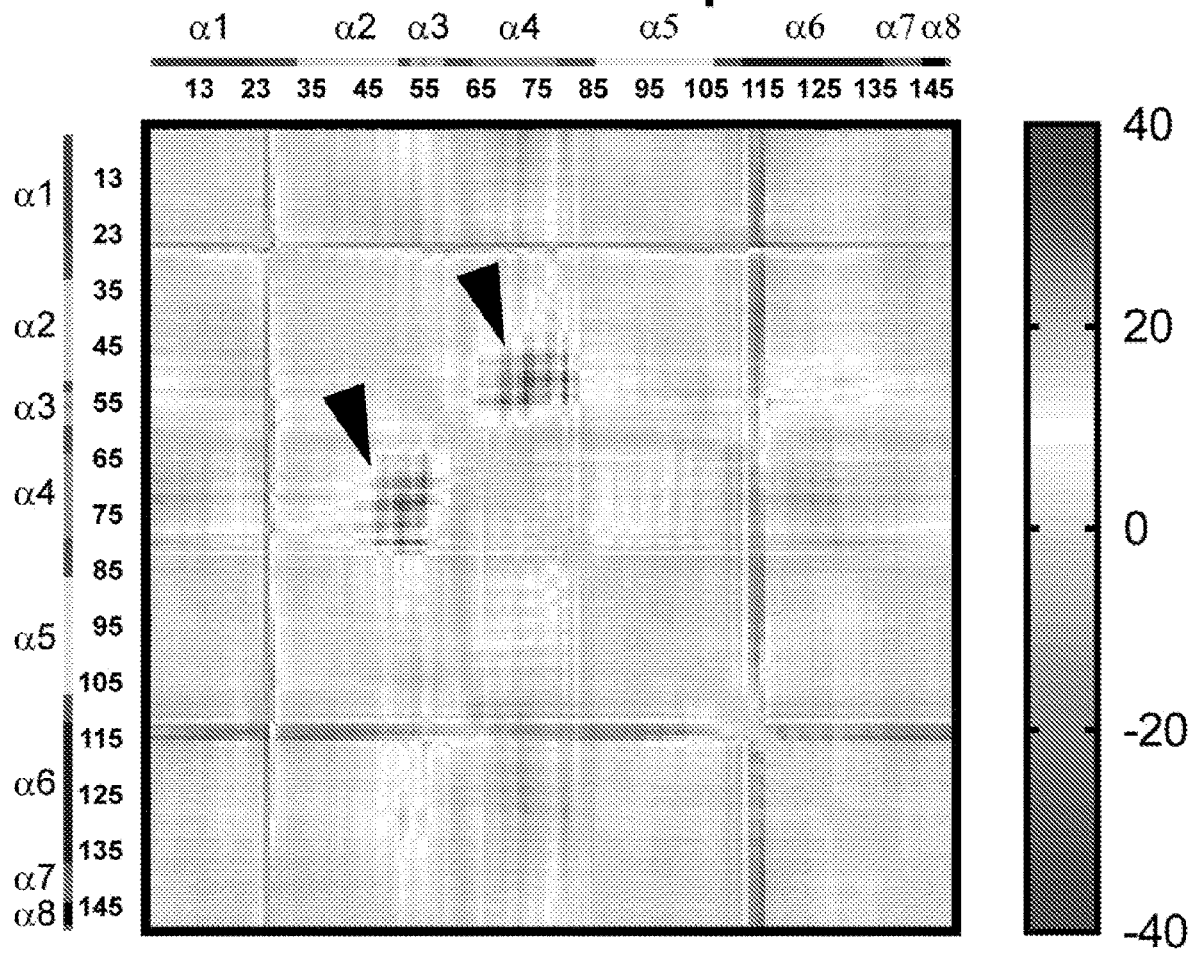
FIG. 35A shows a difference distance matrix plot for NOXA BH3 non-covalent engagement with BFL-1, revealing focal changes in the α2-α4 region (see black arrowheads) similar to that observed upon covalent BH3 targeting.
Figure 35B:
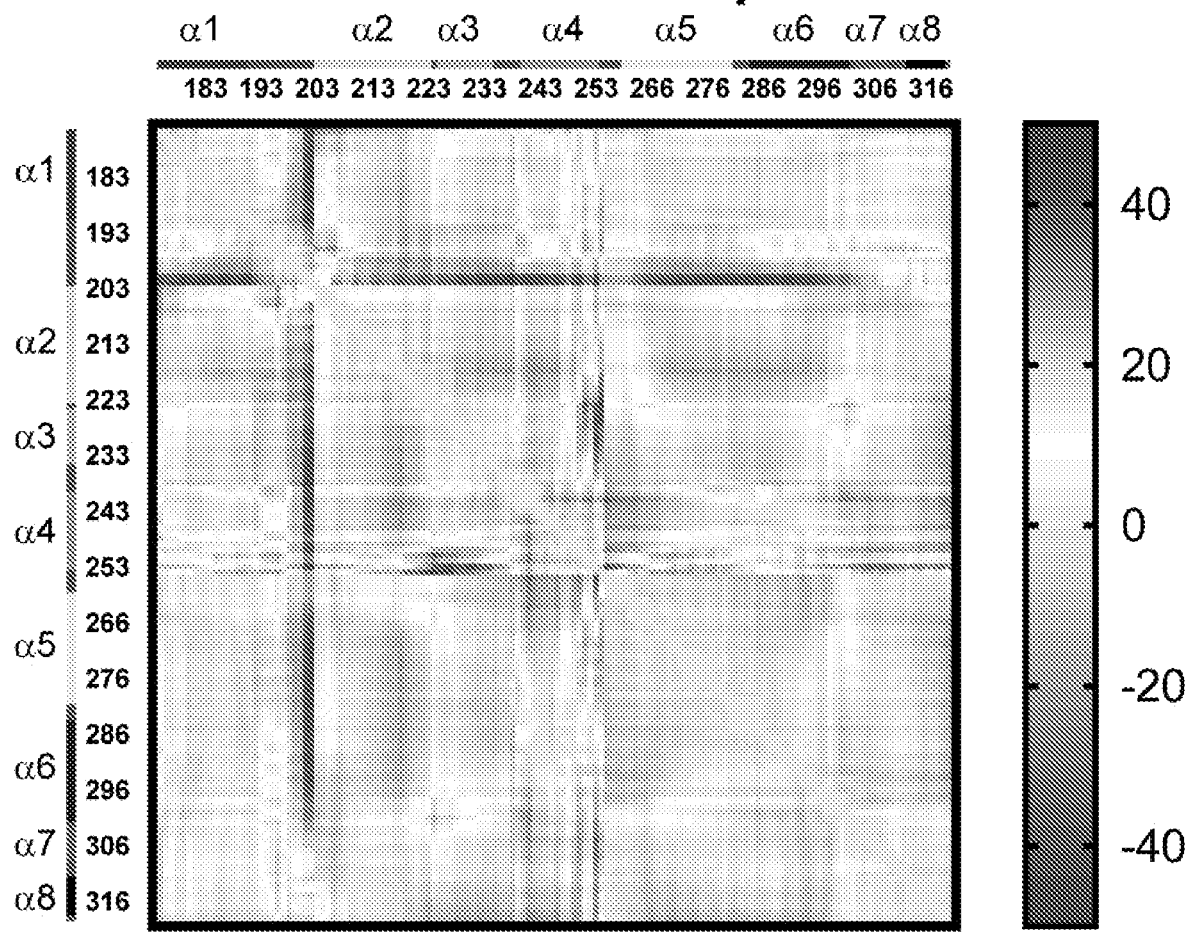
FIG. 35B shows a difference distance matrix plot for murine NOXA BH3 non-covalent engagement with MCL-1, notably lacking the focal α2-α4 region changes observed for the NOXA BH3 interactions (covalent and non-covalent) with BFL-1.

The observed SAHB-induced remodeling of the BFL-1 canonical groove is notable for the formation of a new surface pocket subjacent to BFL-1 C55 (FIG. 34E). This surface change is also evident upon BFL-1 interaction with an unstapled NOXA BH3 peptide, underscoring the general relevance of this finding beyond conformational accommodation to the hydrocarbon staple or the acrylamide moiety (FIG. 35A). Importantly, this change in groove topography upon NOXA BH3 interaction is unique to BFL-1, in that structural comparison of unliganded and NOXA BH3-bound MCL-1 shows no such remodeling, and distance measurements between residues at the top and bottom of the groove are largely unchanged (FIG. 34B, 35B). Indeed, the similarity of the MCL-1 groove between unbound and bound structures, a reflection of BH3-binding accessibility, may explain the relatively high affinity of MCL-1 for diverse BH3 domain helices. This conformational difference between MCL-1 and BFL-1 may likewise explain why both the Ac- and D-NA-derivatized forms of NOXA SAHB can engage MCL-1 non-covalently, whereas the foreshortened Ac-NOXA SAHB has little to no interaction with BFL-1 unless equipped with the cysteine-reactive warhead. Given the potential energetic requirements associated with pocket opening, the irreversible nature of covalent reaction with the surface accessible C55 residue of BFL-1 may provide a substantial binding advantage. Ultimately, compounds that mimic NOXA BH3 in the C25 region and induce formation of this distinctive pocket (FIG. 33F-G, 34E) could yield novel agents with preferential selectivity for BFL-1 over MCL-1, as exemplified by D-NA-NOXA SAHB (FIG. 32C).

Conclusion

Solving the structure of apo BFL-1 provided the first opportunity to compare the BH3-liganded and unliganded forms of BFL-1, revealing structural differences in its surface groove. Importantly, the distinct topography of the unliganded groove can be exploited for small molecule discovery by in silico screening, and the structures of putative hits in complex with BFL-1 obtained by soaking a molecule of interest into the apo crystal. The unoccupied BFL-1 groove likewise demonstrates the surface accessibility of a uniquely-positioned cysteine residue, available for selective covalent targeting by cysteine-reactive stapled peptides and potentially by small molecule mimetics thereof. Indeed, the structure of BFL-1 in complex with a D-nipecotic acid-derivatized NOXA BH3 $\alpha$-helix, reinforced by an i, i+7 staple, reveals both ligand-induced opening of the surface pocket and the creation of a small cavity subjacent to the disulfide bond amenable to supplementary hydrophobic interactions.

In this first structure of a covalent complex between BFL-1 and a stapled BH3 peptide, it was demonstrated that an installed i, i+7 staple localizes to the non-interacting face of the helix, preserves the native interactions between NOXA BH3 and BFL-1, and remodels groove topography to maximize ligand-target engagement. By installing the acrylamide-bearing moiety, which irreversibly reacts with C55 located within the canonical groove of BFL-1, the non-covalent MCL-1-binding preference of this shortened, i, i+7-stapled NOXA BH3 construct was transformed into a robust, covalent inhibitor of BFL-1. Taken together, these structural and biochemical results inform new opportunities to develop highly selective BFL-1-targeting agents and dual BFL-1/MCL-1 inhibitors for clinical use.

Example 5: Further Validation of the Selective Synergy of Cysteine-Reactive NOXA SAHBs and Targeted Inhibition of the DNA Damage Response Pathway in Reactivating Cell Death in BFL-1-Dependent AML Cell Lines To investigate the ability of NOXA-15 R31E SAHB to synergize with a DNA damage response pathway member, U937 cells or MV4;11 cells were treated with D-NA-NOXA SAHB and/or the ATM inhibitor AZD0156 and cell viability and caspase-3/7 activation was measured. NOXA-15 R31E SAHB demonstrated selective cytotoxicity and synergy upon combination with AZD0156 in U937 cells (which are BFL-1-dependent), but not in MV4;11 cells (which are not BFL-1-dependent) (FIGS. 40-43).

Figure 44:
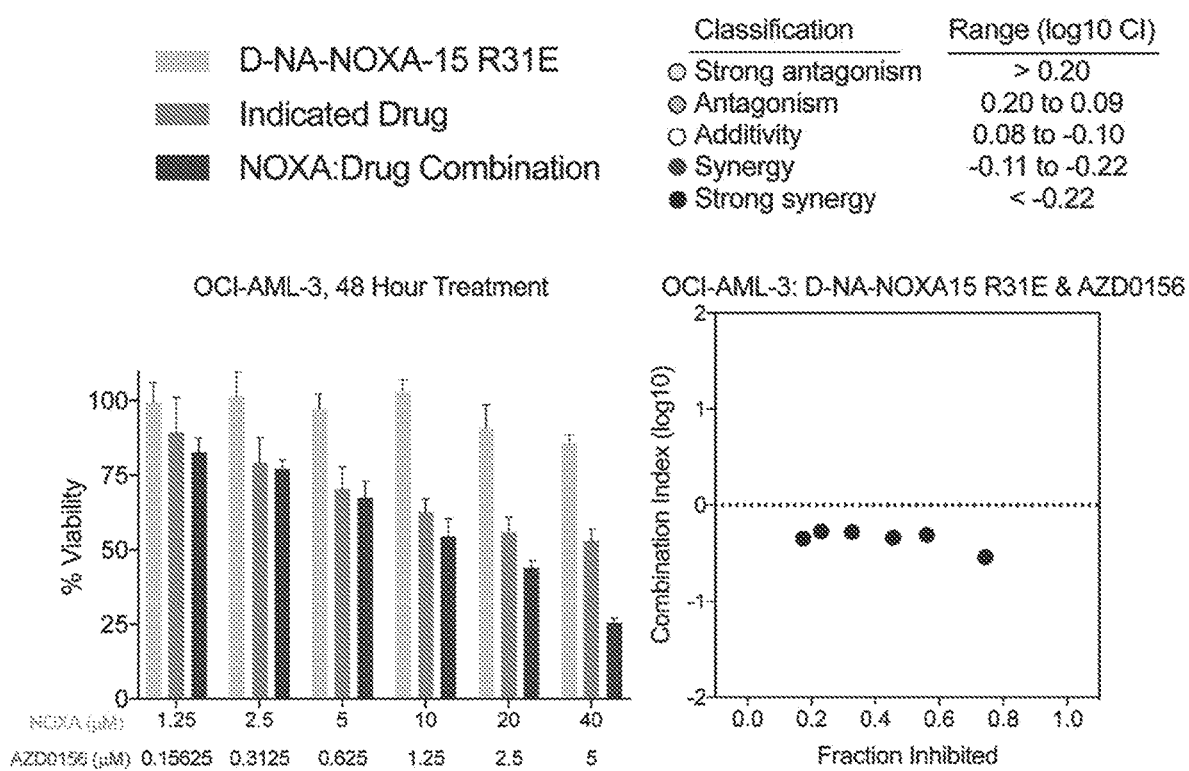
FIG. 44 are graphs showing that treatment of BFL-1-dependent OCI-AML-3 cells with the combination of cysteine-reactive NOXA-15 R31E and the ATM inhibitor AZD0156 caused a synergistic decrease in cell viability (left), as reflected by Calcusyn analysis dose-effect plot (right). Left panel: for each concentration in the left panel, the bars are (from left to right): (i) D-NA-NOXA-15 R31E, (ii) Indicated Drug, and (iii) NOXA:Drug Combination. Right panel: each dot in the plot is classified as "Strong synergy".
Figure 45:
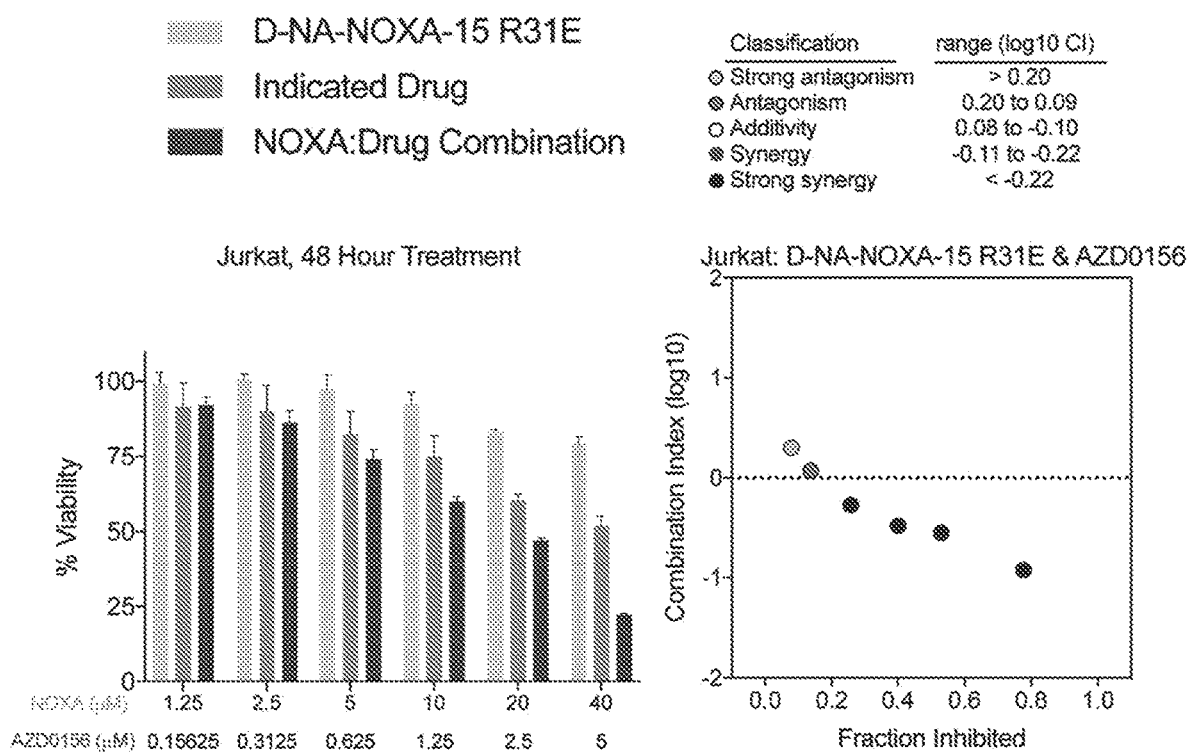
FIG. 45 are graphs showing that treatment of BFL-1-dependent Jurkat cells with the combination of cysteine-reactive NOXA-15 R31E and the ATM inhibitor AZD0156 caused a synergistic decrease in cell viability (left), as reflected by Calcusyn analysis dose-effect plot (right). Left panel: for each concentration in the left panel, the bars are (from left to right): (i) D-NA-NOXA-15 R31E, (ii) Indicated Drug, and (iii) NOXA:Drug Combination. Right panel: the dots are (from left to right): (i) strong antagonism, (ii) antagonism, (iii) strong synergy, (iv) strong synergy, (v) strong synergy, and (vi) strong synergy.
Figure 46:
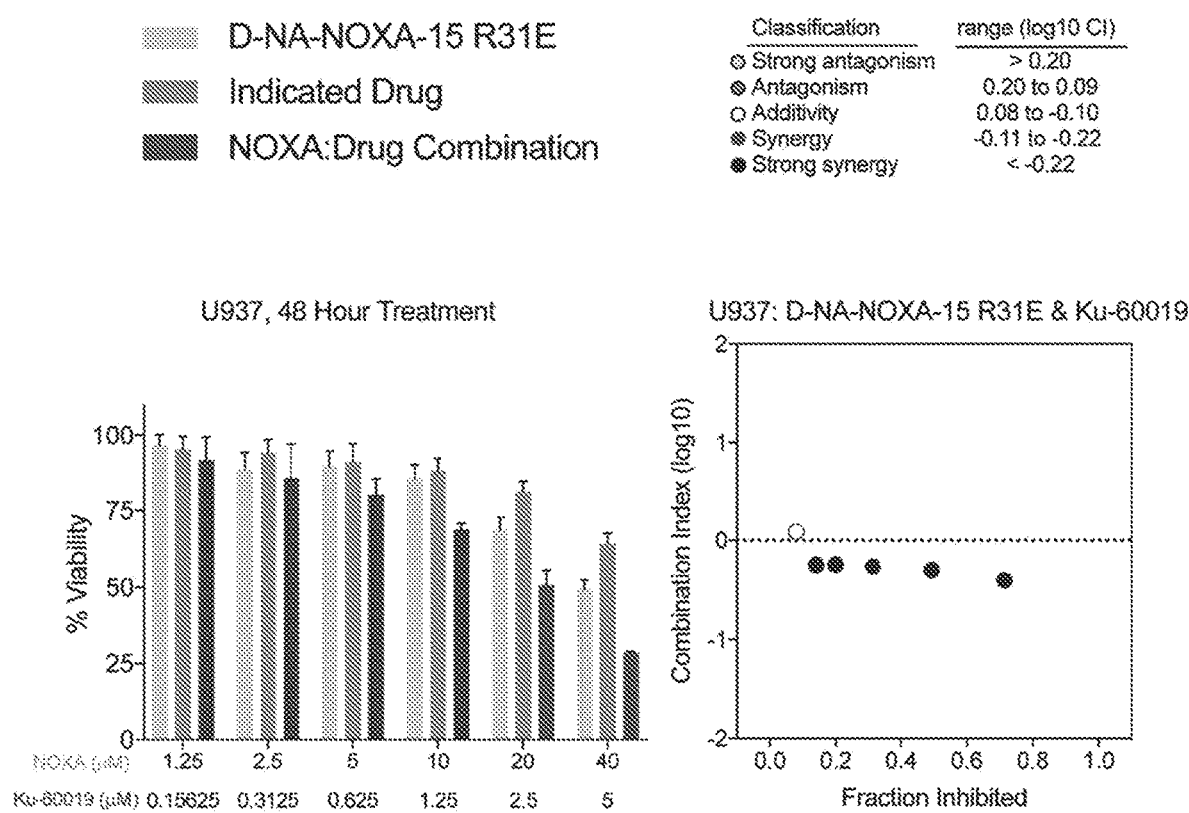
FIG. 46 are graphs showing that treatment of BFL-1-dependent U937 cells with the combination of cysteine-reactive NOXA-15 R31E and the ATM inhibitor Ku-60019 caused a synergistic decrease in cell viability (left), as reflected by Calcusyn analysis dose-effect plot (right). Left panel: for each concentration in the left panel, the bars are (from left to right): (i) D-NA-NOXA-15 R31E, (ii) Indicated Drug, and (iii) NOXA:Drug Combination. Right panel: the dots are (from left to right): (i) additivity, (ii) strong synergy, (iii) strong synergy, (iv) strong synergy, (v) strong synergy, and (vi) strong synergy.
Figure 47:
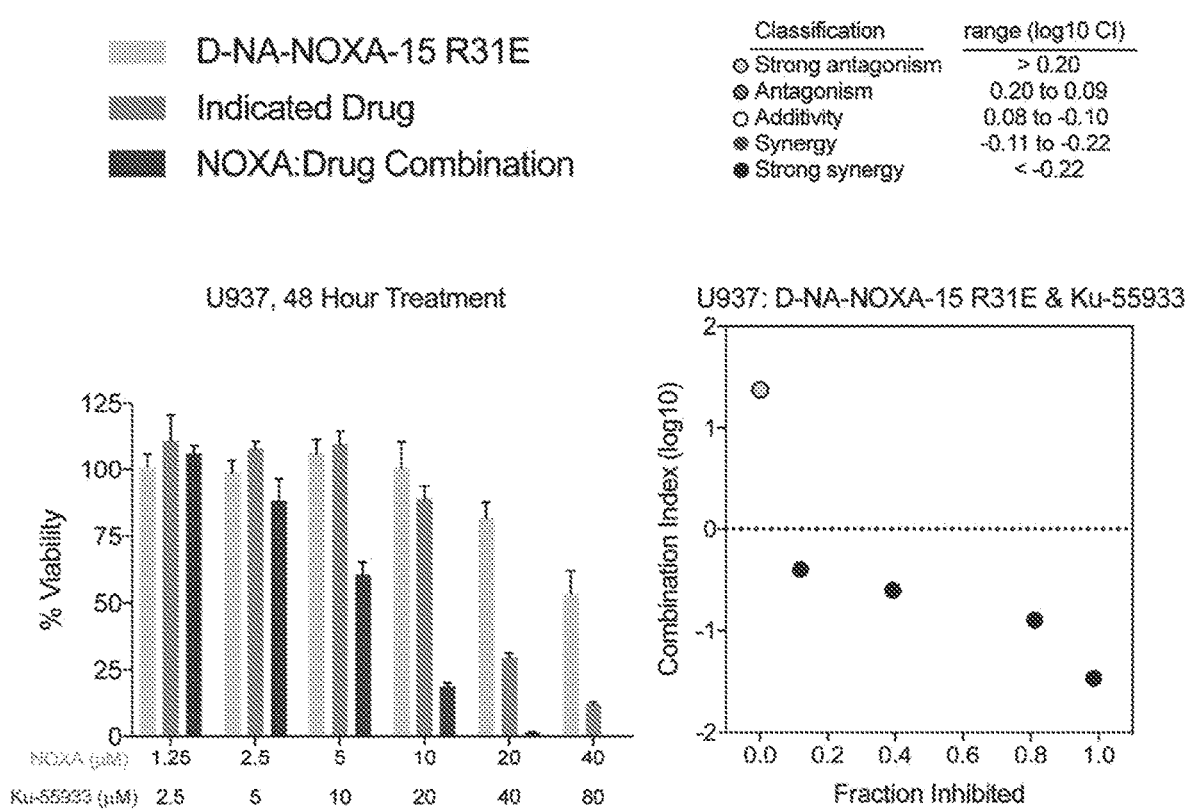
FIG. 47 are graphs showing that treatment of BFL-1-dependent U937 cells with the combination of cysteine-reactive NOXA-15 R31E and the ATM inhibitor Ku-55933 caused a synergistic decrease in cell viability (left), as reflected by Calcusyn analysis dose-effect plot (right). Left panel: for each concentration in the left panel, the bars are (from left to right): (i) D-NA-NOXA-15 R31E, (ii) Indicated Drug, and (iii) NOXA:Drug Combination. Right panel: the dots are (from left to right): (i) strong antagonism, (ii) strong synergy, (iii) strong synergy, (iv) strong synergy, and (v) strong synergy.
Figure 48:
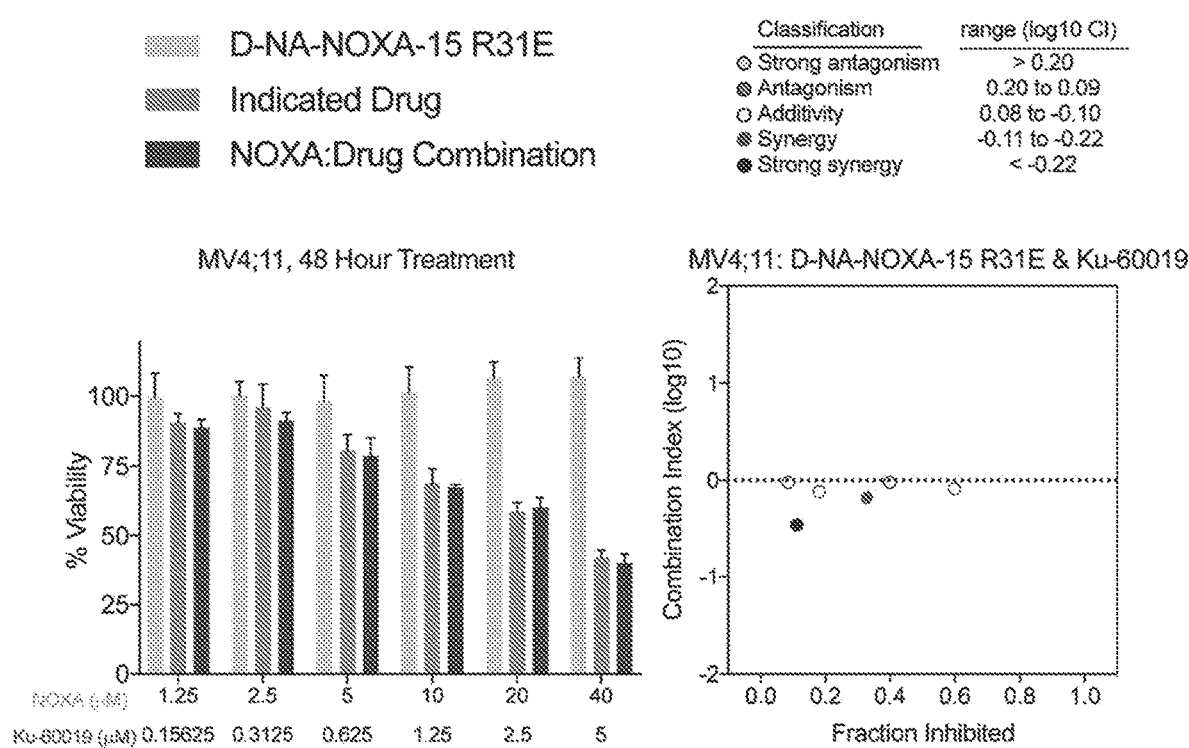
FIG. 48 are graphs showing that co-treatment of the MV4;11 cell line, which is not dependent on BFL-1, resulted in little to no cytotoxic synergy of cysteine-reactive NOXA-15 R31E and the ATM inhibitor Ku-60019. Left panel: for each concentration in the left panel, the bars are (from left to right): (i) D-NA-NOXA-15 R31E, (ii) Indicated Drug, and (iii) NOXA:Drug Combination. Right panel: the dots are (from left to right): (i) additivity, (ii) strong synergy, (iii) additivity, (iv) synergy, (v) additivity, and (vi) additivity.
Figure 49:
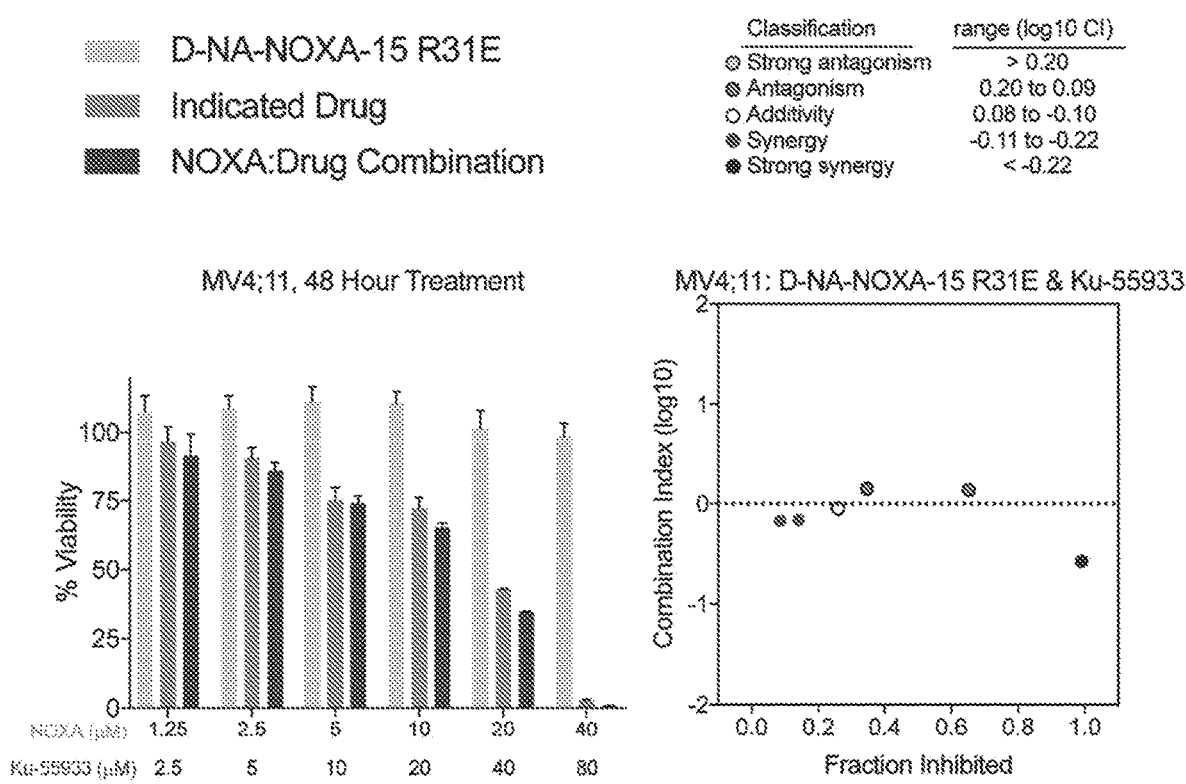
FIG. 49 are graphs showing that co-treatment of the MV4;11 cell line, which is not dependent on BFL-1, resulted in little to no cytotoxic synergy of cysteine-reactive NOXA-15 R31E and the ATM inhibitor Ku-55933. Left panel: for each concentration in the left panel, the bars are (from left to right): (i) D-NA-NOXA-15 R31E, (ii) Indicated Drug, and (iii) NOXA:Drug Combination. Right panel: the dots are (from left to right): (i) synergy, (ii) synergy, (iii) additivity, (iv) antagonism, (v) antagonism, and (vi) strong synergy.
Figure 50:
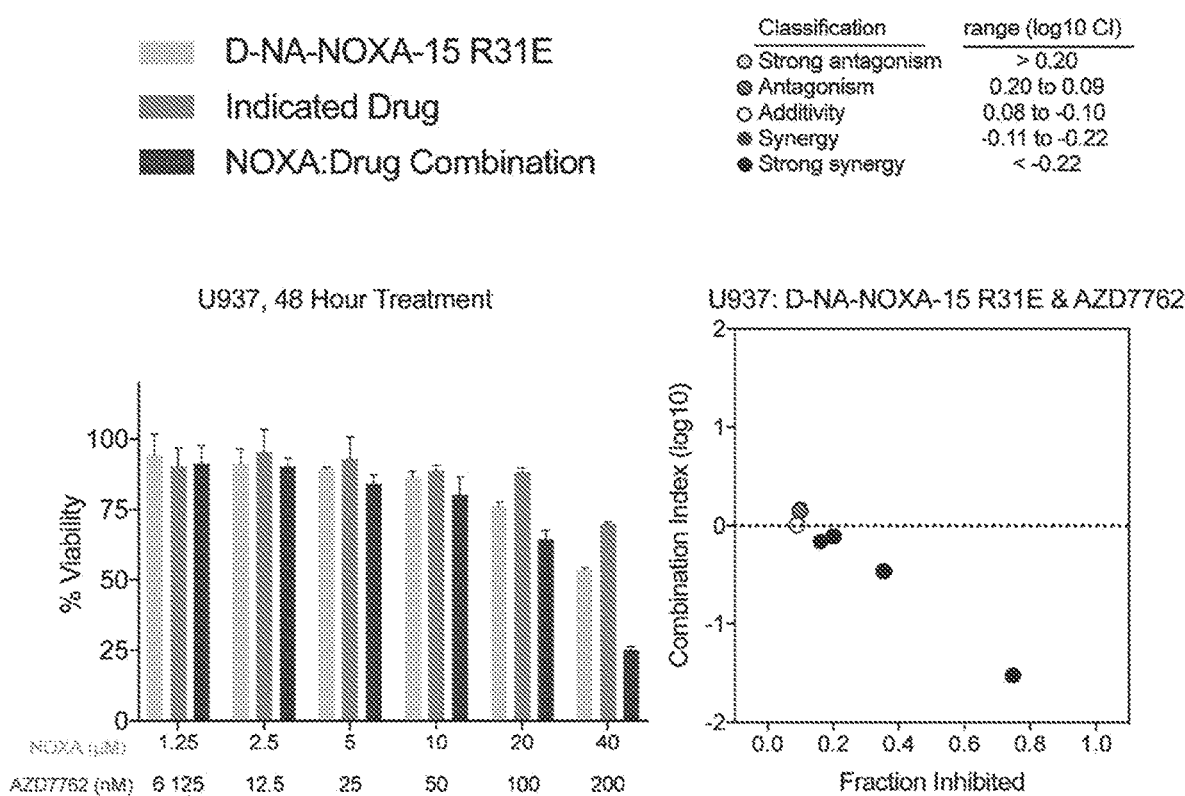
FIG. 50 are graphs showing that treatment of BFL-1-dependent U937 cells with the combination of cysteine-reactive NOXA-15 R31E and the CHK1/2 inhibitor AZD7762 caused a synergistic decrease in cell viability (left), as reflected by Calcusyn analysis dose-effect plot (right). Left panel: for each concentration in the left panel, the bars are (from left to right): (i) D-NA-NOXA-15 R31E, (ii) Indicated Drug, and (iii) NOXA:Drug Combination. Right panel: the dots are (from left to right): (i) additivity, (ii) antagonism, (iii) strong synergy, (iv) strong synergy, (v) strong synergy, and (vi) strong synergy.
Figure 51:
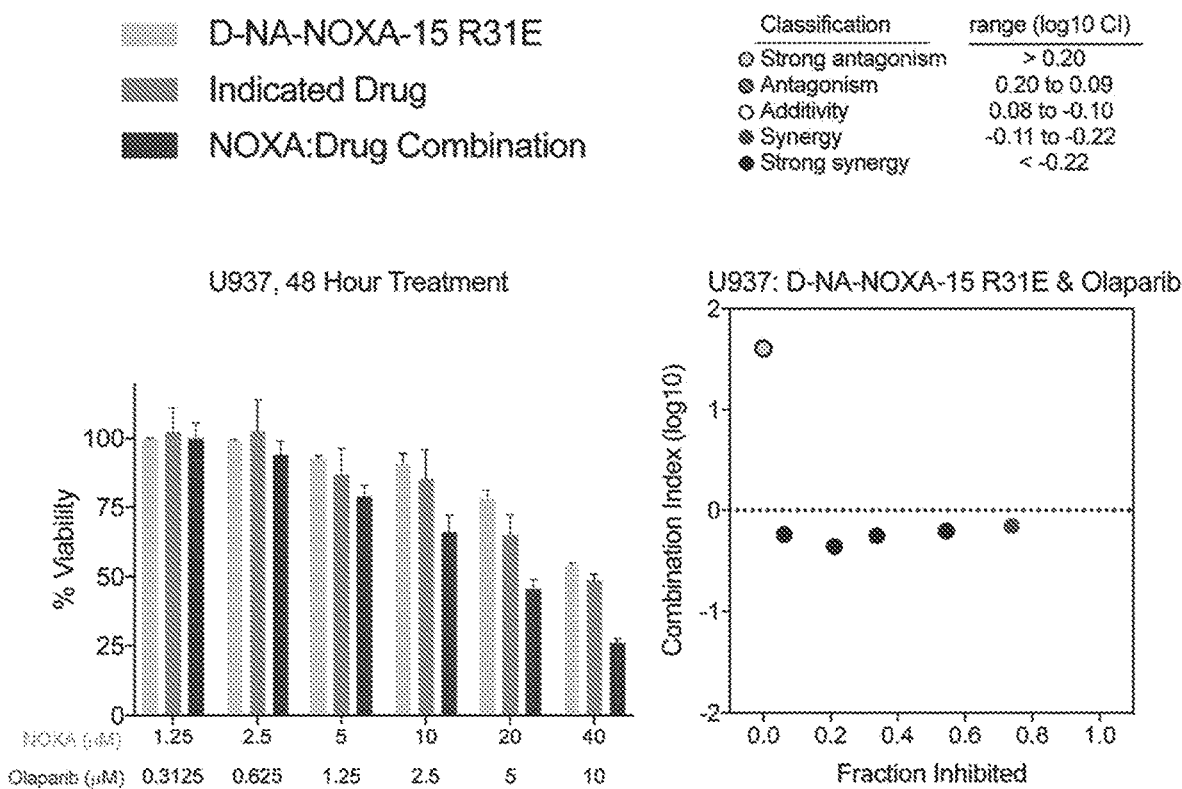
FIG. 51 are graphs showing that treatment of BFL-1-dependent U937 cells with the combination of cysteine-reactive NOXA-15 R31E and the PARP inhibitor Olaparib caused a synergistic decrease in cell viability (left), as reflected by Calcusyn analysis dose-effect plot (right). Left panel: for each concentration in the left panel, the bars are (from left to right): (i) D-NA-NOXA-15 R31E, (ii) Indicated Drug, and (iii) NOXA:Drug Combination. Right panel: the dots are (from left to right): (i) strong antagonism, (ii) strong synergy, (iii) strong synergy, (iv) strong synergy, (v) strong synergy, and (vi) synergy.
Figure 52:
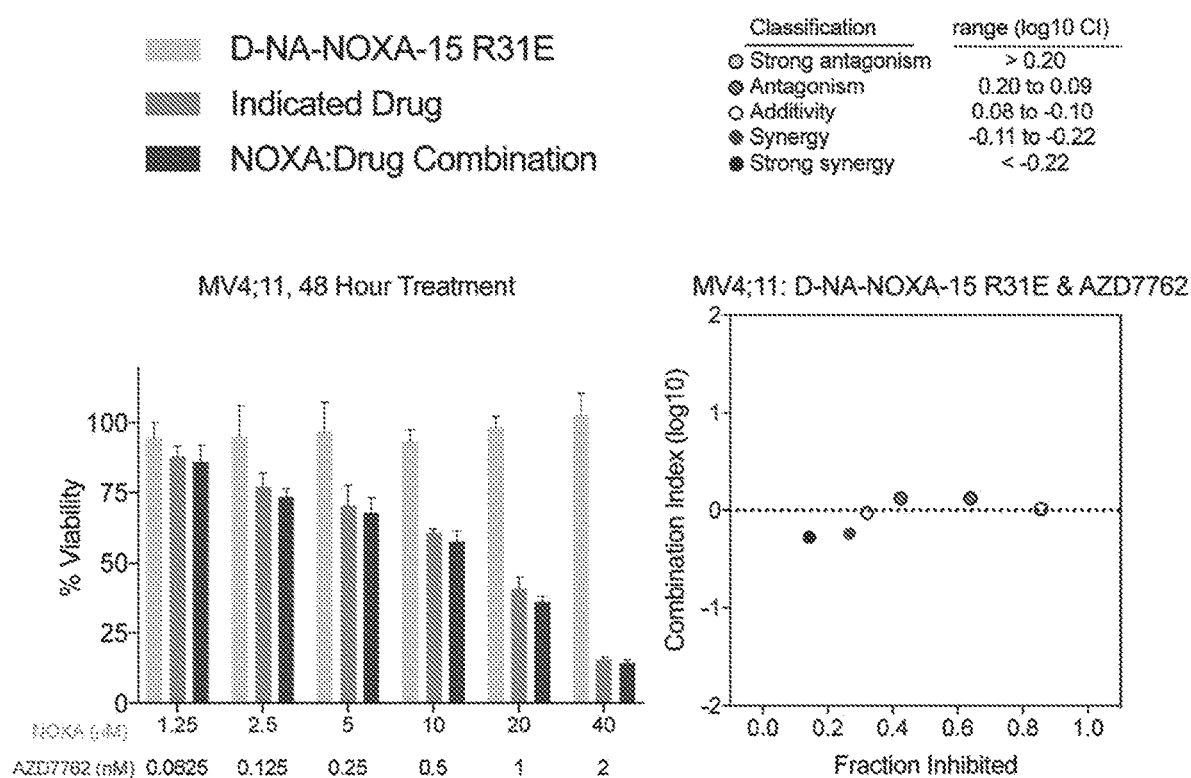
FIG. 52 are graphs showing that co-treatment of the MV4;11 cell line, which is not dependent on BFL-1, resulted in little to no cytotoxic synergy of cysteine-reactive NOXA-15 R31E and the CHK1/2 inhibitor AZD7762. Left panel: for each concentration in the left panel, the bars are (from left to right): (i) D-NA-NOXA-15 R31E, (ii) Indicated Drug, and (iii) NOXA:Drug Combination. Right panel: the dots are (from left to right): (i) strong synergy, (ii) synergy, (iii) additivity, (iv) antagonism, (v) antagonism, and (vi) additivity.
Figure 53:
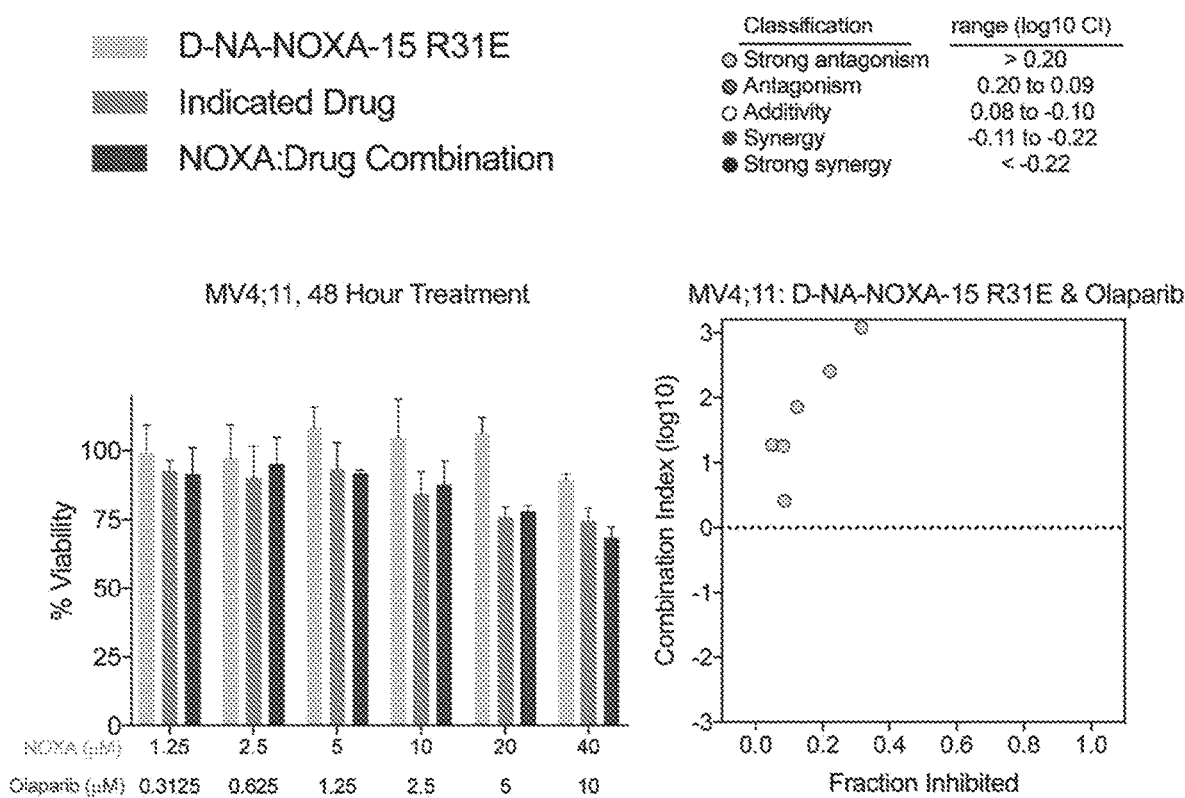
FIG. 53 are graphs showing that co-treatment of the MV4;11 cell line, which is not dependent on BFL-1, resulted in no cytotoxic synergy of cysteine-reactive NOXA-15 R31E and the PARP inhibitor Olaparib. Left panel: for each concentration in the left panel, the bars are (from left to right): (i) D-NA-NOXA-15 R31E, (ii) Indicated Drug, and (iii) NOXA:Drug Combination. Right panel: each of the six dots are strong antagonism.
Figures 54A, 54B, 54C:
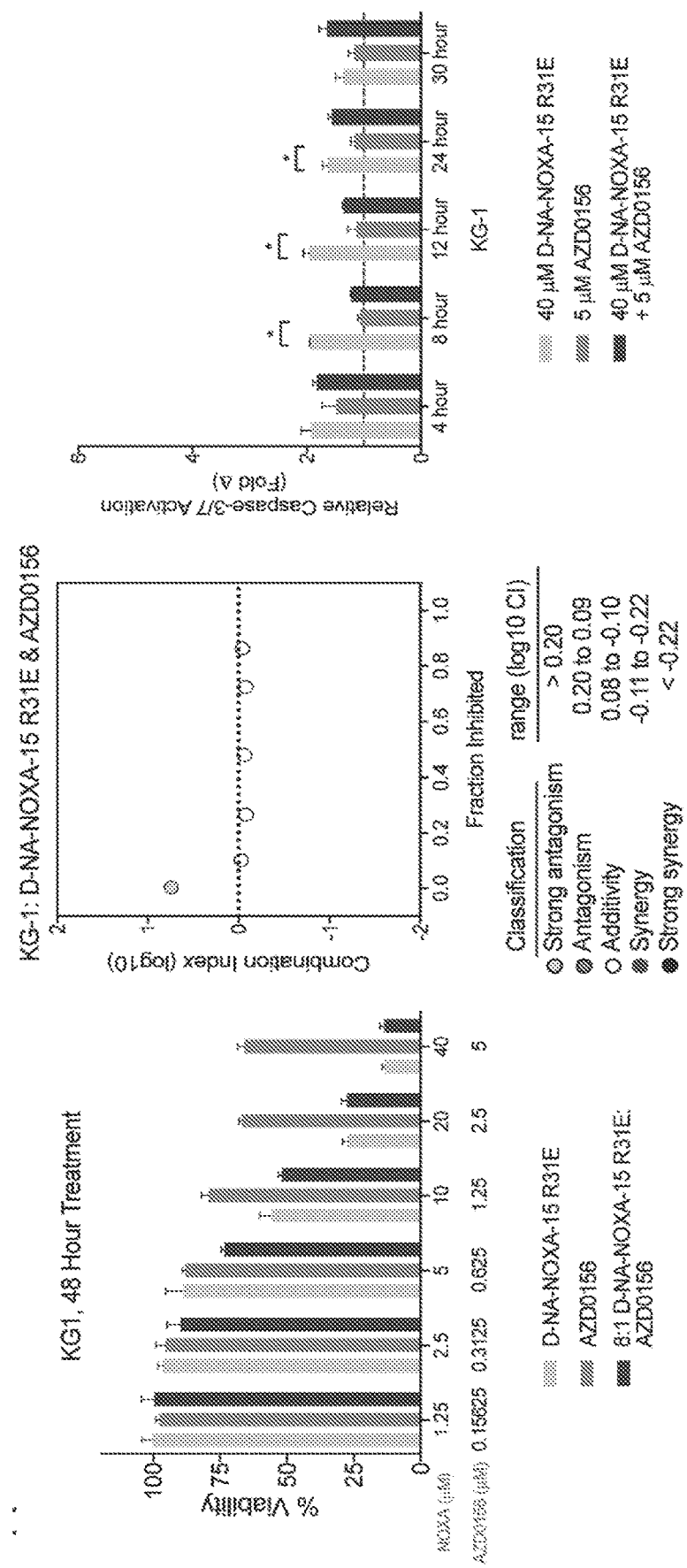
FIG. 54 shows the cell viability (A), Calcusyn dose-effect plots (B), and caspase-3/7 activation (C) results for KG-1 cells treated with D-NA-NOXA SAHB-15 R31E, ATM inhibitor AZD0156, or the combination at the indicated doses. A: for each concentration, the bars are (from left to right): (i) D-NA-NOXA-15 R31E, (ii) Indicated Drug, and (iii) NOXA:Drug Combination. B: the dots are (from left to right): (i) strong antagonism; (ii)-(vi) additivity. C: for each time point, the bars are (from left to right): (i) 40 μM D-NA-NOXA-15 R31E, (ii) 5 μM AZD0156, and (ii) 40 μM D-NA-NOXA-15 R31E+5 μM AZD0156.
Figures 55A, 55B:
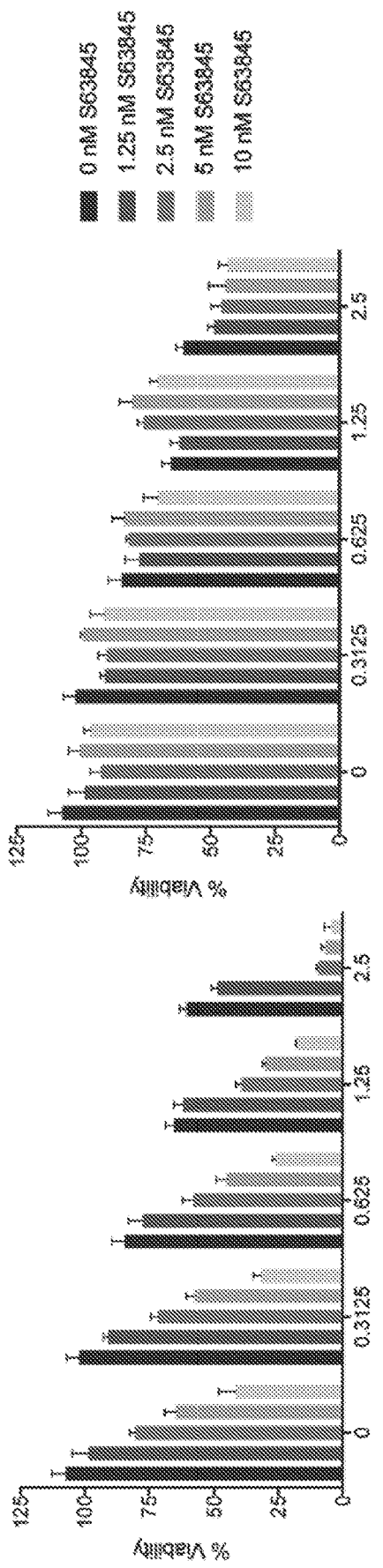
FIG. 55 shows the cell viability of MV4;11 (A) and U937 (B) cells treated with the selective MCL-1 inhibitor S63845, ATM inhibitor AZD0156, or the combination at the indicated doses. For both panels, for each concentration, the bars are (from left to right): (i) 0 nM S63845; (ii) 1.25 nM S63845; (iii) 2.5 nM S63845; (iv) 5 nM S63845; and (v) 10 nM S63845.

To further validate the selective cytotoxicity and synergy of NOXA-15 R31E SAHB upon combination with AZD0156 in BFL-1 dependent U937 but not MV4;11 cell lines (FIGS. 40-43), we performed a series of confirmatory studies. We conducted the above-described cytotoxicity studies on additional cancer cell lines that exhibit dependency on BFL-1, such as OCI-AML-3 AML and Jurkat T cell leukemia cells (Kim et al., 2005, Meyers et al., 2017), and observed pharmacologic synergy similar to that seen in U937 cells (FIGS. 44-45). Next, we tested two additional ATM inhibitors, Ku-60019 (Golding et al., 2009) and Ku-55933 (Hickson et al., 2004), and noted the same pattern of synergy in U937 cells (FIGS. 46-47) but not in MV4;11 cells (FIGS. 48-49) as observed for AZD0156. We found that alternative inhibitors of the DNA damage response (DDR) pathway, including the CHK1/2 inhibitor AZD7762 (Zabludoff et al., 2008) and the PARP inhibitor olaparib (Menear et al., 2008), behaved similarly to the ATM inhibitors in the U937 (FIGS. 50-51) versus MV4;11 (FIGS. 52-53) synergy analyses. As a further measure of specificity, we tested the compounds on KG-1 AML cells, which were previously shown to be relatively unresponsive to the addition of an ATM inhibitor to a pro-apoptotic stimulus (Boehrer et al., 2009). We observed dose-responsive cytotoxicity in response to single agent D-NA-NOXA SAHB-15 R31E treatment, consistent with BFL-1 dependency, but no synergistic effect of AZD0156 when applied in combination (FIG. 54). Finally, we found that the MCL-1 selective inhibitor S63845 exhibits both single agent activity and synergy in combination with ATM inhibition in MV4;11 cells, which are dependent on MCL-1 (Kotschy et al. 2016), but no activity in U937 cells, which are BFL-1 dependent and instead responsive to D-NA-NOXA SAHB-15 R31E (FIG. 55). Indeed, the contrasting activities of S63845 and D-NA-NOXA SAHB-15 R31E in MV4;11 vs. U937 cells underscores the exquisite functional specificities of the two anti-apoptotic inhibitors for MCL-1 and BFL-1, respectively.

Figure 56A:
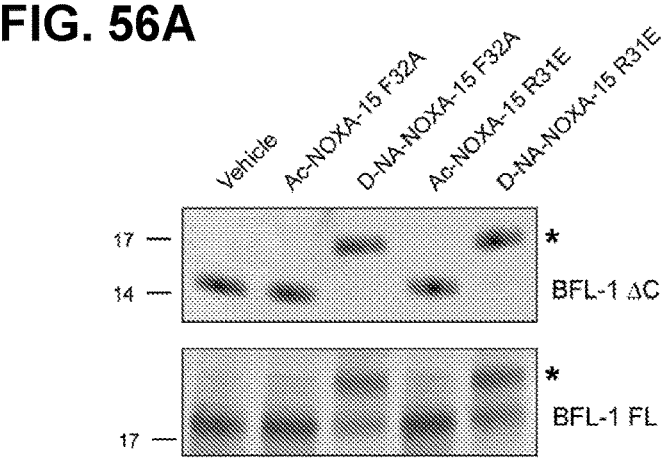
FIG. 56 shows (A) the covalent reactivity of D-NA-NOXA SAHB-15 F32A and R31E peptides with recombinant BFL-1ΔC (top) and full-length BFL-1 (bottom), as reflected by the shift in BFL-1 molecular weight (denoted by *) and detected by reducing and denaturing gel electrophoresis; (B) Covalent reactivity of D-NA-NOXA SAHB-15 F32A and R31E peptides with HA-BFL-1ΔC (top) and full length HA-BFL1 (bottom) expressed in 293T cells, as reflected by the shift in HA-BFL-1 molecular weight (denoted by *) upon treatment with NOXA SAHBs (20 μM) for 12 hours and detected by reducing and denaturing gel electrophoresis of lysates, and anti-HA western analysis; and (C) cysteine-reactive NOXA SAHB-15 R31E and NOXA SAHB-15 F32A peptide targeting of native BFL-1 as assessed by streptavidin pulldown of U937 lysates and anti-BFL-1 western analysis. Of note, native BFL-1 runs at a higher molecular weight than recombinant or expressed BFL-1.
Figure 56B:
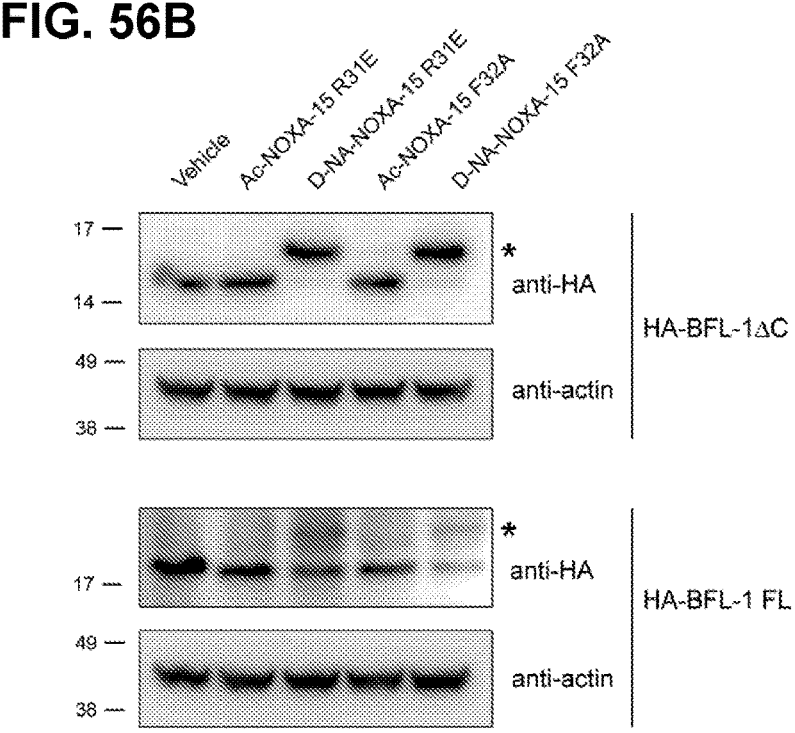
Figure 56C:
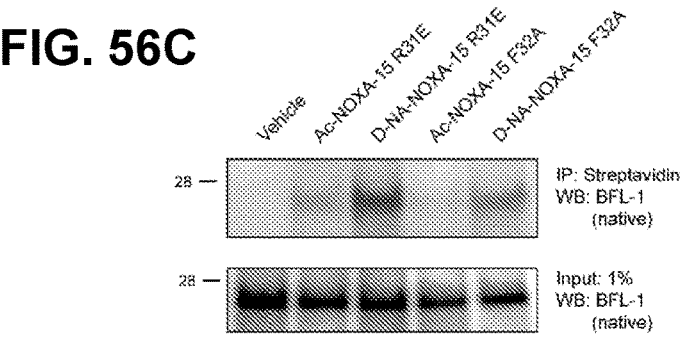

Example 6: Intracellular and Mechanistic Activity of BFL-1 and DNA Damage Response Pathway Inhibitors in Treated Cells We confirmed that both of our lead constructs could covalently crosslink to full-length BFL-1 protein, which bears a C-terminal helix that could potentially compete with D-NA-NOXA SAHBs for interaction at the canonical BH3-binding pocket in cancer cells. We generated recombinant full-length BFL-1 and expressed HA-tagged full-length BFL-1 in 293T cells, and then conducted crosslinking analyses in vitro and in treated cells, respectively. We consistently observed covalent crosslinking to recombinant and expressed full-length BFL-1 for both the F32A and R31E analogs of D-NA-NOXA SAHB-15, albeit at somewhat reduced efficiency compared to treatment of the corresponding C-terminally truncated species (FIG. 56A-B). Thus, to confirm effective targeting of native BFL-1 in AML and identify the superior compound for our battery of planned cytotoxicity analyses, we treated lysates from the AML cell line that demonstrated the strongest BFL-1 dependency score, U937, with biotinylated NOXA SAHB-15 F32A and R31E peptides followed by streptavidin pull-down and BFL-1 western analysis. Consistent with our crosslinking results demonstrated above (e.g. Examples 1-3), incorporation of the acrylamide moiety into the NOXA SAHB-15 peptides markedly enhanced BFL-1 targeting, and in this case, of native BFL-1 protein from U937 AML cells (FIG. 56C). This experiment further identified D-NA-NOXA SAHB-15 R31E as the more effective binder of native BFL-1 protein between the two constructs and was therefore selected for the battery of cancer cell testing.

Figure 57:
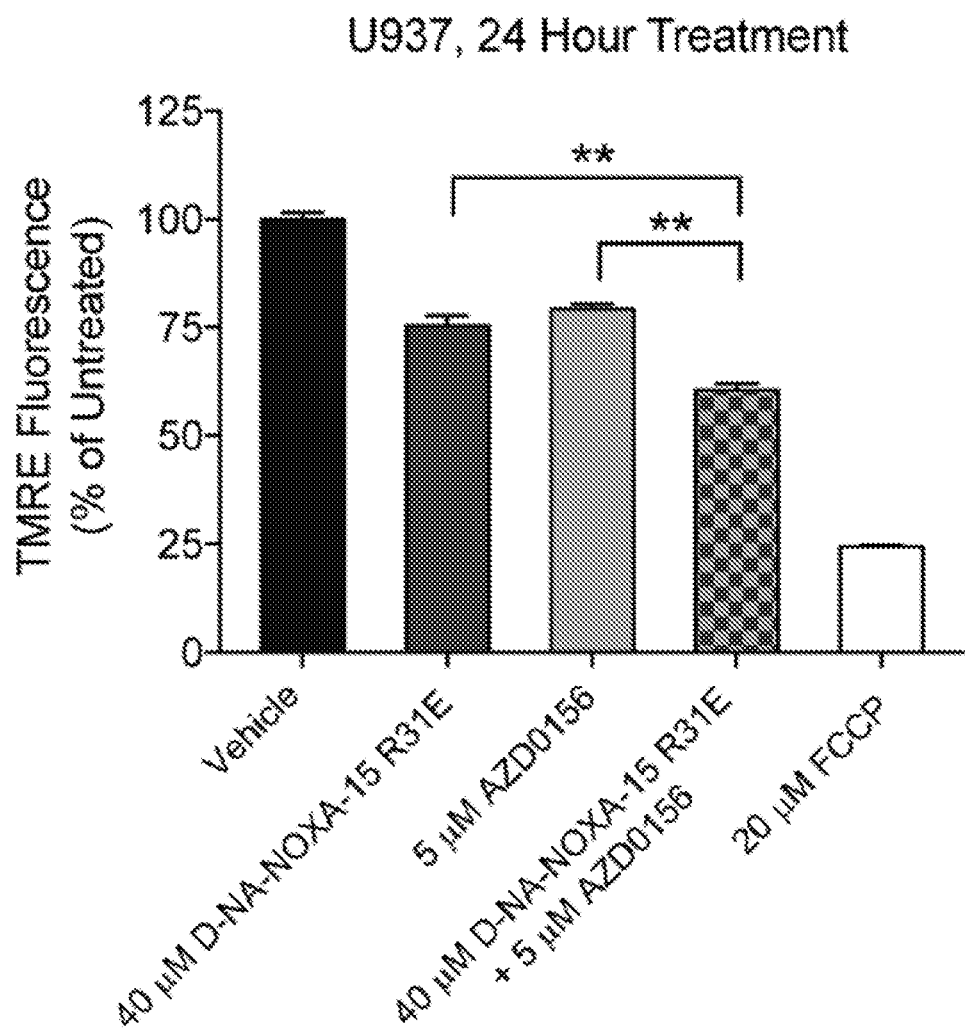
FIG. 57 shows the loss of mitochondrial membrane potential in response to treatment of U937 cells for 24 hours with the indicated doses of D-NA-NOXA SAHB-15 R31E and AZD0156, as single agents and in combination. FCCP is a mitochondrial uncoupler that serves as a positive control for loss of mitochondrial membrane potential.
Figure 58:
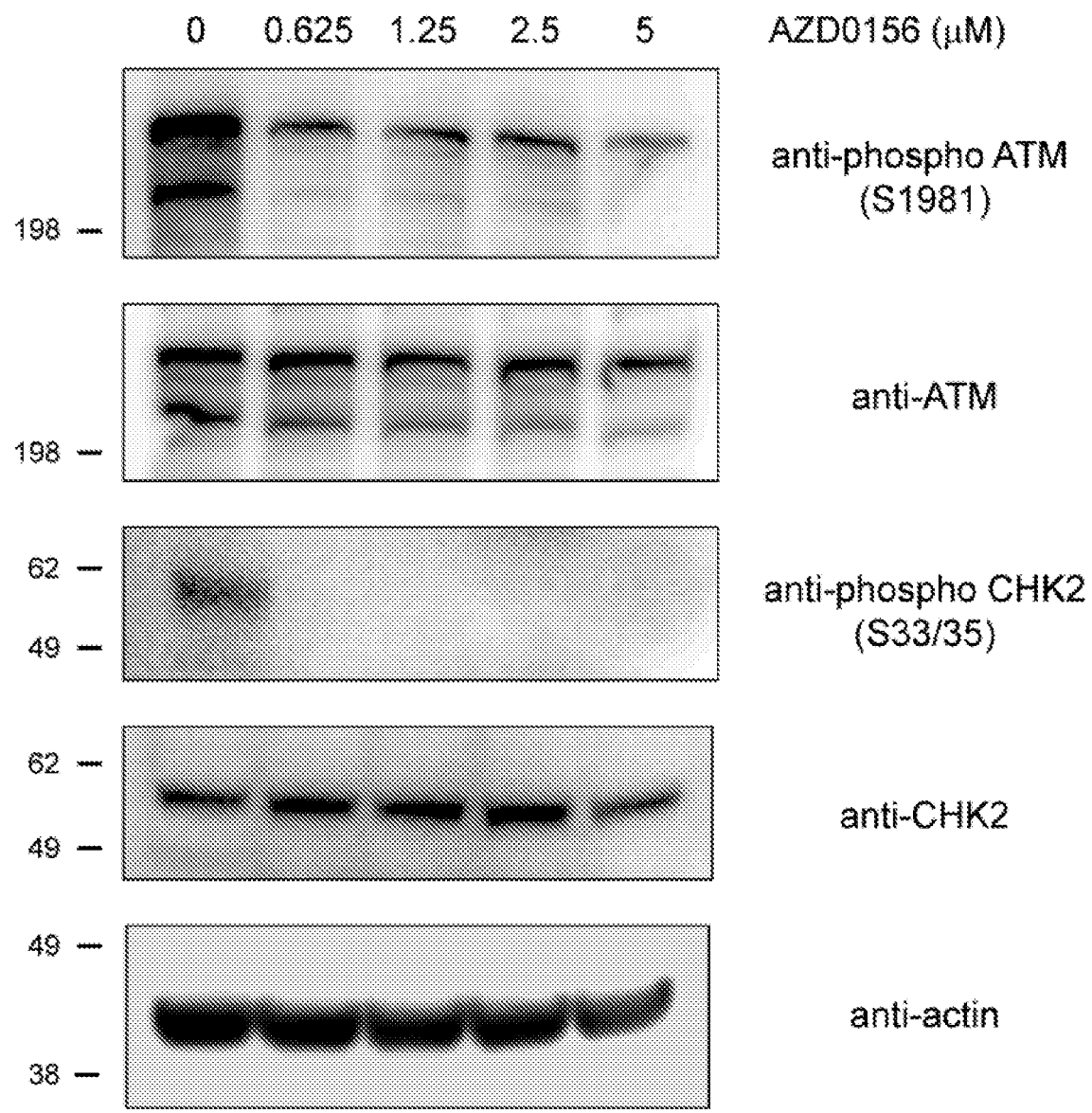
FIG. 58 shows the effects of treatment of U937 cells with the indicated doses of AZD0156 for 2 hours on the phosphorylation status of ATM S1981 and CHK2 S33/35, as monitored by western blot.
Figure 59:
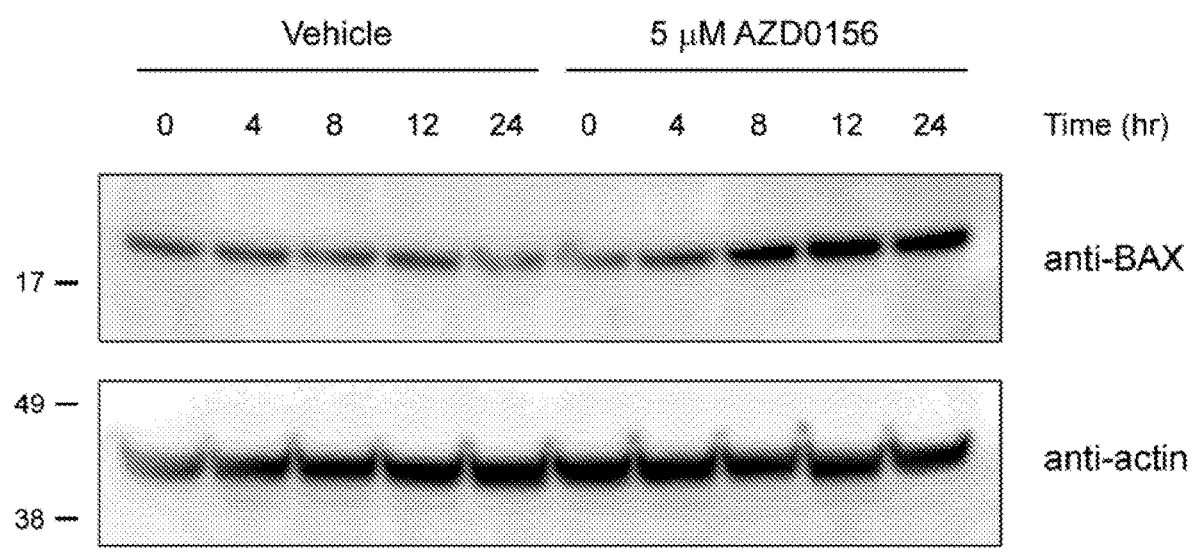
FIG. 59 shows the effect of AZD0156 treatment (5 μM) on the level of BAX protein in U937 cells by BAX western analysis of lysates prepared at the indicated time points.
Figure 61:
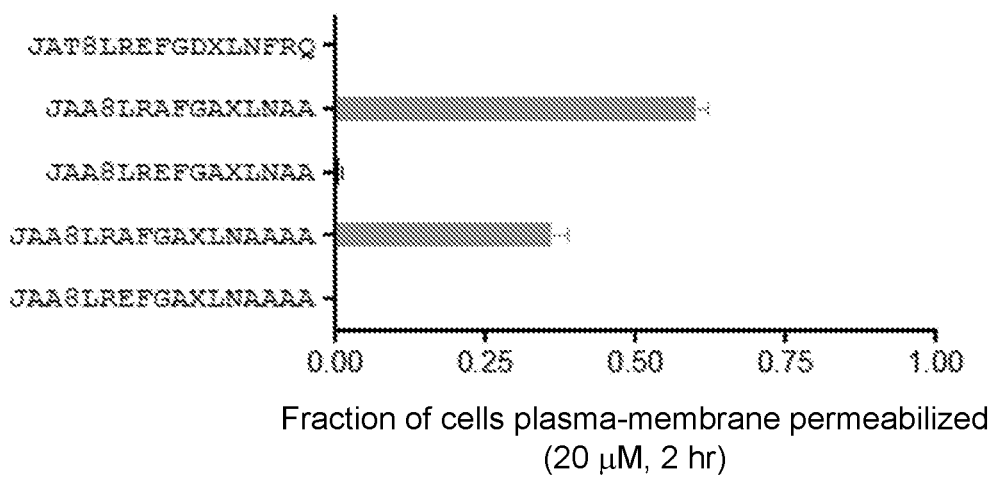
FIG. 61 shows the capacity of select cysteine-reactive NOXA SAHB constructs to induce unwanted, non-specific cytotoxicity by membrane perturbation. SEQ ID NOs: 78 and 150-153 (from top to bottom).

From a mechanistic standpoint, we further confirmed that the cytotoxic effect, synergy, and observed caspase 3/7 activation upon treatment of U937 cells with D-NA-NOXA SAHB-15 R31E and the AZD0156 combination likewise tracked with mitochondrial membrane depolarization, as measured by TMRE staining (FIG. 57). To demonstrate that AZD0156 was effectively targeting ATM at the applied doses, we treated U937 cells with the ATM inhibitor for 2 hr and monitored ATM auto-phosphorylation at S1981 and downstream CHK2 phosphorylation at S33/35 by western blot. Indeed, we observed dose-responsive inhibition of S1981 auto-phosphorylation, which was otherwise constitutively elevated in U937 cells, and potent blockade of CHK2 phosphorylation even at the lowest treatment dose (FIG. 58). In evaluating the potential mechanistic basis for the observed synergy, we noted a time-dependent increase in the protein level of pro-apoptotic BAX in response to AZD0156 treatment (FIG. 59), suggesting that BAX upregulation combined with pharmacologic blockade of the relevant anti-apoptotic inhibitor of BAX-mediated apoptosis in U937 cells, BFL-1, could account for the enhanced cytotoxicity. Finally, we conducted LDH release assays upon treating U937 cells with a serial dilution of D-NA-NOXA SAHB-15 R31E used in single agent and combination treatments, and observed no non-specific cell membrane-lytic activity, as measured at 30 min and 4 hr (FIG. 60). The above-described battery of experiments required for optimizing stapled peptides for selective target protein binding (e.g. BFL-1), cellular penetrance without membrane disruption, and on-mechanism cytotoxic activity highlights the non-obviousness of the design of stapled peptides, such as cysteine-reactive NOXA SAHBs, for therapeutic development. As a further example, a series of D-nipecotic warhead-bearing constructs exhibited varying propensities for non-specific membrane lysis, ranging from 0 to −60% in HeLa cells treated with 20 µM peptide for 2 hours (FIG. 61). Overall, the BFL-1 genetic dependency and co-dependency analyses (FIG. 62) informed the selection of cancer cell subtypes to effectively apply and validate the selective BFL-1 targeting activity of cysteine-reactive NOXA SAHBs and their synergy upon combination with inhibitors of the DNA Damage Response pathway.

Materials and Methods Used in Examples

Stapled Peptide Synthesis

Hydrocarbon-stapled peptides corresponding to the BH3 domains of BCL-2 family proteins, and either N-terminally derivatized with acetyl, FITC-βAla, or electrophilic warheads, or C-terminally derivatized with Lys-biotin or Lys-FITC, were synthesized, purified, and quantitated using our previously reported methods (Bird et al., *Methods Enzymol.*, 446:369-86 (2008); Bird et al., *Curr. Protoc. Chem. Biol.*, 3(3):99-117 (2011)). Acrylamide-bearing peptides were synthesized by either coupling acrylic acid or trans-crotonic acid to the peptide N terminus, or by first coupling the Fmoc-protected cyclic amino acids (Chem-Impex International) followed by Fmoc deprotection and acylation with acrylic acid, using standard Fmoc coupling and deprotection methods (Huhn et al., *Cell Chem Biol.*, 23(9):1123-1134 (2016)).

Recombinant Protein Expression and Purification

Recombinant anti-apoptotic BFL-1ΔC (aa 1-151) and its cysteine to serine mutants were cloned into PET17b (Novagen, N-terminal hexahistidine tag), expressed in *Escherichia coli* LOBSTR BL21(DE3) (Kerafast), and purified by sequential Ni-affinity and size-exclusion chromatography as described (Pitter et al., *Methods Enzymol.*, 446:387-408 (2008)). Recombinant anti-apoptotic BCL-XLΔC (aa 1-212) and MCL-1ΔNΔC (aa 172-329) were cloned into the PGEX-4T-1 (GE Healthcare, N-terminal GST tag) expression vector, expressed in BL21(DE3) *Escherichia coli* (Sigma Aldrich), and purified as described previously (Huhn et al., 2016 (supra), Pitter et al., 2008 (supra)). In purifying BCL-XLΔC, the GST tag was cleaved using thrombin (12-15 units) to provide a size difference between BCL-XLΔC and GST-MCL-1ΔNΔC for facile protein identification by silver stain in streptavidin pull-down experiments.

Recombinant full-length BFL-1 (aa-175) containing an N-terminal hexahistidine tag was cloned into the PTYB1 vector (New England Biolabs) and purified as above except for the addition of a chitin affinity chromatography and DTT elution step. Protein purity and identity was confirmed by Coomassie staining and western blot analysis using a mouse monoclonal anti-His$_6$ tag antibody (Abcam).

In Vitro Covalent Conjugation Assay

His-BFL-1ΔC C4S/C19S protein (5 µM) was pre-treated with 10 mM DTT in 50 mM Tris (pH 8.0) and 100 mM NaCl for 30 min at room temperature (final volume 9.5 µL) and then combined with a 10:1 molar ratio of cysteine-reactive NOXA SAHB for an additional 1-hr incubation at room temperature. The samples were then boiled in 3× loading buffer with DTT and electrophoresed on 12% Bis-Tris gel, then subjected to Coomassie staining.

Cellular Uptake

Cells were cultured using their standard culture medium containing 10% fetal bovine serum (FBS) and penicillin-streptomycin (293T, A375P: DMEM; U937, MV4-11; RMP1). For cysteine-reactive peptide uptake, 293T cells were transfected with 2 µg pCMV plasmid containing HA-BFL-1ΔC C4S/C19S using Lipofectamine LTX Plus (Thermo Scientific). 24 hr post-transfection, cells were treated with 20 µM of the indicated SAHB in DMEM containing 5% FBS for 8 hr. Cells were harvested and lysed by incubation with 1% CHAPS lysis buffer (150 mM NaCl, 50 mM Tris pH 7.4, 100 mM DTT). Protein concentration of the soluble fraction was measured using a BCA kit according to manufacturer's instructions (Thermo Scientific). Samples were then boiled in LDS buffer and subjected to western analysis using 1:1000 dilutions of anti-HA (Sigma Aldrich, #12CA5) and anti-actin (Sigma Aldrich, #A1978) antibodies.

Streptavidin Pulldown

WT His-BFL-1ΔC, BCL-XLΔC (tagless), and GST-MCL-1ΔNΔC (1 µM each) were combined and incubated with 3 mM DTT in PBS for thirty minutes at room temperature. Mixtures were treated with vehicle or the indicated C-terminally biotinylated NOXA SAHB (1 µM) for four hours and were then added to 30 µL PBS-washed high-capacity streptavidin (SA) agarose beads (Thermo Fisher Pierce) and incubated with rotation at room temperature for two hours. The beads were then washed three times with NP-40 lysis buffer (1% NP-40, 50 mM Tris pH 8, 100 mM NaCl, 2.5 mM MgCl2) and three times with PBS. To elute bound protein, beads were boiled for ten minutes with 10% SDS containing 10 mg/mL biotin. After elution, samples were boiled with 3×LDS and 2M DTT for twenty minutes. Gel electrophoresis using a 12% Bis-Tris gel was conducted on inputs (2%) and eluates (5 µL) and gels were developed using the Pierce silver staining kit (Thermo Fisher).

BFL-1 Targeting in Cancer Cell Lysates

Cultured A375P and U937 cells were trypsinized or harvested, respectively, washed with PBS, and lysed by incubating with 1% CHAPS lysis buffer (1% CHAPS, 150 mM NaCl, 50 mM Tris pH 7.4, 100 µM DTT). The protein concentrations of the soluble fraction were measured using a BCA kit according to the manufacturer's instructions (Thermo Scientific). Lysate samples (1 mg) were incubated with vehicle or C-terminally biotinylated NOXA SAHBs (30 µM) overnight in 1% CHAPS lysis buffer at 4° C. Biotin capture was accomplished by incubating the mixture with high-capacity SA agarose (Thermo Scientific) for 2 hours at 4° C., followed by centrifugation and washing the pelleted beads three times with lysis buffer (1 mL). Bead-bound proteins were eluted by boiling in 10% SDS containing 10 mg/mL biotin for 10 minutes and then subjected to electrophoresis and western blotting using BFL-1 (Abcam, #125259) and MCL-1 (Rockland #600-401-394S) antibodies.

BFL-1/BH3 Complex Disruption

To evaluate the capacity of biotinylated SAHBs to compete with tBID for interactions with BFL-1 and MCL-1, 293T cells were transfected with either HA-BFL-1ΔC C4S/C19S or FLAG-MCL-1 in the p3×FLAG-CMV-10 vector (Sigma) as above. After 24 hr, cells were trypsinized, washed with PBS, lysed in 1% CHAPS buffer, and the supernatant collected for protein concentration determination by BCA kit. Lysate samples (0.5 mg) were incubated with 0.25 µM recombinant tBID (R&D Systems) and 5 µM biotinylated NOXA SAHBs for 6 h at RT. The mixtures were then subjected to HA or FLAG immunoprecipitation, followed by western analysis using 1:1000 dilutions of HA (Sigma Aldrich, #12CA5), FLAG (Sigma-Aldrich, F7425), and BID (Santa Cruz sc-11423) antibodies.

Competitive Fluorescence Polarization Binding Assay

Fluorescence polarization (FP) assays were performed as previously described (Putter et al., 2008 (supra)). Briefly, direct binding curves were first generated by FITC-BID BH3 (25 nM) with serial dilutions of anti-apoptotic protein, and FP was measured at 5 min on a SpectraMax M5 microplate reader (Molecular Devices). For competition assays, a serial dilution of acetylated or warhead-bearing NOXA SAHB was added to the indicated recombinant protein at ~EC75 concentration, as determined by the direct binding assay. FITC-BID BH3 (25 nM) was then added and fluorescence polarization was measured at equilibrium. IC50 values were calculated by nonlinear regression analysis of competitive binding curves using PRISM software (Graph-Pad).

LDH Release Assay.

A375P and U937 cancer cells were cultured in DMEM and RPMI, respectively, containing 10% fetal bovine serum (FBS) and penicillin-streptomycin, and plated in 96-well plates ($5\times10^3$ cells per well). After overnight incubation for A375P cells, or immediately upon plating for U937 cells, the cells were treated with the indicated concentrations of D-NA-NOXA SAHBs in DMEM or RPMI supplemented with 5% FBS for the indicated time period (30 min, 4 h). After plate centrifugation at 1,500 rpm (Thermo Scientific Sorvall Four-Place Swinging Bucket Rotor [75006445]; 478×g) for 5 min at 4° C., LDH release was quantified by transferring 100 µL of cell-culture medium to a clear plate (Corning), incubating with 100 µL of LDH reagent (Roche) for 30 min while shaking, and then measuring absorbance at 490 nm on a microplate reader (Spectramax M5, Molecular Devices).

Cell Viability and Caspase-3/7 Activation Assays.

U937, MV4;11, OCI-AML-3, Jurkat, and KG-1 cells cultured in RPMI containing 10% FBS and penicillin-streptomycin were plated in 96-well plates ($5\times10^3$ cells per well) and, after overnight incubation, treated with the indicated concentrations of D-NA-NOXA SAHB and/or AZD0156, Ku-60019, Ku-55933, AZD7762, olaparib, or S63845 (all from Selleck Chemicals) in RPMI supplemented with 5% FBS for the indicated durations. Cell viability and caspase-3/7 activation was measured using CellTiter-Glo and Caspase-Glo 3/7 chemiluminescence reagents (Promega), respectively, and luminescence was detected by a Spectramax M5 microplate reader. Synergy of drug interactions was calculated using the CalcuSyn software (Biosoft).

Preparation of SAHB-Conjugated BFL-1

BFL-1ΔC/D-NA-NOXA SAHB conjugates were prepared for structural analysis by treating BFL-1ΔC (30 µM) with DTT (20 mM) for 30 min at 4° C., followed by sequential incubation with D-NA-NOXA SAHB peptide at peptide:protein molar ratios of 1.2×, 1.2×, and 1× for 1 hour each at 4° C. The resulting conjugate was then purified using size-exclusion chromatography and conjugation efficiency assessed by SDS-PAGE gel electrophoresis and intact mass spectrometry.

X-Ray Crystallography

Apo His-BFL-1ΔC C4S/C19S was expressed and purified as described above and buffer exchanged into 20 mM HEPES pH 7.5, 300 mM NaCl, 5% glycerol, 50 mM arginine, and 1 mM DTT. An equal volume (100 nL) of 6.3 mg/mL (340 µM) apo BFL-1ΔC was mixed with reservoir solution (35% PEG1500 and 0.1 M sodium cacodylate pH 6), and crystals were prepared in hanging drops at 20° C.

The crystals were transferred briefly into crystallization buffer containing 25% glycerol prior to flash-freezing in liquid nitrogen. Diffraction data from apo BFL-1ΔC crystals were collected at beamline 241D-C of the NE-CAT at the Advanced Photon Source (Argonne National Laboratory), and data sets were integrated and scaled using XIA2 package (Evans, *Acta Crystallogr D Biol Crystallogr* 62, 72-82 (2006); Kabsch, *Acta Crystallogr D Biol Crystallogr* 66, 133-144 (2010); Winter, *J Appl Crystallogr* 43, 186-190 (2010)). The structure was solved by molecular replacement using the program Phaser (McCoy et al., *J Appl Crystallogr* 40, 658-674 (2007)) and the search model PDB entry 1NB8. Iterative manual model building and refinement using Phenix (Adams et al., *Acta Crystallogr D Biol Crystallogr* 66, 213-221 (2010)) and Coot (Emsley and Cowtan, *Acta Crystallogr D Biol Crystallogr* 60, 2126-2132, (2004)) led to a model (PDB: 5WHI) with excellent statistics, including maximum diffraction of 1.69 Å.

His-BFL-1ΔC C4S/C19S in complex with D-NA-NOXA SAHB was generated as described above and buffer exchanged into 20 mM HEPES pH 7, 100 mM NaCl, and 1 mM DTT. An equal volume (200 nL) of (400 µM) His-BFL-1ΔC/D-NA-NOXA SAHB complex was mixed with reservoir solution (20% PEG3350 and 0.2 M sodium malonate), and crystals were formed in hanging drops at 20° C. The crystals were transferred briefly into crystallization buffer containing 25% glycerol prior to flash-freezing in liquid nitrogen. Diffraction data from His-BFL-1ΔC/D-NA-NOXA SAHB crystals were collected at beamline 241D-C of the NE-CAT at the Advanced Photon Source (Argonne National Laboratory). After initial molecular replacement, the ligand was positioned and preliminarily refined using Buster and Rhofit (Smart et al., 2012). A model of the crystallographic data (PDB: 5WHH, maximum diffraction of 2.38 Å) was generated as described above.

Difference Distance Matrix Plots

To generate heat maps, alpha carbon coordinates conserved between structures were extracted from PDB files. Difference distance matrix plots were produced using the DDMP program from the Center for Structural Biology at Yale University (New Haven, CT).

Quantification and Statistical Analysis

For the structural analyses, bond length and difference distance matrix plot quantifications were conducted using pymol and the DDMP program. Refinement statistics for the X-ray structures were generated by the Phenix software package. Biochemical and cellular data are mean±SD for experiments performed in technical triplicate and repeated at least two times with similar results. p values less than 0.05 were considered statistically significant by unpaired, two-tailed Student's t test, and indicated by an asterisk. Data were analyzed using Prism Software 7.0 (GraphPad) and CalcuSyn (Biosoft).

Data and Software Availability

X-ray crystallography data was deposited to the PDB under accession numbers 5WHI (apo BFL-1) and 5WHH (BFL-1/D-NA NOXA SAHB).

Mitochondrial Membrane Potential Assay

U937 cells were plated in 6-well plates ($2\times10^6$ cells per well) and treated with the indicated concentrations of D-NA-NOXA SAHB and/or AZD0156. After 24 hr, cells were incubated with TMRE (1 µM) for 30 min according to the manufacturer's instructions (TMRE-Mitochondrial Membrane Potential Assay Kit, Abcam). Cells were then resuspended in 0.2% BSA in PBS and seeded at $2\times10^5$ cells per well in black 96-well plates (Corning). TMRE-mitochondrial membrane potential was read by measuring fluorescence (Ex/Em=549/575 nm) on a Spectramax M5 microplate reader.

Phospho-Signaling Analysis.

U937 cells cultured in RPMI containing 10% FBS and penicillin-streptomycin were plated in 6-well plates ($2\times10^6$ cells per well) and treated with the indicated concentrations of AZD0156 for 2 hr. Cells were then washed with PBS, lysed in 1% CHAPS buffer, and the supernatant collected for protein concentration determination by BCA kit. Samples were subjected to electrophoresis and western analysis using 1:1000 dilutions of phospho-ATM (S1981, Cell Signaling, #4526), ATM (Abcam, #ab78), phospho-CHK2 (Ser33/35, Cell Signaling, #2665), CHK2 (Cell Signaling, #2662), and actin (Sigma #A1978) antibodies.

Dynamic Assessment of BAX Protein Levels.

U937 cells were plated in 6-well plates ($2\times10^6$ cells per well), treated with AZD0156 (5 µM), and the cells harvested and lysed at the indicated time points. Cell lysates were then subjected to electrophoresis and western blotting with BAX (Santa Cruz sc-493) and actin (Sigma #A1978) antibodies.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims

What is claimed is:

1. A peptide that covalently binds to BFL-1/A1, wherein the peptide comprises the sequence JATX$_1$LREFGDX$_2$LNFRQ (SEQ ID NO:62), wherein J is an electrophilic warhead; and wherein X$_1$ is R-octenyl alanine and X$_2$ is S-pentenyl alanine, and wherein X$_1$ is cross-linked to X$_2$.

2. A peptide that covalently binds to BFL-1/A1, wherein the peptide comprises the sequence JATX$_1$LRRAGDX$_2$LNFRQ (SEQ ID NO:60), wherein J is an electrophilic warhead; and wherein X$_1$ is R-octenyl alanine and X$_2$ is S-pentenyl alanine, and wherein X$_1$ is cross-linked to X$_2$.

3. The peptide of claim 1, wherein the peptide consists of the sequence of SEQ ID NO:62.

4. The peptide of claim 1, wherein the electrophilic warhead is a cysteine-reactive acrylamide D-nipecotic acid moiety.

5. The peptide of claim 3, wherein the electrophilic warhead is a cysteine-reactive acrylamide D-nipecotic acid moiety.

6. The peptide of claim 2, wherein the peptide consists of the sequence of SEQ ID NO:60.

7. The peptide of claim 2, wherein the electrophilic warhead is a cysteine-reactive acrylamide D-nipecotic acid moiety.

8. The peptide of claim 6, wherein the electrophilic warhead is a cysteine-reactive acrylamide D-nipecotic acid moiety.

9. The peptide of claim 1, wherein the electrophilic warhead is a non-natural amino acid bearing an electrophilic group.

10. The peptide of claim 9, wherein the non-natural amino acid bearing an electrophilic group has an electrophilic acrylamide or substituted acrylamide linked to the peptide backbone.

11. The peptide of claim 9, wherein the electrophilic group is selected from the group consisting of: (S)-1-acryloylpyrrolidine-3-carboxamide; 1-acryloylpiperidine-4-carboxamide, (R)-1 acryloylpiperidine-3-carboxamide; (S)-1-acryloylpiperidine-3-carboxamide; (S)-1-acryloylpyrrolidine-2-carboxamide; (R)-1-acryloylpyrrolidine-2-carboxamide; (E)-4-(dimethylamino) but-2-enamide; acrylamide; aziridine, diaziridine, azetidine, pyrrolidine, imidazolidine, pyrazolidine, oxazolidine, isoxazolidine, thiazolidine, isothiazolidine, piperidine, piperazine, morpholine, thiomorpholine, azepaneazirine, diazirine, azete, pyrrole, imidazole, pyrazole, oxazole, isoxazole, thiazole, isothiazole, pyridine, diazines, oxazine, thiazine, azepine phenyl (aniline); naphthalene, anthracene, phenanthrene, indole, isoindole, indolizine, quinolone, isoquinoline, quinoxaline, phthalzine, quinazoline, purine, carbazole, indazole, benzimidazole, azaindole, α-cyanoacrylamide, propiolamide, trans 4-dimethylamino-2-butenamide, trans 4-piperidinyl-2-butenamide, a substituted acrylamide, and a vinyl-sulfonamide.

12. The peptide of claim 2, wherein the electrophilic warhead is a non-natural amino acid bearing an electrophilic group.

13. The peptide of claim 12, wherein the non-natural amino acid bearing an electrophilic group has an electrophilic acrylamide or substituted acrylamide linked to the peptide backbone.

14. The peptide of claim 12, wherein the electrophilic group is selected from the group consisting of: (S)-1-acryloylpyrrolidine-3-carboxamide; 1-acryloylpiperidine-4-carboxamide, (R)-1 acryloylpiperidine-3-carboxamide; (S)-1-acryloylpiperidine-3-carboxamide; (S)-1-acryloylpyrrolidine-2-carboxamide; (R)-1-acryloylpyrrolidine-2-carboxamide; (E)-4-(dimethylamino) but-2-enamide; acrylamide; aziridine, diaziridine, azetidine, pyrrolidine, imidazolidine, pyrazolidine, oxazolidine, isoxazolidine, thiazolidine, isothiazolidine, piperidine, piperazine, morpholine, thiomorpholine, azepaneazirine, diazirine, azete, pyrrole, imidazole, pyrazole, oxazole, isoxazole, thiazole, isothiazole, pyridine, diazines, oxazine, thiazine, azepine phenyl (aniline); naphthalene, anthracene, phenanthrene, indole, isoindole, indolizine, quinolone, isoquinoline, quinoxaline, phthalzine, quinazoline, purine, carbazole, indazole, benzimidazole, azaindole, α-cyanoacrylamide, propiolamide, trans 4-dimethylamino-2-butenamide, trans 4-piperidinyl-2-butenamide, a substituted acrylamide, and a vinyl-sulfonamide.

15. A pharmaceutical composition comprising the peptide of claim 1, and a pharmaceutically acceptable carrier.

16. A pharmaceutical composition comprising the peptide of claim 2, and a pharmaceutically acceptable carrier.

17. A pharmaceutical composition comprising the peptide of claim 3, and a pharmaceutically acceptable carrier.

18. A pharmaceutical composition comprising the peptide of claim 4, and a pharmaceutically acceptable carrier.

19. A pharmaceutical composition comprising the peptide of claim 5, and a pharmaceutically acceptable carrier.

20. A pharmaceutical composition comprising the peptide of claim 6, and a pharmaceutically acceptable carrier.

21. A pharmaceutical composition comprising the peptide of claim 7, and a pharmaceutically acceptable carrier.

22. A pharmaceutical composition comprising the peptide of claim 8, and a pharmaceutically acceptable carrier.

23. A method of treating a BFL-1/A1-expressing disease or a BFL-1/A1-dependent disease in a human subject in need thereof, the method comprising administering to the human subject a therapeutically effective amount of the peptide of claim 1; wherein the BFL-1/A1-expressing disease or the BFL-1/A1-dependent disease is a cancer.

24. A method of treating a BFL-1/A1-expressing disease or a BFL-1/A1-dependent disease in a human subject in need thereof, the method comprising administering to the human subject a therapeutically effective amount of the peptide of claim 2; wherein the BFL-1/A1-expressing disease or the BFL-1/A1-dependent disease is a cancer.

25. The method of claim 23, wherein the cancer is acute myeloid leukemia (AML).

26. The method of claim 24, wherein the cancer is AML.

* * * * *

UNITED STATES PATENT AND TRADEMARK OFFICE
CERTIFICATE OF CORRECTION

PATENT NO. : 11,834,520 B2
APPLICATION NO. : 16/766201
DATED : December 5, 2023
INVENTOR(S) : Loren D. Walensky et al.

It is certified that error appears in the above-identified patent and that said Letters Patent is hereby corrected as shown below:

In the Claims

Column 166, Line 56, in Claim 11:
Delete "phthalzine," and insert -- phthalazine, --.

Column 167, Line 16, in Claim 14:
Delete "phthalzine," and insert -- phthalazine, --.

Signed and Sealed this
Seventh Day of May, 2024

Katherine Kelly Vidal
*Director of the United States Patent and Trademark Office*

SEQUENCE LISTING

```
<160> NUMBER OF SEQ ID NOS: 156

<210> SEQ ID NO 1
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Ala Thr Gln Leu Arg Arg Phe Gly Asp Lys Leu Asn Phe Arg Gln
1               5                   10                  15
```

-continued

```
<210> SEQ ID NO 2
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: S-pentenyl alanine
<220> FEATURE:
<221> NAME/KEY: MOD_RES
<222> LOCATION: (5)..(5)
<223> OTHER INFORMATION: S-pentenyl alanine

<400> SEQUENCE: 2

Xaa Thr Gln Leu Xaa Arg Phe Gly Asp Lys Leu Asn Phe Arg Gln
1               5                   10                  15

<210> SEQ ID NO 3
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: S-pentenyl alanine
<220> FEATURE:
<221> NAME/KEY: MOD_RES
<222> LOCATION: (6)..(6)
<223> OTHER INFORMATION: S-pentenyl alanine

<400> SEQUENCE: 3

Ala Xaa Gln Leu Arg Xaa Phe Gly Asp Lys Leu Asn Phe Arg Gln
1               5                   10                  15

<210> SEQ ID NO 4
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: S-pentenyl alanine
<220> FEATURE:
<221> NAME/KEY: MOD_RES
<222> LOCATION: (7)..(7)
<223> OTHER INFORMATION: S-pentenyl alanine

<400> SEQUENCE: 4

Ala Thr Xaa Leu Arg Arg Xaa Gly Asp Lys Leu Asn Phe Arg Gln
1               5                   10                  15

<210> SEQ ID NO 5
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
```

```
<222> LOCATION: (4)..(4)
<223> OTHER INFORMATION: S-pentenyl alanine
<220> FEATURE:
<221> NAME/KEY: MOD_RES
<222> LOCATION: (8)..(8)
<223> OTHER INFORMATION: S-pentenyl alanine

<400> SEQUENCE: 5

Ala Thr Gln Xaa Arg Arg Phe Xaa Asp Lys Leu Asn Phe Arg Gln
1               5                   10                  15

<210> SEQ ID NO 6
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: S-pentenyl alanine
<220> FEATURE:
<221> NAME/KEY: MOD_RES
<222> LOCATION: (9)..(9)
<223> OTHER INFORMATION: S-pentenyl alanine

<400> SEQUENCE: 6

Ala Thr Gln Leu Xaa Arg Phe Gly Xaa Lys Leu Asn Phe Arg Gln
1               5                   10                  15

<210> SEQ ID NO 7
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: S-pentenyl alanine
<220> FEATURE:
<221> NAME/KEY: MOD_RES
<222> LOCATION: (10)..(10)
<223> OTHER INFORMATION: S-pentenyl alanine

<400> SEQUENCE: 7

Ala Thr Gln Leu Arg Xaa Phe Gly Asp Xaa Leu Asn Phe Arg Gln
1               5                   10                  15

<210> SEQ ID NO 8
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: S-pentenyl alanine
<220> FEATURE:
<221> NAME/KEY: MOD_RES
<222> LOCATION: (11)..(11)
<223> OTHER INFORMATION: S-pentenyl alanine

<400> SEQUENCE: 8

Ala Thr Gln Leu Arg Arg Xaa Gly Asp Lys Xaa Asn Phe Arg Gln
```

```
<210> SEQ ID NO 9
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (8)..(8)
<223> OTHER INFORMATION: S-pentenyl alanine
<220> FEATURE:
<221> NAME/KEY: MOD_RES
<222> LOCATION: (12)..(12)
<223> OTHER INFORMATION: S-pentenyl alanine

<400> SEQUENCE: 9

Ala Thr Gln Leu Arg Arg Phe Xaa Asp Lys Leu Xaa Phe Arg Gln
1               5                   10                  15

<210> SEQ ID NO 10
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (9)..(9)
<223> OTHER INFORMATION: S-pentenyl alanine
<220> FEATURE:
<221> NAME/KEY: MOD_RES
<222> LOCATION: (13)..(13)
<223> OTHER INFORMATION: S-pentenyl alanine

<400> SEQUENCE: 10

Ala Thr Gln Leu Arg Arg Phe Gly Xaa Lys Leu Asn Xaa Arg Gln
1               5                   10                  15

<210> SEQ ID NO 11
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (10)..(10)
<223> OTHER INFORMATION: S-pentenyl alanine
<220> FEATURE:
<221> NAME/KEY: MOD_RES
<222> LOCATION: (14)..(14)
<223> OTHER INFORMATION: S-pentenyl alanine

<400> SEQUENCE: 11

Ala Thr Gln Leu Arg Arg Phe Gly Asp Xaa Leu Asn Phe Xaa Gln
1               5                   10                  15

<210> SEQ ID NO 12
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
```

```
        Synthetic peptide"
<220> FEATURE:
<221> NAME/KEY: MOD_RES
<222> LOCATION: (11)..(11)
<223> OTHER INFORMATION: S-pentenyl alanine
<220> FEATURE:
<221> NAME/KEY: MOD_RES
<222> LOCATION: (15)..(15)
<223> OTHER INFORMATION: S-pentenyl alanine

<400> SEQUENCE: 12

Ala Thr Gln Leu Arg Arg Phe Gly Asp Lys Xaa Asn Phe Arg Xaa
1               5                   10                  15

<210> SEQ ID NO 13
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"
<220> FEATURE:
<221> NAME/KEY: MOD_RES
<222> LOCATION: (12)..(12)
<223> OTHER INFORMATION: S-pentenyl alanine
<220> FEATURE:
<221> NAME/KEY: MOD_RES
<222> LOCATION: (16)..(16)
<223> OTHER INFORMATION: S-pentenyl alanine

<400> SEQUENCE: 13

Ala Thr Gln Leu Arg Arg Phe Gly Asp Lys Leu Xaa Phe Arg Gln Xaa
1               5                   10                  15

<210> SEQ ID NO 14
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"
<220> FEATURE:
<221> NAME/KEY: MOD_RES
<222> LOCATION: (1)..(1)
<223> OTHER INFORMATION: R-octenyl alanine
<220> FEATURE:
<221> NAME/KEY: MOD_RES
<222> LOCATION: (8)..(8)
<223> OTHER INFORMATION: S-pentenyl alanine

<400> SEQUENCE: 14

Xaa Thr Gln Leu Arg Arg Phe Xaa Asp Lys Leu Asn Phe Arg Gln
1               5                   10                  15

<210> SEQ ID NO 15
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"
<220> FEATURE:
<221> NAME/KEY: MOD_RES
<222> LOCATION: (2)..(2)
<223> OTHER INFORMATION: R-octenyl alanine
<220> FEATURE:
<221> NAME/KEY: MOD_RES
<222> LOCATION: (9)..(9)
<223> OTHER INFORMATION: S-pentenyl alanine
```

```
<400> SEQUENCE: 15

Ala Xaa Gln Leu Arg Arg Phe Gly Xaa Lys Leu Asn Phe Arg Gln
1               5                   10                  15

<210> SEQ ID NO 16
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 16

Ala Thr Xaa Leu Arg Arg Phe Gly Asp Xaa Leu Asn Phe Arg Gln
1               5                   10                  15

<210> SEQ ID NO 17
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: R-octenyl alanine
<220> FEATURE:
<221> NAME/KEY: MOD_RES
<222> LOCATION: (11)..(11)
<223> OTHER INFORMATION: S-pentenyl alanine

<400> SEQUENCE: 17

Ala Thr Gln Xaa Arg Arg Phe Gly Asp Lys Xaa Asn Phe Arg Gln
1               5                   10                  15

<210> SEQ ID NO 18
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: R-octenyl alanine
<220> FEATURE:
<221> NAME/KEY: MOD_RES
<222> LOCATION: (12)..(12)
<223> OTHER INFORMATION: S-pentenyl alanine

<400> SEQUENCE: 18

Ala Thr Gln Leu Xaa Arg Phe Gly Asp Lys Leu Xaa Phe Arg Gln
1               5                   10                  15

<210> SEQ ID NO 19
<211> LENGTH: 15
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: R-octenyl alanine
<220> FEATURE:
<221> NAME/KEY: MOD_RES
<222> LOCATION: (13)..(13)
<223> OTHER INFORMATION: S-pentenyl alanine

<400> SEQUENCE: 19

Ala Thr Gln Leu Arg Xaa Phe Gly Asp Lys Leu Asn Xaa Arg Gln
1               5                   10                  15

<210> SEQ ID NO 20
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: R-octenyl alanine
<220> FEATURE:
<221> NAME/KEY: MOD_RES
<222> LOCATION: (14)..(14)
<223> OTHER INFORMATION: S-pentenyl alanine

<400> SEQUENCE: 20

Ala Thr Gln Leu Arg Arg Xaa Gly Asp Lys Leu Asn Phe Xaa Gln
1               5                   10                  15

<210> SEQ ID NO 21
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (8)..(8)
<223> OTHER INFORMATION: R-octenyl alanine
<220> FEATURE:
<221> NAME/KEY: MOD_RES
<222> LOCATION: (15)..(15)
<223> OTHER INFORMATION: S-pentenyl alanine

<400> SEQUENCE: 21

Ala Thr Gln Leu Arg Arg Phe Xaa Asp Lys Leu Asn Phe Arg Xaa
1               5                   10                  15

<210> SEQ ID NO 22
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
```

```
<222> LOCATION: (10)..(10)
<223> OTHER INFORMATION: S-pentenyl alanine

<400> SEQUENCE: 22

Glu Thr Xaa Leu Arg Arg Phe Gly Asp Xaa Leu Asn Phe Arg Gln
1               5                   10                  15

<210> SEQ ID NO 23
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 23

Ala Ala Xaa Leu Arg Arg Phe Gly Asp Xaa Leu Asn Phe Arg Gln
1               5                   10                  15

<210> SEQ ID NO 24
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 24

Ala Thr Xaa Ala Arg Arg Phe Gly Asp Xaa Leu Asn Phe Arg Gln
1               5                   10                  15

<210> SEQ ID NO 25
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 25

Ala Thr Xaa Leu Ala Arg Phe Gly Asp Xaa Leu Asn Phe Arg Gln
1               5                   10                  15

<210> SEQ ID NO 26
```

```
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 26

Ala Thr Xaa Leu Arg Ala Phe Gly Asp Xaa Leu Asn Phe Arg Gln
1               5                   10                  15

<210> SEQ ID NO 27
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 27

Ala Thr Xaa Leu Arg Arg Ala Gly Asp Xaa Leu Asn Phe Arg Gln
1               5                   10                  15

<210> SEQ ID NO 28
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 28

Ala Thr Xaa Leu Arg Arg Phe Ala Asp Xaa Leu Asn Phe Arg Gln
1               5                   10                  15

<210> SEQ ID NO 29
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
```

-continued

```
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 29

Ala Thr Xaa Leu Arg Arg Phe Gly Ala Xaa Leu Asn Phe Arg Gln
1               5                   10                  15

<210> SEQ ID NO 30
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 30

Ala Thr Xaa Leu Arg Arg Phe Gly Asp Xaa Ala Asn Phe Arg Gln
1               5                   10                  15

<210> SEQ ID NO 31
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 31

Ala Thr Xaa Leu Arg Arg Phe Gly Asp Xaa Leu Ala Phe Arg Gln
1               5                   10                  15

<210> SEQ ID NO 32
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 32

Ala Thr Xaa Leu Arg Arg Phe Gly Asp Xaa Leu Asn Ala Arg Gln
1               5                   10                  15
```

```
<210> SEQ ID NO 33
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 33

Ala Thr Xaa Leu Arg Arg Phe Gly Asp Xaa Leu Asn Phe Ala Gln
1               5                   10                  15

<210> SEQ ID NO 34
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 34

Ala Thr Xaa Leu Arg Arg Phe Gly Asp Xaa Leu Asn Phe Arg Ala
1               5                   10                  15

<210> SEQ ID NO 35
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 35

Ala Thr Xaa Leu Arg Glu Phe Gly Asp Xaa Leu Asn Phe Arg Gln
1               5                   10                  15

<210> SEQ ID NO 36
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 36

Ala Thr Xaa Leu Arg Arg Phe Gly Asp Xaa Leu Asn Phe Glu Gln
1               5                   10                  15

<210> SEQ ID NO 37
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 37

Ala Thr Xaa Leu Arg Arg Phe Gly Asp Xaa Leu Asp Phe Arg Gln
1               5                   10                  15

<210> SEQ ID NO 38
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 38

Ala Thr Xaa Leu Arg Arg Phe Gly Asp Xaa Leu Asn Phe Arg Leu
1               5                   10                  15

<210> SEQ ID NO 39
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Ala Thr Gln Leu Arg Arg Phe Gly Asp Lys Leu Asn Phe Arg Gln
1               5                   10                  15

<210> SEQ ID NO 40
<211> LENGTH: 15
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any non-natural amino acid which can be
      covalently joined ("stapled together") using a ring-closing
      metathesis (RCM) reaction to form a cross-linked ring
<220> FEATURE:
<221> NAME/KEY: MOD_RES
<222> LOCATION: (10)..(10)
<223> OTHER INFORMATION: Any non-natural amino acid which can be
      covalently joined ("stapled together") using a ring-closing
      metathesis (RCM) reaction to form a cross-linked ring

<400> SEQUENCE: 40

Ala Thr Xaa Leu Arg Arg Ala Gly Asp Xaa Leu Asn Phe Arg Gln
1               5                   10                  15

<210> SEQ ID NO 41
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any non-natural amino acid which can be
      covalently joined ("stapled together") using a ring-closing
      metathesis (RCM) reaction to form a cross-linked ring
<220> FEATURE:
<221> NAME/KEY: MOD_RES
<222> LOCATION: (10)..(10)
<223> OTHER INFORMATION: Any non-natural amino acid which can be
      covalently joined ("stapled together") using a ring-closing
      metathesis (RCM) reaction to form a cross-linked ring

<400> SEQUENCE: 41

Ala Thr Xaa Leu Arg Arg Phe Gly Asp Xaa Ala Asn Phe Arg Gln
1               5                   10                  15

<210> SEQ ID NO 42
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any non-natural amino acid which can be
      covalently joined ("stapled together") using a ring-closing
      metathesis (RCM) reaction to form a cross-linked ring
<220> FEATURE:
<221> NAME/KEY: MOD_RES
<222> LOCATION: (10)..(10)
<223> OTHER INFORMATION: Any non-natural amino acid which can be
      covalently joined ("stapled together") using a ring-closing
      metathesis (RCM) reaction to form a cross-linked ring

<400> SEQUENCE: 42

Ala Thr Xaa Leu Arg Glu Phe Gly Asp Xaa Leu Asn Phe Arg Gln
1               5                   10                  15

<210> SEQ ID NO 43
```

```
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any non-natural amino acid which can be
      covalently joined ("stapled together") using a ring-closing
      metathesis (RCM) reaction to form a cross-linked ring
<220> FEATURE:
<221> NAME/KEY: MOD_RES
<222> LOCATION: (10)..(10)
<223> OTHER INFORMATION: Any non-natural amino acid which can be
      covalently joined ("stapled together") using a ring-closing
      metathesis (RCM) reaction to form a cross-linked ring

<400> SEQUENCE: 43

Ala Thr Xaa Leu Arg Arg Phe Gly Asp Xaa Leu Asn Phe Glu Gln
1               5                   10                  15

<210> SEQ ID NO 44
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 44

Ala Thr Xaa Leu Arg Arg Ala Gly Asp Xaa Leu Asn Phe Arg Gln
1               5                   10                  15

<210> SEQ ID NO 45
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 45

Ala Thr Xaa Leu Arg Arg Phe Gly Asp Xaa Ala Asn Phe Arg Gln
1               5                   10                  15

<210> SEQ ID NO 46
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
```

```
            Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 46

Ala Thr Xaa Leu Arg Glu Phe Gly Asp Xaa Leu Asn Phe Arg Gln
1               5                   10                  15

<210> SEQ ID NO 47
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 47

Ala Thr Xaa Leu Arg Arg Phe Gly Asp Xaa Leu Asn Phe Glu Gln
1               5                   10                  15

<210> SEQ ID NO 48
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 48

Ala Ala Xaa Leu Arg Ala Phe Gly Ala Xaa Leu Asn Ala Ala
1               5                   10

<210> SEQ ID NO 49
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine
```

```
<400> SEQUENCE: 49

Ala Ala Xaa Leu Arg Ala Phe Gly Ala Xaa Leu Asn Ala Ala Ala Ala
1               5                   10                  15

<210> SEQ ID NO 50
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 50

Ala Ala Xaa Leu Arg Ala Phe Gly Ala Xaa Leu Asn Ala Glu
1               5                   10

<210> SEQ ID NO 51
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 51

Ala Ala Xaa Leu Arg Ala Phe Gly Ala Xaa Leu Asn Ala Glu Ala Ala
1               5                   10                  15

<210> SEQ ID NO 52
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 52

Ala Ala Xaa Leu Arg Glu Phe Gly Ala Xaa Leu Asn Ala Ala
1               5                   10

<210> SEQ ID NO 53
<211> LENGTH: 16
<212> TYPE: PRT
<213> ORGANISM: Artificial Sequence
```

-continued

```
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 53

Ala Ala Xaa Leu Arg Glu Phe Gly Ala Xaa Leu Asn Ala Ala Ala Ala
1               5                   10                  15

<210> SEQ ID NO 54
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 54

Ala Ala Xaa Leu Arg Ala Phe Gly Asp Xaa Leu Asn Ala Ala
1               5                   10

<210> SEQ ID NO 55
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 55

Ala Ala Xaa Leu Arg Ala Phe Gly Asp Xaa Leu Asn Ala Ala Ala Ala
1               5                   10                  15

<210> SEQ ID NO 56
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
```

```
<222> LOCATION: (10)..(10)
<223> OTHER INFORMATION: S-pentenyl alanine

<400> SEQUENCE: 56

Ala Ala Xaa Leu Arg Ala Phe Gly Asp Xaa Leu Asn Ala Glu
1               5                   10

<210> SEQ ID NO 57
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 57

Ala Ala Xaa Leu Arg Ala Phe Gly Asp Xaa Leu Asn Ala Glu Ala Ala
1               5                   10                  15

<210> SEQ ID NO 58
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 58

Ala Ala Xaa Leu Arg Glu Phe Gly Asp Xaa Leu Asn Ala Ala
1               5                   10

<210> SEQ ID NO 59
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: S-pentenyl alanine

<400> SEQUENCE: 59

Ala Ala Xaa Leu Arg Glu Phe Gly Asp Xaa Leu Asn Ala Ala Ala Ala
1               5                   10                  15

<210> SEQ ID NO 60
```

```
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent
<220> FEATURE:
<221> NAME/KEY: MOD_RES
<222> LOCATION: (4)..(4)
<223> OTHER INFORMATION: Any non-natural amino acid which can be
      covalently joined ("stapled together") using a ring-closing
      metathesis (RCM) reaction to form a cross-linked ring
<220> FEATURE:
<221> NAME/KEY: MOD_RES
<222> LOCATION: (11)..(11)
<223> OTHER INFORMATION: Any non-natural amino acid which can be
      covalently joined ("stapled together") using a ring-closing
      metathesis (RCM) reaction to form a cross-linked ring

<400> SEQUENCE: 60

Xaa Ala Thr Xaa Leu Arg Arg Ala Gly Asp Xaa Leu Asn Phe Arg Gln
1               5                   10                  15

<210> SEQ ID NO 61
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent
<220> FEATURE:
<221> NAME/KEY: MOD_RES
<222> LOCATION: (4)..(4)
<223> OTHER INFORMATION: Any non-natural amino acid which can be
      covalently joined ("stapled together") using a ring-closing
      metathesis (RCM) reaction to form a cross-linked ring
<220> FEATURE:
<221> NAME/KEY: MOD_RES
<222> LOCATION: (11)..(11)
<223> OTHER INFORMATION: Any non-natural amino acid which can be
      covalently joined ("stapled together") using a ring-closing
      metathesis (RCM) reaction to form a cross-linked ring

<400> SEQUENCE: 61

Xaa Ala Thr Xaa Leu Arg Arg Phe Gly Asp Xaa Ala Asn Phe Arg Gln
1               5                   10                  15

<210> SEQ ID NO 62
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent
<220> FEATURE:
<221> NAME/KEY: MOD_RES
<222> LOCATION: (4)..(4)
```

```
<223> OTHER INFORMATION: Any non-natural amino acid which can be
      covalently joined ("stapled together") using a ring-closing
      metathesis (RCM) reaction to form a cross-linked ring
<220> FEATURE:
<221> NAME/KEY: MOD_RES
<222> LOCATION: (11)..(11)
<223> OTHER INFORMATION: Any non-natural amino acid which can be
      covalently joined ("stapled together") using a ring-closing
      metathesis (RCM) reaction to form a cross-linked ring

<400> SEQUENCE: 62

Xaa Ala Thr Xaa Leu Arg Glu Phe Gly Asp Xaa Leu Asn Phe Arg Gln
1               5                   10                  15

<210> SEQ ID NO 63
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent
<220> FEATURE:
<221> NAME/KEY: MOD_RES
<222> LOCATION: (4)..(4)
<223> OTHER INFORMATION: Any non-natural amino acid which can be
      covalently joined ("stapled together") using a ring-closing
      metathesis (RCM) reaction to form a cross-linked ring
<220> FEATURE:
<221> NAME/KEY: MOD_RES
<222> LOCATION: (11)..(11)
<223> OTHER INFORMATION: Any non-natural amino acid which can be
      covalently joined ("stapled together") using a ring-closing
      metathesis (RCM) reaction to form a cross-linked ring

<400> SEQUENCE: 63

Xaa Ala Thr Xaa Leu Arg Arg Phe Gly Asp Xaa Leu Asn Phe Glu Gln
1               5                   10                  15

<210> SEQ ID NO 64
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent
<220> FEATURE:
<221> NAME/KEY: MOD_RES
<222> LOCATION: (4)..(4)
<223> OTHER INFORMATION: Any non-natural amino acid which can be
      covalently joined ("stapled together") using a ring-closing
      metathesis (RCM) reaction to form a cross-linked ring
<220> FEATURE:
<221> NAME/KEY: MOD_RES
<222> LOCATION: (11)..(11)
<223> OTHER INFORMATION: Any non-natural amino acid which can be
      covalently joined ("stapled together") using a ring-closing
      metathesis (RCM) reaction to form a cross-linked ring

<400> SEQUENCE: 64

Xaa Ala Ala Xaa Leu Arg Ala Phe Gly Ala Xaa Leu Asn Ala Ala
1               5                   10                  15
```

```
<210> SEQ ID NO 65
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent
<220> FEATURE:
<221> NAME/KEY: MOD_RES
<222> LOCATION: (4)..(4)
<223> OTHER INFORMATION: Any non-natural amino acid which can be
      covalently joined ("stapled together") using a ring-closing
      metathesis (RCM) reaction to form a cross-linked ring
<220> FEATURE:
<221> NAME/KEY: MOD_RES
<222> LOCATION: (11)..(11)
<223> OTHER INFORMATION: Any non-natural amino acid which can be
      covalently joined ("stapled together") using a ring-closing
      metathesis (RCM) reaction to form a cross-linked ring

<400> SEQUENCE: 65

Xaa Ala Ala Xaa Leu Arg Ala Phe Gly Ala Xaa Leu Asn Ala Ala Ala
1               5                   10                  15

Ala

<210> SEQ ID NO 66
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent
<220> FEATURE:
<221> NAME/KEY: MOD_RES
<222> LOCATION: (4)..(4)
<223> OTHER INFORMATION: Any non-natural amino acid which can be
      covalently joined ("stapled together") using a ring-closing
      metathesis (RCM) reaction to form a cross-linked ring
<220> FEATURE:
<221> NAME/KEY: MOD_RES
<222> LOCATION: (11)..(11)
<223> OTHER INFORMATION: Any non-natural amino acid which can be
      covalently joined ("stapled together") using a ring-closing
      metathesis (RCM) reaction to form a cross-linked ring

<400> SEQUENCE: 66

Xaa Ala Ala Xaa Leu Arg Ala Phe Gly Ala Xaa Leu Asn Ala Glu
1               5                   10                  15

<210> SEQ ID NO 67
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
```

```
        or absent
<220> FEATURE:
<221> NAME/KEY: MOD_RES
<222> LOCATION: (4)..(4)
<223> OTHER INFORMATION: Any non-natural amino acid which can be
      covalently joined ("stapled together") using a ring-closing
      metathesis (RCM) reaction to form a cross-linked ring
<220> FEATURE:
<221> NAME/KEY: MOD_RES
<222> LOCATION: (11)..(11)
<223> OTHER INFORMATION: Any non-natural amino acid which can be
      covalently joined ("stapled together") using a ring-closing
      metathesis (RCM) reaction to form a cross-linked ring

<400> SEQUENCE: 67

Xaa Ala Ala Xaa Leu Arg Ala Phe Gly Ala Xaa Leu Asn Ala Glu Ala
1               5                   10                  15

Ala

<210> SEQ ID NO 68
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent
<220> FEATURE:
<221> NAME/KEY: MOD_RES
<222> LOCATION: (4)..(4)
<223> OTHER INFORMATION: Any non-natural amino acid which can be
      covalently joined ("stapled together") using a ring-closing
      metathesis (RCM) reaction to form a cross-linked ring
<220> FEATURE:
<221> NAME/KEY: MOD_RES
<222> LOCATION: (11)..(11)
<223> OTHER INFORMATION: Any non-natural amino acid which can be
      covalently joined ("stapled together") using a ring-closing
      metathesis (RCM) reaction to form a cross-linked ring

<400> SEQUENCE: 68

Xaa Ala Ala Xaa Leu Arg Glu Phe Gly Ala Xaa Leu Asn Ala Ala
1               5                   10                  15

<210> SEQ ID NO 69
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent
<220> FEATURE:
<221> NAME/KEY: MOD_RES
<222> LOCATION: (4)..(4)
<223> OTHER INFORMATION: Any non-natural amino acid which can be
      covalently joined ("stapled together") using a ring-closing
      metathesis (RCM) reaction to form a cross-linked ring
<220> FEATURE:
<221> NAME/KEY: MOD_RES
<222> LOCATION: (11)..(11)
<223> OTHER INFORMATION: Any non-natural amino acid which can be
      covalently joined ("stapled together") using a ring-closing
      metathesis (RCM) reaction to form a cross-linked ring
```

<400> SEQUENCE: 69

Xaa Ala Ala Xaa Leu Arg Glu Phe Gly Ala Xaa Leu Asn Ala Ala Ala
1               5                   10                  15

Ala

<210> SEQ ID NO 70
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent
<220> FEATURE:
<221> NAME/KEY: MOD_RES
<222> LOCATION: (4)..(4)
<223> OTHER INFORMATION: Any non-natural amino acid which can be
      covalently joined ("stapled together") using a ring-closing
      metathesis (RCM) reaction to form a cross-linked ring
<220> FEATURE:
<221> NAME/KEY: MOD_RES
<222> LOCATION: (11)..(11)
<223> OTHER INFORMATION: Any non-natural amino acid which can be
      covalently joined ("stapled together") using a ring-closing
      metathesis (RCM) reaction to form a cross-linked ring

<400> SEQUENCE: 70

Xaa Ala Ala Xaa Leu Arg Ala Phe Gly Asp Xaa Leu Asn Ala Ala
1               5                   10                  15

<210> SEQ ID NO 71
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent
<220> FEATURE:
<221> NAME/KEY: MOD_RES
<222> LOCATION: (4)..(4)
<223> OTHER INFORMATION: Any non-natural amino acid which can be
      covalently joined ("stapled together") using a ring-closing
      metathesis (RCM) reaction to form a cross-linked ring
<220> FEATURE:
<221> NAME/KEY: MOD_RES
<222> LOCATION: (11)..(11)
<223> OTHER INFORMATION: Any non-natural amino acid which can be
      covalently joined ("stapled together") using a ring-closing
      metathesis (RCM) reaction to form a cross-linked ring

<400> SEQUENCE: 71

Xaa Ala Ala Xaa Leu Arg Ala Phe Gly Asp Xaa Leu Asn Ala Ala Ala
1               5                   10                  15

Ala

<210> SEQ ID NO 72
<211> LENGTH: 15
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent
<220> FEATURE:
<221> NAME/KEY: MOD_RES
<222> LOCATION: (4)..(4)
<223> OTHER INFORMATION: Any non-natural amino acid which can be
      covalently joined ("stapled together") using a ring-closing
      metathesis (RCM) reaction to form a cross-linked ring
<220> FEATURE:
<221> NAME/KEY: MOD_RES
<222> LOCATION: (11)..(11)
<223> OTHER INFORMATION: Any non-natural amino acid which can be
      covalently joined ("stapled together") using a ring-closing
      metathesis (RCM) reaction to form a cross-linked ring

<400> SEQUENCE: 72

Xaa Ala Ala Xaa Leu Arg Ala Phe Gly Asp Xaa Leu Asn Ala Glu
1               5                   10                  15

<210> SEQ ID NO 73
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent
<220> FEATURE:
<221> NAME/KEY: MOD_RES
<222> LOCATION: (4)..(4)
<223> OTHER INFORMATION: Any non-natural amino acid which can be
      covalently joined ("stapled together") using a ring-closing
      metathesis (RCM) reaction to form a cross-linked ring
<220> FEATURE:
<221> NAME/KEY: MOD_RES
<222> LOCATION: (11)..(11)
<223> OTHER INFORMATION: Any non-natural amino acid which can be
      covalently joined ("stapled together") using a ring-closing
      metathesis (RCM) reaction to form a cross-linked ring

<400> SEQUENCE: 73

Xaa Ala Ala Xaa Leu Arg Ala Phe Gly Asp Xaa Leu Asn Ala Glu Ala
1               5                   10                  15

Ala

<210> SEQ ID NO 74
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent
<220> FEATURE:
<221> NAME/KEY: MOD_RES
<222> LOCATION: (4)..(4)
<223> OTHER INFORMATION: Any non-natural amino acid which can be
``` covalently joined ("stapled together") using a ring-closing
        metathesis (RCM) reaction to form a cross-linked ring
<220> FEATURE:
<221> NAME/KEY: MOD_RES
<222> LOCATION: (11)..(11)
<223> OTHER INFORMATION: Any non-natural amino acid which can be
        covalently joined ("stapled together") using a ring-closing
        metathesis (RCM) reaction to form a cross-linked ring

<400> SEQUENCE: 74

Xaa Ala Ala Xaa Leu Arg Glu Phe Gly Asp Xaa Leu Asn Ala Ala
1               5                   10                  15

<210> SEQ ID NO 75
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"
<220> FEATURE:
<221> NAME/KEY: MOD_RES
<222> LOCATION: (1)..(1)
<223> OTHER INFORMATION: Non-natural electrophile containing amino acid
        or absent
<220> FEATURE:
<221> NAME/KEY: MOD_RES
<222> LOCATION: (4)..(4)
<223> OTHER INFORMATION: Any non-natural amino acid which can be
        covalently joined ("stapled together") using a ring-closing
        metathesis (RCM) reaction to form a cross-linked ring
<220> FEATURE:
<221> NAME/KEY: MOD_RES
<222> LOCATION: (11)..(11)
<223> OTHER INFORMATION: Any non-natural amino acid which can be
        covalently joined ("stapled together") using a ring-closing
        metathesis (RCM) reaction to form a cross-linked ring

<400> SEQUENCE: 75

Xaa Ala Ala Xaa Leu Arg Glu Phe Gly Asp Xaa Leu Asn Ala Ala Ala
1               5                   10                  15

Ala

<210> SEQ ID NO 76
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"
<220> FEATURE:
<221> NAME/KEY: MOD_RES
<222> LOCATION: (1)..(1)
<223> OTHER INFORMATION: Non-natural electrophile containing amino acid
        or absent
<220> FEATURE:
<221> NAME/KEY: MOD_RES
<222> LOCATION: (4)..(4)
<223> OTHER INFORMATION: R-octenyl alanine
<220> FEATURE:
<221> NAME/KEY: MOD_RES
<222> LOCATION: (11)..(11)
<223> OTHER INFORMATION: S-pentenyl alanine

<400> SEQUENCE: 76

Xaa Ala Thr Xaa Leu Arg Arg Ala Gly Asp Xaa Leu Asn Phe Arg Gln
1               5                   10                  15

<210> SEQ ID NO 77
<211> LENGTH: 16

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent
<220> FEATURE:
<221> NAME/KEY: MOD_RES
<222> LOCATION: (4)..(4)
<223> OTHER INFORMATION: R-octenyl alanine
<220> FEATURE:
<221> NAME/KEY: MOD_RES
<222> LOCATION: (11)..(11)
<223> OTHER INFORMATION: S-pentenyl alanine

<400> SEQUENCE: 77

Xaa Ala Thr Xaa Leu Arg Arg Phe Gly Asp Xaa Ala Asn Phe Arg Gln
1               5                   10                  15

<210> SEQ ID NO 78
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent
<220> FEATURE:
<221> NAME/KEY: MOD_RES
<222> LOCATION: (4)..(4)
<223> OTHER INFORMATION: R-octenyl alanine
<220> FEATURE:
<221> NAME/KEY: MOD_RES
<222> LOCATION: (11)..(11)
<223> OTHER INFORMATION: S-pentenyl alanine

<400> SEQUENCE: 78

Xaa Ala Thr Xaa Leu Arg Glu Phe Gly Asp Xaa Leu Asn Phe Arg Gln
1               5                   10                  15

<210> SEQ ID NO 79
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent
<220> FEATURE:
<221> NAME/KEY: MOD_RES
<222> LOCATION: (4)..(4)
<223> OTHER INFORMATION: R-octenyl alanine
<220> FEATURE:
<221> NAME/KEY: MOD_RES
<222> LOCATION: (11)..(11)
<223> OTHER INFORMATION: S-pentenyl alanine

<400> SEQUENCE: 79

Xaa Ala Thr Xaa Leu Arg Arg Phe Gly Asp Xaa Leu Asn Phe Glu Gln
```

<210> SEQ ID NO 80
<211> LENGTH: 350
<212> TYPE: PRT
<213> ORGANISM: Homo sapiens

<400> SEQUENCE: 80

```
Met Phe Gly Leu Lys Arg Asn Ala Val Ile Gly Leu Asn Leu Tyr Cys
1               5                   10                  15

Gly Gly Ala Gly Leu Gly Ala Gly Ser Gly Gly Ala Thr Arg Pro Gly
            20                  25                  30

Gly Arg Leu Leu Ala Thr Glu Lys Glu Ala Ser Ala Arg Arg Glu Ile
        35                  40                  45

Gly Gly Gly Glu Ala Gly Ala Val Ile Gly Ser Ala Gly Ala Ser
    50                  55                  60

Pro Pro Ser Thr Leu Thr Pro Asp Ser Arg Arg Val Ala Arg Pro Pro
65                  70                  75                  80

Pro Ile Gly Ala Glu Val Pro Asp Val Thr Ala Thr Pro Ala Arg Leu
                85                  90                  95

Leu Phe Phe Ala Pro Thr Arg Arg Ala Ala Pro Leu Glu Glu Met Glu
            100                 105                 110

Ala Pro Ala Ala Asp Ala Ile Met Ser Pro Glu Glu Glu Leu Asp Gly
        115                 120                 125

Tyr Glu Pro Glu Pro Leu Gly Lys Arg Pro Ala Val Leu Pro Leu Leu
    130                 135                 140

Glu Leu Val Gly Glu Ser Gly Asn Asn Thr Ser Thr Asp Gly Ser Leu
145                 150                 155                 160

Pro Ser Thr Pro Pro Pro Ala Glu Glu Glu Asp Glu Leu Tyr Arg
                165                 170                 175

Gln Ser Leu Glu Ile Ile Ser Arg Tyr Leu Arg Glu Gln Ala Thr Gly
            180                 185                 190

Ala Lys Asp Thr Lys Pro Met Gly Arg Ser Gly Ala Thr Ser Arg Lys
        195                 200                 205

Ala Leu Glu Thr Leu Arg Arg Val Gly Asp Gly Val Gln Arg Asn His
    210                 215                 220

Glu Thr Ala Phe Gln Gly Met Leu Arg Lys Leu Asp Ile Lys Asn Glu
225                 230                 235                 240

Asp Asp Val Lys Ser Leu Ser Arg Val Met Ile His Val Phe Ser Asp
                245                 250                 255

Gly Val Thr Asn Trp Gly Arg Ile Val Thr Leu Ile Ser Phe Gly Ala
            260                 265                 270

Phe Val Ala Lys His Leu Lys Thr Ile Asn Gln Glu Ser Cys Ile Glu
        275                 280                 285

Pro Leu Ala Glu Ser Ile Thr Asp Val Leu Val Arg Thr Lys Arg Asp
    290                 295                 300

Trp Leu Val Lys Gln Arg Gly Trp Asp Gly Phe Val Glu Phe Phe His
305                 310                 315                 320

Val Glu Asp Leu Glu Gly Gly Ile Arg Asn Val Leu Leu Ala Phe Ala
                325                 330                 335

Gly Val Ala Gly Val Gly Ala Gly Leu Ala Tyr Leu Ile Arg
            340                 345                 350
```

<210> SEQ ID NO 81
<211> LENGTH: 175

```
<212> TYPE: PRT
<213> ORGANISM: Homo sapiens

<400> SEQUENCE: 81

Met Thr Asp Cys Glu Phe Gly Tyr Ile Tyr Arg Leu Ala Gln Asp Tyr
1               5                   10                  15

Leu Gln Cys Val Leu Gln Ile Pro Gln Pro Gly Ser Gly Pro Ser Lys
            20                  25                  30

Thr Ser Arg Val Leu Gln Asn Val Ala Phe Ser Val Gln Lys Glu Val
        35                  40                  45

Glu Lys Asn Leu Lys Ser Cys Leu Asp Asn Val Asn Val Val Ser Val
50                  55                  60

Asp Thr Ala Arg Thr Leu Phe Asn Gln Val Met Glu Lys Glu Phe Glu
65                  70                  75                  80

Asp Gly Ile Ile Asn Trp Gly Arg Ile Val Thr Ile Phe Ala Phe Glu
                85                  90                  95

Gly Ile Leu Ile Lys Lys Leu Leu Arg Gln Gln Ile Ala Pro Asp Val
            100                 105                 110

Asp Thr Tyr Lys Glu Ile Ser Tyr Phe Val Ala Glu Phe Ile Met Asn
        115                 120                 125

Asn Thr Gly Glu Trp Ile Arg Gln Asn Gly Gly Trp Glu Asn Gly Phe
130                 135                 140

Val Lys Lys Phe Glu Pro Lys Ser Gly Trp Met Thr Phe Leu Glu Val
145                 150                 155                 160

Thr Gly Lys Ile Cys Glu Met Leu Ser Leu Leu Lys Gln Tyr Cys
                165                 170                 175

<210> SEQ ID NO 82
<211> LENGTH: 54
<212> TYPE: PRT
<213> ORGANISM: Homo sapiens

<400> SEQUENCE: 82

Met Pro Gly Lys Lys Ala Arg Lys Asn Ala Gln Pro Ser Pro Ala Arg
1               5                   10                  15

Ala Pro Ala Glu Leu Glu Val Glu Cys Ala Thr Gln Leu Arg Arg Phe
            20                  25                  30

Gly Asp Lys Leu Asn Phe Arg Gln Lys Leu Leu Asn Leu Ile Ser Lys
        35                  40                  45

Leu Phe Cys Ser Gly Thr
        50

<210> SEQ ID NO 83
<211> LENGTH: 151
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Met Thr Asp Cys Glu Phe Gly Tyr Ile Tyr Arg Leu Ala Gln Asp Tyr
1               5                   10                  15

Leu Gln Cys Val Leu Gln Ile Pro Gln Pro Gly Ser Gly Pro Ser Lys
            20                  25                  30

Thr Ser Arg Val Leu Gln Asn Val Ala Phe Ser Val Gln Lys Glu Val
        35                  40                  45
```

-continued

```
Glu Lys Asn Leu Lys Ser Cys Leu Asp Asn Val Asn Val Val Ser Val
 50                  55                  60

Asp Thr Ala Arg Thr Leu Phe Asn Gln Val Met Glu Lys Glu Phe Glu
 65                  70                  75                  80

Asp Gly Ile Ile Asn Trp Gly Arg Ile Val Thr Ile Phe Ala Phe Glu
                 85                  90                  95

Gly Ile Leu Ile Lys Lys Leu Leu Arg Gln Gln Ile Ala Pro Asp Val
                100                 105                 110

Asp Thr Tyr Lys Glu Ile Ser Tyr Phe Val Ala Glu Phe Ile Met Asn
            115                 120                 125

Asn Thr Gly Glu Trp Ile Arg Gln Asn Gly Gly Trp Glu Asn Gly Phe
130                 135                 140

Val Lys Lys Phe Glu Pro Lys
145                 150

<210> SEQ ID NO 84
<211> LENGTH: 75
<212> TYPE: PRT
<213> ORGANISM: Unknown
<220> FEATURE:
<221> NAME/KEY: source
<223> OTHER INFORMATION: /note="Description of Unknown:
      BFL-1 sequence"

<400> SEQUENCE: 84

Lys Thr Ser Arg Val Leu Gln Asn Val Ala Phe Ser Val Gln Lys Glu
 1               5                  10                  15

Val Glu Lys Asn Leu Lys Ser Cys Leu Asp Asn Val Asn Val Val Ser
                20                  25                  30

Val Asp Thr Ala Arg Thr Leu Phe Asn Gln Val Met Glu Lys Glu Phe
            35                  40                  45

Glu Asp Gly Ile Ile Asn Trp Gly Arg Ile Val Thr Ile Phe Ala Phe
 50                  55                  60

Glu Gly Ile Leu Ile Lys Lys Leu Leu Arg Gln
 65                  70                  75

<210> SEQ ID NO 85
<211> LENGTH: 76
<212> TYPE: PRT
<213> ORGANISM: Unknown
<220> FEATURE:
<221> NAME/KEY: source
<223> OTHER INFORMATION: /note="Description of Unknown:
      MCL-1 sequence"

<400> SEQUENCE: 85

Thr Ser Arg Lys Ala Leu Glu Thr Leu Arg Arg Val Gly Asp Gly Val
 1               5                  10                  15

Gln Arg Asn His Glu Thr Ala Phe Gln Gly Met Leu Arg Lys Leu Asp
                20                  25                  30

Ile Lys Asn Glu Asp Asp Val Lys Ser Leu Ser Arg Val Met Ile His
            35                  40                  45

Val Phe Ser Asp Gly Val Thr Asn Trp Gly Arg Ile Val Thr Leu Ile
 50                  55                  60

Ser Phe Gly Ala Phe Val Ala Lys His Leu Lys Thr
 65                  70                  75

<210> SEQ ID NO 86
<211> LENGTH: 72
<212> TYPE: PRT
```

```
<213> ORGANISM: Unknown
<220> FEATURE:
<221> NAME/KEY: source
<223> OTHER INFORMATION: /note="Description of Unknown:
      BCL-2 sequence"

<400> SEQUENCE: 86

Val Val His Leu Thr Leu Arg Gln Ala Gly Asp Asp Phe Ser Arg Arg
1               5                   10                  15

Tyr Arg Arg Asp Phe Ala Glu Met Ser Ser Gln Leu His Leu Thr Pro
                20                  25                  30

Phe Thr Ala Arg Gly Arg Phe Ala Thr Val Val Glu Glu Leu Phe Arg
            35                  40                  45

Asp Gly Val Asn Trp Gly Arg Ile Val Ala Phe Phe Glu Phe Gly Gly
        50                  55                  60

Val Met Cys Val Glu Ser Val Asn
65                  70

<210> SEQ ID NO 87
<211> LENGTH: 74
<212> TYPE: PRT
<213> ORGANISM: Unknown
<220> FEATURE:
<221> NAME/KEY: source
<223> OTHER INFORMATION: /note="Description of Unknown:
      BCL-XL sequence"

<400> SEQUENCE: 87

Met Ala Ala Val Lys Gln Ala Leu Arg Glu Ala Gly Asp Glu Phe Glu
1               5                   10                  15

Leu Arg Tyr Arg Arg Ala Phe Ser Asp Leu Thr Ser Gln Leu His Ile
                20                  25                  30

Thr Pro Gly Thr Ala Tyr Gln Ser Phe Glu Gln Val Val Asn Glu Leu
            35                  40                  45

Phe Arg Asp Gly Val Asn Trp Gly Arg Ile Val Ala Phe Phe Ser Phe
        50                  55                  60

Gly Gly Ala Leu Cys Val Glu Ser Val Asp
65                  70

<210> SEQ ID NO 88
<211> LENGTH: 72
<212> TYPE: PRT
<213> ORGANISM: Unknown
<220> FEATURE:
<221> NAME/KEY: source
<223> OTHER INFORMATION: /note="Description of Unknown:
      BCL-W sequence"

<400> SEQUENCE: 88

Pro Leu His Gln Ala Met Arg Ala Ala Gly Asp Glu Phe Glu Thr Arg
1               5                   10                  15

Phe Arg Arg Thr Phe Ser Asp Leu Ala Ala Gln Leu His Val Thr Pro
                20                  25                  30

Gly Ser Ala Gln Gln Arg Phe Thr Gln Val Ser Asp Glu Leu Phe Gln
            35                  40                  45

Gly Gly Pro Asn Trp Gly Arg Leu Val Ala Phe Val Phe Gly Ala
        50                  55                  60

Ala Leu Cys Ala Glu Ser Val Asn
65                  70

<210> SEQ ID NO 89
```

```
<211> LENGTH: 64
<212> TYPE: PRT
<213> ORGANISM: Unknown
<220> FEATURE:
<221> NAME/KEY: source
<223> OTHER INFORMATION: /note="Description of Unknown:
      BCL-b sequence"

<400> SEQUENCE: 89

Pro Glu Ala Ala Val Leu Arg Ser Ala Ala Arg Leu Arg Gln Ile
1               5                   10                  15

His Arg Ser Phe Phe Ser Ala Tyr Leu Gly Tyr Pro Gly Asn Arg Phe
                20                  25                  30

Glu Leu Val Ala Leu Met Ala Asp Ser Val Leu Ser Asp Ser Pro Gly
                35                  40                  45

Pro Thr Trp Gly Arg Val Val Thr Leu Val Thr Phe Ala Gly Thr Leu
    50                  55                  60

<210> SEQ ID NO 90
<211> LENGTH: 73
<212> TYPE: PRT
<213> ORGANISM: Unknown
<220> FEATURE:
<221> NAME/KEY: source
<223> OTHER INFORMATION: /note="Description of Unknown:
      BAX sequence"

<400> SEQUENCE: 90

Ala Ser Thr Lys Lys Leu Ser Glu Cys Leu Lys Arg Ile Gly Asp Glu
1               5                   10                  15

Leu Asp Ser Asn Met Glu Leu Gln Arg Met Ile Ala Ala Val Asp Thr
                20                  25                  30

Asp Ser Pro Arg Glu Val Phe Phe Arg Val Ala Ala Asp Met Phe Ser
                35                  40                  45

Asp Gly Asn Phe Asn Trp Gly Arg Val Val Ala Leu Phe Tyr Phe Ala
    50                  55                  60

Ser Lys Leu Val Leu Lys Ala Leu Cys
65                  70

<210> SEQ ID NO 91
<211> LENGTH: 75
<212> TYPE: PRT
<213> ORGANISM: Unknown
<220> FEATURE:
<221> NAME/KEY: source
<223> OTHER INFORMATION: /note="Description of Unknown:
      BAK sequence"

<400> SEQUENCE: 91

Thr Met Gly Gln Val Gly Arg Gln Leu Ala Ile Ile Gly Asp Asp Ile
1               5                   10                  15

Asn Arg Arg Tyr Asp Ser Glu Phe Gln Thr Met Leu Gln His Leu Gln
                20                  25                  30

Pro Thr Ala Glu Asn Ala Tyr Glu Tyr Phe Thr Lys Ile Ala Thr Ser
                35                  40                  45

Leu Phe Glu Ser Gly Ile Asn Trp Gly Arg Val Val Ala Leu Leu Gly
    50                  55                  60

Phe Gly Tyr Arg Leu Ala Leu His Val Val Gln
65                  70                  75

<210> SEQ ID NO 92
<211> LENGTH: 16
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Nipecotic Acid or absent
<220> FEATURE:
<221> NAME/KEY: MOD_RES
<222> LOCATION: (4)..(4)
<223> OTHER INFORMATION: R-octenyl alanine
<220> FEATURE:
<221> NAME/KEY: MOD_RES
<222> LOCATION: (11)..(11)
<223> OTHER INFORMATION: S-pentenyl alanine

<400> SEQUENCE: 92

Xaa Ala Thr Xaa Leu Arg Arg Phe Gly Asp Xaa Leu Asn Phe Arg Gln
1               5                   10                  15

<210> SEQ ID NO 93
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace=" " or "D-alanine" or "alpha-
      aminoisobutyric acid" or "a non-natural amino acids that can form
      a staple and/or stitch"
<220> FEATURE:
<221> NAME/KEY: VARIANT
<222> LOCATION: (2)..(2)
<223> OTHER INFORMATION: /replace=" " or "Ala" or "D-alanine" or "alpha-
      aminoisobutyric acid" or "Ile" or "Met" or "Norleucine" or "a non-
      natural amino acids that can form a staple and/or stitch"
<220> FEATURE:
<221> NAME/KEY: VARIANT
<222> LOCATION: (3)..(3)
<223> OTHER INFORMATION: /replace=" " or "Ala" or "D-alanine" or "alpha-
      aminoisobutyric acid" or "a non-natural amino acids that can form
      a staple and/or stitch"
<220> FEATURE:
<221> NAME/KEY: VARIANT
<222> LOCATION: (4)..(4)
<223> OTHER INFORMATION: /replace=" " or "Ala" or "D-alanine" or "alpha-
      aminoisobutyric acid" or "Ile" or "Phe"
<220> FEATURE:
<221> NAME/KEY: VARIANT
<222> LOCATION: (5)..(5)
<223> OTHER INFORMATION: /replace="Ala" or "D-alanine" or "alpha-
      aminoisobutyric acid" or "a non-natural amino acids that can form
      a staple and/or stitch"
<220> FEATURE:
<221> NAME/KEY: VARIANT
<222> LOCATION: (6)..(6)
<223> OTHER INFORMATION: /replace="Ala" or "D-alanine" or "alpha-
      aminoisobutyric acid" "Glu" or "a non-natural amino acids that can
      form a staple and/or stitch"
<220> FEATURE:
<221> NAME/KEY: VARIANT
<222> LOCATION: (7)..(7)
<223> OTHER INFORMATION: /replace="Ala" or "D-alanine" or "alpha-
      aminoisobutyric acid" "Ile" or "Leu" or "Val" or "a non-natural
      amino acids that can form a staple and/or stitch"
<220> FEATURE:
<221> NAME/KEY: VARIANT
<222> LOCATION: (8)..(8)
<223> OTHER INFORMATION: /replace="Ala" or "D-alanine" or "alpha-
      aminoisobutyric acid" or "a non-natural amino acids that can form
```

```
      a staple and/or stitch"
<220> FEATURE:
<221> NAME/KEY: VARIANT
<222> LOCATION: (10)..(10)
<223> OTHER INFORMATION: /replace=" " or "Ala" or "D-alanine" or "alpha-
      aminoisobutyric acid" or "a non-natural amino acids that can form
      a staple and/or stitch"
<220> FEATURE:
<221> NAME/KEY: VARIANT
<222> LOCATION: (11)..(11)
<223> OTHER INFORMATION: /replace=" " or "Ala" or "D-alanine" or "alpha-
      aminoisobutyric acid" "Trp" or "Val" or "a non-natural amino acids
      that can form a staple and/or stitch"
<220> FEATURE:
<221> NAME/KEY: VARIANT
<222> LOCATION: (12)..(12)
<223> OTHER INFORMATION: /replace=" " or "Ala" or "D-alanine" or "alpha-
      aminoisobutyric acid" "Ser" or "Asp" or "a non-natural amino acids
      that can form a staple and/or stitch"
<220> FEATURE:
<221> NAME/KEY: VARIANT
<222> LOCATION: (13)..(13)
<223> OTHER INFORMATION: /replace=" " or "Ala" or "Leu" or "D-alanine"
      or "alpha-aminoisobutyric acid" or "a non-natural amino acids that
      can form a staple and/or stitch"
<220> FEATURE:
<221> NAME/KEY: VARIANT
<222> LOCATION: (14)..(14)
<223> OTHER INFORMATION: /replace=" " or "Ala" or "D-alanine" or "alpha-
      aminoisobutyric acid" or "Glu" or "a non-natural amino acids that
      can form a staple and/or stitch"
<220> FEATURE:
<221> NAME/KEY: VARIANT
<222> LOCATION: (15)..(15)
<223> OTHER INFORMATION: /replace=" " or "Ala" or "D-alanine" or "alpha-
      aminoisobutyric acid" "Leu" or "a non-natural amino acids that can
      form a staple and/or stitch"
<220> FEATURE:
<221> NAME/KEY: SITE
<222> LOCATION: (1)..(15)
<223> OTHER INFORMATION: /note="Variant residues given in the sequence
      have no preference with respect to those in the annotations
      for variant positions"

<400> SEQUENCE: 93

Ala Thr Gln Leu Arg Arg Phe Gly Asp Lys Leu Asn Phe Arg Gln
1               5                   10                  15

<210> SEQ ID NO 94
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Ala Thr Gln Leu Arg Arg Ala Gly Asp Lys Leu Asn Phe Arg Gln
1               5                   10                  15

<210> SEQ ID NO 95
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Ala Thr Gln Leu Arg Arg Phe Gly Asp Lys Ala Asn Phe Arg Gln
1               5                   10                  15
```

```
<210> SEQ ID NO 96
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Ala Thr Gln Leu Arg Glu Phe Gly Asp Lys Leu Asn Phe Arg Gln
1               5                   10                  15

<210> SEQ ID NO 97
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Ala Thr Gln Leu Arg Arg Phe Gly Asp Lys Leu Asn Phe Glu Gln
1               5                   10                  15

<210> SEQ ID NO 98
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Ala Ala Gln Leu Arg Ala Phe Gly Ala Lys Leu Asn Ala Ala
1               5                   10

<210> SEQ ID NO 99
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Ala Ala Gln Leu Arg Ala Phe Gly Ala Lys Leu Asn Ala Ala Ala Ala
1               5                   10                  15

<210> SEQ ID NO 100
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Ala Ala Gln Leu Arg Ala Phe Gly Ala Lys Leu Asn Ala Glu
1               5                   10

<210> SEQ ID NO 101
<211> LENGTH: 16
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Ala Ala Gln Leu Arg Ala Phe Gly Ala Lys Leu Asn Ala Glu Ala Ala
1               5                   10                  15

<210> SEQ ID NO 102
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Ala Ala Gln Leu Arg Glu Phe Gly Ala Lys Leu Asn Ala Ala
1               5                   10

<210> SEQ ID NO 103
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Ala Ala Gln Leu Arg Glu Phe Gly Ala Lys Leu Asn Ala Ala Ala Ala
1               5                   10                  15

<210> SEQ ID NO 104
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Ala Ala Gln Leu Arg Ala Phe Gly Asp Lys Leu Asn Ala Ala
1               5                   10

<210> SEQ ID NO 105
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Ala Ala Gln Leu Arg Ala Phe Gly Asp Lys Leu Asn Ala Ala Ala Ala
1               5                   10                  15

<210> SEQ ID NO 106
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 106

Ala Ala Gln Leu Arg Ala Phe Gly Asp Lys Leu Asn Ala Glu
1               5                   10

<210> SEQ ID NO 107
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Ala Ala Gln Leu Arg Ala Phe Gly Asp Lys Leu Asn Ala Glu Ala Ala
1               5                   10                  15

<210> SEQ ID NO 108
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Ala Ala Gln Leu Arg Glu Phe Gly Asp Lys Leu Asn Ala Ala
1               5                   10

<210> SEQ ID NO 109
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Ala Ala Gln Leu Arg Glu Phe Gly Asp Lys Leu Asn Ala Ala Ala Ala
1               5                   10                  15

<210> SEQ ID NO 110
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Ala Thr Gln Leu Arg
1               5

<210> SEQ ID NO 111
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

```
Ala Thr Gln Leu Arg Arg
1               5

<210> SEQ ID NO 112
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Ala Thr Gln Leu Arg Arg Phe
1               5

<210> SEQ ID NO 113
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

Ala Thr Gln Leu Arg Arg Phe Gly Asp
1               5

<210> SEQ ID NO 114
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 114

Ala Thr Gln Leu Arg Arg Phe Gly Asp Lys
1               5                   10

<210> SEQ ID NO 115
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115

Ala Thr Gln Leu Arg Arg Phe Gly Asp Lys Leu
1               5                   10

<210> SEQ ID NO 116
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Thr Gln Leu Arg Arg Phe
1               5
```

-continued

```
<210> SEQ ID NO 117
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Leu Arg Arg Phe Gly Asp
1               5

<210> SEQ ID NO 118
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Phe Gly Asp Lys Leu Asn
1               5

<210> SEQ ID NO 119
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Gly Asp Lys Leu Asn Phe
1               5

<210> SEQ ID NO 120
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

Asp Lys Leu Asn Phe Arg
1               5

<210> SEQ ID NO 121
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Arg Phe Gly Asp Lys Leu Asn Phe Arg Gln
1               5                   10

<210> SEQ ID NO 122
<211> LENGTH: 9
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 122

Phe Gly Asp Lys Leu Asn Phe Arg Gln
1               5

<210> SEQ ID NO 123
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

Gly Asp Lys Leu Asn Phe Arg Gln
1               5

<210> SEQ ID NO 124
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

Leu Asn Phe Arg Gln
1               5

<210> SEQ ID NO 125
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Asp Lys Leu Asn Phe Arg Gln
1               5

<210> SEQ ID NO 126
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent

<400> SEQUENCE: 126

Xaa Ala Thr Gln Leu Arg Arg Ala Gly Asp Lys Leu Asn Phe Arg Gln
1               5                   10                  15

<210> SEQ ID NO 127
<211> LENGTH: 16
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent

<400> SEQUENCE: 127

Xaa Ala Thr Gln Leu Arg Arg Phe Gly Asp Lys Ala Asn Phe Arg Gln
1               5                   10                  15

<210> SEQ ID NO 128
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent

<400> SEQUENCE: 128

Xaa Ala Thr Gln Leu Arg Glu Phe Gly Asp Lys Leu Asn Phe Arg Gln
1               5                   10                  15

<210> SEQ ID NO 129
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent

<400> SEQUENCE: 129

Xaa Ala Thr Gln Leu Arg Arg Phe Gly Asp Lys Leu Asn Phe Glu Gln
1               5                   10                  15

<210> SEQ ID NO 130
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent

<400> SEQUENCE: 130

Xaa Ala Ala Gln Leu Arg Ala Phe Gly Ala Lys Leu Asn Ala Ala
1               5                   10                  15

<210> SEQ ID NO 131
<211> LENGTH: 17
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent

<400> SEQUENCE: 131

Xaa Ala Ala Gln Leu Arg Ala Phe Gly Ala Lys Leu Asn Ala Ala Ala
1               5                   10                  15

Ala

<210> SEQ ID NO 132
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent

<400> SEQUENCE: 132

Xaa Ala Ala Gln Leu Arg Ala Phe Gly Ala Lys Leu Asn Ala Glu
1               5                   10                  15

<210> SEQ ID NO 133
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent

<400> SEQUENCE: 133

Xaa Ala Ala Gln Leu Arg Ala Phe Gly Ala Lys Leu Asn Ala Glu Ala
1               5                   10                  15

Ala

<210> SEQ ID NO 134
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent

<400> SEQUENCE: 134

Xaa Ala Ala Gln Leu Arg Glu Phe Gly Ala Lys Leu Asn Ala Ala
```

<210> SEQ ID NO 135
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent

<400> SEQUENCE: 135

Xaa Ala Ala Gln Leu Arg Glu Phe Gly Ala Lys Leu Asn Ala Ala Ala
1               5                   10                  15

Ala

<210> SEQ ID NO 136
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent

<400> SEQUENCE: 136

Xaa Ala Ala Gln Leu Arg Ala Phe Gly Asp Lys Leu Asn Ala Ala
1               5                   10                  15

<210> SEQ ID NO 137
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent

<400> SEQUENCE: 137

Xaa Ala Ala Gln Leu Arg Ala Phe Gly Asp Lys Leu Asn Ala Ala Ala
1               5                   10                  15

Ala

<210> SEQ ID NO 138
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid or absent

<400> SEQUENCE: 138

Xaa Ala Ala Gln Leu Arg Ala Phe Gly Asp Lys Leu Asn Ala Glu
1               5                   10                  15

<210> SEQ ID NO 139
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent

<400> SEQUENCE: 139

Xaa Ala Ala Gln Leu Arg Ala Phe Gly Asp Lys Leu Asn Ala Glu Ala
1               5                   10                  15

Ala

<210> SEQ ID NO 140
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent

<400> SEQUENCE: 140

Xaa Ala Ala Gln Leu Arg Glu Phe Gly Asp Lys Leu Asn Ala Ala
1               5                   10                  15

<210> SEQ ID NO 141
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent

<400> SEQUENCE: 141

Xaa Ala Ala Gln Leu Arg Glu Phe Gly Asp Lys Leu Asn Ala Ala Ala
1               5                   10                  15

Ala

<210> SEQ ID NO 142
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 142

Arg Arg Phe Gly Asp
1               5

<210> SEQ ID NO 143
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 143

Arg Phe Gly Asp Lys
1               5

<210> SEQ ID NO 144
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 144

Lys Leu Asn Phe Arg
1               5

<210> SEQ ID NO 145
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 145

Thr Gln Leu Arg Arg
1               5

<210> SEQ ID NO 146
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 146

Phe Gly Asp Lys Leu
1               5

<210> SEQ ID NO 147
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 147

```
Gln Leu Arg Arg Phe
1               5

<210> SEQ ID NO 148
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 148

Gly Asp Lys Leu Asn
1               5

<210> SEQ ID NO 149
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 149

Leu Arg Arg Phe Gly
1               5

<210> SEQ ID NO 150
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 150

Asp Lys Leu Asn Phe
1               5

<210> SEQ ID NO 151
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent
<220> FEATURE:
<221> NAME/KEY: MOD_RES
<222> LOCATION: (4)..(4)
<223> OTHER INFORMATION: R-octenyl alanine
<220> FEATURE:
<221> NAME/KEY: MOD_RES
<222> LOCATION: (11)..(11)
<223> OTHER INFORMATION: S-pentenyl alanine

<400> SEQUENCE: 151

Xaa Ala Ala Xaa Leu Arg Glu Phe Gly Ala Xaa Leu Asn Ala Ala
1               5                   10                  15

<210> SEQ ID NO 152
<211> LENGTH: 17
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent
<220> FEATURE:
<221> NAME/KEY: MOD_RES
<222> LOCATION: (4)..(4)
<223> OTHER INFORMATION: R-octenyl alanine
<220> FEATURE:
<221> NAME/KEY: MOD_RES
<222> LOCATION: (11)..(11)
<223> OTHER INFORMATION: S-pentenyl alanine

<400> SEQUENCE: 152

Xaa Ala Ala Xaa Leu Arg Ala Phe Gly Ala Xaa Leu Asn Ala Ala Ala
1               5                   10                  15

Ala

<210> SEQ ID NO 153
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent
<220> FEATURE:
<221> NAME/KEY: MOD_RES
<222> LOCATION: (4)..(4)
<223> OTHER INFORMATION: R-octenyl alanine
<220> FEATURE:
<221> NAME/KEY: MOD_RES
<222> LOCATION: (11)..(11)
<223> OTHER INFORMATION: S-pentenyl alanine

<400> SEQUENCE: 153

Xaa Ala Ala Xaa Leu Arg Glu Phe Gly Ala Xaa Leu Asn Ala Ala Ala
1               5                   10                  15

Ala

<210> SEQ ID NO 154
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Non-natural electrophile containing amino acid
      or absent
<220> FEATURE:
<221> NAME/KEY: MOD_RES
<222> LOCATION: (4)..(4)
<223> OTHER INFORMATION: R-octenyl alanine
<220> FEATURE:
<221> NAME/KEY: MOD_RES
<222> LOCATION: (11)..(11)
<223> OTHER INFORMATION: S-pentenyl alanine
```

<400> SEQUENCE: 154

Xaa Ala Ala Xaa Leu Arg Ala Phe Gly Ala Xaa Leu Asn Ala Ala
1               5                   10                  15

<210> SEQ ID NO 155
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(4)
<223> OTHER INFORMATION: Any amino acid

<400> SEQUENCE: 155

Leu Xaa Xaa Xaa Gly Asp Glu
1               5

<210> SEQ ID NO 156
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 156

His His His His His His
1               5